(12) United States Patent
Lundergan et al.

(10) Patent No.: US 7,550,300 B1
(45) Date of Patent: Jun. 23, 2009

(54) PREDICTION OF BARE METAL STENT RESTENOSIS

(75) Inventors: Conor F. Lundergan, Ellicott City, MD (US); Harry B. Burke, Glen Allen, VA (US); Timothy A. McCaffrey, Silver Spring, MD (US)

(73) Assignee: CapGen Sciences, Inc., Elliocott City, MD (US)

( * ) Notice: Subject to any disclaimer, the term of this patent is extended or adjusted under 35 U.S.C. 154(b) by 0 days.

(21) Appl. No.: 11/947,119

(22) Filed: Nov. 29, 2007

(51) Int. Cl.
*G01N 33/00* (2006.01)
*C12Q 1/68* (2006.01)
*C12M 1/34* (2006.01)
*C07H 21/04* (2006.01)

(52) U.S. Cl. .................. 436/94; 435/6; 435/287.2; 536/23.1; 536/23.5; 536/24.31

(58) Field of Classification Search ............... None
See application file for complete search history.

(56) References Cited

U.S. PATENT DOCUMENTS

| 6,790,635 | B1 | 9/2004 | Seiki et al. |
| 2006/0099590 | A1 | 5/2006 | Yamada et al. |
| 2006/0134663 | A1 | 6/2006 | Harkin et al. |

| 2007/0037144 | A1 | 2/2007 | Wohlgemuth et al. |

FOREIGN PATENT DOCUMENTS

WO  WO 03/031650 A2  4/2003

OTHER PUBLICATIONS

Patino et al.; "Circulating Transcriptome Reveals Markers of Atherosclerosis"; article; PNAS; Mar. 1, 2005; pp. 3423-3428; vol. 102, No. 9.
Zohlnhofer et al.; Transcriptome Analysis Reveals a Role of Interferon-y in Human Neointima Formation: article; Molecular Cell; May 2005; pp. 1059-1069; vol. 7.
Welt, F., et al, "Leukocyte Recruitment and Exprression of Chemokines Following Different Forms of Vascular Injury", Vascular Medicine, 2003., vol. 8, pp. 1-7.

*Primary Examiner*—Bradley L Sisson
(74) *Attorney, Agent, or Firm*—Whitham Curtis Christofferson & Cook, PC

(57) ABSTRACT

Methods for predicting whether or not a patient is likely to experience restenosis after the placement of a bare metal stent are provided. The methods involve detecting and analyzing gene expression patterns of the cellular components of whole blood, where activation of selected genes has been found to be indicative of a high probability of restenosis. The method thus allows the identification, prior to placement of a stent, of patients who are i) likely to experience restenosis, and thus should receive a stent that includes anti-restenosis agents; or ii) unlikely to experience restenosis, and thus should receive a stent without anti-stenosis agents.

3 Claims, 2 Drawing Sheets

SEQUENCE LISTING

```
<160> NUMBER OF SEQ ID NOS: 1174

<210> SEQ ID NO 1
<211> LENGTH: 492
<212> TYPE: DNA
<213> ORGANISM: Homo sapiens
<220> FEATURE:
<221> NAME/KEY: misc_feature
<222> LOCATION: (83)..(83)
<223> OTHER INFORMATION: n is a, c, g, or t
<220> FEATURE:
<221> NAME/KEY: misc_feature
<222> LOCATION: (177)..(177)
<223> OTHER INFORMATION: n is a, c, g, or t
<220> FEATURE:
<221> NAME/KEY: misc_feature
<222> LOCATION: (284)..(284)
<223> OTHER INFORMATION: n is a, c, g, or t
<220> FEATURE:
<221> NAME/KEY: misc_feature
<222> LOCATION: (335)..(335)
<223> OTHER INFORMATION: n is a, c, g, or t
<220> FEATURE:
<221> NAME/KEY: misc_feature
<222> LOCATION: (348)..(348)
<223> OTHER INFORMATION: n is a, c, g, or t
<220> FEATURE:
<221> NAME/KEY: misc_feature
<222> LOCATION: (388)..(390)
<223> OTHER INFORMATION: n is a, c, g, or t
<220> FEATURE:
<221> NAME/KEY: misc_feature
<222> LOCATION: (444)..(445)
<223> OTHER INFORMATION: n is a, c, g, or t

<400> SEQUENCE: 1
agaaggtcct taacacagtc gtgaacaaac acaaggacct gaagacacac gggttcacac       60
tggagtcctg ccgtagcatg atngcgctca tggatacaga tggctctgga aagctcaacc      120
tgcaggagtt ccaccacctc tggaacaaga ttaaggcctg gcagaaaatt ttcaaanact      180
atgacacaga ccagtccggc accatcaaca gctacgagat gcgaaatgca gtcaacgacg      240
caggattcca cctcaacaac cagctctatg acatcattac catngcggta cgcagacaaa      300
cacatgaaca tcgactttga cagtttcatc tgctngcttc gttaggcntg gagggcatgt      360
tcagagcttt tcatgcattt gacaaggnnn gagatgtgat catcaagctc aacgttctgg      420
agtggctgca gctcaccatg tatnnctgaa ccaggctggc ctcatccaaa gccatgcagg      480
```
atcactcagg at                                                          492

<210> SEQ ID NO 2
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 2
agaaggtcct taacacagtc gtgaa                                            25

<210> SEQ ID NO 3
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 3
gacacacggg ttcacactgg agtcc                                            25

<210> SEQ ID NO 4
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 4
gatggctctg gaaagctcaa cctgc                                            25

<210> SEQ ID NO 5
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 5
aaagctcaac ctgcaggagt tccac                                            25

<210> SEQ ID NO 6
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 6
tgcagtcaac gacgcaggat tccac                                            25

<210> SEQ ID NO 7
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 7
acctcaacaa ccagctctat gacat                                            25

<210> SEQ ID NO 8
<211> LENGTH: 25
<212> TYPE: DNA

-continued

```
<213> ORGANISM: Artificial
<220> FEATURE:
<223> OTHER INFORMATION: synthetic oligonucleotide primer

<400> SEQUENCE: 8
gaacatcgac tttgacagtt tcatc                                             25

<210> SEQ ID NO 9
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 9
ggagggcatg ttcagagctt ttcat                                             25

<210> SEQ ID NO 10
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 10
ggtatcatca agctcaacgt tctgg                                             25

<210> SEQ ID NO 11
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 11
caacgttctg gagtggctgc agctc                                             25

<210> SEQ ID NO 12
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 12
aaagccatgc aggatcactc aggat                                             25

<210> SEQ ID NO 13
<211> LENGTH: 457
<212> TYPE: DNA
<213> ORGANISM: Homo sapiens

<400> SEQUENCE: 13
cacggccgtg gacatgtggt cagtgggttg catcttcggg gagctgctga ctcagaagcc       60
tctgttcccc gggaagtcag aaatcgatca gatcaacaag gtgttcaagg atctggggac      120
ccctagtgag aaaatctggc ccggctacag cgagctccca gcagtcaaga agatgaccct      180
cagcgagcac ccctacaaca acctccgcaa gcgcttcggg gctctgctct cagaccaggg      240
cttcgacctc atgaacaagt tcctgaccta cttccccggg aggaggatca gcgctgagga      300
cggcctcaag catgagtatt ccgcgagac cccctcccc atcgacccct ccatgttccc       360
cacgtggccc gccaagagcg agcagcagcg tgtgaagcgg ggcaccagcc cgaggccccc      420
tgagggaggc ctgggctaca gccagctggg tgacgac                               457
```

<210> SEQ ID NO 14
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 14
cacggccgtg gacatgtggt cagtg					25

<210> SEQ ID NO 15
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 15
agctgctgac tcagaagcct ctgtt					25

<210> SEQ ID NO 16
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 16
gcctctgttc cccgggaagt cagaa					25

<210> SEQ ID NO 17
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 17
ggtgttcaag gatctgggga cccct					25

<210> SEQ ID NO 18
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 18
cgagctccca gcagtcaaga agatg					25

<210> SEQ ID NO 19
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 19
ggcttcgacc tcatgaacaa gttcc					25

<210> SEQ ID NO 20
<211> LENGTH: 25
<212> TYPE: DNA
<213> ORGANISM: Artificial
<220> FEATURE:

<223> OTHER INFORMATION: synthetic oligonucleotide primer

<400> SEQUENCE: 20
tgacctactt ccccgggagg aggat                                        25

<210> SEQ ID NO 21
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 21
gaggatcagc gctgaggacg gcctc                                        25

<210> SEQ ID NO 22
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 22
caagcatgag tatttccgcg agacc                                        25

<210> SEQ ID NO 23
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 23
gagcagcagc gtgtgaagcg gggca                                        25

<210> SEQ ID NO 24
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 24
gggctacagc cagctgggtg acgac                                        25

<210> SEQ ID NO 25
<211> LENGTH: 504
<212> TYPE: DNA
<213> ORGANISM: Homo sapiens

<400> SEQUENCE: 25
gcgtacagca acctcttggt caaacaggca tgccaccatc tttttcaaag cccaatattg      60
aaggtgcccc aggggctcct attggaaata ccttccagca tgtgcagtct ttgccaacaa     120
aaaaaattac caagaaacct attccagatg agcacctcat tctaaagacc acatttgagg     180
atcttattca gcgctgcctt tcttcagcaa cagaccctca aaccaagagg aagctagatg     240
atgccagcaa acgtttggag tttctgtatg ataaacttag ggaacagaca ctttcaccaa     300
caatcaccag tggtttacac aacattgcaa ggagcattga aactcgaaac tactcagaag     360
gattgaccat gcatacccac atagttagca ccagcaactt cagtgagacc tctgctttca     420
tgccagttct caaagttgtt ctcacccagg ccaataagct gggtgtctaa aaggacagct     480
tctcttccac tcaatattgc catt                                           504

```
<210> SEQ ID NO 26
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 26
gcgtacagca acctcttggt caaac                                              25

<210> SEQ ID NO 27
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 27
tgaaggtgcc ccaggggctc ctatt                                              25

<210> SEQ ID NO 28
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 28
ttgaggatct tattcagcgc tgcct                                              25

<210> SEQ ID NO 29
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 29
gctgcctttc ttcagcaaca gaccc                                              25

<210> SEQ ID NO 30
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 30
aacagacact ttcaccaaca atcac                                              25

<210> SEQ ID NO 31
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 31
agaaggattg accatgcata cccac                                              25

<210> SEQ ID NO 32
<211> LENGTH: 25
<212> TYPE: DNA
<213> ORGANISM: Artificial
<220> FEATURE:
```

```
<223> OTHER INFORMATION: synthetic oligonucleotide primer

<400> SEQUENCE: 32
catacccaca tagttagcac cagca                                            25

<210> SEQ ID NO 33
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 33
gcaccagcaa cttcagtgag acctc                                            25

<210> SEQ ID NO 34
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 34
ttcagtgaga cctctgcttt catgc                                            25

<210> SEQ ID NO 35
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 35
gccagttctc aaagttgttc tcacc                                            25

<210> SEQ ID NO 36
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 36
ttctcttcca ctcaatattg ccatt                                            25

<210> SEQ ID NO 37
<211> LENGTH: 546
<212> TYPE: DNA
<213> ORGANISM: Homo sapiens

<400> SEQUENCE: 37
agtgccagga cctgtgtacc gggacacgtg ggagtcctcc cagcatgatg cttgactgac       60
ccgaggaagg tcctcatgtt tcgtgcctgt cattctcgga tggctgtgag gcattccttg      120
gcaagggacg ctgcgtacca gcggtcctca ccgcatctca catggctcct gtgatgcatg      180
ttgtcgcttt cccacccggg atctccatct ctcttccctt cctgctgtca gtaagagatc      240
acatgtctgt gtagtgtgaa tgccttgtcg ctgtcctgtg cttttgcacc attgagttga      300
ctgcctctga gaagcagcac taggcctgtt gaaatgcaat gtgctgccct gagatccagt      360
ttcaagaatg ggcaggtaaa cgcagtgtgg gaaaggaatg tggaatgaga acttggtggt      420
tcaccgctgt actatttgtg taaatgttta cgtatgtgat aagctacatg tatgtaaatg      480
ttgcaatacc cctaacagtc gagtagtagt ctcccttaca ggaattttg acggggttcc       540
```

```
tcatca                                                              546

<210> SEQ ID NO 38
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 38
agtgccagga cctgtgtacc gggac                                          25

<210> SEQ ID NO 39
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 39
agtcctccca gcatgatgct tgact                                          25

<210> SEQ ID NO 40
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 40
tgcctgtcat tctcggatgg ctgtg                                          25

<210> SEQ ID NO 41
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 41
ggctgtgagg cattccttgg caagg                                          25

<210> SEQ ID NO 42
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 42
tggctcctgt gatgcatgtt gtcgc                                          25

<210> SEQ ID NO 43
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 43
gtagtgtgaa tgccttgtcg ctgtc                                          25

<210> SEQ ID NO 44
<211> LENGTH: 25
<212> TYPE: DNA
```

```
<213> ORGANISM: Artificial
<220> FEATURE:
<223> OTHER INFORMATION: synthetic oligonucleotide primer

<400> SEQUENCE: 44
gcaccattga gttgactgcc tctga                                              25

<210> SEQ ID NO 45
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 45
gctgccctga gatccagttt caaga                                              25

<210> SEQ ID NO 46
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 46
gtggttcacc gctgtactat ttgtg                                              25

<210> SEQ ID NO 47
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 47
tcgagtagta gtctcccttLa cagga                                             25

<210> SEQ ID NO 48
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 48
gaatttttga cggggttcct catca                                              25

<210> SEQ ID NO 49
<211> LENGTH: 568
<212> TYPE: DNA
<213> ORGANISM: Homo sapiens

<400> SEQUENCE: 49
ggacttggtc acaggttttt caaagggcta cgccttcatc gaatacaagg aggagcgtgc        60
cgtgatcaaa gcttaccgag atgctgatgg cctggttatt gaccagcatg agatatttgt       120
ggactacgag ctggaaagga ctctcaaagg gtggatccct cggcgacttg gaggcggtct       180 tggggggaaaa aaggagtctg gcaactgag atttggggga cgggaccggc cttttcgaaa      240
acctattaac ttgccagttg ttaaaaacga cctctataga gagggaaaac gggaaaggcg       300
ggagcgatct cgatcccgag aaagacactg ggactcgagg acaagggatc gagaccatga       360
caggggccgg gagaagagat ggcaagaaag agagccgacc aggtgtggcc cgacaatga       420 ctgggagaga gagagggact tcagagatga caggatcaag gggagggaga agaaggaaag       480
```

```
aggcaagtag aggcccaaca gcagaacccc aaagtgaagt tacagtggaa atgagtggag    540
ggggattgtc tttcaacgca gcgtgagt                                       568
```

<210> SEQ ID NO 50
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 50

```
ggacttggtc acaggttttt caaag                                          25
```

<210> SEQ ID NO 51
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 51

```
ttcaaagggc tacgccttca tcgaa                                          25
```

<210> SEQ ID NO 52
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 52

```
aaggaggagc gtgccgtgat caaag                                          25
```

<210> SEQ ID NO 53
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 53

```
gcttaccgag atgctgatgg cctgg                                          25
```

<210> SEQ ID NO 54
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 54

```
ctcaaagggt ggatccctcg gcgac                                          25
```

<210> SEQ ID NO 55
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 55

```
ggaaaggcgg gagcgatctc gatcc                                          25
```

<210> SEQ ID NO 56

```
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 56
agggatcgag accatgacag gggcc                                          25

<210> SEQ ID NO 57
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 57
aagagagccg accagggtgt ggccc                                          25

<210> SEQ ID NO 58
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 58
gggtgtggcc cgacaatgac tggga                                          25

<210> SEQ ID NO 59
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 59
aagtagaggc ccaacagcag aaccc                                          25

<210> SEQ ID NO 60
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 60
gattgtcttt caacgcagcg tgagt                                          25

<210> SEQ ID NO 61
<211> LENGTH: 377
<212> TYPE: DNA
<213> ORGANISM: Homo sapiens

<400> SEQUENCE: 61
tggactgctc aatgccttgg atggtgtggc ttccaccgag gcccgcatcg tgttcatgac      60
caccaaccac gttgacaggc tggaccctgc cctgatacgc ccggggcgag tggacctgaa     120
ggagtacgtg ggctactgct cacactggca gctgacccag atgttccaga ggttctatcc     180
agggcaggca ccttccttag ctgagaactt tgcagaacat gtccttcgag ctacaaacca     240
gatcagtcct gcccaggtgc aggatactt catgctgtat aaaaatgacc ctgtaggggc     300
aattcacaat gctgagtctc tgaggaggtg atcaggctgg gctcagctca gctctcctcc     360
tctagctcaa taaacat                                                   377
```

<210> SEQ ID NO 62
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 62
tggactgctc aatgccttgg atggt                                              25

<210> SEQ ID NO 63
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 63
cttggatggt gtggcttcca ccgag                                              25

<210> SEQ ID NO 64
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 64
tcgtgttcat gaccaccaac cacgt                                              25

<210> SEQ ID NO 65
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 65
ccaaccacgt tgacaggctg gaccc                                              25

<210> SEQ ID NO 66
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 66
gccctgatac gcccggggcg agtgg                                              25

<210> SEQ ID NO 67
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 67
gaaggagtac gtgggctact gctca                                              25

<210> SEQ ID NO 68
<211> LENGTH: 25
<212> TYPE: DNA
<213> ORGANISM: Artificial
<220> FEATURE:

-continued

<223> OTHER INFORMATION: synthetic oligonucleotide primer

<400> SEQUENCE: 68
ctggcagctg acccagatgt tccag                                        25

<210> SEQ ID NO 69
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 69
tgttccagag gttctatcca gggca                                        25

<210> SEQ ID NO 70
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 70
gcaccttcct tagctgagaa ctttg                                        25

<210> SEQ ID NO 71
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 71
gaacatgtcc ttcgagctac aaacc                                        25

<210> SEQ ID NO 72
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 72
tctcctcctc tagctcaata aacat                                        25

<210> SEQ ID NO 73
<211> LENGTH: 513
<212> TYPE: DNA
<213> ORGANISM: Homo sapiens

<400> SEQUENCE: 73
catgactgtc tgtgcaccga gaagaggcgg caggtcctgc cctggccaat caggcgagac        60
gcctttgtga gctgtgagtg cctcctgtgg tctcaggctt gcgctggacc tggttcttag       120
cccttgggca ctgcaccctg tttaacattt cacccactc tgtacagctg ctcttaccca        180 tttttttac ctcacaccca aagcattttg cctacctggg tcagagagag gagtcctttt        240
tgtcatgccc ttaagttcag caactgttta acctgttttc agtcttattt acgtcgtcaa       300
aaatgattta gtacttgttc cctctgttgg gatgccagtt gtggcagggg gaggggaacc       360
tgtccagttt gtacgatttc tttgtatgta tttctgatgt gttctctgat ctgccccac        420 tgtcctgtga ggacagctga ggccaaggag tgaaaaacct attactacta agagaagggg       480
tgcagagtgt ttacctggtg ctctcaacag gac                                    513

```
<210> SEQ ID NO 74
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 74
catgactgtc tgtgcaccga gaaga                                  25

<210> SEQ ID NO 75
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 75
tgccctggcc aatcaggcga gacgc                                  25

<210> SEQ ID NO 76
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 76
cgagacgcct ttgtgagctg tgagt                                  25

<210> SEQ ID NO 77
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 77
ctgcaccctg tttaacattt caccc                                  25

<210> SEQ ID NO 78
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 78
acctcacacc caaagcattt tgcct                                  25

<210> SEQ ID NO 79
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 79
gcattttgcc tacctgggtc agaga                                  25

<210> SEQ ID NO 80
<211> LENGTH: 25
<212> TYPE: DNA
<213> ORGANISM: Artificial
<220> FEATURE:
```

```
<223> OTHER INFORMATION: synthetic oligonucleotide primer

<400> SEQUENCE: 80
tcctttttgt catgcccttá agttc                                          25

<210> SEQ ID NO 81
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 81
gttttcagtc ttatttacgt cgtca                                          25

<210> SEQ ID NO 82
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 82
gtacttgttc cctctgttgg gatgc                                          25

<210> SEQ ID NO 83
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 83
tttctgatgt gttctctgat ctgcc                                          25

<210> SEQ ID NO 84
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 84
gtttacctgg tgctctcaac aggac                                          25

<210> SEQ ID NO 85
<211> LENGTH: 429
<212> TYPE: DNA
<213> ORGANISM: Homo sapiens

<400> SEQUENCE: 85
ccagctgttc caagactggg ccgtagaatt ccatgtttca ggagcctaag accctcccag    60
agcccagggg cttcaccgca gaccccaagc cattgagcac atcacccaaa gcagtggcca   120
acatcgcgga cccctgtgcc ttgtcacaga tgggtgctgg tcctcaggcg ttggggacac   180
tgctgggtcg atggggtcgg attctgccag tttctgctct gcagccaaag atggtcagaa   240
gcattgtcac ttcagtaaca tcaagtgctc aaagacatgg caaccgttca gtggtactta   300
agtattcaaa atatacaact acagattctc tgacagaaac cagcacgggg tcttcacctt   360
cattcacccc acaggcgaca cgcgagggag aacagcatct cagtggtgat tccaaaacca   420
agcctttgt                                                           429
```

```
<210> SEQ ID NO 86
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 86
ccagctgttc caagactggg ccgta                                           25

<210> SEQ ID NO 87
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 87
gggccgtaga attccatgtt tcagg                                           25

<210> SEQ ID NO 88
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 88
caaagcagtg gccaacatcg cggac                                           25

<210> SEQ ID NO 89
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 89
gtgccttgtc acagatgggt gctgg                                           25

<210> SEQ ID NO 90
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 90
ggtcctcagg cgttggggac actgc                                           25

<210> SEQ ID NO 91
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 91
tgggtcgatg gggtcggatt ctgcc                                           25

<210> SEQ ID NO 92
<211> LENGTH: 25
<212> TYPE: DNA
<213> ORGANISM: Artificial
<220> FEATURE:
<223> OTHER INFORMATION: synthetic oligonucleotide primer
```

```
<400> SEQUENCE: 92
tctgctctgc agccaaagat ggtca                                          25

<210> SEQ ID NO 93
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 93
aagcattgtc acttcagtaa catca                                          25

<210> SEQ ID NO 94
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 94
gacatggcaa ccgttcagtg gtact                                          25

<210> SEQ ID NO 95
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 95
gaacagcatc tcagtggtga tttcc                                          25

<210> SEQ ID NO 96
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 96
ggtgatttcc aaaccaagcc tttgt                                          25

<210> SEQ ID NO 97
<211> LENGTH: 543
<212> TYPE: DNA
<213> ORGANISM: Homo sapiens

<400> SEQUENCE: 97
atcgtggaga tcatgcagca aggttctcag cttccttgct tccatggctc cagcaccatt    60
cgaaacctca agagaggtt ccacatgagc atgactgagg agcagctgca gctgctggtg    120
gagcagatgg tggatggcag tatgcggtct atcaccacca aactctatga cggcttccag    180
tacctcacca acggcatcat gtgacacgct cctcagccca ggagtggtgg ggggtccagg    240
gcaccctccc tagagggccc ttgtttgaga aaccccaaac caggaaaccc cacctaccca    300
accatccacc caagggaaat ggaaggcaag aaacacgaag gatcatgtgg taactgcgag    360
agcttgctga ggggtgggag agccagctgt ggggtccaga cttgttgggg cttccctgcc    420
cctcctggtc tgtgtcagta ttaccaccag actgactcca ggactcactg ccctccagaa    480
aacagaggtg acaaatgtga gggacactgg ggcctttctt ctccttgtag gggtctctca    540
gag                                                                 543
```

```
<210> SEQ ID NO 98
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 98
atcgtggaga tcatgcagca aggtt                                    25

<210> SEQ ID NO 99
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 99
gcaaggttct cagcttcctt gcttc                                    25

<210> SEQ ID NO 100
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 100
aagagaggtt ccacatgagc atgac                                    25

<210> SEQ ID NO 101
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 101
atggcagtat gcggtctatc accac                                    25

<210> SEQ ID NO 102
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 102
tcaccaccaa actctatgac ggctt                                    25

<210> SEQ ID NO 103
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 103
gtacctcacc aacggcatca tgtga                                    25

<210> SEQ ID NO 104
<211> LENGTH: 25
<212> TYPE: DNA
<213> ORGANISM: Artificial
<220> FEATURE:
```

```
<223> OTHER INFORMATION: synthetic oligonucleotide primer

<400> SEQUENCE: 104
caccaacggc atcatgtgac acgct                                          25

<210> SEQ ID NO 105
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 105
gaaggatcat gtggtaactg cgaga                                          25

<210> SEQ ID NO 106
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 106
ccagctgtgg ggtccagact tgttg                                          25

<210> SEQ ID NO 107
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 107
cactgccctc cagaaaacag aggtg                                          25

<210> SEQ ID NO 108
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 108
ttctccttgt agggtctct cagag                                           25

<210> SEQ ID NO 109
<211> LENGTH: 537
<212> TYPE: DNA
<213> ORGANISM: Homo sapiens

<400> SEQUENCE: 109
cccgtgggca cccacggacg tggcttggtg ctgagatagc agagccccca gccatcactg    60
ctggcagcct gggcaaaccg ggtgagcaac aggaggacga ggggccgggg cggtgccagg   120
ctaccacaag aacctgcgtc ttggaccatt gcccctcccg gccccaaacc acaggggctc   180
aggtcgtgtg ggccccagtg ctagatctct ccctcccttc gtctctgtct gtgctgttgg   240
cgacccctct gtctgtctcc agccctgtct ttctgttctc ttatctcttt gtttcacctt   300
ttccctctct ggcgtccccg gctgcttgta ctcttggcct tttctgtgtc tccttttctgg  360 ctcttgcctc cgcctctctc tctcatcctc tttgtcctca gctcctcctg ctttcttggg   420
tcccaccagt gtcactttc tgccgttttc tttcctgttc tcctctgctt cattctcgtc    480
cagccattgc tccctctcc ctgccaccct tcccagttc accaaacctt acatgtt        537
```

```
<210> SEQ ID NO 110
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 110
cccgtgggca cccacggacg tggct                                   25

<210> SEQ ID NO 111
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 111
acggacgtgg cttggtgctg agata                                   25

<210> SEQ ID NO 112
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 112
tggtgctgag atagcagagc cccca                                   25

<210> SEQ ID NO 113
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 113
cagcctgggc aaaccgggtg agcaa                                   25

<210> SEQ ID NO 114
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 114
ggcaaaccgg gtgagcaaca ggagg                                   25

<210> SEQ ID NO 115
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 115
agcaacagga ggacgagggg ccggg                                   25

<210> SEQ ID NO 116
<211> LENGTH: 25
<212> TYPE: DNA
<213> ORGANISM: Artificial
<220> FEATURE:
```

<223> OTHER INFORMATION: synthetic oligonucleotide primer

<400> SEQUENCE: 116
gtgccaggct accacaagaa cctgc                                              25

<210> SEQ ID NO 117
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 117
accacaagaa cctgcgtctt ggacc                                              25

<210> SEQ ID NO 118
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 118
cggccccaaa ccacaggggc tcagg                                              25

<210> SEQ ID NO 119
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 119 cagggctca ggtcgtgtgg gcccc                                               25

<210> SEQ ID NO 120
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 120
cccagttcac caaaccttac atgtt                                              25

<210> SEQ ID NO 121
<211> LENGTH: 560
<212> TYPE: DNA
<213> ORGANISM: Homo sapiens

<400> SEQUENCE: 121
gcaaacctcc tgaagtgggc agccaacagt tttgagagag ccatgttcat aaactacgaa        60
caggtgaaca tgggtgatcg gtttgggcag atcatgattg aaaacctgcg gagacgccag       120
tgtgacctgg cgggagtgga gacctgcaag tcattagagt cacagaaaga acggctcctg       180
tcgaatgggt gggaaacagc atcggccgtc gacatgatga gttgtacaa caggttacct       240 cgagctgaag tgagcaggat agaatcactt gaattcctgg atgaaatgga gctgctggag       300
cagctcatgc ggcattactg cctttgctgg gcaaccaaag gaggaaatga gcttgggctg       360
aaggagataa cttattaatc tgtcgaaggc ttatgccgag ccagaagccg aagccacttg       420
ccctcctgga ggagacctgc aagctccctg agcggtgggc gggcctcgtc cgcaggtctc       480
atcccacact cttgagaagc cttggtcact acagtggtcg cacatgttcc tcttcctgtt       540

-continued

```
cctgttgaca tgtcgttgtt                                              560

<210> SEQ ID NO 122
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 122
gcaaacctcc tgaagtgggc agcca                                         25

<210> SEQ ID NO 123
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 123
gaacatgggt gatcggtttg ggcag                                         25

<210> SEQ ID NO 124
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 124
gaaaacctgc ggagacgcca gtgtg                                         25

<210> SEQ ID NO 125
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 125
aaagaacggc tcctgtcgaa tgggt                                         25

<210> SEQ ID NO 126
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 126
cagcatcggc cgtcgacatg atgga                                         25

<210> SEQ ID NO 127
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 127
ggagttgtac aacaggttac ctcga                                         25

<210> SEQ ID NO 128
<211> LENGTH: 25
<212> TYPE: DNA
```

```
<213> ORGANISM: Artificial
<220> FEATURE:
<223> OTHER INFORMATION: synthetic oligonucleotide primer

<400> SEQUENCE: 128
cattactgcc tttgctgggc aacca                                              25

<210> SEQ ID NO 129
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 129
gtctcatccc acactcttga gaagc                                              25

<210> SEQ ID NO 130
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 130
agccttggtc actacagtgg tcgca                                              25

<210> SEQ ID NO 131
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 131
actacagtgg tcgcacatgt tcctc                                              25

<210> SEQ ID NO 132
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 132
ctgttcctgt tgacatgtcg ttgtt                                              25

<210> SEQ ID NO 133
<211> LENGTH: 348
<212> TYPE: DNA
<213> ORGANISM: Homo sapiens

<400> SEQUENCE: 133
caagaccgaa aagctggagc ggctcatggt gcgcatcggc gtcttctccg tgctctacac        60
agtgcccgcc accatcgtca tcgcttgcta cttctacgag caggccttcc gcgagcactg       120
ggagcgctcg tgggtgagcc agcactgcaa gagcctggcc atcccgtgcc ggcgcacta        180 cacgccgcgc atgtcgcccg acttcacggt ctacatgatc aaatacctca tgacgctcat       240
cgtgggcatc acgtcgggct tctggatctg gtcgggcaag acgctgcact cgtggaggaa       300
gttctacact cgcctcacca acagccgaca cggtgagacc accgtgtg                    348

<210> SEQ ID NO 134
<211> LENGTH: 25
```

```
<212> TYPE: DNA
<213> ORGANISM: Artificial
<220> FEATURE:
<223> OTHER INFORMATION: synthetic oligonucleotide primer

<400> SEQUENCE: 134
caagaccgaa aagctggagc ggctc                                           25

<210> SEQ ID NO 135
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 135
gtgagccagc actgcaagag cctgg                                           25

<210> SEQ ID NO 136
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 136
gagccagcac tgcaagagcc tggcc                                           25

<210> SEQ ID NO 137
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 137
cccgacttca cggtctacat gatca                                           25

<210> SEQ ID NO 138
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 138
cacggtctac atgatcaaat acctc                                           25

<210> SEQ ID NO 139
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 139
gatcaaatac ctcatgacgc tcatc                                           25

<210> SEQ ID NO 140
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 140
```

```
caaatacctc atgacgctca tcgtg                                              25

<210> SEQ ID NO 141
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 141
caagacgctg cactcgtgga ggaag                                              25

<210> SEQ ID NO 142
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 142
gctgcactcg tggaggaagt tctac                                              25

<210> SEQ ID NO 143
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 143
caacagccga cacggtgaga ccacc                                              25

<210> SEQ ID NO 144
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 144
gccgacacgg tgagaccacc gtgtg                                              25

<210> SEQ ID NO 145
<211> LENGTH: 488
<212> TYPE: DNA
<213> ORGANISM: Homo sapiens

<400> SEQUENCE: 145
aaagcattct gcattagtac taaaataagc catcaatgcc agtccaccct ctctattcat        60
ggctaaatat ttaaaggtta tttatagctt ctttaatgaa ttcttcttaa acaaagtgaa       120
attatgtcct agaaaagtag aagctattcg taactagagc agtgcaactt taaagtttta       180
tgaatatgta ttttaatgac aaggggcga gcttgcatcc ccactagtta atggataatt       240
caaaccgagg actgattttg aaagatcacc taaaaatgta gatttgttct ttagtaaatt       300
tagatcaact atgcatatat tttgtaggta aatctttcag tccatgcccc aaccctcacc       360
aaaaccaaag cagaaattac acacacaaag atgctcccgt taggaattgc tattcacatg       420
aggctttctg tgctagattt ttttctcaga aacaaacttt actgtaggac tattgtggtg       480
ttcttaac                                                                488

<210> SEQ ID NO 146
<211> LENGTH: 25
```

```
<212> TYPE: DNA
<213> ORGANISM: Artificial
<220> FEATURE:
<223> OTHER INFORMATION: synthetic oligonucleotide primer

<400> SEQUENCE: 146
aaagcattct gcattagtac taaaa                                              25

<210> SEQ ID NO 147
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 147
aaataagcca tcaatgccag tccac                                              25

<210> SEQ ID NO 148
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 148
ccaccctctc tattcatggc taaat                                              25

<210> SEQ ID NO 149
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 149 gacaagggggg cgagcttgca tcccc                                             25

<210> SEQ ID NO 150
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 150
gcttgcatcc ccactagtta atgga                                              25

<210> SEQ ID NO 151
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 151
taggtaaatc tttcagtcca tgccc                                              25

<210> SEQ ID NO 152
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 152
```
acacacaaag atgctcccgt tagga                                                25

<210> SEQ ID NO 153
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 153
gatgctcccg ttaggaattg ctatt                                                25

<210> SEQ ID NO 154
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 154
attgctattc acatgaggct ttctg                                                25

<210> SEQ ID NO 155
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 155
aggctttctg tgctagattt ttttc                                                25

<210> SEQ ID NO 156
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 156
gtaggactat tgtggtgttc ttaac                                                25

<210> SEQ ID NO 157
<211> LENGTH: 250
<212> TYPE: DNA
<213> ORGANISM: Homo sapiens

<400> SEQUENCE: 157
gacagagagc gagaccgtga tcgggacaga gaaagagaac gcaccagaga gagagagagg          60
gagcgtgatc acagtcctac accaagtgtt ttcaacagcg atgaagaacg atacagatac         120
agggaatatg cagaaagagg ttatgagcgt cacagagcaa gtcgagaaaa agaagaacga         180
catagagaaa gacgacacag ggagaaagag gaaaccagac ataagtcttc tcgaagtaat         240
agtagacgtc                                                                250

<210> SEQ ID NO 158
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 158
gacagagagc gagaccgtga tcggg                                                25

```
<210> SEQ ID NO 159
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 159
gagcgagacc gtgatcggga cagag                                              25

<210> SEQ ID NO 160
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 160
gaccgtgatc gggacagaga aagag                                              25

<210> SEQ ID NO 161
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 161
gagaaagaga acgcaccaga gagag                                              25

<210> SEQ ID NO 162
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 162
gagggagcgt gatcacagtc ctaca                                              25

<210> SEQ ID NO 163
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 163
gtgttttcaa cagcgatgaa gaacg                                              25

<210> SEQ ID NO 164
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 164
gaagaacgat acagatacag ggaat                                              25

<210> SEQ ID NO 165
<211> LENGTH: 25
<212> TYPE: DNA
<213> ORGANISM: Artificial
<220> FEATURE:
```

<223> OTHER INFORMATION: synthetic oligonucleotide primer

<400> SEQUENCE: 165
gcagaaagag gttatgagcg tcaca                                          25

<210> SEQ ID NO 166
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 166
tgagcgtcac agagcaagtc gagaa                                          25

<210> SEQ ID NO 167
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 167
gaaaccagac ataagtcttc tcgaa                                          25

<210> SEQ ID NO 168
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 168
tcttctcgaa gtaatagtag acgtc                                          25

<210> SEQ ID NO 169
<211> LENGTH: 550
<212> TYPE: DNA
<213> ORGANISM: Homo sapiens
<220> FEATURE:
<221> NAME/KEY: misc_feature
<222> LOCATION: (80)..(80)
<223> OTHER INFORMATION: n is a, c, g, or t
<220> FEATURE:
<221> NAME/KEY: misc_feature
<222> LOCATION: (82)..(82)
<223> OTHER INFORMATION: n is a, c, g, or t
<220> FEATURE:
<221> NAME/KEY: misc_feature
<222> LOCATION: (157)..(157)
<223> OTHER INFORMATION: n is a, c, g, or t
<220> FEATURE:
<221> NAME/KEY: misc_feature
<222> LOCATION: (321)..(321)
<223> OTHER INFORMATION: n is a, c, g, or t
<220> FEATURE:
<221> NAME/KEY: misc_feature
<222> LOCATION: (333)..(333)
<223> OTHER INFORMATION: n is a, c, g, or t
<220> FEATURE:
<221> NAME/KEY: misc_feature
<222> LOCATION: (380)..(380)
<223> OTHER INFORMATION: n is a, c, g, or t

<400> SEQUENCE: 169
ctcacccaag tgctccggag agtgacagga aacccacggc tccccgcgcc caagagcgtc     60
ctgcggtctc gctggcacan cnccccgtac actaggggt cctacagcta cgtggccgtg    120
ggcagtactg ggggcgacct ggacctgctg gctcagnccc tccctgcaga cggcgccggc    180

```
gcccagctcc agatcctgtt tgcgggggaa gccacacatc gcacgtttta ctccacgacg    240 cacgggctc tgctgtcggg atggagggag gccgaccgcc tcctcagtct gtgggccccg    300
caggtgcagc agcccaggcc naggctctag ctnggcccag cctactctgt tccacccgtg   360 tcggggtag gctgggaccn tcatttcttc tgacagattt cagtctggct tgaaatttgg    420
ggatgttaat gagggtcctc tggttttggg taaccagggc caccttctca gttcttgtgt   480
ctgttattgg agtctggcca gggttgactt gagctgagac accagatgct cacggagatg   540
ctggacacat                                                           550

<210> SEQ ID NO 170
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 170
ctcacccaag tgctccggag agtga                                          25

<210> SEQ ID NO 171
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 171
gagagtgaca ggaaacccac ggctc                                          25

<210> SEQ ID NO 172
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 172 actaggggt cctacagcta cgtgg                                           25

<210> SEQ ID NO 173
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 173
agctacgtgg ccgtgggcag tactg                                          25

<210> SEQ ID NO 174
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 174
gtttgcgggg gaagccacac atcgc                                          25

<210> SEQ ID NO 175
<211> LENGTH: 25
<212> TYPE: DNA
```

```
<213> ORGANISM: Artificial
<220> FEATURE:
<223> OTHER INFORMATION: synthetic oligonucleotide primer

<400> SEQUENCE: 175
ggctctgctg tcgggatgga gggag                                          25

<210> SEQ ID NO 176
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 176
ttccacccgt gtcgggggta ggctg                                          25

<210> SEQ ID NO 177
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 177
caccttctca gttcttgtgt ctgtt                                          25

<210> SEQ ID NO 178
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 178
gtctggccag ggttgacttg agctg                                          25

<210> SEQ ID NO 179
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 179
gagctgagac accagatgct cacgg                                          25

<210> SEQ ID NO 180
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 180
atgctcacgg agatgctgga cacat                                          25

<210> SEQ ID NO 181
<211> LENGTH: 448
<212> TYPE: DNA
<213> ORGANISM: Homo sapiens

<400> SEQUENCE: 181
gcctacagcc ggacctgata gagggcagga aggggcgca gatagtgaag cgggccagcc     60
tgaaaagggg gaaacagtga ccccgagccg ctctccttgg agtagcctct cgggaggatc   120
```

```
acacctcgac acccaacccc tgaaccccac acactctctg ccatgcacac aggaggagag    180
ctggacctga gggccaccgc agcggtgcac acattcctct gggctgacgg catgacctct    240
gtaagggact cctgctagtc ccctcttggc atgaatgact gactgtagac gcatgacctc    300
caggcttcaa tcctgcctct tgcaatgaca gctgatctgt cggaaccagg acacaaaagc    360
agcaagaagc ggggagagag agggatagaa aacaagcgca ggagagcctg cgaacgcaaa    420
agtgaatgag ggcttttgt ggctgggg                                       448
```

<210> SEQ ID NO 182
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 182
gcctacagcc ggacctgata gaggg    25

<210> SEQ ID NO 183
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 183
agatagtgaa gcgggccagc ctgaa    25

<210> SEQ ID NO 184
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 184
tctccttgga gtagcctctc gggag    25

<210> SEQ ID NO 185
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 185
ctctcgggag gatcacacct cgaca    25

<210> SEQ ID NO 186
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 186
ctctctgcca tgcacacagg aggag    25

<210> SEQ ID NO 187
<211> LENGTH: 25
<212> TYPE: DNA
<213> ORGANISM: Artificial
<220> FEATURE:

-continued

<223> OTHER INFORMATION: synthetic oligonucleotide primer

<400> SEQUENCE: 187
gcatgacctc tgtaagggac tcctg                                          25

<210> SEQ ID NO 188
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 188
ctagtcccct cttggcatga atgac                                          25

<210> SEQ ID NO 189
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 189
tgactgactg tagacgcatg acctc                                          25

<210> SEQ ID NO 190
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 190
aatcctgcct cttgcaatga cagct                                          25

<210> SEQ ID NO 191
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 191
acagctgatc tgtcggaacc aggac                                          25

<210> SEQ ID NO 192
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 192
gaatgagggc ttttgtggc tgggg                                           25

<210> SEQ ID NO 193
<211> LENGTH: 545
<212> TYPE: DNA
<213> ORGANISM: Homo sapiens

<400> SEQUENCE: 193
atgtaattta gggaggactg gtctgtaatt tctgaatgta tatagaataa tatttatgtt    60
tacaatgtaa cttttcaaaa tttacaaatc aggattatat acataagaat tccactaaga   120
aatgccaaga ttcttaaatt tgccagcgtt aaagtagaaa ataacatttc agaagagcac   180

-continued

```
aatatgcata aaacatttt  caaaattgaa atattttcct gggcattaaa aacctttact    240
attggctaca aatttattgt acctgatgaa aacatatttt ctggacttaa atgttattac    300
aaatatctta attttcagta attgttttgc actttcaaag attgtaaata gttcattcaa    360
tcaatggtat agagttattt atttgctaca taatagatac tgtgccaaat aattacttt    420 tatttatttt atttagtacg taattttgaa gtacatttt  tcctgttttc acaattagac    480
tacatttaat gtgtaggaat tgtatgtatg tatatcttct gtaaataaca tctagtatct    540
tcact                                                                545

<210> SEQ ID NO 194
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 194
atgtaattta gggaggactg gtctg                                           25

<210> SEQ ID NO 195
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 195
ggactggtct gtaatttctg aatgt                                           25

<210> SEQ ID NO 196
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 196
agaattccac taagaaatgc caaga                                           25

<210> SEQ ID NO 197
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 197
gattcttaaa tttgccagcg ttaaa                                           25

<210> SEQ ID NO 198
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 198
ttgaaatatt ttcctgggca ttaaa                                           25

<210> SEQ ID NO 199
<211> LENGTH: 25
<212> TYPE: DNA
```

```
<213> ORGANISM: Artificial
<220> FEATURE:
<223> OTHER INFORMATION: synthetic oligonucleotide primer

<400> SEQUENCE: 199
gcattaaaaa cctttactat tggct                                              25

<210> SEQ ID NO 200
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 200
ttcagtaatt gttttgcact ttcaa                                              25

<210> SEQ ID NO 201
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 201
gctacataat agatactgtg ccaaa                                              25

<210> SEQ ID NO 202
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 202
gtacattttt tcctgttttc acaat                                              25

<210> SEQ ID NO 203
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 203
tcctgttttc acaattagac tacat                                              25

<210> SEQ ID NO 204
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 204
gtaaataaca tctagtatct tcact                                              25

<210> SEQ ID NO 205
<211> LENGTH: 586
<212> TYPE: DNA
<213> ORGANISM: Homo sapiens
<220> FEATURE:
<221> NAME/KEY: misc_feature
<222> LOCATION: (33)..(410)
<223> OTHER INFORMATION: n is a, c, g, or t

<400> SEQUENCE: 205
```

```
catgggcatg ggagacctgc tcagtgccat gtnnnnnnnn nnnnnnnnnn nnnnnnnnnn      60
nnnnnnnnnn nnnnnnnnnn nnnnnnnnnn nnnnnnnnnn nnnnnnnnnn nnnnnnnnnn     120
nnnnnnnnnn nnnnnnnnnn nnnnnnnnnn nnnnnnnnnn nnnnnnnnnn nnnnnnnnnn     180
nnnnnnnnnn nnnnnnnnnn nnnnnnnnnn nnnnnnnnnn nnnnnnnnnn nnnnnnnnnn     240
nnnnnnnnnn nnnnnnnnnn nnnnnnnnnn nnnnnnnnnn nnnnnnnnnn nnnnnnnnnn     300
nnnnnnnnnn nnnnnnnnnn nnnnnnnnnn nnnnnnnnnn nnnnnnnnnn nnnnnnnnnn     360
nnnnnnnnnn nnnnnnnnnn nnnnnnnnnn nnnnnnnnnn nnnnnnnnnn aatcttattt     420
atattgttat aaaatattcc aagatgagcc tctggccccc tgagccttct tgtaaatacc     480
tgcctccctc ccccatcacc gaacttcccc tcctccccta tttaaaccac tctgtctccc     540
ccacaaccct ccctggccc tctgatttgt tctgttcctg tctcaa                    586

<210> SEQ ID NO 206
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 206
catgggcatg ggagacctgc tcagt                                           25

<210> SEQ ID NO 207
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 207
tctggccccc tgagccttct tgtaa                                           25

<210> SEQ ID NO 208
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 208 gcccctgag ccttcttgta aatac                                            25

<210> SEQ ID NO 209
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 209
ccctgagcct tcttgtaaat acctg                                           25

<210> SEQ ID NO 210
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 210
```

-continued

```
cctgagcctt cttgtaaata cctgc                                              25

<210> SEQ ID NO 211
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 211
ctgagccttc ttgtaaatac ctgcc                                              25

<210> SEQ ID NO 212
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 212
tcccctggcc ctctgatttg ttctg                                              25

<210> SEQ ID NO 213
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 213
cccctggccc tctgatttgt tctgt                                              25

<210> SEQ ID NO 214
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 214
ccctggccct ctgatttgtt ctgtt                                              25

<210> SEQ ID NO 215
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 215
cctggccctc tgatttgttc tgttc                                              25

<210> SEQ ID NO 216
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 216
ctggccctct gatttgttct gttcc                                              25

<210> SEQ ID NO 217
<211> LENGTH: 25
<212> TYPE: DNA
<213> ORGANISM: Artificial
```

```
<220> FEATURE:
<223> OTHER INFORMATION: synthetic oligonucleotide primer

<400> SEQUENCE: 217
tggccctctg atttgttctg ttcct                                          25

<210> SEQ ID NO 218
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 218
ggccctctga tttgttctgt tcctg                                          25

<210> SEQ ID NO 219
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 219
gccctctgat tgttctgtt cctgt                                           25

<210> SEQ ID NO 220
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 220
ccctctgatt tgttctgttc ctgtc                                          25

<210> SEQ ID NO 221
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 221
ctgatttgtt ctgttcctgt ctcaa                                          25

<210> SEQ ID NO 222
<211> LENGTH: 476
<212> TYPE: DNA
<213> ORGANISM: Homo sapiens

<400> SEQUENCE: 222
ccccagctgc gacctgtggg ggagctcagt tgggccgaca ttgaccacct gcagacacac    60
ttccgctgcc agtgctactt gggctggagt ggtgagcaat gccagtggga ccataggcag   120
gcagctggag gtgccaacga ggcctgggct gggtcccacc tcaccagtct gctggctctg   180
gcagccctgg cctttacctg gaccttgtag gggtctcctg cctagctgcc tagcaagctg   240
gcctctacac aagggctctc ttaggcatgt aggaccctgc aggggggtggt caaactggag   300 tctggagtgc agagccccca ggaaaccagg gagggcatcc ataccagctc gcaccccct    360 gttctaaggg ggaggggaag tccctggag gcccccttctc tccctgccag agggaagga    420 gggtacagct gggctgggga ggacctgacc ctactccctt gccctagata gtttat       476
```

```
<210> SEQ ID NO 223
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 223
ccccagctgc gacctgtggg ggagc                                 25

<210> SEQ ID NO 224
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 224
agctcagttg ggccgacatt gacca                                 25

<210> SEQ ID NO 225
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 225
gggctggagt ggtgagcaat gccag                                 25

<210> SEQ ID NO 226
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 226
ggtgagcaat gccagtggga ccata                                 25

<210> SEQ ID NO 227
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 227
gcaatgccag tgggaccata ggcag                                 25

<210> SEQ ID NO 228
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 228
acctggacct tgtagggggtc tcctg                                25

<210> SEQ ID NO 229
<211> LENGTH: 25
<212> TYPE: DNA
<213> ORGANISM: Artificial
<220> FEATURE:
<223> OTHER INFORMATION: synthetic oligonucleotide primer
```

<400> SEQUENCE: 229
cacaagggct ctcttaggca tgtag                                             25

<210> SEQ ID NO 230
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 230
ggctctctta ggcatgtagg accct                                             25

<210> SEQ ID NO 231
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 231
ttaggcatgt aggaccctgc agggg                                             25

<210> SEQ ID NO 232
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 232
gcatgtagga ccctgcaggg ggtgg                                             25

<210> SEQ ID NO 233
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 233
tactcccttg ccctagatag tttat                                             25

<210> SEQ ID NO 234
<211> LENGTH: 420
<212> TYPE: DNA
<213> ORGANISM: Homo sapiens

<400> SEQUENCE: 234
ggaactggtg ctgtactggg tacacagtag gcgcccagga caagtgggtt gcaagacagg        60
aagaaaggaa aaggaagggc agagtgctgg tttctccagg ttgggttggg ggcactgctg       120 tccccctcc agctaggacc cagcccatcc ccagatgcct gagcctttgt ccaaagtgag        180
gtcactcgag aattcatgga cacggccccc agtcaggggg catcttgcaa gacctttagt      240
gccacaaata agcatcgagc acctccccat tcacaccccc attcctcctg gctccttatc      300
ccccatggtg tttattattt atttccctcc ccatgcccct ggggacccca aggcccagc        360 ttccctctgc accccagcc tatcccagag gccttgcagg tgaccagcag tgtcattgta       420

<210> SEQ ID NO 235
<211> LENGTH: 25
<212> TYPE: DNA

```
<213> ORGANISM: Artificial
<220> FEATURE:
<223> OTHER INFORMATION: synthetic oligonucleotide primer

<400> SEQUENCE: 235
ggaactggtg ctgtactggg tacac                                         25

<210> SEQ ID NO 236
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 236
tgggtacaca gtaggcgccc aggac                                         25

<210> SEQ ID NO 237
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 237
ggaagggcag agtgctggtt tctcc                                         25

<210> SEQ ID NO 238
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 238
gctggtttct ccaggttggg ttggg                                         25

<210> SEQ ID NO 239
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 239
atgcctgagc ctttgtccaa agtga                                         25

<210> SEQ ID NO 240
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 240
gtgaggtcac tcgagaattc atgga                                         25

<210> SEQ ID NO 241
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 241
agtcaggggg catcttgcaa gacct                                         25
```

<210> SEQ ID NO 242
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 242
atcttgcaag acctttagtg ccaca    25

<210> SEQ ID NO 243
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 243
cacaaataag catcgagcac ctccc    25

<210> SEQ ID NO 244
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 244
tccttatccc ccatggtgtt tatta    25

<210> SEQ ID NO 245
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 245
gcaggtgacc agcagtgtca ttgta    25

<210> SEQ ID NO 246
<211> LENGTH: 531
<212> TYPE: DNA
<213> ORGANISM: Homo sapiens

<400> SEQUENCE: 246
gggcttgtat gtgttctatg tggtcactgt gattctctgc acctggatct accaacggca    60
acggagagga tctctgttct gccccatgcc agtactccca gagatcctct cagactccga    120
ggaggaccgg gtatcttcta ataccaacag ctatgactac ggtgatgagt accggccgct    180
gttcttctac caggagacca cggctcagat cctggtccgg ccctcaatc ccctggatta    240
catgaagtgg agaaggaaat cagcatactg gaaagccctc aaggtgttca agctgcctgt    300
ggagttcctg ctgctcctca cagtccccgt cgtggacccg gacaaggatg accagaactg    360
gaaacggccc ctcaactgtc tgcatctggt tatcagcccc ctggttgtgg tcctgaccct    420
gcagtcgggg acctatggtg tctatgagat aggcggcctc gttcccgtct gggtcgtggt    480
ggtgatcgca ggcacagcct tggcttcagt gacctttttt gccacatctg a    531

<210> SEQ ID NO 247
<211> LENGTH: 25
<212> TYPE: DNA

-continued

<213> ORGANISM: Artificial
<220> FEATURE:
<223> OTHER INFORMATION: synthetic oligonucleotide primer

<400> SEQUENCE: 247
gggcttgtat gtgttctatg tggtc                                  25

<210> SEQ ID NO 248
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 248
agttactcca gagatcctct cagac                                  25

<210> SEQ ID NO 249
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 249
gactccgagg aggaccgggt atctt                                  25

<210> SEQ ID NO 250
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 250
tacggtgatg agtaccggcc gctgt                                  25

<210> SEQ ID NO 251
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 251
ttctaccagg agaccacggc tcaga                                  25

<210> SEQ ID NO 252
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 252
ccctcaaggt gttcaagctg cctgt                                  25

<210> SEQ ID NO 253
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 253
actgtctgca tctggttatc agccc                                  25

<210> SEQ ID NO 254
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 254
accctgcagt cggggaccta tggtg                                             25

<210> SEQ ID NO 255
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 255
ctatgagata ggcggcctcg ttccc                                             25

<210> SEQ ID NO 256
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 256
gtcgtggtgg tgatcgcagg cacag                                             25

<210> SEQ ID NO 257
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 257
cagtgacctt ttttgccaca tctga                                             25

<210> SEQ ID NO 258
<211> LENGTH: 421
<212> TYPE: DNA
<213> ORGANISM: Homo sapiens

<400> SEQUENCE: 258
gaagtaagag actcagcctg cagttaatta gcattctggc agttttgaca tcagccagct        60
gccctaaata acccttcaac gtttcttcac ttttgcaagt tccacagagt aagacattgg       120
gtctattcca gctcattcat tttatattga aaaaaataat tttaaaaatg gtggcttcag       180
ctccagcccc tttccaaaat ttttcaaccc caccctgttt ggatttttaa ttaaaaacta       240
gtagttctct tggtgttaaa acacttctgt cctgtgaggt ttcccaatgg tgttttttctt      300 gtaaatgtgt tggacaaatg tgaagatgca ttgtagttta accatatgcc cacatttagt       360
ctctttattc ctagttggtg agaaacctgt atctttctat gctgctttta tatctgtatg       420
t                                                                       421

<210> SEQ ID NO 259
<211> LENGTH: 25
<212> TYPE: DNA
<213> ORGANISM: Artificial
<220> FEATURE:

<223> OTHER INFORMATION: synthetic oligonucleotide primer

<400> SEQUENCE: 259
gaagtaagag actcagcctg cagtt                                             25

<210> SEQ ID NO 260
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 260
gcctgcagtt aattagcatt ctggc                                             25

<210> SEQ ID NO 261
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 261
ccttcaacgt ttcttcactt ttgca                                             25

<210> SEQ ID NO 262
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 262
gacattgggt ctattccagc tcatt                                             25

<210> SEQ ID NO 263
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 263
gtgttaaaac acttctgtcc tgtga                                             25

<210> SEQ ID NO 264
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 264
tgaggtttcc caatggtgtt tttct                                             25

<210> SEQ ID NO 265
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 265
gtgaagatgc attgtagttt aacca                                             25

<210> SEQ ID NO 266
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 266
taaccatatg cccacattta gtctc                                            25

<210> SEQ ID NO 267
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 267
gcccacattt agtctcttta ttcct                                            25

<210> SEQ ID NO 268
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 268
aaacctgtat ctttctatgc tgctt                                            25

<210> SEQ ID NO 269
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 269
ctatgctgct tttatatctg tatgt                                            25

<210> SEQ ID NO 270
<211> LENGTH: 525
<212> TYPE: DNA
<213> ORGANISM: Homo sapiens

<400> SEQUENCE: 270
cctggccagt caaagtagtc tctcccctgg ccacagtaat tggtcatgtg atgcaagcca      60
gcttactagc actttgagaa tgagtctcct gttgagctgg taggatgtaa gcctggagct     120
aatggcgatc atctttgcca ccgcctgggg agagcctgct tgggaatgaa attaacacaa     180
aggaagtcca acctgagaaa tggccaaata tatttcctga taacattatg tggccctctg     240
gatccagcca tgcctgaggt ctaccoctgg gcttttggat tatgtgtaca gttggttcat     300
cccttttct gctaattcga gtcatggcta atttaacacc ctttagaacc ttaaagaacc     360
atcagcatca cccgggaact tttttagaaa tgcaaaatct ctactgcttt ggatcctggg     420
tcaaaaaaaa gaaaaaaaaa agaaatgcaa aactttaggc cctgccccag atttactaaa     480
tcaatctgca gtttaacaaa atcctcaggt gatttgtatg ctcat                     525

<210> SEQ ID NO 271
<211> LENGTH: 25
<212> TYPE: DNA
<213> ORGANISM: Artificial
<220> FEATURE:

<223> OTHER INFORMATION: synthetic oligonucleotide primer

<400> SEQUENCE: 271
cctggccagt caaagtagtc tctcc                                          25

<210> SEQ ID NO 272
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 272
ctcccctggc cacagtaatt ggtca                                          25

<210> SEQ ID NO 273
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 273
aattggtcat gtgatgcaag ccagc                                          25

<210> SEQ ID NO 274
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 274
gcaagccagc ttactagcac tttga                                          25

<210> SEQ ID NO 275
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 275
gctaatggcg atcatctttg ccacc                                          25

<210> SEQ ID NO 276
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 276
cctgggcttt tggattatgt gtaca                                          25

<210> SEQ ID NO 277
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 277
tgtacagttg gttcatccct ttttc                                          25

<210> SEQ ID NO 278
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 278
atcccttttt ctgctaattc gagtc                                           25

<210> SEQ ID NO 279
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 279
atgcaaaatc tctactgctt tggat                                           25

<210> SEQ ID NO 280
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 280
ccctgcccca gatttactaa atcaa                                           25

<210> SEQ ID NO 281
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 281
atcctcaggt gatttgtatg ctcat                                           25

<210> SEQ ID NO 282
<211> LENGTH: 173
<212> TYPE: DNA
<213> ORGANISM: Homo sapiens
<220> FEATURE:
<221> NAME/KEY: misc_feature
<222> LOCATION: (146)..(146)
<223> OTHER INFORMATION: n is a, c, g, or t

<400> SEQUENCE: 282
gtggaaggtg gctgctgcga agaagctcgt tagaactgtg gtgcgccatc acgaggagaa     60
gcagctccgt gaagaaaggg ggaagaagga agagcagagc agactgaggc ggatagccgc    120
ctccacggcc cgggagatag agtgcntttg gtcgaatatt gaacaggttg tgg           173

<210> SEQ ID NO 283
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 283
gtggaaggtg gctgctgcga agaag                                           25

<210> SEQ ID NO 284

```
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 284
gaaggtggct gctgcgaaga agctc                                        25

<210> SEQ ID NO 285
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 285
gtggctgctg cgaagaagct cgtta                                        25

<210> SEQ ID NO 286
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 286
ggctgctgcg aagaagctcg ttaga                                        25

<210> SEQ ID NO 287
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 287
gaagctcgtt agaactgtgg tgcgc                                        25

<210> SEQ ID NO 288
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 288
gctcgttaga actgtggtgc gccat                                        25

<210> SEQ ID NO 289
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 289
ttagaactgt ggtgcgccat cacga                                        25

<210> SEQ ID NO 290
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 290
```

```
gtggtgcgcc atcacgagga gaagc                                          25

<210> SEQ ID NO 291
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 291
tgcgccatca cgaggagaag cagct                                          25

<210> SEQ ID NO 292
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 292
cctccacggc ccgggagata gagtg                                          25

<210> SEQ ID NO 293
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 293
tggtcgaata ttgaacaggt tgtgg                                          25

<210> SEQ ID NO 294
<211> LENGTH: 523
<212> TYPE: DNA
<213> ORGANISM: Homo sapiens
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (34)..(34)
<223> OTHER INFORMATION: n is a, c, g, or t
<220> FEATURE:
<221> NAME/KEY: misc_feature
<222> LOCATION: (207)..(207)
<223> OTHER INFORMATION: n is a, c, g, or t
<220> FEATURE:
<221> NAME/KEY: misc_feature
<222> LOCATION: (335)..(335)
<223> OTHER INFORMATION: n is a, c, g, or t
<220> FEATURE:
<221> NAME/KEY: misc_feature
<222> LOCATION: (337)..(337)
<223> OTHER INFORMATION: n is a, c, g, or t
<220> FEATURE:
<221> NAME/KEY: misc_feature
<222> LOCATION: (339)..(339)
<223> OTHER INFORMATION: n is a, c, g, or t

<400> SEQUENCE: 294
gcccagaatt acaggagtta gcacaccnag ctcntacaga taagaaaaca ttgaaattca     60
aagattaagg ccaaaaatat ctcacttgca attttaatat tttcatttgg atttatataa    120
atgaaacata tatatgtttt ggaatggcca gagtgaggca aagggatcc ctgaaataac     180 attagaacat acaggaaaaa cgaggcnggc agatcacttt aggtcaggag ttcaagacca    240
```

-continued

```
gcctgtacgt gcgtgcctgt agtcccagct actcgggagg ctgagatggg agaatcactt    300
gaacctggga ggcagagttt gcagtgagct gagantntnc cactgcactc cagtctgtgt    360
gacagaatga gaccttgtct tgaaacaaac acaaaaacaa aaaaccacat acaggaaaca    420
agagagggat ggagtcaact gtgccccaga cattaagcgc ccttcagtga ggaggggcaa    480
agtgctcagg cctgcctgtg tggcccacag gagtcagaac tcg                     523
```

<210> SEQ ID NO 295
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 295
gcccagaatt acaggagtta gcaca                                          25

<210> SEQ ID NO 296
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 296
aggccaaaaa tatctcactt gcaat                                          25

<210> SEQ ID NO 297
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 297
gagtgaggca aagggatcc ctgaa                                           25

<210> SEQ ID NO 298
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 298
ctgcactcca gtctgtgtga cagaa                                          25

<210> SEQ ID NO 299
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 299
gagaccttgt cttgaaacaa acaca                                          25

<210> SEQ ID NO 300
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 300
gagggatgga gtcaactgtg cccca                                          25

<210> SEQ ID NO 301
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 301
tcaactgtgc cccagacatt aagcg                                          25

<210> SEQ ID NO 302
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 302
gacattaagc gcccttcagt gagga                                          25

<210> SEQ ID NO 303
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 303 gaggagggc aaagtgctca ggcct                                           25

<210> SEQ ID NO 304
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 304
aaagtgctca ggcctgcctg tgtgg                                          25

<210> SEQ ID NO 305
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 305
tgtggcccac aggagtcaga actcg                                          25

<210> SEQ ID NO 306
<211> LENGTH: 375
<212> TYPE: DNA
<213> ORGANISM: Homo sapiens

<400> SEQUENCE: 306
gcaaccccaa cagcttgaag aggacaggga cggagagctc cagacctaac actgccttgt    60
tggatccaag ctcccctgaa ttctctgctg tggtatcagt gggcgattgg ctccaggcca   120
ttaaaatgga ccggtataag gataacttca cagctgctgg ttataccaca ctagaggctg   180
tggtgcacgt gaaccaggag gacctggcaa gaattggtat cacagccatc acgcaccaga   240

-continued

```
ataagatttt gagcagtgtc caggcaatgc gaacccaaat gcagcagatg cacggcagaa    300
tggttcccgt ctgagccagt actgaataaa ctcaaaactc ttgaaattag tttacctcat    360
ccatgcactt taatt                                                     375
```

<210> SEQ ID NO 307
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 307

```
gcaaccccaa cagcttgaag aggac                                           25
```

<210> SEQ ID NO 308
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 308

```
tccagaccta acactgcctt gttgg                                           25
```

<210> SEQ ID NO 309
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 309

```
ccctgaattc tctgctgtgg tatca                                           25
```

<210> SEQ ID NO 310
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 310

```
tatcagtggg cgattggctc caggc                                           25
```

<210> SEQ ID NO 311
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 311

```
acagctgctg gttataccac actag                                           25
```

<210> SEQ ID NO 312
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 312

```
ggtgcacgtg aaccaggagg acctg                                           25
```

```
<210> SEQ ID NO 313
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 313
cagccatcac gcaccagaat aagat                                           25

<210> SEQ ID NO 314
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 314
gcagtgtcca ggcaatgcga accca                                           25

<210> SEQ ID NO 315
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 315
tgcacggcag aatggttccc gtctg                                           25

<210> SEQ ID NO 316
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 316
ttcccgtctg agccagtact gaata                                           25

<210> SEQ ID NO 317
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 317
tttacctcat ccatgcactt taatt                                           25

<210> SEQ ID NO 318
<211> LENGTH: 561
<212> TYPE: DNA
<213> ORGANISM: Homo sapiens
<220> FEATURE:
<221> NAME/KEY: misc_feature
<222> LOCATION: (135)..(135)
<223> OTHER INFORMATION: n is a, c, g, or t

<400> SEQUENCE: 318
agcgccccag tgaacactac aacatacgta gctgacacag aatcagagca agcagataca     60
tgggatttga gtgaaaggcc aaagaaatc aaagtctcca aaatggaaca aaaattcaga     120
atgctttcac aagangcacc cactgtaaag gagtcctgca aaacaagctc taataataat    180
agtatggtat caaatacttt ggctaagatg agaatcccaa actatcagct ttcaccaact    240
```

```
aaattgccaa gtataaataa aagtaaagat agggcttctc agcagcagca gaccaactcc    300
atcagaaact actttcagcc gtctaccaaa aaagggaaa gggatgaaga aaatcaagaa    360
atgtcttcat gcaaatcagc aagaatagaa acgtcttgtt ctcttttaga acaaacacaa    420
cctgctacac cctcattgtg gaaaaataag gagcagcatc tatctgagaa tgagcctgtg    480
gacacaaact cagacaataa cttatttaca gatacagatt taaaatctat tgtgaaaaat    540
tctgccagta aatctcatgc t                                              561

<210> SEQ ID NO 319
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 319
agcgccccag tgaacactac aacat                                          25

<210> SEQ ID NO 320
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 320
gcacccactg taaaggagtc ctgca                                          25

<210> SEQ ID NO 321
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 321
gaatcccaaa ctatcagctt tcacc                                          25

<210> SEQ ID NO 322
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 322
agctttcacc aactaaattg ccaag                                          25

<210> SEQ ID NO 323
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 323
aagatagggc ttctcagcag cagca                                          25

<210> SEQ ID NO 324
<211> LENGTH: 25
<212> TYPE: DNA
<213> ORGANISM: Artificial
<220> FEATURE:
<223> OTHER INFORMATION: synthetic oligonucleotide primer
```

<400> SEQUENCE: 324
gcagaccaac tccatcagaa actac                                    25

<210> SEQ ID NO 325
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 325
tcagaaacta ctttcagccg tctac                                    25

<210> SEQ ID NO 326
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 326
tagaaacgtc ttgttctctt ttaga                                    25

<210> SEQ ID NO 327
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 327
tagaacaaac acaacctgct acacc                                    25

<210> SEQ ID NO 328
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 328
cctgctacac cctcattgtg gaaaa                                    25

<210> SEQ ID NO 329
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 329
aaattctgcc agtaaatctc atgct                                    25

<210> SEQ ID NO 330
<211> LENGTH: 400
<212> TYPE: DNA
<213> ORGANISM: Homo sapiens

<400> SEQUENCE: 330
gccattgact ccctgagcat tgagaaaggc taccggcact ggcacgcgga cctgcggcca      60
gacgacagcc ccctggaggc aggcctggcc ttcacctgca agctcaagtc gccggtgccc     120
ttcctgggga gggaggccct ggagcagcag cgggccgcag gcctccgccg gcgcctggtg     180

-continued

```
tgcttcacca tggaggacaa agtacccatg tttggcctgg aggccatctg gaggaacggc    240
caagtggtgg gccatgtccg gagggctgac tttgggttcg ccatcgacaa gaccatcgcc    300
tacggttaca tccatgaccc cagcggtggg ccggtctcgc tggactttgt gaagagcggg    360
gactatgccc tggagagaat gggggtgacc tatggtgccc                          400
```

```
<210> SEQ ID NO 331
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 331
gccattgact ccctgagcat tgaga                                          25

<210> SEQ ID NO 332
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 332
ttgagaaagg ctaccggcac tggca                                          25

<210> SEQ ID NO 333
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 333
cacctgcaag ctcaagtcgc cggtg                                          25

<210> SEQ ID NO 334
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 334
cgcctggtgt gcttcaccat ggagg                                          25

<210> SEQ ID NO 335
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 335
aagtacccat gtttggcctg gaggc                                          25

<210> SEQ ID NO 336
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 336
gcctggaggc catctggagg aacgg                                          25
```

```
<210> SEQ ID NO 337
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 337
ctggaggaac ggccaagtgg tgggc                                    25

<210> SEQ ID NO 338
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 338
tttgggttcg ccatcgacaa gacca                                    25

<210> SEQ ID NO 339
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 339
cggtctcgct ggactttgtg aagag                                    25

<210> SEQ ID NO 340
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 340
tgaagagcgg ggactatgcc ctgga                                    25

<210> SEQ ID NO 341
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 341
agaatggggg tgacctatgg tgccc                                    25

<210> SEQ ID NO 342
<211> LENGTH: 364
<212> TYPE: DNA
<213> ORGANISM: Homo sapiens

<400> SEQUENCE: 342
cacttcagac cagccaggtg tcttcccggg ccctgccaga ccctgctcac attccctctg    60
ctggtctgtg ctggtctcag aaggccaccg cgcccgcatt ccactcagcc agggtccagc   120
tgcagccccc gccaccctte cttcccttcc ctgtcctggg tcatgttgtt gccaccctgt   180
gtgacttttg aagctgtaaa atgagcttcc agggcttggg tggcgtcggg gcagggccgc   240
cgaggctggg aggaagccct tctgccttttt gctggtgttt ctggaatttg ctttccctca   300
```

```
cctctcactt ccttctagaa ggagcttcct gactggaacc agagaatgca tgtctgtcca    360
cttg                                                                364

<210> SEQ ID NO 343
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 343
cacttcagac cagccaggtg tcttc                                          25

<210> SEQ ID NO 344
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 344
gctggtctgt gctggtctca gaagg                                          25

<210> SEQ ID NO 345
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 345
ttccctgtcc tgggtcatgt tgttg                                          25

<210> SEQ ID NO 346
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 346
caccctgtgt gactttgaa gctgt                                           25

<210> SEQ ID NO 347
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 347
gtgtgacttt tgaagctgta aaatg                                          25

<210> SEQ ID NO 348
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 348
aaatgagctt ccagggcttg ggtgg                                          25

<210> SEQ ID NO 349
<211> LENGTH: 25
```

```
<212> TYPE: DNA
<213> ORGANISM: Artificial
<220> FEATURE:
<223> OTHER INFORMATION: synthetic oligonucleotide primer

<400> SEQUENCE: 349
cttttgctgg tgtttctgga atttg                                         25

<210> SEQ ID NO 350
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 350
gctggtgttt ctggaatttg ctttc                                         25

<210> SEQ ID NO 351
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 351
acctctcact tccttctaga aggag                                         25

<210> SEQ ID NO 352
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 352
gcttcctgac tggaaccaga gaatg                                         25

<210> SEQ ID NO 353
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 353
cagagaatgc atgtctgtcc acttg                                         25

<210> SEQ ID NO 354
<211> LENGTH: 394
<212> TYPE: DNA
<213> ORGANISM: Homo sapiens

<400> SEQUENCE: 354
aatccttatt gttcagagtt gtttgggggt tctgtttcag agcataaaac ctaaaggtta    60
tagtagaaca aggcaccttc ttaaaagaaa tcttgcttca gaccatcagt tacagagaat   120
ttcctaaagt aaaattgaag caactacaac ttctccttag acactttgga atctaaccac   180
ttaaggacct ttttaaagag atagcttctc ttctttctga agatcaattt ctcccaaggc   240
caagattgtc cttttctccc atttcttgct agctattgca aatgagggaa gaacattatt   300
catctctcct cccctttttt ttctgattct ttttcagtc agtttgctc ctgggttcaa    360 gtagtattac caccctttca caagcaacag actc                              394
```

<210> SEQ ID NO 355
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 355
aatccttatt gttcagagtt gtttg            25

<210> SEQ ID NO 356
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 356
gaaatcttgc ttcagaccat cagtt            25

<210> SEQ ID NO 357
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 357
gaccatcagt tacagagaat ttcct            25

<210> SEQ ID NO 358
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 358
aactacaact tctccttaga cactt            25

<210> SEQ ID NO 359
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 359
gacactttgg aatctaacca cttaa            25

<210> SEQ ID NO 360
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 360
ctgaagatca atttctccca aggcc            25

<210> SEQ ID NO 361
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 361
ctcccaaggc caagattgtc cttt                                25

<210> SEQ ID NO 362
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 362
ctcccatttc ttgctagcta ttgca                                25

<210> SEQ ID NO 363
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 363
gaagaacatt attcatctct cctcc                                25

<210> SEQ ID NO 364
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 364 tttttcagt cagttttgct cctgg                                 25

<210> SEQ ID NO 365
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 365 ccacccttc acaagcaaca gactc                                 25

<210> SEQ ID NO 366
<211> LENGTH: 408
<212> TYPE: DNA
<213> ORGANISM: Homo sapiens
<220> FEATURE:
<221> NAME/KEY: misc_feature
<222> LOCATION: (68)..(68)
<223> OTHER INFORMATION: n is a, c, g, or t

<400> SEQUENCE: 366
gctgcctctg gtggatatgc ggaggtgggc cgagttcttt tggataaagg tgctgatgtt      60
aatgcccntc cagttccctc ctcaagagat acagctttaa ccatagcagc agataaaggg     120
cattacaaat tctgtgagct tcttattggc aggggagctc atattgatgt acgtaacaag     180
aaggggaaca ctccattgtg gctagcagca aatggtggac acctcgatgt ggttcagtta     240
ctggtgcaag caggtgcaga tgtggatgca gcagataacc gcaagataac tcctcttatg     300
gcagcattta gaaagggtca gtgaaggtg gtgcgctact tagtcaaaga agtcaatcag      360
tttccatcag attctgaatg tatgagatac atagcaacca tcactgat                 408

<210> SEQ ID NO 367
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 367
gctgcctctg gtggatatgc ggagg                                   25

<210> SEQ ID NO 368
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 368
gaggtgggcc gagttctttt ggata                                   25

<210> SEQ ID NO 369
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 369
agttccctcc tcaagagata cagct                                   25

<210> SEQ ID NO 370
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 370
tgtgagcttc ttattggcag gggag                                   25

<210> SEQ ID NO 371
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 371
ggaacactcc attgtggcta gcagc                                   25

<210> SEQ ID NO 372
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 372
gtggacacct cgatgtggtt cagtt                                   25

<210> SEQ ID NO 373
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 373
gcagataacc gcaagataac tcctc    25

<210> SEQ ID NO 374
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 374
agataactcc tcttatggca gcatt    25

<210> SEQ ID NO 375
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 375
gaaggtggtg cgctacttag tcaaa    25

<210> SEQ ID NO 376
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 376
agaagtcaat cagtttccat cagat    25

<210> SEQ ID NO 377
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 377
gagatacata gcaaccatca ctgat    25

<210> SEQ ID NO 378
<211> LENGTH: 453
<212> TYPE: DNA
<213> ORGANISM: Homo sapiens

<400> SEQUENCE: 378
taagccgaat atgtgggagt ccatgtcctg cagtgtggcc tgatgtaatc aaactaccat    60
atttcaacac catgaaacca agaagcaat atcgtcgaaa gttaagagaa gaatttgttt   120
ttattcctgc agctgcgcta gacttatttg attacatgct tgccttggat cctagtaagc   180
gctgcactgc tgaacaggct cttcagtgcg agttcctccg agatgtggaa ccctcaaaat   240
gcctccacca gatctccctt tatggcaaga ttgtcatgag ttatggagta aaaagcgaag   300
aagacagaag cagatgggca tgactgatgt ttccaccatt aaagccccca ggaaggactt   360
gtctctgggc ttggatgaca gcagaaccaa cacaccccag ggtgtgctgc catcttcaca   420
gctgaaatct cagggcagct caaatgtggc acc   453

<210> SEQ ID NO 379

```
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 379
taagccgaat atgtgggagt ccatg                                              25

<210> SEQ ID NO 380
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 380
gcagtgtggc ctgatgtaat caaac                                              25

<210> SEQ ID NO 381
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 381
tcaaactacc atatttcaac accat                                              25

<210> SEQ ID NO 382
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 382
ttcctgcagc tgcgctagac ttatt                                              25

<210> SEQ ID NO 383
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 383
gcgctagact tatttgatta catgc                                              25

<210> SEQ ID NO 384
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 384
tgccttggat cctagtaagc gctgc                                              25

<210> SEQ ID NO 385
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 385
```
taagcgctgc actgctgaac aggct                                           25

<210> SEQ ID NO 386
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 386
gaacaggctc ttcagtgcga gttcc                                           25

<210> SEQ ID NO 387
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 387
caccagatct ccctttatgg caaga                                           25

<210> SEQ ID NO 388
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 388
tggatgacag cagaaccaac acacc                                           25

<210> SEQ ID NO 389
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 389
ctcagggcag ctcaaatgtg gcacc                                           25

<210> SEQ ID NO 390
<211> LENGTH: 390
<212> TYPE: DNA
<213> ORGANISM: Homo sapiens

<400> SEQUENCE: 390
gcagctaggt gagtttgttt tccgggtctg tcttaactgg cagcttcctg tacatactgg      60
tacttatttg ctgtaaacgt ctgtttcata catttgccat gcagtgactg tgctcgaaag     120
gtgaaatcaa tggtaaagaa gcctaggatt ttatggtatg agaaactgat cgcaggattt     180
tctgatccat agctattaat tgaaaacttc tgatagtgct gtaggctcta tagtaggctt     240
aagagtgagt cttatactat gaagccagcc acaagatact aacaaatgta taaattgaaa     300
agtaccaata cttttttgcac atagatcaaa atagagtgga gaatttgggc tccaaaaatc    360
aggttagtag gctcatttcc atgtgcttaa                                     390

<210> SEQ ID NO 391
<211> LENGTH: 25
<212> TYPE: DNA
<213> ORGANISM: Artificial
<220> FEATURE:

<223> OTHER INFORMATION: synthetic oligonucleotide primer

<400> SEQUENCE: 391
gcagctaggt gagtttgttt tccgg                                          25

<210> SEQ ID NO 392
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 392
ttttccgggt ctgtcttaac tggca                                          25

<210> SEQ ID NO 393
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 393
taactggcag cttcctgtac atact                                          25

<210> SEQ ID NO 394
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 394
ggtacttatt tgctgtaaac gtctg                                          25

<210> SEQ ID NO 395
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 395
tttgccatgc agtgactgtg ctcga                                          25

<210> SEQ ID NO 396
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 396
gattttctga tccatagcta ttaat                                          25

<210> SEQ ID NO 397
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 397
aacttctgat agtgctgtag gctct                                          25

```
<210> SEQ ID NO 398
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 398
gctgtaggct ctatagtagg cttaa                                            25

<210> SEQ ID NO 399
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 399
gagtcttata ctatgaagcc agcca                                            25

<210> SEQ ID NO 400
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 400
gaagccagcc acaagatact aacaa                                            25

<210> SEQ ID NO 401
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 401
agtaggctca tttccatgtg cttaa                                            25

<210> SEQ ID NO 402
<211> LENGTH: 512
<212> TYPE: DNA
<213> ORGANISM: Homo sapiens

<400> SEQUENCE: 402
gttgacgatt ttaactggct ggcccgggat atggcctccc caaactggag tattcttcct      60
gaagaggagc gaaatatcca gtgggactaa gcagttgtca ctctgttctt cactcctacc     120
aaatactttc cacgttggac tttcccccctt attgggtctc gaagtttact tattgtcaca    180
ctgtgtatgt tttcagcatt ttaaggctag agattgtaat gggctcctac ttgtaatttc     240
cattaaattc gtaacaggta taacactaaa gcattttttgc tattttcgtc atgcctttga    300
gactgagtct tactccgtcc cccagcgtgg tggcgcgctg ggattacagg cgcgcgccac     360
cacgcgaact cgtatttta gtagagacgg ggtttcgcca tgttgtccgg gctgctctcg      420
aactcctgac ctcaggtgat ccacccgctt cagcttccca aagtgctggc attacaggcg    480
tgagccacca cgccagggct ttatttattt at                                  512

<210> SEQ ID NO 403
<211> LENGTH: 25
<212> TYPE: DNA
<213> ORGANISM: Artificial
<220> FEATURE:
```

<223> OTHER INFORMATION: synthetic oligonucleotide primer

<400> SEQUENCE: 403
gttgacgatt ttaactggct ggccc    25

<210> SEQ ID NO 404
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 404
aactggctgg cccgggatat ggcct    25

<210> SEQ ID NO 405
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 405
atggcctccc caaactggag tattc    25

<210> SEQ ID NO 406
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 406
gactaagcag ttgtcactct gttct    25

<210> SEQ ID NO 407
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 407
ctcctaccaa atactttcca cgttg    25

<210> SEQ ID NO 408
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 408
gaagtttact tattgtcaca ctgtg    25

<210> SEQ ID NO 409
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 409
gggctcctac ttgtaatttc catta    25

```
<210> SEQ ID NO 410
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 410 tttgctatttt tcgtcatgcc tttga                                       25

<210> SEQ ID NO 411
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 411
cccccagcgt ggtggcgcgc tggga                                        25

<210> SEQ ID NO 412
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 412
ccaccacgcg aactcgtatt tttag                                        25

<210> SEQ ID NO 413
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 413
ccacgccagg gctttatttta tttat                                       25

<210> SEQ ID NO 414
<211> LENGTH: 210
<212> TYPE: DNA
<213> ORGANISM: Homo sapiens

<400> SEQUENCE: 414
gtcacgtgtc agaggacaca ctcgggagaa accttcatgg agtgagagta aggtgttggc     60
tggaagtggc cccttaagag atacttggag tcaaatctat ccactgtacg cccaccccac    120
tcttgttcta agagctttgg ggacagtctt ttgaccccett acattccttt agatgtgaag   180
atgacagaga tctaacttct gagagcagag                                     210

<210> SEQ ID NO 415
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 415
gtcacgtgtc agaggacaca ctcgg                                        25

<210> SEQ ID NO 416
<211> LENGTH: 25
<212> TYPE: DNA
```

-continued

```
<213> ORGANISM: Artificial
<220> FEATURE:
<223> OTHER INFORMATION: synthetic oligonucleotide primer

<400> SEQUENCE: 416
cacactcggg agaaaccttc atgga                                              25

<210> SEQ ID NO 417
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 417
tcgggagaaa ccttcatgga gtgag                                              25

<210> SEQ ID NO 418
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 418
catggagtga gagtaaggtg ttggc                                              25

<210> SEQ ID NO 419
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 419
tggctggaag tggcccctta agaga                                              25

<210> SEQ ID NO 420
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 420
gtggcccctt aagagatact tggag                                              25

<210> SEQ ID NO 421
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 421
gagatacttg gagtcaaatc tatcc                                              25

<210> SEQ ID NO 422
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 422
gagtcaaatc tatccactgt acgcc                                              25
```

<210> SEQ ID NO 423
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 423
ccaccccact cttgttctaa gagct                                      25

<210> SEQ ID NO 424
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 424
tgacccctta cattcctttta gatgt                                     25

<210> SEQ ID NO 425
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 425
agagatctaa cttctgagag cagag                                      25

<210> SEQ ID NO 426
<211> LENGTH: 520
<212> TYPE: DNA
<213> ORGANISM: Homo sapiens

<400> SEQUENCE: 426
tgcagggttt ggcttgtggg ctgcttgctg ctcatctgat ttttgtccca gtagtccctg    60
cgttcttcat tcaacccctt ctgggacttc agctcagaga gcaccatccc gggggtcagg   120
gcctccccac aggagccctg cagtgtggta gcgccatggc tgtctcaaac caagcaaagg   180
aaggaccctg aggccttcac gctaaccatc ctcgagcaac tgctgttgga aggcctccct   240
gggcctggcc cccaccctct gccacccagt cctcccagct gccatgtttc aaagacgacc   300
tttacctcct gcctttggat tgactctgca tttgaccacg gactccagtc tgtgtgtagg   360
gagagagctg agtaggaggc ctccactccg gatcgaggcc tgtatagggc tcgtttcccc   420
acacatgcct atttctgaag aggcttctgt cttatttgaa ggccagccca cacccagcta   480
ctttaacacc aggtttatgg aaaatgtcag gccttcccca                        520

<210> SEQ ID NO 427
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 427
tgcagggttt ggcttgtggg ctgct                                      25

<210> SEQ ID NO 428
<211> LENGTH: 25
<212> TYPE: DNA

```
<213> ORGANISM: Artificial
<220> FEATURE:
<223> OTHER INFORMATION: synthetic oligonucleotide primer

<400> SEQUENCE: 428
gctgctcatc tgattttttgt cccag                                              25

<210> SEQ ID NO 429
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 429
cccttctggg acttcagctc agaga                                               25

<210> SEQ ID NO 430
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 430
gagcaactgc tgttggaagg cctcc                                               25

<210> SEQ ID NO 431
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 431
agctgccatg tttcaaagac gacct                                               25

<210> SEQ ID NO 432
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 432
accacggact ccagtctgtg tgtag                                               25

<210> SEQ ID NO 433
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 433
gagagctgag taggaggcct ccact                                               25

<210> SEQ ID NO 434
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 434
cactccggat cgaggcctgt atagg                                               25
```

<210> SEQ ID NO 435
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 435
tgtcttattt gaaggccagc ccaca                                           25

<210> SEQ ID NO 436
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 436
acacccagct actttaacac caggt                                           25

<210> SEQ ID NO 437
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 437
tatggaaaat gtcaggcctt cccca                                           25

<210> SEQ ID NO 438
<211> LENGTH: 538
<212> TYPE: DNA
<213> ORGANISM: Homo sapiens

<400> SEQUENCE: 438
ccacgagtag cagccgcaac tggacggagg acatggaagg aggcatctcg tccccggtga     60
agaagacaga gatggacaag tcaccattca acagcccgtc cccccaggac tctcccgcc    120 tctccagctt cacccagcac caccggcccg tcatcgccgt gcacagcggg atcgcccga    180 gcccacaccc gtcctccgct ctgcatttcc ctacgacgtc catcctaccc agacggcct    240 ccacctactt ccccacacg gccatccgct acccacctca tctcaacccc caggacccgc    300
tcaaagatct tgtctcgctg gcctgcgacc cagccagcca gcaacctgga ccgtcctggt    360
atctgggata gcaaaggtct tcttccctcg ccccttctcc atcgtcccag gaatcccagg    420
gggcagcaca gccggccccc ggcccacgtt ttcggtggaa aattagagtg aacaagaaca    480
cccctgccga ctcccagccc ggccaaaaag acaaaacaca tagacgcaca cactcagg     538

<210> SEQ ID NO 439
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 439
ccacgagtag cagccgcaac tggac                                           25

<210> SEQ ID NO 440
<211> LENGTH: 25
<212> TYPE: DNA

```
<213> ORGANISM: Artificial
<220> FEATURE:
<223> OTHER INFORMATION: synthetic oligonucleotide primer

<400> SEQUENCE: 440
gtagcagccg caactggacg gagga                                              25

<210> SEQ ID NO 441
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 441
gcaactggac ggaggacatg gaagg                                              25

<210> SEQ ID NO 442
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 442
acatggaagg aggcatctcg tcccc                                              25

<210> SEQ ID NO 443
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 443
gcatctcgtc cccggtgaag aagac                                              25

<210> SEQ ID NO 444
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 444
tctcgtcccc ggtgaagaag acaga                                              25

<210> SEQ ID NO 445
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 445
tggacaagtc accattcaac agccc                                              25

<210> SEQ ID NO 446
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 446
gtcctggtat ctgggatagc aaagg                                              25
```

<210> SEQ ID NO 447
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 447
ctgggatagc aaaggtcttc ttccc                                        25

<210> SEQ ID NO 448
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 448
tagagtgaac aagaacaccc ctgcc                                        25

<210> SEQ ID NO 449
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 449
aaacacatag acgcacacac tcagg                                        25

<210> SEQ ID NO 450
<211> LENGTH: 534
<212> TYPE: DNA
<213> ORGANISM: Homo sapiens
<220> FEATURE:
<221> NAME/KEY: misc_feature
<222> LOCATION: (423)..(423)
<223> OTHER INFORMATION: n is a, c, g, or t
<220> FEATURE:
<221> NAME/KEY: misc_feature
<222> LOCATION: (477)..(485)
<223> OTHER INFORMATION: n is a, c, g, or t
<220> FEATURE:
<221> NAME/KEY: misc_feature
<222> LOCATION: (489)..(496)
<223> OTHER INFORMATION: n is a, c, g, or t
<220> FEATURE:
<221> NAME/KEY: misc_feature
<222> LOCATION: (498)..(498)
<223> OTHER INFORMATION: n is a, c, g, or t
<220> FEATURE:
<221> NAME/KEY: misc_feature
<222> LOCATION: (502)..(503)
<223> OTHER INFORMATION: n is a, c, g, or t
<220> FEATURE:
<221> NAME/KEY: misc_feature
<222> LOCATION: (505)..(505)
<223> OTHER INFORMATION: n is a, c, g, or t
<220> FEATURE:
<221> NAME/KEY: misc_feature
<222> LOCATION: (509)..(509)
<223> OTHER INFORMATION: n is a, c, g, or t

<400> SEQUENCE: 450
tattcagcca aaattaccgt tttagaccag aatgaataga ctacactgat aaaatgtact      60
ggataatgcc acatcctata tggtgttata gaaatagtgc aaggaaagta catttgtttg     120
cctgtctttt cattttgtac attcttccca ttctgtattc ttgtacaaaa gatctcattg     180

```
aaaatttaaa gtcatcataa tttgttgcca taaatatgta agtgtcaata ccaaaatgtc    240
tgagtaactt cttaaatccc tgttctagca aactaatatt ggttcatgtg cttgtgtata    300
tgtaaatctt aaattatgtg aactattaaa tagaccctac tgtactgtgc tttggacatt    360
tgaattaatg taaatatatg taatctgtga cttgatattt tgttttattt ggctatttaa    420
aancataaat ctaaaatgtc ttatgttatc agattatgct attttgtata aagcacnnnn    480
nnnnncaann nnnnnncnaa annanaaant cactggaccg acgttttaac aacg          534
```

<210> SEQ ID NO 451
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 451
tattcagcca aaattaccgt tttag                                           25

<210> SEQ ID NO 452
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 452
aatgccacat cctatatggt gttat                                           25

<210> SEQ ID NO 453
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 453
gaaagtacat ttgtttgcct gtctt                                           25

<210> SEQ ID NO 454
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 454
ttcattttgt acattcttcc cattc                                           25

<210> SEQ ID NO 455
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 455
aagtcatcat aatttgttgc cataa                                           25

<210> SEQ ID NO 456
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 456
gagtaacttc ttaaatccct gttct                                    25

<210> SEQ ID NO 457
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 457
aaatccctgt tctagcaaac taata                                    25

<210> SEQ ID NO 458
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 458
atattggttc atgtgcttgt gtata                                    25

<210> SEQ ID NO 459
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 459
aatagaccct actgtactgt gcttt                                    25

<210> SEQ ID NO 460
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 460
actgtactgt gctttggaca tttga                                    25

<210> SEQ ID NO 461
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 461
tcactggacc gacgttttaa caacg                                    25

<210> SEQ ID NO 462
<211> LENGTH: 482
<212> TYPE: DNA
<213> ORGANISM: Homo sapiens

<400> SEQUENCE: 462
cttcccggat tggcaggag ctggaggctg aggaggagcc ggtgcctgag gggtctgggc    60
ccctgggtcc ctgggggccc caagactggg tgggcccccct accacgtggc cctaccacac   120
cagatgaggg ctgcctccgg tactttgtcc tgggcaccgt ggcggctttg gtggccctcg   180

-continued

```
tgctcaacgt gttctatcct ctggtatccc agagtcgctg gagatgagct cgcctgcagg    240
cagctgctgt gagctggcct acctgcctgc cccaggccat gcctgccttt gttgtgggga    300
acacctctgg gctttgggcc tcagcttatg catctggtgg gagagggtgg ggaggttgtg    360 gccctgcag gggcagagta tcctagggtg tgtatccatc tggctgtctg tccattcatc     420
ctgctgctct gacccttggc ctcaggcttg gccctgccca agctacttcc tgtacttaaa    480
ag                                                                  482
```

<210> SEQ ID NO 463
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 463
cttcccggat ttggcaggag ctgga                                          25

<210> SEQ ID NO 464
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 464
tgttctatcc tctggtatcc cagag                                          25

<210> SEQ ID NO 465
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 465
tctggtatcc cagagtcgct ggaga                                          25

<210> SEQ ID NO 466
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 466
agagtcgctg gagatgagct cgcct                                          25

<210> SEQ ID NO 467
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 467
gcctcagctt atgcatctgg tggga                                          25

<210> SEQ ID NO 468
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 468
tcagcttatg catctggtgg gagag                                25

<210> SEQ ID NO 469
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 469
gcccctgcag gggcagagta tccta                                25

<210> SEQ ID NO 470
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 470
ggggcagagt atcctagggt gtgta                                25

<210> SEQ ID NO 471
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 471
gagtatccta gggtgtgtat ccatc                                25

<210> SEQ ID NO 472
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 472
ctagggtgtg tatccatctg gctgt                                25

<210> SEQ ID NO 473
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 473
ccaagctact tcctgtactt aaaag                                25

<210> SEQ ID NO 474
<211> LENGTH: 88
<212> TYPE: DNA
<213> ORGANISM: Homo sapiens

<400> SEQUENCE: 474
ccggaggcga ccgtgagttg ctacagtggc tggagagacg acatctgctc catgggctgg    60
tggccgacag taatctcacg ctgggacc                                      88

<210> SEQ ID NO 475

<211> LENGTH: 25
<212> TYPE: DNA
<213> ORGANISM: Artificial
<220> FEATURE:
<223> OTHER INFORMATION: synthetic oligonucleotide primer

<400> SEQUENCE: 475
ccggaggcga ccgtgagttg ctaca                                    25

<210> SEQ ID NO 476
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 476
gcgaccgtga gttgctacag tggct                                    25

<210> SEQ ID NO 477
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 477
gaccgtgagt tgctacagtg gctgg                                    25

<210> SEQ ID NO 478
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 478
cgtgagttgc tacagtggct ggaga                                    25

<210> SEQ ID NO 479
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 479
gctggagaga cgacatctgc tccat                                    25

<210> SEQ ID NO 480
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 480
ggagagacga catctgctcc atggg                                    25

<210> SEQ ID NO 481
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 481
ccatgggctg gtggccgaca gtaat                                        25

<210> SEQ ID NO 482
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 482
atgggctggt ggccgacagt aatct                                        25

<210> SEQ ID NO 483
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 483
ctggtggccg acagtaatct cacgc                                        25

<210> SEQ ID NO 484
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 484
gccgacagta atctcacgct gggac                                        25

<210> SEQ ID NO 485
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 485
ccgacagtaa tctcacgctg ggacc                                        25

<210> SEQ ID NO 486
<211> LENGTH: 490
<212> TYPE: DNA
<213> ORGANISM: Homo sapiens
<220> FEATURE:
<221> NAME/KEY: misc_feature
<222> LOCATION: (195)..(198)
<223> OTHER INFORMATION: n is a, c, g, or t
<220> FEATURE:
<221> NAME/KEY: misc_feature
<222> LOCATION: (409)..(411)
<223> OTHER INFORMATION: n is a, c, g, or t

<400> SEQUENCE: 486
gttacagcca catcgtgggt gcagcagggt gtaggcgatt ccaaagagca gatgattcaa      60
attcgtgtgc gatgggtaca gagagatacg cttggctcca gacccacgcg tctccctgtt     120
tccctctctt gtggtggggg cacagtagcc ttcgtgtgtc ttcctctagc acagacccct     180
gagctgaggg taggnnnnat gaaggcagca cgagggacgc tcccacctcc cactctatcc     240
tcaagaacct cggccaatga acgggccact cttgctagtt ggggtactga tcacttcctg     300
tcctctctgt gaggttggag atgtggcctt ggaacacacc ttcgtgaccc ccaggagttg     360

```
ctgtaaatcc atcggaagtg tgtcctgtga cggacgcgat gtgtctccnn ncgtcatcca    420
ccagaaggta actggagatt ttgtgtgttg ccttgacaga cccctgaggg ctggtgactt    480
cattttatt                                                             490
```

<210> SEQ ID NO 487
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 487

```
gttacagcca catcgtgggt gcagc                                            25
```

<210> SEQ ID NO 488
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 488

```
ggtgcagcag ggtgtaggcg attcc                                            25
```

<210> SEQ ID NO 489
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 489

```
cagagagata cgcttggctc cagac                                            25
```

<210> SEQ ID NO 490
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 490

```
gcacagaccc ctgagctgag ggtag                                            25
```

<210> SEQ ID NO 491
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 491

```
atgaaggcag cacgagggac gctcc                                            25
```

<210> SEQ ID NO 492
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 492

```
gaacctcggc caatgaacgg gccac                                            25
```

```
<210> SEQ ID NO 493
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 493
ggccactctt gctagttggg gtact                                              25

<210> SEQ ID NO 494
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 494
ttcctgtcct ctctgtgagg ttgga                                              25

<210> SEQ ID NO 495
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 495
ctggagattt tgtgtgttgc cttga                                              25

<210> SEQ ID NO 496
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 496
ccttgacaga cccctgaggg ctggt                                              25

<210> SEQ ID NO 497
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 497
gagggctggt gacttcattt ttatt                                              25

<210> SEQ ID NO 498
<211> LENGTH: 486
<212> TYPE: DNA
<213> ORGANISM: Homo sapiens

<400> SEQUENCE: 498
gacgatcagt cagtacatct ggagagacag gaggacctgg aggactgctg tcagctgctc        60
agccacatcc tggaggtgct gtacaggaag gacgtggggc caacccagag gcacgtccag       120
attatcatgg agaaacttct ccggaccgtg aaccgaaccg tcatttccat gggacgagat       180
tctgaactca ttgtaagtgc ttggtgacat atgtttggat atttaactgg ggctgacagc       240
atccttctcc aactgctgtt tgaacatagc ttattatact gcaatgtagt gagcagttga       300
gatacagctt ggtatataaa atgtcctcat tttccaaatg aatgtcaaag ttgaagggta       360
```

-continued

```
agcaaaccaa ctttaaagat ggaaacattt ggctcttgtt ttctcattac ttacttatag      420
caaaagacat gtattttctg ctgagtcgtc attcttctgg cagtttctcc atagtgttta      480
cactta                                                                 486
```

<210> SEQ ID NO 499
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 499

```
gacgatcagt cagtacatct ggaga                                            25
```

<210> SEQ ID NO 500
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 500

```
gaactcattg taagtgcttg gtgac                                            25
```

<210> SEQ ID NO 501
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 501

```
taactggggc tgacagcatc cttct                                            25
```

<210> SEQ ID NO 502
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 502

```
ctccaactgc tgtttgaaca tagct                                            25
```

<210> SEQ ID NO 503
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 503

```
gaacatagct tattatactg caatg                                            25
```

<210> SEQ ID NO 504
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 504

```
gtgagcagtt gagatacagc ttggt                                            25
```

```
<210> SEQ ID NO 505
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 505
agcttggtat ataaaatgtc ctcat                                    25

<210> SEQ ID NO 506
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 506
atggaaacat ttggctcttg ttttc                                    25

<210> SEQ ID NO 507
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 507
ttctcattac ttacttatag caaaa                                    25

<210> SEQ ID NO 508
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 508
acatgtattt tctgctgagt cgtca                                    25

<210> SEQ ID NO 509
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 509
agtttctcca tagtgtttac actta                                    25

<210> SEQ ID NO 510
<211> LENGTH: 487
<212> TYPE: DNA
<213> ORGANISM: Homo sapiens

<400> SEQUENCE: 510
ctggaagact gttgtggcct ctcagttctc tttgagtctg actgactgtg gccagtccct      60
ggactggtag ctgctggagg ccttcttgtt tctccagtcc ctggaagctg agctctatgt     120
gtatttgatg acattgtcag ctcttaccaa acgtcaagac ctcttcctgc ttgaccactc     180
gcacatggct ctaggcttct cctgctgagt cctggtcttg gcctgtgaat gtgcctcgtt     240
catccctggt gcttgagccc ctcaagctcc agtcaatgat ccagtccttc cccttttgaag    300 ttttctgctc tactttcctt ggcagcagcc tgtgaactac tcaaaagagt cccctt gggt    360
```

```
ttggaattat cagtggcttt gccactagta aatgtgtgat cttcggcaag taacctaacc    420
tagggacatc agtttactca tctgcgaagt ggggataata aaacctacct cagggttgct    480
tcaagga                                                              487
```

<210> SEQ ID NO 511
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 511

```
ctggaagact gttgtggcct ctcag                                           25
```

<210> SEQ ID NO 512
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 512

```
gcctctcagt tctctttgag tctga                                           25
```

<210> SEQ ID NO 513
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 513

```
tccctggact ggtagctgct ggagg                                           25
```

<210> SEQ ID NO 514
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 514

```
gctggaggcc ttcttgtttc tccag                                           25
```

<210> SEQ ID NO 515
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 515

```
gacattgtca gctcttacca aacgt                                           25
```

<210> SEQ ID NO 516
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 516

```
ggtcttggcc tgtgaatgtg cctcg                                           25
```

```
<210> SEQ ID NO 517
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 517
aagctccagt caatgatcca gtcct                                             25

<210> SEQ ID NO 518
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 518
ttgaagtttt ctgctctact ttcct                                             25

<210> SEQ ID NO 519
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 519
ctttccttgg cagcagcctg tgaac                                             25

<210> SEQ ID NO 520
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 520
gggacatcag tttactcatc tgcga                                             25

<210> SEQ ID NO 521
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 521
acctacctca gggttgcttc aagga                                             25

<210> SEQ ID NO 522
<211> LENGTH: 468
<212> TYPE: DNA
<213> ORGANISM: Homo sapiens

<400> SEQUENCE: 522
aactgaggca gcatgcacgg aggcggggtc aggggagacg aggccaagct gaggaggtgc        60
tgcaggtccc gtctggctcc agcccttgtc agattcaccc agggtgaagc cttcaaagct       120
ttttgctacc aaagcccact cacccttgga gctacagaac actttgctag agatactct        180 tctgcctcct agacctgttc tttccatctt tagaaacatc agtttttgta tggaagccac       240
cgggagattt ctggatggtg gtgcatccgt gaatgcgctg atcgtttctt ccagttagag       300
tcttcatctg tccgacaagt tcactcgcct cggttgcgga cctaggacca tttctctgca       360
```

```
ggccacttac cttcccctga gtcaggctta ctaatgctgc cctcactgcc tctttgcagt    420
aggggagaga gcagagaagt acaggtcatc tgctgggatc tagttttc                 468

<210> SEQ ID NO 523
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 523
aactgaggca gcatgcacgg aggcg                                          25

<210> SEQ ID NO 524
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 524
aggggagacg aggccaagct gagga                                          25

<210> SEQ ID NO 525
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 525
agcccttgtc agattcaccc agggt                                          25

<210> SEQ ID NO 526
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 526
ttgctaggag atactcttct gcctc                                          25

<210> SEQ ID NO 527
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 527
ggaagccacc gggagatttc tggat                                          25

<210> SEQ ID NO 528
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 528
tgaatgcgct gatcgtttct tccag                                          25

<210> SEQ ID NO 529
<211> LENGTH: 25
```

<212> TYPE: DNA
<213> ORGANISM: Artificial
<220> FEATURE:
<223> OTHER INFORMATION: synthetic oligonucleotide primer

<400> SEQUENCE: 529
ccagttagag tcttcatctg tccga					25

<210> SEQ ID NO 530
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 530
tcatctgtcc gacaagttca ctcgc					25

<210> SEQ ID NO 531
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 531
tcaggcttac taatgctgcc ctcac					25

<210> SEQ ID NO 532
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 532
ccctcactgc ctctttgcag taggg					25

<210> SEQ ID NO 533
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 533
ggtcatctgc tgggatctag ttttc					25

<210> SEQ ID NO 534
<211> LENGTH: 533
<212> TYPE: DNA
<213> ORGANISM: Homo sapiens

<400> SEQUENCE: 534
atcctacaac ccaccttgaa ggtataactg gatccagaga gggaaggact gacaagaagg			60 aattattcag aaaaacactg acagatgttt tataaattgt acagaaaaat agttaaaaat		120 gcaataggtt gaagttttcc agatatgttt ctctctgaaa ttactgtgaa tatttaacaa		180 acacttactt gatctatgtt atgaaataag tagcaaattg ccagcaaaat gtcttgtacc		240 ttttctaaag tgtatttctc gatgtgaact tccttcccct tacttgctag gtttcaataa		300 tttaaaagag tcaaacacta taatgagta agttgacgat gttttaagat tgcacctggc		360 agtgtgcctt tttgcaacaa atatttacct ggcagtgtgc cttttttgcaa caaatattta		420

```
ctttgcactt ggagctgctt ttaattttag caaaatgttt tatgcaaggc acaataggaa    480
gtcagttctc ctgcacttcc tcctcatgta gtctggagta ctttctaaag ggc          533
```

<210> SEQ ID NO 535
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 535

```
atcctacaac ccaccttgaa ggtat                                          25
```

<210> SEQ ID NO 536
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 536

```
accttgaagg tataactgga tccag                                          25
```

<210> SEQ ID NO 537
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 537

```
gatatgtttc tctctgaaat tactg                                          25
```

<210> SEQ ID NO 538
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 538

```
taacaaacac ttacttgatc tatgt                                          25
```

<210> SEQ ID NO 539
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 539

```
gcaaaatgtc ttgtaccttt tctaa                                          25
```

<210> SEQ ID NO 540
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 540

```
gttttaagat tgcacctggc agtgt                                          25
```

<210> SEQ ID NO 541
<211> LENGTH: 25

<210> SEQ ID NO 541
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 541
gcacttggag ctgcttttaa tttta                                    25

<210> SEQ ID NO 542
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 542
gcaaaatgtt ttatgcaagg cacaa                                    25

<210> SEQ ID NO 543
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 543
ggcacaatag gaagtcagtt ctcct                                    25

<210> SEQ ID NO 544
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 544
cacttcctcc tcatgtagtc tggag                                    25

<210> SEQ ID NO 545
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 545
tagtctggag tactttctaa agggc                                    25

<210> SEQ ID NO 546
<211> LENGTH: 502
<212> TYPE: DNA
<213> ORGANISM: Homo sapiens

<400> SEQUENCE: 546
tggctccgag actttcatga tcccattgtc gaggttgagg tgtccgtgtt cccggccggg      60
acgaccacag cctccagccc ccagagctcc atgggcacct caggtcctcc cacgaagctg     120
cccgtgcaca cctggcccag cgtgaccaga aggacagcc ccgaacccag cccacaccct      180
ggctccctgt tcagcaatgt ccgcttcctg ctcctggtcc tcttggagct gcccctgctc     240
ctgagcatgc tgggtgccgt cctctgggtg aacagacctc agagaagctc tagaagcagg     300
cagaattggc ccaagggtga gaaccagtag catctgctgt ccatcaaggc cctgtgctgc     360
aacagagccc ctctggggac tggaatgacc tcctgaccat caaggcctgc aacagagccc     420

```
ctctggggga ctggaatgac ctcctgacca ctccctcccg ggctgctctc tccaacatct    480
cctggaatcc tttgtgagcc tc                                             502
```

<210> SEQ ID NO 547
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 547

```
tggctccgag actttcatga tccca                                          25
```

<210> SEQ ID NO 548
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 548

```
atgatcccat tgtcgaggtt gaggt                                          25
```

<210> SEQ ID NO 549
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 549

```
ccagcgtgac cagaaaggac agccc                                          25
```

<210> SEQ ID NO 550
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 550

```
cgtcctctgg gtgaacagac ctcag                                          25
```

<210> SEQ ID NO 551
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 551

```
ggcccaaggg tgagaaccag tagca                                          25
```

<210> SEQ ID NO 552
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 552

```
gaaccagtag catctgctgt ccatc                                          25
```

<210> SEQ ID NO 553
<211> LENGTH: 25

```
<212> TYPE: DNA
<213> ORGANISM: Artificial
<220> FEATURE:
<223> OTHER INFORMATION: synthetic oligonucleotide primer

<400> SEQUENCE: 553
tcaaggccct gtgctgcaac agagc                                            25

<210> SEQ ID NO 554
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 554
acagagcccc tctggggact ggaat                                            25

<210> SEQ ID NO 555
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 555
tgaccatcaa ggcctgcaac agagc                                            25

<210> SEQ ID NO 556
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 556
cagagcccct ctggggact ggaat                                             25

<210> SEQ ID NO 557
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 557
tctcctggaa tcctttgtga gcctc                                            25

<210> SEQ ID NO 558
<211> LENGTH: 462
<212> TYPE: DNA
<213> ORGANISM: Homo sapiens

<400> SEQUENCE: 558
gtcatgaggc agctttcatc acacccttt aacatttatc taaaagaatt taaattcttt        60
ttcaaaaatt acactacaag tttataagcc caaatggctc tgtgaaatca gaagtgcaaa      120
ggtgtgcaaa cttgtatctg aagacctacc agggacaagc aggtaagagc tgatgtgagt     180
gtgtgtgatg ggatctgtaa ggaactggaa cacacatgtc ctatccaaag gaatcagctg     240
cagctgcttg ttgtcaagta taaagtcagg acctggcttg gctttaaccg ttttccaaga     300
aaactggaaa tctggatttt cagcgaacat gcctgatttt aaaaggttga ctcaagtttt     360
tacaaaatac tatgtgggac acctcaaata catacctact gactgatgac aaacccagga     420
```

```
gtttgtgtgt cttttataaa aagtttgccc tggatgtcat at              462
```

<210> SEQ ID NO 559
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 559

```
gtcatgaggc agctttcatc acacc                                 25
```

<210> SEQ ID NO 560
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 560

```
tcatcacacc cttttaacat ttatc                                 25
```

<210> SEQ ID NO 561
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 561

```
aaaggtgtgc aaacttgtat ctgaa                                 25
```

<210> SEQ ID NO 562
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 562

```
gtatctgaag acctaccagg gacaa                                 25
```

<210> SEQ ID NO 563
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 563

```
ggaacacaca tgtcctatcc aaagg                                 25
```

<210> SEQ ID NO 564
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 564

```
ctatccaaag gaatcagctg cagct                                 25
```

<210> SEQ ID NO 565
<211> LENGTH: 25
<212> TYPE: DNA
<213> ORGANISM: Artificial

```
<220> FEATURE:
<223> OTHER INFORMATION: synthetic oligonucleotide primer

<400> SEQUENCE: 565
taaagtcagg acctggcttg gcttt                                        25

<210> SEQ ID NO 566
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 566
tctggatttt cagcgaacat gcctg                                        25

<210> SEQ ID NO 567
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 567
ggacacctca aatacatacc tactg                                        25

<210> SEQ ID NO 568
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 568
actgactgat gacaaaccca ggagt                                        25

<210> SEQ ID NO 569
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 569
aaaaagtttg ccctggatgt catat                                        25

<210> SEQ ID NO 570
<211> LENGTH: 356
<212> TYPE: DNA
<213> ORGANISM: Homo sapiens

<400> SEQUENCE: 570
gatattcggt tactacacgt gcacctgtag cagtatttct agaaacatcc cttttgttg    60 agaacctccc ttgaatgtct gtcacactca cacctgacgg gatggttact ggattagaga  120
gtagatttgg cacatctttt cttagtcttt tgattcaaat tcaaaactta acagcacaaa  180
ccaggtcaga gttactttcg gttagaattt attgccattt attccttttt ataaatttct  240
atagattata ctgttatttt tatgttattg gcctagagct acacgtatat gggtttgtcc  300
tgagtccgtt ttcaaatgac cttgtgatag ggaaatggtt ttgtccatgt tcttgg      356

<210> SEQ ID NO 571
<211> LENGTH: 25
<212> TYPE: DNA
```

```
<213> ORGANISM: Artificial
<220> FEATURE:
<223> OTHER INFORMATION: synthetic oligonucleotide primer

<400> SEQUENCE: 571
gatattcggt tactacacgt gcacc                                           25

<210> SEQ ID NO 572
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 572
acacgtgcac ctgtagcagt atttc                                           25

<210> SEQ ID NO 573
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 573
ttgagaacct cccttgaatg tctgt                                           25

<210> SEQ ID NO 574
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 574
cacactcaca cctgacggga tggtt                                           25

<210> SEQ ID NO 575
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 575
ggcacatctt ttcttagtct tttga                                           25

<210> SEQ ID NO 576
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 576
aacttaacag cacaaaccag gtcag                                           25

<210> SEQ ID NO 577
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 577
ccaggtcaga gttactttcg gttag                                           25
```

<210> SEQ ID NO 578
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 578
gttattggcc tagagctaca cgtat                                        25

<210> SEQ ID NO 579
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 579
gtatatgggt ttgtcctgag tccgt                                        25

<210> SEQ ID NO 580
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 580
ctgagtccgt tttcaaatga ccttg                                        25

<210> SEQ ID NO 581
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 581
gaaatggttt tgtccatgtt cttgg                                        25

<210> SEQ ID NO 582
<211> LENGTH: 504
<212> TYPE: DNA
<213> ORGANISM: Homo sapiens

<400> SEQUENCE: 582
cacactggag ggcacacacg taccccgcac ccagcaactc ctgacagaaa gctcctccca    60
cccaaatggg ccaggcccca gcatgatcct gaaatctgca tccgccgtgg tttgtattca   120
ttgtgcatat cagggatacc ctcaagctgg actgtgggtt ccaaattact catagaggag   180
aaaaccagag aaagatgaag aggaggagtt aggtctattt gaaatgccag gggctcgctg   240
tgaggaatag gtaaaaaaaa acttttcacc agcctttgag agactagact gaccccaccc   300
ttccttcagt gagcagaatc actgtggtca gtcctgtc ccagcttcag ttcatgaata   360
ctcctgttcc tccagtttcc catcctttgt ccctgctgtc cccacttttt aaagatgggt   420 ctcaaccccct ccccaccacg tcatgatgga tggggcaagg tggtggggac taggggagcc   480
tggtatacat gcggcttcat tgcc                                         504

<210> SEQ ID NO 583
<211> LENGTH: 25
<212> TYPE: DNA

```
<213> ORGANISM: Artificial
<220> FEATURE:
<223> OTHER INFORMATION: synthetic oligonucleotide primer

<400> SEQUENCE: 583
cacactggag ggcacacacg taccc                                              25

<210> SEQ ID NO 584
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 584
caactcctga cagaaagctc ctccc                                              25

<210> SEQ ID NO 585
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 585
gcatgatcct gaaatctgca tccgc                                              25

<210> SEQ ID NO 586
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 586
tgcatccgcc gtggtttgta ttcat                                              25

<210> SEQ ID NO 587
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 587
gccaggggct cgctgtgagg aatag                                              25

<210> SEQ ID NO 588
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 588 aaaactttc accagccttt gagag                                               25

<210> SEQ ID NO 589
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 589
tttgagagac tagactgacc ccacc                                              25
```

<210> SEQ ID NO 590
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 590
acccttcctt cagtgagcag aatca 25

<210> SEQ ID NO 591
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 591
gcagaatcac tgtggtcagt ctcct 25

<210> SEQ ID NO 592
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 592
cagttcatga atactcctgt tcctc 25

<210> SEQ ID NO 593
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 593
ctggtataca tgcggcttca ttgcc 25

<210> SEQ ID NO 594
<211> LENGTH: 423
<212> TYPE: DNA
<213> ORGANISM: Homo sapiens

<400> SEQUENCE: 594
ataagcgaac ggcaggtgtc tacagaagaa gcccaagctt ggtgcaggga caacggcgac 60
tatccttatt ttgaaacaag tgcaaaagat gccacaaatg tggcagcagc ctttgaggaa 120
gcggttcgaa gagttcttgc taccgaggat aggtcagatc atttgattca gacagacaca 180
gtcaatcttc accgaaagcc caagcctagc tcatcttgct gttgattgtt agattgttga 240
tgcattctaa ccaactcaca catatacaca aaatcaacat ggggatggag aagagaatta 300
gcgtttgcag cagtgtatca tctactaata aaattaaact aatgttgctg cttcattagt 360
tggtgggaga agggacacat ccactcttgg aggaatatat ttactcaata atggcacctt 420
aca 423

<210> SEQ ID NO 595
<211> LENGTH: 25
<212> TYPE: DNA
<213> ORGANISM: Artificial
<220> FEATURE:

-continued

<223> OTHER INFORMATION: synthetic oligonucleotide primer

<400> SEQUENCE: 595
ataagcgaac ggcaggtgtc tacag                                    25

<210> SEQ ID NO 596
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 596
caagcttggt gcagggacaa cggcg                                    25

<210> SEQ ID NO 597
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 597
gacaacggcg actatcctta ttttg                                    25

<210> SEQ ID NO 598
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 598
ggaagcggtt cgaagagttc ttgct                                    25

<210> SEQ ID NO 599
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 599
gagttcttgc taccgaggat aggtc                                    25

<210> SEQ ID NO 600
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 600
cacagtcaat cttcaccgaa agccc                                    25

<210> SEQ ID NO 601
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 601
gatgcattct aaccaactca cacat                                    25

```
<210> SEQ ID NO 602
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 602
gcgtttgcag cagtgtatca tctac                                          25

<210> SEQ ID NO 603
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 603
gttgctgctt cattagttgg tggga                                          25

<210> SEQ ID NO 604
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 604
agaagggaca catccactct tggag                                          25

<210> SEQ ID NO 605
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 605
atttactcaa taatggcacc ttaca                                          25

<210> SEQ ID NO 606
<211> LENGTH: 436
<212> TYPE: DNA
<213> ORGANISM: Homo sapiens

<400> SEQUENCE: 606
ctgccatcct tgactttgaa ctaatgataa agtaatgatc tcaaactatg acagaaaagt     60
aatgtaaaat ccatccaatc tattatttct ctaattatgc aattagcctc atagttatta    120
tccagaggac ccaactgaac tgaactaatc cttctggcag attcaaatcg tttatttcac    180
acgctgttct aatggcactt atcattagaa tcttaccttg tgcagtcatc agaaattcca    240
gcgtactata atgaaaacat ccttgttttg aaaacctaaa agacaggctc tgtatatata    300
tatacttaag aatatgctga cttcacttat tagtcttagg gatttatttt caattaatat    360
taattttcta caaataattt tagtgtcatt tccatttggg gatattgtca tatcagcaca    420
tattttctgt ttggaa                                                   436

<210> SEQ ID NO 607
<211> LENGTH: 25
<212> TYPE: DNA
<213> ORGANISM: Artificial
<220> FEATURE:
<223> OTHER INFORMATION: synthetic oligonucleotide primer
```

-continued

<400> SEQUENCE: 607
ctgccatcct tgactttgaa ctaat                                    25

<210> SEQ ID NO 608
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 608
aaaatccatc caatctatta tttct                                    25

<210> SEQ ID NO 609
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 609
atgcaattag cctcatagtt attat                                    25

<210> SEQ ID NO 610
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 610
agaggaccca actgaactga actaa                                    25

<210> SEQ ID NO 611
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 611
tgaactaatc cttctggcag attca                                    25

<210> SEQ ID NO 612
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 612
aatcgtttat ttcacacgct gttct                                    25

<210> SEQ ID NO 613
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 613
cacgctgttc taatggcact tatca                                    25

<210> SEQ ID NO 614
<211> LENGTH: 25

```
<212> TYPE: DNA
<213> ORGANISM: Artificial
<220> FEATURE:
<223> OTHER INFORMATION: synthetic oligonucleotide primer

<400> SEQUENCE: 614
cattagaatc ttaccttgtg cagtc                                         25

<210> SEQ ID NO 615
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 615
cttgtgcagt catcagaaat tccag                                         25

<210> SEQ ID NO 616
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 616
ttagtgtcat ttccatttgg ggata                                         25

<210> SEQ ID NO 617
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 617
atcagcacat attttctgtt tggaa                                         25

<210> SEQ ID NO 618
<211> LENGTH: 556
<212> TYPE: DNA
<213> ORGANISM: Homo sapiens

<400> SEQUENCE: 618
ggagacttga gcttgaccta aggatatgca ttaaccactc tacagactcc cactcagtac    60
tgtacagggt ggctgtggtc ctagaagttc agttttttact gaggaaatat ttccattaac  120
agcaattatt atattgaagg ctttaataaa ggccacagga gacattacta tagcatagat  180
tgtcaaatgt aaatttactg agcgtgtttt ataaaaaact cacaggtgtt tgaggccaaa  240
acagatttta gacttacctt gaacggataa gaatctatag ttcactgaca cagtaaaatt  300
aactctgtgg gtgggggcgg ggggcatagc tctaatctaa tatataaaat gtgtgatgaa  360
tcaacaagat ttccacaatt cttctgtcaa gcttactaca gtgaaagaat gggattggca  420
agtaacttct gacttactgt cagttgtact tctgctccat agacatcagt attctgccat  480 cattttttgat gactacctca gaacataaaa aggaacgtat atcacataat tccagtcaca  540
gtttttggtt cctctt                                                  556

<210> SEQ ID NO 619
<211> LENGTH: 25
<212> TYPE: DNA
<213> ORGANISM: Artificial
<220> FEATURE:
```

<223> OTHER INFORMATION: synthetic oligonucleotide primer

<400> SEQUENCE: 619
ggagacttga gcttgaccta aggat                                25

<210> SEQ ID NO 620
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 620
atgcattaac cactctacag actcc                                25

<210> SEQ ID NO 621
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 621
ggctgtggtc ctagaagttc agttt                                25

<210> SEQ ID NO 622
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 622
aggccacagg agacattact atagc                                25

<210> SEQ ID NO 623
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 623 cgggggggcat agctctaatc taata                               25

<210> SEQ ID NO 624
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 624
gatttccaca attcttctgt caagc                                25

<210> SEQ ID NO 625
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 625
ggcaagtaac ttctgactta ctgtc                                25

```
<210> SEQ ID NO 626
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 626
tactgtcagt tgtacttctg ctcca                                              25

<210> SEQ ID NO 627
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 627
gacatcagta ttctgccatc atttt                                              25

<210> SEQ ID NO 628
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 628
acgtatatca cataattcca gtcac                                              25

<210> SEQ ID NO 629
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 629
ccagtcacag tttttggttc ctctt                                              25

<210> SEQ ID NO 630
<211> LENGTH: 503
<212> TYPE: DNA
<213> ORGANISM: Homo sapiens
<220> FEATURE:
<221> NAME/KEY: misc_feature
<222> LOCATION: (263)..(263)
<223> OTHER INFORMATION: n is a, c, g, or t
<220> FEATURE:
<221> NAME/KEY: misc_feature
<222> LOCATION: (269)..(269)
<223> OTHER INFORMATION: n is a, c, g, or t
<220> FEATURE:
<221> NAME/KEY: misc_feature
<222> LOCATION: (272)..(272)
<223> OTHER INFORMATION: n is a, c, g, or t
<220> FEATURE:
<221> NAME/KEY: misc_feature
<222> LOCATION: (274)..(274)
<223> OTHER INFORMATION: n is a, c, g, or t
<220> FEATURE:
<221> NAME/KEY: misc_feature
<222> LOCATION: (376)..(376)
<223> OTHER INFORMATION: n is a, c, g, or t
<220> FEATURE:
<221> NAME/KEY: misc_feature
<222> LOCATION: (381)..(381)
<223> OTHER INFORMATION: n is a, c, g, or t

<400> SEQUENCE: 630
```

```
ggactggccg ccgtacaggc ggccctggag gacatgggcg acaagccccc cggcttccgg        60
ggctcccggg actggatcgg ctgcgtggag gccagcctct gcctcgctca cttcggaggg       120
ccccaggacg cctctgccac gtaccccggg gagtgggggct gcacggggag ctggagaggc      180
tttactcgca cattcgcacg gggtgggggc ccagtcatgg ttgggggggga cgcagatgcc     240 aggtccaagg ccttgctggg agntctgcng tngnggtcag gcacggaagc ctatgtcctg      300
gtattggacc ctcactactg gggcactcca aaaagccccca gtgaactaca ggctgctggg    360
tgggtgggct ggcaanaggt nagtgcagcc tttgacccca actccttcta caacctgtgc      420
ttgaccagcc ttagctccca acagcagcag cgcaccttgg actgaggacg aagttacaga     480
actgagattc tcgggtccca gac                                              503
```

```
<210> SEQ ID NO 631
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 631
ggactggccg ccgtacaggc ggccc                                            25

<210> SEQ ID NO 632
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 632
tacaggcggc cctggaggac atggg                                            25

<210> SEQ ID NO 633
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 633
tggaggacat gggcgacaag ccccc                                            25

<210> SEQ ID NO 634
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 634
gctggagagg ctttactcgc acatt                                            25

<210> SEQ ID NO 635
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 635
caggcacgga agcctatgtc ctggt                                            25
```

```
<210> SEQ ID NO 636
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 636
tgtcctggta ttggaccctc actac                                              25

<210> SEQ ID NO 637
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 637
ctcactactg gggcactcca aaaag                                              25

<210> SEQ ID NO 638
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 638
gtgaactaca ggctgctggg tgggt                                              25

<210> SEQ ID NO 639
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 639
ttctacaacc tgtgcttgac cagcc                                              25

<210> SEQ ID NO 640
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 640
cagcgcacct tggactgagg acgaa                                              25

<210> SEQ ID NO 641
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 641
gaactgagat tctcgggtcc cagac                                              25

<210> SEQ ID NO 642
<211> LENGTH: 537
<212> TYPE: DNA
<213> ORGANISM: Homo sapiens

<400> SEQUENCE: 642
```

-continued

```
gtattctgtg gattctatat ttcatattga gatcagcatt caaaatagtt ctatttctat      60
ctgcaaatag tttcaaatga gtttaaaaaa ataacatctg aaagaaatg ctaatgtaat      120 catttatctt atctagcaag aagattctaa acattcttt aacatacatc taagtcagtt      180
tcacatattt gtagctagaa tatcctatac tggttatagt tgatatgtaa cagttggtga      240
ttttagattt ctttgattgt gaaacaggga gctatgagag atgtgtccat gtgaaattta      300
cagttactgc ctaggagtta atgatcgttc tgggtcagct tgaatgtccc cattctataa      360
attcaacact tattttctga attcataaaa ataaccaaaa aatgtgagct ataatgtttc      420
cctcaagaac aaacagaaac gagatttgcc aaaaactaaa attcaacaaa tgatgttgag      480
tgggagattg ctttgcctt tagcgtgtaa atggaagcac tgccattaga ctgaatt        537
```

<210> SEQ ID NO 643
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 643
gtattctgtg gattctatat ttcat     25

<210> SEQ ID NO 644
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 644
catacatcta agtcagtttc acata     25

<210> SEQ ID NO 645
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 645
gtagctagaa tatcctatac tggtt     25

<210> SEQ ID NO 646
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 646
ggagctatga gagatgtgtc catgt     25

<210> SEQ ID NO 647
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 647
gcctaggagt taatgatcgt tctgg     25

```
<210> SEQ ID NO 648
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 648
gatcgttctg ggtcagcttg aatgt                                    25

<210> SEQ ID NO 649
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 649 aatgtccccca ttctataaat tcaac                                   25

<210> SEQ ID NO 650
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 650
gagctataat gtttccctca agaac                                    25

<210> SEQ ID NO 651
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 651
tgagtgggag attggctttg cctt                                     25

<210> SEQ ID NO 652
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 652
gattggcttt gcctttagcg tgtaa                                    25

<210> SEQ ID NO 653
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 653
ggaagcactg ccattagact gaatt                                    25

<210> SEQ ID NO 654
<211> LENGTH: 151
<212> TYPE: DNA
<213> ORGANISM: Homo sapiens
<220> FEATURE:
<221> NAME/KEY: misc_feature
<222> LOCATION: (39)..(39)
```

```
<223> OTHER INFORMATION: n is a, c, g, or t
<220> FEATURE:
<221> NAME/KEY: misc_feature
<222> LOCATION: (76)..(76)
<223> OTHER INFORMATION: n is a, c, g, or t

<400> SEQUENCE: 654
gttaggcaat cattctaggg cagaaagaag tacaggatng gaagagcata atacactgtt      60
tttctcaaca aggagncagt atgtacacag tcataatgat gtgactgctt agcccctaaa    120
tatggtaact actctgggac aatatgggag g                                   151

<210> SEQ ID NO 655
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 655
gttaggcaat cattctaggg cagaa                                           25

<210> SEQ ID NO 656
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 656
ggcaatcatt ctagggcaga aagaa                                           25

<210> SEQ ID NO 657
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 657
tcattctagg gcagaaagaa gtaca                                           25

<210> SEQ ID NO 658
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 658
cattctaggg cagaaagaag tacag                                           25

<210> SEQ ID NO 659
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 659
atacactgtt tttctcaaca aggag                                           25

<210> SEQ ID NO 660
<211> LENGTH: 25
<212> TYPE: DNA
<213> ORGANISM: Artificial
```

```
<220> FEATURE:
<223> OTHER INFORMATION: synthetic oligonucleotide primer

<400> SEQUENCE: 660
tacacagtca taatgatgtg actgc                                              25

<210> SEQ ID NO 661
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 661
acacagtcat aatgatgtga ctgct                                              25

<210> SEQ ID NO 662
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 662
cataatgatg tgactgctta gcccc                                              25

<210> SEQ ID NO 663
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 663
ataatgatgt gactgcttag ccccct                                             25

<210> SEQ ID NO 664
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 664
taatgatgtg actgcttagc ccta                                               25

<210> SEQ ID NO 665
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 665
gatgtgactg cttagcccct aaata                                              25

<210> SEQ ID NO 666
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 666
atgtgactgc ttagccccta aatat                                              25
```

<210> SEQ ID NO 667
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 667
aatatggtaa ctactctggg acaat                                    25

<210> SEQ ID NO 668
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 668
atggtaacta ctctgggaca atatg                                    25

<210> SEQ ID NO 669
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 669
tggtaactac tctgggacaa tatgg                                    25

<210> SEQ ID NO 670
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 670
aactactctg ggacaatatg ggagg                                    25

<210> SEQ ID NO 671
<211> LENGTH: 524
<212> TYPE: DNA
<213> ORGANISM: Homo sapiens

<400> SEQUENCE: 671
agagtgcttc ttattcggca gggcttcgtg agaatgccac caagttatcc aaaaccaaag    60
gatgagagag gcttccaaga gagggaagac tgtccaagtt caaggagaag gggtttggtt   120
ccctgtctgc cagggacaga aagttctttc cacatgtgtc tcctggtccc gagagctttc   180
aaaaggggat gtattctgct ccaagaaaga atcacctccc agtaaagtag ccatgaaggg   240
ctcctgtata aaatatgcac acttcccctg ccctgagttt gtggagggaa aggctgtcgg   300
aagtagggac tcttaggaga gcccgtgtgc cctgtttggt tcagctgtca ggcgtgtgcc   360
acacacatcc cacctcatct tctggtccca taattctcca tggatgggct gcttttagct   420
ccagttttcc agtagaatgc ttgagttttc cttttttccg tacctcctgg aggatgaaac   480
tcataacctg tcatcatcag tactcactgt gttttccact ttga                   524

<210> SEQ ID NO 672
<211> LENGTH: 25
<212> TYPE: DNA
<213> ORGANISM: Artificial

```
<220> FEATURE:
<223> OTHER INFORMATION: synthetic oligonucleotide primer

<400> SEQUENCE: 672
agagtgcttc ttattcggca gggct                                          25

<210> SEQ ID NO 673
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 673
gcagggcttc gtgagaatgc cacca                                          25

<210> SEQ ID NO 674
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 674
gagaaggggt ttggttccct gtctg                                          25

<210> SEQ ID NO 675
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 675
gctccaagaa agaatcacct cccag                                          25

<210> SEQ ID NO 676
<211> LENGTH: 50
<212> TYPE: DNA
<213> ORGANISM: Artificial
<220> FEATURE:
<223> OTHER INFORMATION: synthetic oligonucleotide primer

<400> SEQUENCE: 676
atcacctccc agtaaagtag ccatgatcac ctcccagtaa agtagccatg               50

<210> SEQ ID NO 677
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 677
agggactctt aggagagccc gtgtg                                          25

<210> SEQ ID NO 678
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 678
ttggttcagc tgtcaggcgt gtgcc                                          25
```

<210> SEQ ID NO 679
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 679
atcttctggt cccataattc tccat                                              25

<210> SEQ ID NO 680
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 680
ccatggatgg gctgctttta gctcc                                              25

<210> SEQ ID NO 681
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 681 tttttccgt acctcctgga ggatg                                               25

<210> SEQ ID NO 682
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 682
gtactcactg tgttttccac tttga                                              25

<210> SEQ ID NO 683
<211> LENGTH: 473
<212> TYPE: DNA
<213> ORGANISM: Homo sapiens

<400> SEQUENCE: 683
actacactag tctgtttctt tgccctggtc tcaagtctct aagacgctgg tgtgtattat         60
gtgggctaag ttcatgtgtt atcctaaggc acaagagttg aggaatgggt gagcttggtg        120
tcagagcact gtgtggttgg agggtggact cttgtgatgc tgtggggatg aaattggccc        180
tcttttagca taagttgggg agtgtgcact ggctggaggc ttccagaggc ttccagccat        240
gaggtgtgag ctgaaaccaa ttttctct ttccttatag catgttgaga aaatctgttg         300
ggttttcagc agtcagggaa ggccggagtt ctgctttaat ctgggtaact gaggctaata        360
tgagcaagac tttggttaat taactgggtt ctcagatgcc acagactccg tgagaagtca        420
ccattatttt caatggttgt gatagaattt cccccagtag ccattatttt aag              473

<210> SEQ ID NO 684
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 684
actacactag tctgtttctt tgccc                                            25

<210> SEQ ID NO 685
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 685
tgccctggtc tcaagtctct aagac                                            25

<210> SEQ ID NO 686
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 686
gacgctggtg tgtattatgt gggct                                            25

<210> SEQ ID NO 687
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 687
tgggtgagct tggtgtcaga gcact                                            25

<210> SEQ ID NO 688
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 688
ggagggtgga ctcttgtgat gctgt                                            25

<210> SEQ ID NO 689
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 689
gatgaaattg gccctctttt agcat                                            25

<210> SEQ ID NO 690
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 690
ttcctctttc cttatagcat gttga                                            25

<210> SEQ ID NO 691

```
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 691
gggttttcag cagtcaggga aggcc                                              25

<210> SEQ ID NO 692
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 692
gaaggccgga gttctgcttt aatct                                              25

<210> SEQ ID NO 693
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 693
gccacagact ccgtgagaag tcacc                                              25

<210> SEQ ID NO 694
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 694
ttcccccagt agccattatt ttaag                                              25

<210> SEQ ID NO 695
<211> LENGTH: 456
<212> TYPE: DNA
<213> ORGANISM: Homo sapiens

<400> SEQUENCE: 695
taccccctgc tgcttttgag aaatttgtga acattttcag aggcctcagt gtagtggaag        60
tgataatcct taaatgaaca ttttctaccc taatttcact ggagtgactt attctaagcc       120
tcatctatcc cctacctatt tctcaaaatc attctatgct gattttacaa aagatcattt       180
ttacatttga actgagaacc ccttttaatt gaatcagtgg tgtctgaaat catattaaat       240
acccacattt gacataaatg cggtaccctt tactacactc atgagtggca tatttatgct       300
taggtctttt caaaagactt gacaagaaat cttcatattc tctgtagcct ttgtcaagtg       360
aggaaatcag tggttaaaga attccactat aaactttttag gcctgaatag gagtagtaaa      420
gcctcaagga catctgcctg tcacaatata ttctca                                 456

<210> SEQ ID NO 696
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 696
```

-continued tacccoctgc tgcttttgag aaatt   25

<210> SEQ ID NO 697
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 697
gtgaacattt tcagaggcct cagtg   25

<210> SEQ ID NO 698
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 698
gaacattttc taccctaatt tcact   25

<210> SEQ ID NO 699
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 699
ggagtgactt attctaagcc tcatc   25

<210> SEQ ID NO 700
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 700
tgaactgaga acccttttta attga   25

<210> SEQ ID NO 701
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 701
gacataaatg cggtacccett tacta   25

<210> SEQ ID NO 702
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 702
gtacccttta ctacactcat gagtg   25

<210> SEQ ID NO 703
<211> LENGTH: 25
<212> TYPE: DNA

```
<213> ORGANISM: Artificial
<220> FEATURE:
<223> OTHER INFORMATION: synthetic oligonucleotide primer

<400> SEQUENCE: 703
gcatatttat gcttaggtct tttca                                          25

<210> SEQ ID NO 704
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 704
aaatcttcat attctctgta gcctt                                          25

<210> SEQ ID NO 705
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 705
taaagcctca aggacatctg cctgt                                          25

<210> SEQ ID NO 706
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 706
atctgcctgt cacaatatat tctca                                          25

<210> SEQ ID NO 707
<211> LENGTH: 565
<212> TYPE: DNA
<213> ORGANISM: Homo sapiens
<220> FEATURE:
<221> NAME/KEY: misc_feature
<222> LOCATION: (399)..(399)
<223> OTHER INFORMATION: n is a, c, g, or t
<220> FEATURE:
<221> NAME/KEY: misc_feature
<222> LOCATION: (442)..(442)
<223> OTHER INFORMATION: n is a, c, g, or t

<400> SEQUENCE: 707
caaaaccttg ggacctcagc agtcccaagg ctgccctgac aatcaggcag gctccccacc    60
gtgaggccaa gctcctctg ccactgccag catgcccaa gggaggcttg gccttgggct     120
tgccagcctc agctctgccc tgacaagggt cttgtatcca gggcagaggc ctgaggtgac   180
ccaggcttgc tttgtggctg atgccagcag gcttggttct agtgggcacc actggtgggc   240
aacctccata actggcccctt aggccctacc ttcctacaca gctaggctat aatgggcctg   300
agtgagaggg tagcttcccc agccccaagc acaggcagag gggtggagag caattttggt   360 ttttatttt gttctgaag tggtgcctgt acctccagnc cccaggggc cttccctggc      420 cacacttctc tgccccaccc angcatcgcc atccagcac tttgctccat gtcacccgta    480
agatgccctt tgctgaatgt acctgagtgt atgtatttaa aaggactcac atgggcatca   540
gagaatttat ggctctgtat ccaat                                         565
```

```
<210> SEQ ID NO 708
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 708
caaaaccttg ggacctcagc agtcc                                           25

<210> SEQ ID NO 709
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 709
tgccctgaca atcaggcagg ctccc                                           25

<210> SEQ ID NO 710
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 710
gcatggccca agggaggctt ggcct                                           25

<210> SEQ ID NO 711
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 711
tgccctgaca agggtcttgt atcca                                           25

<210> SEQ ID NO 712
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 712
ggtcttgtat ccagggcaga ggcct                                           25

<210> SEQ ID NO 713
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 713
gaggcctgag gtgacccagg cttgc                                           25

<210> SEQ ID NO 714
<211> LENGTH: 25
<212> TYPE: DNA
<213> ORGANISM: Artificial
<220> FEATURE:
```

<223> OTHER INFORMATION: synthetic oligonucleotide primer

<400> SEQUENCE: 714
ccaggcttgc tttgtggctg atgcc                                              25

<210> SEQ ID NO 715
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 715
gctttgtggc tgatgccagc aggct                                              25

<210> SEQ ID NO 716
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 716
tttctgaagt ggtgcctgta cctcc                                              25

<210> SEQ ID NO 717
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 717
agatgccctt tgctgaatgt acctg                                              25

<210> SEQ ID NO 718
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 718
gagaatttat ggctctgtat ccaat                                              25

<210> SEQ ID NO 719
<211> LENGTH: 514
<212> TYPE: DNA
<213> ORGANISM: Homo sapiens

<400> SEQUENCE: 719
cagactgttc agtgtttgtc aagcttctgg tctaatatgt actcgaaaga ctttccgctt        60
acaatttgta gaaacacaaa tatcgttttc catacagcag tgcctatata gtgactgatt       120
ttaactttca atgtccatct ttcaaaggaa gtaacaccaa ggtacaatgt taaaggaata       180
ttcactttac ctagcaggga aaaatacaca aaaactgcag atacttcata tagcccattt       240
taacttgtat aaactgtgtg acttgtggcg tcttataaat aatgcactgt aaagattact       300
gaatagttgt gtcatgttaa tgtgcctaat ttcatgtatc ttgtaatcat gattgagcct       360
cagaatcatt tggagaaact atattttaaa gaacaagaca tacttcaatg tattatacag       420
ataaagtatt acatgtgttt gattttaaaa gggcggacat tttattaaaa tcaatattgt       480
ttttgctttt tctgaggagt ctctttcagt ttca                                   514

```
<210> SEQ ID NO 720
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 720
cagactgttc agtgtttgtc aagct                                   25

<210> SEQ ID NO 721
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 721
gtgtttgtca agcttctggt ctaat                                   25

<210> SEQ ID NO 722
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 722
agcttctggt ctaatatgta ctcga                                   25

<210> SEQ ID NO 723
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 723
gaaagacttt ccgcttacaa tttgt                                   25

<210> SEQ ID NO 724
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 724
atatcgtttt ccatacagca gtgcc                                   25

<210> SEQ ID NO 725
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 725
ttaactttca atgtccatct ttcaa                                   25

<210> SEQ ID NO 726
<211> LENGTH: 25
<212> TYPE: DNA
<213> ORGANISM: Artificial
<220> FEATURE:
```

```
<223> OTHER INFORMATION: synthetic oligonucleotide primer

<400> SEQUENCE: 726
gatacttcat atagcccatt ttaac                                              25

<210> SEQ ID NO 727
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 727
tgtgtgactt gtggcgtctt ataaa                                              25

<210> SEQ ID NO 728
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 728
gttgtgtcat gttaatgtgc ctaat                                              25

<210> SEQ ID NO 729
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 729
tgtgcctaat ttcatgtatc ttgta                                              25

<210> SEQ ID NO 730
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 730
ttctgaggag tctctttcag tttca                                              25

<210> SEQ ID NO 731
<211> LENGTH: 271
<212> TYPE: DNA
<213> ORGANISM: Homo sapiens

<400> SEQUENCE: 731
aaagacactg tgtacaacgt tggacactgt gcaggatgat gccacttcat cttggatgct        60
aatctgccat gttgacttct gattaacccc aggcccagga atgcctcaag atttctactt       120
tacttactgt tgcttgtgta agccaagaca accttgatgt tatcataaac atgtacttac       180
ctaagtcctg tcctttggca aattatgggc tatgagacac agcattcttg cctttccctg       240
aggggtcaat ttcagcgatc ctacacattc c                                     271

<210> SEQ ID NO 732
<211> LENGTH: 25
<212> TYPE: DNA
<213> ORGANISM: Artificial
<220> FEATURE:
<223> OTHER INFORMATION: synthetic oligonucleotide primer
```

<400> SEQUENCE: 732
aaagacactg tgtacaacgt tggac                                  25

<210> SEQ ID NO 733
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 733
gacactgtgt acaacgttgg acact                                  25

<210> SEQ ID NO 734
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 734
ctgtgtacaa cgttggacac tgtgc                                  25

<210> SEQ ID NO 735
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 735
ggcaaattat gggctatgag acaca                                  25

<210> SEQ ID NO 736
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 736
ggctatgaga cacagcattc ttgcc                                  25

<210> SEQ ID NO 737
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 737
tgagacacag cattcttgcc tttcc                                  25

<210> SEQ ID NO 738
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 738
tgcctttccc tgagggtca atttc                                   25

<210> SEQ ID NO 739

```
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 739
ctttccctga ggggtcaatt tcagc                                              25

<210> SEQ ID NO 740
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 740
gaggggtcaa tttcagcgat cctac                                              25

<210> SEQ ID NO 741
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 741
gtcaatttca gcgatcctac acatt                                              25

<210> SEQ ID NO 742
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 742
caatttcagc gatcctacac attcc                                              25

<210> SEQ ID NO 743
<211> LENGTH: 394
<212> TYPE: DNA
<213> ORGANISM: Homo sapiens

<400> SEQUENCE: 743
aaggcgccgt caagtcaaat aaataaatgc cctacaacac caacccagga ctgagatctg        60
catgctggaa tgacggtggt ggtggtggct ttcagtattc cccaggtttt gtccggagca       120
ccggcacgcc ctctcttgaa gtccgctctc cgcacagtgg ttagacggga agatccggag       180
ctgtccagtg tcttgggtaa tgcacggcat cgcctgatgt ctgacgctag aacaccacgt       240
aaagtcaagc agagggaagt gaatgcgccc taggcccctg caggccacca agaagagcta       300
gagggagttg gtgcaatcct agagatgccg gcaggtgcac caatctgtgg cacacgtacg       360
ctctccaatg gaagacaact caagaccaca ccaa                                   394

<210> SEQ ID NO 744
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 744
aaggcgccgt caagtcaaat aaata                                              25
```

<210> SEQ ID NO 745
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 745
ctacaacacc aacccaggac tgaga                                      25

<210> SEQ ID NO 746
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 746
acaccaaccc aggactgaga tctgc                                      25

<210> SEQ ID NO 747
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 747
ggactgagat ctgcatgctg gaatg                                      25

<210> SEQ ID NO 748
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 748
tgctggaatg acggtggtgg tggtg                                      25

<210> SEQ ID NO 749
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 749
ccaggttttg tccggagcac cggca                                      25

<210> SEQ ID NO 750
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 750
cgctctccgc acagtggtta gacgg                                      25

<210> SEQ ID NO 751
<211> LENGTH: 25
<212> TYPE: DNA
<213> ORGANISM: Artificial
<220> FEATURE:

<223> OTHER INFORMATION: synthetic oligonucleotide primer

<400> SEQUENCE: 751
gctagaggga gttggtgcaa tccta                                              25

<210> SEQ ID NO 752
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 752
acacgtacgc tctccaatgg aagac                                              25

<210> SEQ ID NO 753
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 753
gtacgctctc caatggaaga caact                                              25

<210> SEQ ID NO 754
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 754
ggaagacaac tcaagaccac accaa                                              25

<210> SEQ ID NO 755
<211> LENGTH: 421
<212> TYPE: DNA
<213> ORGANISM: Homo sapiens
<220> FEATURE:
<221> NAME/KEY: misc_feature
<222> LOCATION: (109)..(109)
<223> OTHER INFORMATION: n is a, c, g, or t
<220> FEATURE:
<221> NAME/KEY: misc_feature
<222> LOCATION: (113)..(115)
<223> OTHER INFORMATION: n is a, c, g, or t
<220> FEATURE:
<221> NAME/KEY: misc_feature
<222> LOCATION: (117)..(117)
<223> OTHER INFORMATION: n is a, c, g, or t
<220> FEATURE:
<221> NAME/KEY: misc_feature
<222> LOCATION: (122)..(122)
<223> OTHER INFORMATION: n is a, c, g, or t
<220> FEATURE:
<221> NAME/KEY: misc_feature
<222> LOCATION: (125)..(125)
<223> OTHER INFORMATION: n is a, c, g, or t
<220> FEATURE:
<221> NAME/KEY: misc_feature
<222> LOCATION: (134)..(134)
<223> OTHER INFORMATION: n is a, c, g, or t
<220> FEATURE:
<221> NAME/KEY: misc_feature
<222> LOCATION: (150)..(150)
<223> OTHER INFORMATION: n is a, c, g, or t
<220> FEATURE:
<221> NAME/KEY: misc_feature
<222> LOCATION: (153)..(153)
<223> OTHER INFORMATION: n is a, c, g, or t

```
<220> FEATURE:
<221> NAME/KEY: misc_feature
<222> LOCATION: (172)..(172)
<223> OTHER INFORMATION: n is a, c, g, or t
<220> FEATURE:
<221> NAME/KEY: misc_feature
<222> LOCATION: (176)..(176)
<223> OTHER INFORMATION: n is a, c, g, or t
<220> FEATURE:
<221> NAME/KEY: misc_feature
<222> LOCATION: (198)..(198)
<223> OTHER INFORMATION: n is a, c, g, or t
<220> FEATURE:
<221> NAME/KEY: misc_feature
<222> LOCATION: (200)..(200)
<223> OTHER INFORMATION: n is a, c, g, or t
<220> FEATURE:
<221> NAME/KEY: misc_feature
<222> LOCATION: (203)..(203)
<223> OTHER INFORMATION: n is a, c, g, or t
<220> FEATURE:
<221> NAME/KEY: misc_feature
<222> LOCATION: (209)..(209)
<223> OTHER INFORMATION: n is a, c, g, or t
<220> FEATURE:
<221> NAME/KEY: misc_feature
<222> LOCATION: (216)..(216)
<223> OTHER INFORMATION: n is a, c, g, or t
<220> FEATURE:
<221> NAME/KEY: misc_feature
<222> LOCATION: (233)..(233)
<223> OTHER INFORMATION: n is a, c, g, or t
<220> FEATURE:
<221> NAME/KEY: misc_feature
<222> LOCATION: (264)..(264)
<223> OTHER INFORMATION: n is a, c, g, or t
<220> FEATURE:
<221> NAME/KEY: misc_feature
<222> LOCATION: (268)..(271)
<223> OTHER INFORMATION: n is a, c, g, or t

<400> SEQUENCE: 755
tggggagagt cttacaatga ataactcaga aaaaagtttt caaaataatc ctagattgta      60
agatatctac gaccattatc catagccata tctttaaaaa aaaaaaaana aannnanaaa     120
anaanaaaca aggngttttct ttacccaggn cangtgagca ctaaagcttc cngtcntaat    180
gaggaggcag tgggggcnan ttngctttng agactnggag tcccagtatt acnggggagtg   240 ccctgacccc tcaggtaggg actngtcnnn nctccagaag acctaaggta cagtcagagc    300
tgagccacgc ctttgtccat gaagagaatg gggttgaaag tggagactga ggccgaggcg    360
ggtggatcac gaggtcagga gatccagacc atcctatcct ggctaataca gtgaacccct    420
g                                                                   421

<210> SEQ ID NO 756
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 756
tggggagagt cttacaatga ataac                                           25

<210> SEQ ID NO 757
<211> LENGTH: 25
<212> TYPE: DNA
<213> ORGANISM: Artificial
<220> FEATURE:
<223> OTHER INFORMATION: synthetic oligonucleotide primer
```

```
<400> SEQUENCE: 757
gattgtaaga tatctacgac catta                                     25

<210> SEQ ID NO 758
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 758
atctacgacc attatccata gccat                                     25

<210> SEQ ID NO 759
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 759
gaccattatc catagccata tcttt                                     25

<210> SEQ ID NO 760
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 760
gaagacctaa ggtacagtca gagct                                     25

<210> SEQ ID NO 761
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 761
ggtacagtca gagctgagcc acgcc                                     25

<210> SEQ ID NO 762
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 762
ccacgccttt gtccatgaag agaat                                     25

<210> SEQ ID NO 763
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 763
gagaatgggg ttgaaagtgg agact                                     25

<210> SEQ ID NO 764
<211> LENGTH: 25
```

```
<212> TYPE: DNA
<213> ORGANISM: Artificial
<220> FEATURE:
<223> OTHER INFORMATION: synthetic oligonucleotide primer

<400> SEQUENCE: 764
aaagtggaga ctgaggccga ggcgg                                               25

<210> SEQ ID NO 765
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 765
tcaggagatc cagaccatcc tatcc                                               25

<210> SEQ ID NO 766
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 766
tcctggctaa tacagtgaaa ccctg                                               25

<210> SEQ ID NO 767
<211> LENGTH: 484
<212> TYPE: DNA
<213> ORGANISM: Homo sapiens
<220> FEATURE:
<221> NAME/KEY: misc_feature
<222> LOCATION: (143)..(143)
<223> OTHER INFORMATION: n is a, c, g, or t
<220> FEATURE:
<221> NAME/KEY: misc_feature
<222> LOCATION: (147)..(147)
<223> OTHER INFORMATION: n is a, c, g, or t
<220> FEATURE:
<221> NAME/KEY: misc_feature
<222> LOCATION: (230)..(230)
<223> OTHER INFORMATION: n is a, c, g, or t

<400> SEQUENCE: 767
ctgtccgaag cggcaagtgc gtccactacc actcatgctg gagaggacag gccgcctgtc         60
ttctgtggcc agggacacag gcttggggcc caccctcaga cctctgagaa ctgcctgcca        120 gccccgatg cagaacccctt gantagncaa gcctcagttt ctccacaccc cactcctctt        180
tctcctctcc tcagccttac agctggaggg caggggctg gggaagggn tcacccccaat         240 gccctggact gggccccaca gctccccgg ctgcttgctt ccttctcctg acggccggct         300
ccttcccact tcagcctcct ctgtgggcac cgaggcccag gagcttcaaa agtcagacca        360
agactgtcct tggtcccaca ggggcagagg tgagatctgt gcgtgccccc tctccacact        420
cacggggaca gggcgtgaga tctttgcgcc ccctcccat gatctcccctt tccagatttt       480 caaa                                                                    484

<210> SEQ ID NO 768
<211> LENGTH: 25
<212> TYPE: DNA
<213> ORGANISM: Artificial
<220> FEATURE:
<223> OTHER INFORMATION: synthetic oligonucleotide primer
```

```
<400> SEQUENCE: 768
ctgtccgaag cggcaagtgc gtcca                                    25

<210> SEQ ID NO 769
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 769
gtccactacc actcatgctg gagag                                    25

<210> SEQ ID NO 770
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 770
gagaggacag gccgcctgtc ttctg                                    25

<210> SEQ ID NO 771
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 771
caccctcaga cctctgagaa ctgcc                                    25

<210> SEQ ID NO 772
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 772
ctctcctcag ccttacagct ggagg                                    25

<210> SEQ ID NO 773
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 773
ccgaggccca ggagcttcaa aagtc                                    25

<210> SEQ ID NO 774
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 774
gaccaagact gtccttggtc ccaca                                    25

<210> SEQ ID NO 775
<211> LENGTH: 25
```

```
<212> TYPE: DNA
<213> ORGANISM: Artificial
<220> FEATURE:
<223> OTHER INFORMATION: synthetic oligonucleotide primer

<400> SEQUENCE: 775
cagaggtgag atctgtgcgt gcccc                                          25

<210> SEQ ID NO 776
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 776
tccacactca cggggacagg gcgtg                                          25

<210> SEQ ID NO 777
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 777
cagggcgtga gatctttgcg ccccc                                          25

<210> SEQ ID NO 778
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 778
tgatctccct ttccagattt tcaaa                                          25

<210> SEQ ID NO 779
<211> LENGTH: 247
<212> TYPE: DNA
<213> ORGANISM: Homo sapiens

<400> SEQUENCE: 779
gggtttggtt aatttgtcct gcagcagcat cgtccctgat taacatcgtg atattaagcc    60
attcactgtg tcctgtaaca gtctctaatc gttcataaac acatagtaga aagtgggccc   120
caattacccc caaaattatt ctctacaata catgtcagct aacaaatgga actttctgga   180
aattttcttc ttgtcacttc caacactgaa ttgtgatatt tggcctttaa caggacattc   240
ttgatca                                                             247

<210> SEQ ID NO 780
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 780
gggtttggtt aatttgtcct gcagc                                          25

<210> SEQ ID NO 781
<211> LENGTH: 25
<212> TYPE: DNA
```

-continued

```
<213> ORGANISM: Artificial
<220> FEATURE:
<223> OTHER INFORMATION: synthetic oligonucleotide primer

<400> SEQUENCE: 781
cagcagcatc gtccctgatt aacat                                          25

<210> SEQ ID NO 782
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 782
atcgtccctg attaacatcg tgata                                          25

<210> SEQ ID NO 783
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 783
gatattaagc cattcactgt gtcct                                          25

<210> SEQ ID NO 784
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 784
cactgtgtcc tgtaacagtc tctaa                                          25

<210> SEQ ID NO 785
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 785
acagtctcta atcgttcata aacac                                          25

<210> SEQ ID NO 786
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 786
acatagtaga aagtgggccc caatt                                          25

<210> SEQ ID NO 787
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 787
tacccccaaa attattctct acaat                                          25
```

<210> SEQ ID NO 788
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 788
tattctctac aatacatgtc agcta                                    25

<210> SEQ ID NO 789
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 789
atgtcagcta acaaatggaa ctttc                                    25

<210> SEQ ID NO 790
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 790
gcctttaaca ggacattctt gatca                                    25

<210> SEQ ID NO 791
<211> LENGTH: 445
<212> TYPE: DNA
<213> ORGANISM: Homo sapiens
<220> FEATURE:
<221> NAME/KEY: misc_feature
<222> LOCATION: (393)..(393)
<223> OTHER INFORMATION: n is a, c, g, or t
<220> FEATURE:
<221> NAME/KEY: misc_feature
<222> LOCATION: (406)..(410)
<223> OTHER INFORMATION: n is a, c, g, or t
<220> FEATURE:
<221> NAME/KEY: misc_feature
<222> LOCATION: (413)..(413)
<223> OTHER INFORMATION: n is a, c, g, or t

<400> SEQUENCE: 791
aacaccagca atacatcagc tttacacagc aggcaagttt cctgctctct acaagtacag     60
atggaacttg tcttgtgaat taacatcctg actactttg ttgatcatca catttttcc     120 tcatgagaga aataatagtg ttttataggc tcctgagaat aggtttacta aagtcatcga    180
gatctgggtt caaatgacac tgcttaggga ggcattcact gatcaagtta cctaaaatag    240
caacaatcta tcatccaaaa tatcatttgc cagctttgat tttgcatata acacttactt    300
tatatatgta catatatgtg tatatatata tttgtgtgtg tgtgtgtgta tacatgtata    360
tatatatgca gtctgcaata aaatgtatgc ttntcagggg agaaannnnn ttntaataca    420
ttcagtgctc tatcccaga acctg                                          445

<210> SEQ ID NO 792
<211> LENGTH: 25
<212> TYPE: DNA
<213> ORGANISM: Artificial
<220> FEATURE:

<223> OTHER INFORMATION: synthetic oligonucleotide primer

<400> SEQUENCE: 792
aacaccagca atacatcagc tttac                                    25

<210> SEQ ID NO 793
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 793
agctttacac agcaggcaag tttcc                                    25

<210> SEQ ID NO 794
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 794
agtttcctgc tctctacaag tacag                                    25

<210> SEQ ID NO 795
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 795
acatcctgac tactttgtt gatca                                     25

<210> SEQ ID NO 796
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 796
gatcatcaca tttttcctc atgag                                     25

<210> SEQ ID NO 797
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 797
aatagtgttt tataggctcc tgaga                                    25

<210> SEQ ID NO 798
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 798
gatctgggtt caaatgacac tgctt                                    25

```
<210> SEQ ID NO 799
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 799
gacactgctt agggaggcat tcact                                          25

<210> SEQ ID NO 800
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 800
ggcattcact gatcaagtta cctaa                                          25

<210> SEQ ID NO 801
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 801
tcatttgcca gctttgattt tgcat                                          25

<210> SEQ ID NO 802
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 802
ttcagtgctc tatacccaga acctg                                          25

<210> SEQ ID NO 803
<211> LENGTH: 388
<212> TYPE: DNA
<213> ORGANISM: Homo sapiens

<400> SEQUENCE: 803
atcctccctt gattcgtgga tggacaacta tggaggccaa tctggctgag gtgaagactg     60
cttgagtcta aattcctctc tcctcaaacc caattcaaac tggcctgagc aaaatgaatg    120
tattgatcca taactgaaaa gtccagaatg atcaggcatc aggcatggtt gcatccaggg    180
gcccatgtat tagaaccatc tccttccagt tctgggctct gcttgcctcc cagttggttt    240
tactgcacag aggcttattc aagtccagag agatcttatc tttccctaca agtctgtgac    300
cttgattctg aacctgcatc tatgggaagg gcttgcagtg tctgagtgag cttggactgt    360
gtaaactttc ccacttctga agctgggg                                       388

<210> SEQ ID NO 804
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 804
```

```
atcctccctt gattcgtgga tggac                                              25

<210> SEQ ID NO 805
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 805
tgcttgagtc taaattcctc tctcc                                              25

<210> SEQ ID NO 806
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 806
ctctcctcaa acccaattca aactg                                              25

<210> SEQ ID NO 807
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 807
ggcatcaggc atggttgcat ccagg                                              25

<210> SEQ ID NO 808
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 808
gggcccatgt attagaacca tctcc                                              25

<210> SEQ ID NO 809
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 809
tgcctcccag ttggttttac tgcac                                              25

<210> SEQ ID NO 810
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 810
gcacagaggc ttattcaagt ccaga                                              25

<210> SEQ ID NO 811
<211> LENGTH: 25
<212> TYPE: DNA
<213> ORGANISM: Artificial
```

```
<220> FEATURE:
<223> OTHER INFORMATION: synthetic oligonucleotide primer

<400> SEQUENCE: 811
tatctttccc tacaagtctg tgacc                                              25

<210> SEQ ID NO 812
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 812
gattctgaac ctgcatctat gggaa                                              25

<210> SEQ ID NO 813
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 813
gtgagcttgg actgtgtaaa ctttc                                              25

<210> SEQ ID NO 814
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 814
aactttccca cttctgaagc tgggg                                              25

<210> SEQ ID NO 815
<211> LENGTH: 395
<212> TYPE: DNA
<213> ORGANISM: Homo sapiens
<220> FEATURE:
<221> NAME/KEY: misc_feature
<222> LOCATION: (63)..(63)
<223> OTHER INFORMATION: n is a, c, g, or t
<220> FEATURE:
<221> NAME/KEY: misc_feature
<222> LOCATION: (100)..(100)
<223> OTHER INFORMATION: n is a, c, g, or t

<400> SEQUENCE: 815
tccccttatc cagatgcagg tgcctatagc tgaagccatg tgtggtacat ttggtccagc        60
canagccttg catgaagctg gcacttgtgc tggtgcctgn agctgtctgc cttgccacag       120
cagctagcat gcgtggctgt gcacagtggc tggaccccat gctcattcgc tcatacactc       180
tttgccactc cgtgcctggc tccccttgg caggtgtgag atcgaggcca gtagtgtgag        240
ccaagcgcag cctgccaggc caagtgggtg gaacgagccc tgtgggcgcg agcaatactc       300
aggcagaagg cgctgcctgc cacagaggtt tctggctggc aaatcgacat cccaagggtc       360
ccgtgacaat tatagcccct gcttctggat agagt                                  395

<210> SEQ ID NO 816
<211> LENGTH: 25
<212> TYPE: DNA
<213> ORGANISM: Artificial
<220> FEATURE:
```

<223> OTHER INFORMATION: synthetic oligonucleotide primer

<400> SEQUENCE: 816
tccccttatc cagatgcagg tgcct                                              25

<210> SEQ ID NO 817
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 817
atgtgtggta catttggtcc agcca                                              25

<210> SEQ ID NO 818
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 818
aagctggcac ttgtgctggt gcctg                                              25

<210> SEQ ID NO 819
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 819
ctagcatgcg tggctgtgca cagtg                                              25

<210> SEQ ID NO 820
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 820
gcaggtgtga gatcgaggcc agtag                                              25

<210> SEQ ID NO 821
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 821
cagtagtgtg agccaagcgc agcct                                              25

<210> SEQ ID NO 822
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 822
tgggcgcgag caatactcag gcaga                                              25

<210> SEQ ID NO 823
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 823
ggtttctggc tggcaaatcg acatc                                            25

<210> SEQ ID NO 824
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 824
caaatcgaca tcccaagggt cccgt                                            25

<210> SEQ ID NO 825
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 825
gggtcccgtg acaattatag cccct                                            25

<210> SEQ ID NO 826
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 826
tatagcccct gcttctggat agagt                                            25

<210> SEQ ID NO 827
<211> LENGTH: 508
<212> TYPE: DNA
<213> ORGANISM: Homo sapiens
<220> FEATURE:
<221> NAME/KEY: misc_feature
<222> LOCATION: (40)..(40)
<223> OTHER INFORMATION: n is a, c, g, or t
<220> FEATURE:
<221> NAME/KEY: misc_feature
<222> LOCATION: (52)..(52)
<223> OTHER INFORMATION: n is a, c, g, or t
<220> FEATURE:
<221> NAME/KEY: misc_feature
<222> LOCATION: (59)..(59)
<223> OTHER INFORMATION: n is a, c, g, or t
<220> FEATURE:
<221> NAME/KEY: misc_feature
<222> LOCATION: (75)..(75)
<223> OTHER INFORMATION: n is a, c, g, or t
<220> FEATURE:
<221> NAME/KEY: misc_feature
<222> LOCATION: (77)..(77)
<223> OTHER INFORMATION: n is a, c, g, or t
<220> FEATURE:
<221> NAME/KEY: misc_feature
<222> LOCATION: (79)..(79)
<223> OTHER INFORMATION: n is a, c, g, or t
<220> FEATURE:
<221> NAME/KEY: misc_feature
<222> LOCATION: (82)..(83)

```
<223> OTHER INFORMATION: n is a, c, g, or t
<220> FEATURE:
<221> NAME/KEY: misc_feature
<222> LOCATION: (92)..(92)
<223> OTHER INFORMATION: n is a, c, g, or t
<220> FEATURE:
<221> NAME/KEY: misc_feature
<222> LOCATION: (95)..(95)
<223> OTHER INFORMATION: n is a, c, g, or t
<220> FEATURE:
<221> NAME/KEY: misc_feature
<222> LOCATION: (102)..(102)
<223> OTHER INFORMATION: n is a, c, g, or t
<220> FEATURE:
<221> NAME/KEY: misc_feature
<222> LOCATION: (108)..(108)
<223> OTHER INFORMATION: n is a, c, g, or t
<220> FEATURE:
<221> NAME/KEY: misc_feature
<222> LOCATION: (123)..(123)
<223> OTHER INFORMATION: n is a, c, g, or t
<220> FEATURE:
<221> NAME/KEY: misc_feature
<222> LOCATION: (150)..(150)
<223> OTHER INFORMATION: n is a, c, g, or t
<220> FEATURE:
<221> NAME/KEY: misc_feature
<222> LOCATION: (170)..(170)
<223> OTHER INFORMATION: n is a, c, g, or t
<220> FEATURE:
<221> NAME/KEY: misc_feature
<222> LOCATION: (480)..(480)
<223> OTHER INFORMATION: n is a, c, g, or t

<400> SEQUENCE: 827
aattgtcgag cacctctgac acttggcagt gcctacctgn ttgtgttcca gngggcagnt      60
tcagagaaaa cgggnanana cnntccaagc cnagntcaat cntcagangg ccagtaatta     120
ccnattggaa ttacacagca gcaatggatn gttcatatag gataataatn ataattatac    180
atgagcatcg ctgtagaata atgatgccta ttggcttatc ctgggaagac tccaaaaatg    240
tgattcagtc ctgaggcctc ggcaatgggc atgatgaggg caggctcagg ggcaggaggg    300
caccctgcta gagctgggtg tggggcacgt aggaaagggg tggttttcaa aaaggcttga    360
gacagatccc tggccttgag gacgtgcttc gcatgcagcc tgcaacccag ggagtgcaga    420
aaagaaaaag tgcatttgtt tatggagcac atatttgtgt ggcaggtacc attctagatn    480
ctggagattc agaaataagc cccctcc                                        508

<210> SEQ ID NO 828
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 828
aattgtcgag caccetctgac acttg                                          25

<210> SEQ ID NO 829
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 829
tctgacactt ggcagtgcct acctg                                           25
```

```
<210> SEQ ID NO 830
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 830
atgcctattg gcttatcctg ggaag                                  25

<210> SEQ ID NO 831
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 831
aatgtgattc agtcctgagg cctcg                                  25

<210> SEQ ID NO 832
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 832
gaggcctcgg caatgggcat gatga                                  25

<210> SEQ ID NO 833
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 833
gagggcaccc tgctagagct gggtg                                  25

<210> SEQ ID NO 834
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 834
gctgggtgtg gggcacgtag gaaag                                  25

<210> SEQ ID NO 835
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 835
aggcttgaga cagatccctg gcctt                                  25

<210> SEQ ID NO 836
<211> LENGTH: 25
<212> TYPE: DNA
<213> ORGANISM: Artificial
<220> FEATURE:
<223> OTHER INFORMATION: synthetic oligonucleotide primer
```

<400> SEQUENCE: 836
tgcagcctgc aacccaggga gtgca                                              25

<210> SEQ ID NO 837
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 837
ttgtgtggca ggtaccattc tagat                                              25

<210> SEQ ID NO 838
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 838
gagattcaga ataagccccc cctcc                                              25

<210> SEQ ID NO 839
<211> LENGTH: 508
<212> TYPE: DNA
<213> ORGANISM: Homo sapiens

<400> SEQUENCE: 839
atgacatcac ttgtcagatt ttctggtgta tggaaagatt taataatcct gcctcttttg        60
aagcctgaaa cttacaattt aaagcctgaa atctaccata aggaacttgg taaattgtgt       120
cagataccat gaaatgcat cttttcatag ttaaccacag attgtttatg taaaggcaaa        180
ttggtggtca ggttcaaggt aaaatggatt attgggttga ttagtagcca aaaactaaat       240
gcatgttcag gtcaaaatga atttgtttgt tttagttggt gccatttttcc tttattatt      300 cagaactaca gagtgtgcat tttattaata ggaatgaaag ctcatgcttg aggatttgaa       360
tagggtggat gtatatattt tataaaactca agttgcaaaa tatgtaaagt cactacttttt   420 taaatagaat ataatgttca aaacagacaa atctatgtta tatatttttt aatacatgta     480
tcagacttgt tagttgaatg cagattac                                         508

<210> SEQ ID NO 840
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 840
atgacatcac ttgtcagatt ttctg                                              25

<210> SEQ ID NO 841
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 841
ctcttttgaa gcctgaaact tacaa                                              25

```
<210> SEQ ID NO 842
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 842
tttaaagcct gaaatctacc ataag                                      25

<210> SEQ ID NO 843
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 843
gcatcttttc atagttaacc acaga                                      25

<210> SEQ ID NO 844
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 844
ggcaaattgg tggtcaggtt caagg                                      25

<210> SEQ ID NO 845
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 845
actaaatgca tgttcaggtc aaaat                                      25

<210> SEQ ID NO 846
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 846
tttcctttta ttattcagaa ctaca                                      25

<210> SEQ ID NO 847
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 847
gaactacaga gtgtgcattt tatta                                      25

<210> SEQ ID NO 848
<211> LENGTH: 25
<212> TYPE: DNA
<213> ORGANISM: Artificial
<220> FEATURE:
<223> OTHER INFORMATION: synthetic oligonucleotide primer
```

```
<400> SEQUENCE: 848
gaaagctcat gcttgaggat ttgaa                                          25

<210> SEQ ID NO 849
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 849
aatacatgta tcagacttgt tagtt                                          25

<210> SEQ ID NO 850
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 850
gacttgttag ttgaatgcag attac                                          25

<210> SEQ ID NO 851
<211> LENGTH: 527
<212> TYPE: DNA
<213> ORGANISM: Homo sapiens
<220> FEATURE:
<221> NAME/KEY: misc_feature
<222> LOCATION: (470)..(470)
<223> OTHER INFORMATION: n is a, c, g, or t
<220> FEATURE:
<221> NAME/KEY: misc_feature
<222> LOCATION: (472)..(472)
<223> OTHER INFORMATION: n is a, c, g, or t
<220> FEATURE:
<221> NAME/KEY: misc_feature
<222> LOCATION: (500)..(500)
<223> OTHER INFORMATION: n is a, c, g, or t

<400> SEQUENCE: 851
agagctctgc aaagaacacc gccagctctt tccttccggg tgctcttgct gggggggtcag    60 gctggtcccc tctgactggc actgcccacg ctgggacatg ggaggagggc catctgggca   120
ctgcaggagc agatcctggg tgcacatggg agacaggtg tgctggcagg aacagcaggc    180
ggggctgagc tcaggaggcg cctcacagcg ggtgcctcca gcctggtctg agcacgggat   240
gaagaaccag gcaccgctca tcgtgcatct ccacaaggca ctgtgtgact tcatgcaagc   300
cgctcaacct ctctggcccc acgtccttgt ccacaggggc agagtggact gaatggaggc   360
tgaggtccct ctcagcttgg gtggtgtggc agagggtgag gaggagccca tgggccctgg   420
atcaccagcc tccctccacc cagaatgccc cgtccactcc actgcccacn ancctctgtg   480
caattgacaa acgtcctggn tgttaacgcc taagcataaa gagtcgg                 527

<210> SEQ ID NO 852
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 852
agagctctgc aaagaacacc gccag                                          25
```

<210> SEQ ID NO 853
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 853
aaagaacacc gccagctctt tcctt                                              25

<210> SEQ ID NO 854
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 854
tttccttccg ggtgctcttg ctggg                                              25

<210> SEQ ID NO 855
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 855
aggctggtcc cctctgactg gcact                                              25

<210> SEQ ID NO 856
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 856
cagcctggtc tgagcacggg atgaa                                              25

<210> SEQ ID NO 857
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 857
gtctgagcac gggatgaaga accag                                              25

<210> SEQ ID NO 858
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 858
gaagaaccag gcaccgctca tcgtg                                              25

<210> SEQ ID NO 859
<211> LENGTH: 25
<212> TYPE: DNA
<213> ORGANISM: Artificial
<220> FEATURE:
<223> OTHER INFORMATION: synthetic oligonucleotide primer

```
<400> SEQUENCE: 859
gtgtgacttc atgcaagccg ctcaa                                           25

<210> SEQ ID NO 860
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 860
tgaatggagg ctgaggtccc tctca                                           25

<210> SEQ ID NO 861
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 861
aggtccctct cagcttgggt ggtgt                                           25

<210> SEQ ID NO 862
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 862
ttaacgccta agcataaaga gtcgg                                           25

<210> SEQ ID NO 863
<211> LENGTH: 506
<212> TYPE: DNA
<213> ORGANISM: Homo sapiens
<220> FEATURE:
<221> NAME/KEY: misc_feature
<222> LOCATION: (44)..(44)
<223> OTHER INFORMATION: n is a, c, g, or t
<220> FEATURE:
<221> NAME/KEY: misc_feature
<222> LOCATION: (46)..(46)
<223> OTHER INFORMATION: n is a, c, g, or t
<220> FEATURE:
<221> NAME/KEY: misc_feature
<222> LOCATION: (93)..(93)
<223> OTHER INFORMATION: n is a, c, g, or t
<220> FEATURE:
<221> NAME/KEY: misc_feature
<222> LOCATION: (122)..(122)
<223> OTHER INFORMATION: n is a, c, g, or t
<220> FEATURE:
<221> NAME/KEY: misc_feature
<222> LOCATION: (131)..(131)
<223> OTHER INFORMATION: n is a, c, g, or t
<220> FEATURE:
<221> NAME/KEY: misc_feature
<222> LOCATION: (200)..(200)
<223> OTHER INFORMATION: n is a, c, g, or t
<220> FEATURE:
<221> NAME/KEY: misc_feature
<222> LOCATION: (231)..(231)
<223> OTHER INFORMATION: n is a, c, g, or t

<400> SEQUENCE: 863
ccttcccagc tgcaagcatg gatgcgggca tgagaagaac aagncntggc acttctgctc     60
ctgcagctgc cgcagcagcc cctcccccct ccncattgaa ccccacgttg gggtcactac    120
```

```
tngagtggat ngaggccctt cacatttctg ggcctcagcc acagctgcag caggtgccca    180
gaggtcagaa ccagagatcn cagacctccc ggaccagctc gtgccccaaa ngaaaggcca    240
tctccagctc ctacagctct acggaggcc tcccggaacg aaagcggagg aggggggccag    300 cctcatccca ctgccagctg accctcagtt cctcaaacac agacccaggg tgcgtgccca    360
tctccagccc agggcagctc ccctgtaagc tgggtgagct actgaagcca aggcgggagg    420
cagctgacaa cacccacggc ccatgtggag gtggtggaaa ggctggactc agcagcaaca    480
ccaaatcccg gaccaggcag aaacca                                         506
```

```
<210> SEQ ID NO 864
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 864
ccttcccagc tgcaagcatg gatgc                                           25

<210> SEQ ID NO 865
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 865
aggcccttca catttctggg cctca                                           25

<210> SEQ ID NO 866
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 866
gcaggtgccc agaggtcaga accag                                           25

<210> SEQ ID NO 867
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 867
gaaagcggag gagggggcca gcctc                                           25

<210> SEQ ID NO 868
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 868
aaacacagac ccagggtgcg tgccc                                           25

<210> SEQ ID NO 869
<211> LENGTH: 25
<212> TYPE: DNA
```

<213> ORGANISM: Artificial
<220> FEATURE:
<223> OTHER INFORMATION: synthetic oligonucleotide primer

<400> SEQUENCE: 869
gcagctcccc tgtaagctgg gtgag                                    25

<210> SEQ ID NO 870
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 870
ggtgagctac tgaagccaag gcggg                                    25

<210> SEQ ID NO 871
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 871
aggcgggagg cagctgacaa caccc                                    25

<210> SEQ ID NO 872
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 872
cacccacggc ccatgtggag gtggt                                    25

<210> SEQ ID NO 873
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 873
aaggctggac tcagcagcaa cacca                                    25

<210> SEQ ID NO 874
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 874
caaatcccgg accaggcaga aacca                                    25

<210> SEQ ID NO 875
<211> LENGTH: 508
<212> TYPE: DNA
<213> ORGANISM: Homo sapiens

<400> SEQUENCE: 875
ggatgggccg tcaaagtcta agtcagagca tcctgatgtt ggaggcaaag caggagagtg    60
tggattaagc agctagacat tggttactgg ggcaacaacc gtttgggtgg agaactggat   120

```
cagaaatcaa ctggagtgga tcgaggtgtg catagaaggc gaggaagtgg cgaggcgttt      180
ggctgcgagg ggtagaacta gggtgcacca agcaggagaa acagatggaa gtttggacat      240
gattgaacac aaatgggaag agtacagaaa caagagtgga ccaggctcat atgtgtaatc      300
ccagcacttg gggaggctga ggcgggagga ttgcttgaca ctaggagttt gaggccaacc      360
tgggcaatat ggcgagaccc catctctaca aaaacattta aaaattagcc agatgcggtg      420
gcgcatacct gtggtcccag gctaagatgg gacgattgct tgagcccagg aggtcaaggc      480
ctcagtcatg ccactgcttg agtgacag                                         508

<210> SEQ ID NO 876
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 876
ggatgggccg tcaaagtcta agtca                                             25

<210> SEQ ID NO 877
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 877
aagtctaagt cagagcatcc tgatg                                             25

<210> SEQ ID NO 878
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 878
gattaagcag ctagacattg gttac                                             25

<210> SEQ ID NO 879
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 879
caaccgtttg ggtggagaac tggat                                             25

<210> SEQ ID NO 880
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 880
aatcaactgg agtggatcga ggtgt                                             25

<210> SEQ ID NO 881
<211> LENGTH: 25
<212> TYPE: DNA
```

```
<213> ORGANISM: Artificial
<220> FEATURE:
<223> OTHER INFORMATION: synthetic oligonucleotide primer

<400> SEQUENCE: 881
ggtagaacta gggtgcacca agcag                                     25

<210> SEQ ID NO 882
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 882
gtgcaccaag caggagaaac agatg                                     25

<210> SEQ ID NO 883
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 883
agtggaccag gctcatatgt gtaat                                     25

<210> SEQ ID NO 884
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 884
tacctgtggt cccaggctaa gatgg                                     25

<210> SEQ ID NO 885
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 885
aggtcaaggc ctcagtcatg ccact                                     25

<210> SEQ ID NO 886
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 886
agtcatgcca ctgcttgagt gacag                                     25

<210> SEQ ID NO 887
<211> LENGTH: 489
<212> TYPE: DNA
<213> ORGANISM: Homo sapiens

<400> SEQUENCE: 887
gcattgtcta ctgaaaagct gtggcagcga gtggtattat tgaccatgtg ttctcatgtc    60
tttttgcaga tttaaaggtt ttattgtagt gtccatttaa tatctgcatg tgtgtttaat   120
```

```
ctctgaatac catgtaatta aactgattaa cttgtgatgg tgatggtgat tagcacacac    180
taaaaaccca atgaagcaat tgtctccctc ttcttaactg gaaatcacac ttgtgaggta    240
tggtatccat tatcaacagt ggattcatga ttgacttcat attttgtgta tctggttata    300
aattttgtat agcatttaat ttggcactta atataaatcc atttgatttg aatagtgtgt    360
gtgtgtacat ggtgtgtgtg tgtgtgtgca ctttagtttc gtgagccttg ggaaactgat    420
tctacaaata tcttatatag agataaatgt atcaggcatt tttttgcaaa gcgatatata    480
cattcctct                                                            489
```

<210> SEQ ID NO 888
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 888
gcattgtcta ctgaaaagct gtggc                                           25

<210> SEQ ID NO 889
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 889
gctgtggcag cgagtggtat tattg                                           25

<210> SEQ ID NO 890
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 890
ggtattattg accatgtgtt ctcat                                           25

<210> SEQ ID NO 891
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 891
tgtagtgtcc atttaatatc tgcat                                           25

<210> SEQ ID NO 892
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 892
atctgcatgt gtgtttaatc tctga                                           25

<210> SEQ ID NO 893
<211> LENGTH: 25
<212> TYPE: DNA

```
<213> ORGANISM: Artificial
<220> FEATURE:
<223> OTHER INFORMATION: synthetic oligonucleotide primer

<400> SEQUENCE: 893
aatgaagcaa ttgtctccct cttct                                          25

<210> SEQ ID NO 894
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 894
gtctccctct tcttaactgg aaatc                                          25

<210> SEQ ID NO 895
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 895
ttgacttcat attttgtgta tctgg                                          25

<210> SEQ ID NO 896
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 896
gtgtgcactt tagtttcgtg agcct                                          25

<210> SEQ ID NO 897
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 897
gtgagccttg ggaaactgat tctac                                          25

<210> SEQ ID NO 898
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 898
tgcaaagcga tatatacatt cctct                                          25

<210> SEQ ID NO 899
<211> LENGTH: 533
<212> TYPE: DNA
<213> ORGANISM: Homo sapiens
<220> FEATURE:
<221> NAME/KEY: misc_feature
<222> LOCATION: (487)..(489)
<223> OTHER INFORMATION: n is a, c, g, or t

<400> SEQUENCE: 899
```

-continued

```
agacttcctg agttcagatc tctcagccat aactagctat ctgaccttgg ccaagtatgc    60
tcaaagtcac aaaaccttag tttccttatg tgcatgatga ttataatacc ttttgtacag   120
ttatgaggaa acttagacaa tgcctgtgtt gtatggtaag cgttttcata aatgctgcct   180
acctgtaagt agcattatag tgtgtagtta ttggttaatt tccttttttct ttaccagaag   240 tgtgggtttt gcccagcctt tatacaactt cagtatttct ggttaatctg tctctctatg   300
gctctaaact tttcagagtg gtgggggagt taccaacact tttgtaaaag gccagatagt   360
aaatgtttta tgctttatgt agtctctgtt gcaagtactc aattctgtaa ttatagcgtg   420
aaagcggcca cagacttgta aatgaatgag tacagctatg ttctaataaa attttttattt   480 acaaaannna tgtggtggac tggatttggc ctttgggcca tattttgctg acc           533
```

<210> SEQ ID NO 900
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 900

```
agacttcctg agttcagatc tctca                                          25
```

<210> SEQ ID NO 901
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 901

```
taactagcta tctgaccttg gccaa                                          25
```

<210> SEQ ID NO 902
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 902

```
accttggcca agtatgctca aagtc                                          25
```

<210> SEQ ID NO 903
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 903

```
aaccttagtt tccttatgtg catga                                          25
```

<210> SEQ ID NO 904
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 904

```
gcgttttcat aaatgctgcc tacct                                          25
```

```
<210> SEQ ID NO 905
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 905
tgcccagcct ttatacaact tcagt                                             25

<210> SEQ ID NO 906
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 906
tttctggtta atctgtctct ctatg                                             25

<210> SEQ ID NO 907
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 907
gtctctctat ggctctaaac ttttc                                             25

<210> SEQ ID NO 908
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 908
gtagtctctg ttgcaagtac tcaat                                             25

<210> SEQ ID NO 909
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 909
gcgtgaaagc ggccacagac ttgta                                             25

<210> SEQ ID NO 910
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 910
gcctttgggc catattttgc tgacc                                             25

<210> SEQ ID NO 911
<211> LENGTH: 380
<212> TYPE: DNA
<213> ORGANISM: Homo sapiens
<220> FEATURE:
<221> NAME/KEY: misc_feature
```

```
<222> LOCATION: (84)..(84)
<223> OTHER INFORMATION: n is a, c, g, or t
<220> FEATURE:
<221> NAME/KEY: misc_feature
<222> LOCATION: (94)..(94)
<223> OTHER INFORMATION: n is a, c, g, or t
<220> FEATURE:
<221> NAME/KEY: misc_feature
<222> LOCATION: (99)..(99)
<223> OTHER INFORMATION: n is a, c, g, or t
<220> FEATURE:
<221> NAME/KEY: misc_feature
<222> LOCATION: (103)..(103)
<223> OTHER INFORMATION: n is a, c, g, or t
<220> FEATURE:
<221> NAME/KEY: misc_feature
<222> LOCATION: (169)..(169)
<223> OTHER INFORMATION: n is a, c, g, or t
<220> FEATURE:
<221> NAME/KEY: misc_feature
<222> LOCATION: (202)..(202)
<223> OTHER INFORMATION: n is a, c, g, or t
<220> FEATURE:
<221> NAME/KEY: misc_feature
<222> LOCATION: (273)..(273)
<223> OTHER INFORMATION: n is a, c, g, or t
<220> FEATURE:
<221> NAME/KEY: misc_feature
<222> LOCATION: (275)..(277)
<223> OTHER INFORMATION: n is a, c, g, or t

<400> SEQUENCE: 911
gcgtggtgac tgatgtgtgc ctgtagtctc agctactcag gaggctgagg caggaggatc    60
acttgagccc aggagtttga gtcnagtctg ggcnaacant agnaaacccc atctctaaaa   120
taaataaaat aaatgactga gctgttgtga aagggttagt gatagaganc cagaactctt   180
aactgtcagg ccaatgtctt tnccacttcc tcacactgat cccacataac tctgggtatg   240
atagtgagtg tcaggggtca gacatgggtc tgntnnngct gagctgcctg attgttcctt   300
ataaagtttg tcaacctctt cttttttttg aacaagttaa gaggaaagga attaaagctt   360
tatggatgat cacttttcaa                                                380

<210> SEQ ID NO 912
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 912
gcgtggtgac tgatgtgtgc ctgta                                          25

<210> SEQ ID NO 913
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 913
atgactgagc tgttgtgaaa gggtt                                          25

<210> SEQ ID NO 914
<211> LENGTH: 25
<212> TYPE: DNA
<213> ORGANISM: Artificial
<220> FEATURE:
<223> OTHER INFORMATION: synthetic oligonucleotide primer
```

```
<400> SEQUENCE: 914
ccagaactct taactgtcag gccaa                                            25

<210> SEQ ID NO 915
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 915
tcttaactgt caggccaatg tcttt                                            25

<210> SEQ ID NO 916
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 916
tcacactgat cccacataac tctgg                                            25

<210> SEQ ID NO 917
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 917
tcccacataa ctctgggtat gatag                                            25

<210> SEQ ID NO 918
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 918
ggtatgatag tgagtgtcag gggtc                                            25

<210> SEQ ID NO 919
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 919
gtgtcagggg tcagacatgg gtctg                                            25

<210> SEQ ID NO 920
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 920
agctgcctga ttgttcctta taaag                                            25

<210> SEQ ID NO 921
<211> LENGTH: 25
```

```
<212> TYPE: DNA
<213> ORGANISM: Artificial
<220> FEATURE:
<223> OTHER INFORMATION: synthetic oligonucleotide primer

<400> SEQUENCE: 921
ttataaagtt tgtcaacctc ttctt                                          25

<210> SEQ ID NO 922
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 922
agctttatgg atgatcactt ttcaa                                          25

<210> SEQ ID NO 923
<211> LENGTH: 472
<212> TYPE: DNA
<213> ORGANISM: Homo sapiens
<220> FEATURE:
<221> NAME/KEY: misc_feature
<222> LOCATION: (154)..(154)
<223> OTHER INFORMATION: n is a, c, g, or t
<220> FEATURE:
<221> NAME/KEY: misc_feature
<222> LOCATION: (292)..(293)
<223> OTHER INFORMATION: n is a, c, g, or t
<220> FEATURE:
<221> NAME/KEY: misc_feature
<222> LOCATION: (295)..(296)
<223> OTHER INFORMATION: n is a, c, g, or t

<400> SEQUENCE: 923
tgggcttggg gacatctcaa tggccataga taggtagcct gggtttgggg acacctcagt    60
gggctgatat gaataggctg cacttgggga cacctcagtg agctgatatg ggtgggctgg   120
gcttggagat acctcagtgg gctgaaatgg ctgngccagg gttgggtact ccctaatggc   180
ctgagatggg taggttggac ttggggacac ctcagtgggc tgaaatggct gagccagcat   240
tgggtactcc ccaacagact gagatgggta gtctggactt ggagacaccc cnnanngctt   300
gagatggctg ggccagattt gaggttaccc caggggcttg agatggctgg gctaggcttg   360
agggctcccc actgtccata gatggctggg ctaggttttg gaccccag ttagccattg     420 attggtgacc ttggtctgag gccactctaa aggtccttga tgggtgtcct cg           472

<210> SEQ ID NO 924
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 924
tgggcttggg gacatctcaa tggcc                                          25

<210> SEQ ID NO 925
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 925
```

```
tgggctgggc ttggagatac ctcag                                              25

<210> SEQ ID NO 926
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 926
gccagggttg ggtactccct aatgg                                              25

<210> SEQ ID NO 927
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 927
tggctgagcc agcattgggt actcc                                              25

<210> SEQ ID NO 928
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 928
ggtactcccc aacagactga gatgg                                              25

<210> SEQ ID NO 929
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 929
gatttgaggt taccccaggg gcttg                                              25

<210> SEQ ID NO 930
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 930
gggcttgaga tggctgggct aggct                                              25

<210> SEQ ID NO 931
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 931
gatggctggg ctaggttttg ggacc                                              25

<210> SEQ ID NO 932
<211> LENGTH: 25
<212> TYPE: DNA
<213> ORGANISM: Artificial
```

```
<220> FEATURE:
<223> OTHER INFORMATION: synthetic oligonucleotide primer

<400> SEQUENCE: 932 gaccccccagt tagccattga ttggt                                  25

<210> SEQ ID NO 933
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 933
ttggtgacct tggtctgagg ccact                                   25

<210> SEQ ID NO 934
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 934
taaaggtcct tgatgggtgt cctcg                                   25

<210> SEQ ID NO 935
<211> LENGTH: 398
<212> TYPE: DNA
<213> ORGANISM: Homo sapiens

<400> SEQUENCE: 935
acaatgggag cccttcatca cagctttgta gttacctcaa ctctggctgt tgagtaattt    60
gctcagttaa atctgtttgt gggtgtagtg aattacaacc tcctctggtt ccctcgagat   120
caagtctaac ctggtgattg cgtcatctgg tgggagagca cggctacaac agcaggtgga   180
aaccatgctc gggtcctggc cactttgcct aggatgaaag ctgttgtggc aaacagggga   240
aagagcttca agctttgtag taaaaggaat ctgggcttaa attcctctta tcagcactgt   300
gaccttggag aattaatcat tcttggttgt ggtgagggtt aattgagatc aggtatttaa   360
aggacatctg acagtgcctg gcacgggata ggtgctcc                          398

<210> SEQ ID NO 936
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 936
acaatgggag cccttcatca cagct                                   25

<210> SEQ ID NO 937
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 937
gctttgtagt tacctcaact ctggc                                   25

<210> SEQ ID NO 938
```

```
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 938
agtgaattac aacctcctct ggttc                                          25

<210> SEQ ID NO 939
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 939
gttccctcga gatcaagtct aacct                                          25

<210> SEQ ID NO 940
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 940
gtctaacctg gtgattgcgt catct                                          25

<210> SEQ ID NO 941
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 941
ggtgggagag cacggctaca acagc                                          25

<210> SEQ ID NO 942
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 942
tcctggccac tttgcctagg atgaa                                          25

<210> SEQ ID NO 943
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 943
atctgggctt aaattcctct tatca                                          25

<210> SEQ ID NO 944
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 944
```
cctcttatca gcactgtgac cttgg                                     25

<210> SEQ ID NO 945
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 945
aaggacatct gacagtgcct ggcac                                     25

<210> SEQ ID NO 946
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 946
gtgcctggca cgggataggt gctcc                                     25

<210> SEQ ID NO 947
<211> LENGTH: 99
<212> TYPE: DNA
<213> ORGANISM: Homo sapiens

<400> SEQUENCE: 947
ttttttttac caactattgt cacatacata taacgcatat agacatatgg acacacagaa    60
gatacttctt acctggagtt atatactagc aatattttc                           99

<210> SEQ ID NO 948
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 948
ttttttttac caactattgt cacat                                     25

<210> SEQ ID NO 949
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 949
ttttaccaac tattgtcaca tacat                                     25

<210> SEQ ID NO 950
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 950
taccaactat tgtcacatac atata                                     25

<210> SEQ ID NO 951
<211> LENGTH: 25
<212> TYPE: DNA

```
<213> ORGANISM: Artificial
<220> FEATURE:
<223> OTHER INFORMATION: synthetic oligonucleotide primer

<400> SEQUENCE: 951
actattgtca catacatata acgca                                             25

<210> SEQ ID NO 952
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 952
gtcacataca taaacgcat ataga                                              25

<210> SEQ ID NO 953
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 953
aacgcatata gacatatgga cacac                                             25

<210> SEQ ID NO 954
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 954
catatggaca cacagaagat acttc                                             25

<210> SEQ ID NO 955
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 955
gaagatactt cttacctgga gttat                                             25

<210> SEQ ID NO 956
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 956
gatacttctt acctggagtt atata                                             25

<210> SEQ ID NO 957
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 957
tcttacctgg agttatatac tagca                                             25
```

<210> SEQ ID NO 958
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 958
ggagttatat actagcaata ttttc                                          25

<210> SEQ ID NO 959
<211> LENGTH: 489
<212> TYPE: DNA
<213> ORGANISM: Homo sapiens
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (115)..(115)
<223> OTHER INFORMATION: n is a, c, g, or t

<400> SEQUENCE: 959
cccagccgag gaagagccgg gaaagggcgt cgncgctcat gtaggctcac ctttcgagtg     60
cggagggtga cggacgcccc ccgttcaagc agcagctcag ccacctcgaa gtggncacag    120
ttgagggcat cgtggagggg ggtgatgcct tcgcagccct ggccacctgg gtcgtccact    180
gcggccccgt ggtccagcag gaagcggaca atttctgcag accaggagac gtaagcccag    240
ctcccgatgc cccgccagga ctgactcttc gccccacgtg tccaccaagg gtctcactcc    300
agcctgggtg acagagcgag actccatctc aagaaaaaaa aacaacacaa catggatggt    360
gcctggctca aagtgagggc tgacggctgc caacctccaa tggtggtctc tgccatcagc    420
actcctggac cacgcgtgcc atctcctctc ccaccctggg aggctagggg tacaactact    480
gtctccagt                                                           489

<210> SEQ ID NO 960
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 960
cccagccgag gaagagccgg gaaag                                          25

<210> SEQ ID NO 961
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 961
tcatgtaggc tcacctttcg agtgc                                          25

<210> SEQ ID NO 962
<211> LENGTH: 25
<212> TYPE: DNA
<213> ORGANISM: Artificial
<220> FEATURE:
<223> OTHER INFORMATION: synthetic oligonucleotide primer

```
<400> SEQUENCE: 962
cgagtgcgga gggtgacgga cgccc                                              25

<210> SEQ ID NO 963
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 963
atcgtggagg ggggtgatgc cttcg                                              25

<210> SEQ ID NO 964
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 964
ggaagcggac aatttctgca gacca                                              25

<210> SEQ ID NO 965
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 965
gcagaccagg agacgtaagc ccagc                                              25

<210> SEQ ID NO 966
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 966
aacaacacaa catggatggt gcctg                                              25

<210> SEQ ID NO 967
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 967
ggtgcctggc tcaaagtgag ggctg                                              25

<210> SEQ ID NO 968
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 968
aaagtgaggg ctgacggctg ccaac                                              25

<210> SEQ ID NO 969
<211> LENGTH: 25
```

```
<212> TYPE: DNA
<213> ORGANISM: Artificial
<220> FEATURE:
<223> OTHER INFORMATION: synthetic oligonucleotide primer

<400> SEQUENCE: 969
ggaggctagg ggtacaacta ctgtc                                         25

<210> SEQ ID NO 970
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 970 tagggggtaca actactgtct ccagt                                        25

<210> SEQ ID NO 971
<211> LENGTH: 397
<212> TYPE: DNA
<213> ORGANISM: Homo sapiens

<400> SEQUENCE: 971
ggcagcgtat ccagaagggg gcagggaatg ggtgaagagg ttgtgctcta gggcagagct    60
gagctctgat ctagaaagga cagcaaagat acctggaagg cctcccgatt cttgcgttgt   120
tggcgtcgct cccgaagccg ggcccgctcc cgttcctcct cctcttccct ctccaaagct   180
cggatgtgct cctcaaaaca gatcagtgca tcttccttgt ccatgtctaa agacaggcag   240
gaggttccgc gggcattgtc ccagcaggat accctctcag accccagcac ccctaatgtt   300
tcaacgatgc tgtcctacag gtgctaggga tacccagggt ggtgggggaa gggcctggag   360
ggggctctgt gggagcagcc actgcaatgg tagttct                           397

<210> SEQ ID NO 972
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 972
ggcagcgtat ccagaagggg gcagg                                         25

<210> SEQ ID NO 973
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 973
gaggttgtgc tctagggcag agctg                                         25

<210> SEQ ID NO 974
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 974
gagctgagct ctgatctaga aagga                                         25
```

<210> SEQ ID NO 975
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 975
agcaaagata cctggaaggc ctccc                                           25

<210> SEQ ID NO 976
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 976
cgattcttgc gttgttggcg tcgct                                           25

<210> SEQ ID NO 977
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 977
atgtgctcct caaaacagat cagtg                                           25

<210> SEQ ID NO 978
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 978
aacagatcag tgcatcttcc ttgtc                                           25

<210> SEQ ID NO 979
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 979
agcaccccta atgtttcaac gatgc                                           25

<210> SEQ ID NO 980
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 980
tgtttcaacg atgctgtcct acagg                                           25

<210> SEQ ID NO 981
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 981
gtcctacagg tgctagggat accca 25

<210> SEQ ID NO 982
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 982
gagcagccac tgcaatggta gttct 25

<210> SEQ ID NO 983
<211> LENGTH: 234
<212> TYPE: DNA
<213> ORGANISM: Homo sapiens
<220> FEATURE:
<221> NAME/KEY: misc_feature
<222> LOCATION: (88)..(88)
<223> OTHER INFORMATION: n is a, c, g, or t
<220> FEATURE:
<221> NAME/KEY: misc_feature
<222> LOCATION: (126)..(126)
<223> OTHER INFORMATION: n is a, c, g, or t
<220> FEATURE:
<221> NAME/KEY: misc_feature
<222> LOCATION: (142)..(142)
<223> OTHER INFORMATION: n is a, c, g, or t
<220> FEATURE:
<221> NAME/KEY: misc_feature
<222> LOCATION: (188)..(188)
<223> OTHER INFORMATION: n is a, c, g, or t

<400> SEQUENCE: 983
acaatgataa caacagctaa cacttagaaa ggaaatacaa tgaactgttc tcttcgagat 60
ccagaataaa agtctggcag ctagaacncc gtttttatac accgaacccc tcgtgctctc 120
cctgcntttt ttttgttgtt gntgttgtgc ttaatgttag aaaataacat tactactatg 180
aaacgaanag aattttttt caaaaccatg tcttgccatt acagatgaga caag 234

<210> SEQ ID NO 984
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 984
acaatgataa caacagctaa cactt 25

<210> SEQ ID NO 985
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 985
aaggaaatac aatgaactgt tctct 25

<210> SEQ ID NO 986
<211> LENGTH: 25
<212> TYPE: DNA
<213> ORGANISM: Artificial
<220> FEATURE:

-continued

```
<223> OTHER INFORMATION: synthetic oligonucleotide primer

<400> SEQUENCE: 986
tgaactgttc tcttcgagat ccaga                                    25

<210> SEQ ID NO 987
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 987
aactgttctc ttcgagatcc agaat                                    25

<210> SEQ ID NO 988
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 988
tgttctcttc gagatccaga ataaa                                    25

<210> SEQ ID NO 989
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 989
agaataaaag tctggcagct agaac                                    25

<210> SEQ ID NO 990
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 990
aataacatta ctactatgaa acgaa                                    25

<210> SEQ ID NO 991
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 991 tttttcaaa accatgtctt gccat                                     25

<210> SEQ ID NO 992
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 992
ttcaaaacca tgtcttgcca ttaca                                    25
```

```
<210> SEQ ID NO 993
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 993
accatgtctt gccattacag atgag                                          25

<210> SEQ ID NO 994
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 994
gtcttgccat tacagatgag acaag                                          25

<210> SEQ ID NO 995
<211> LENGTH: 437
<212> TYPE: DNA
<213> ORGANISM: Homo sapiens

<400> SEQUENCE: 995
ccctaccatc cacagtatca ttttcaggaa tattggtgga aggtcctggt tctccaggtg    60
gttccaagct atccaataaa cgattcactt tatttcgaag ttctatcagt tctcgacgga   120
gatatttcac ctgacttgat tcaaggggtc ttggctggcc attaacaaat aatgtcagtt   180
tcagtatcct actgcactga attgcaaagg aaaggtcaga actatcaaaa attgttataa   240
gatctccatc ttcatcttta tactttattg ttacttcatc attactcaga agttttcctc   300
tgaaaactcg ttgcatcatt agcactaatt catcataagt aatatcttca ttatgaatag   360
gaattcgccg aatatcctcc ccaagttgag ctttgatgat tagcttccca cttagatcca   420
actgtccgtt catggtg                                                 437

<210> SEQ ID NO 996
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 996
ccctaccatc cacagtatca ttttc                                          25

<210> SEQ ID NO 997
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 997
ggtggttcca agctatccaa taaac                                          25

<210> SEQ ID NO 998
<211> LENGTH: 25
<212> TYPE: DNA
<213> ORGANISM: Artificial
<220> FEATURE:
<223> OTHER INFORMATION: synthetic oligonucleotide primer
```

```
<400> SEQUENCE: 998
gaagttctat cagttctcga cggag                                    25

<210> SEQ ID NO 999
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 999
ctcgacggag atatttcacc tgact                                    25

<210> SEQ ID NO 1000
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1000
tgattcaagg ggtcttggct ggcca                                    25

<210> SEQ ID NO 1001
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1001
cagtatccta ctgcactgaa ttgca                                    25

<210> SEQ ID NO 1002
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1002
tttcctctga aaactcgttg catca                                    25

<210> SEQ ID NO 1003
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1003
taggaattcg ccgaatatcc tcccc                                    25

<210> SEQ ID NO 1004
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1004
tatcctcccc aagttgagct ttgat                                    25

<210> SEQ ID NO 1005
<211> LENGTH: 25
```

<212> TYPE: DNA
<213> ORGANISM: Artificial
<220> FEATURE:
<223> OTHER INFORMATION: synthetic oligonucleotide primer

<400> SEQUENCE: 1005
gatgattagc ttcccactta gatcc                                            25

<210> SEQ ID NO 1006
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1006
tagatccaac tgtccgttca tggtg                                            25

<210> SEQ ID NO 1007
<211> LENGTH: 338
<212> TYPE: DNA
<213> ORGANISM: Homo sapiens
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (55)..(55)
<223> OTHER INFORMATION: n is a, c, g, or t
<220> FEATURE:
<221> NAME/KEY: misc_feature
<222> LOCATION: (70)..(70)
<223> OTHER INFORMATION: n is a, c, g, or t
<220> FEATURE:
<221> NAME/KEY: misc_feature
<222> LOCATION: (77)..(77)
<223> OTHER INFORMATION: n is a, c, g, or t
<220> FEATURE:
<221> NAME/KEY: misc_feature
<222> LOCATION: (98)..(98)
<223> OTHER INFORMATION: n is a, c, g, or t
<220> FEATURE:
<221> NAME/KEY: misc_feature
<222> LOCATION: (107)..(107)
<223> OTHER INFORMATION: n is a, c, g, or t
<220> FEATURE:
<221> NAME/KEY: misc_feature
<222> LOCATION: (115)..(115)
<223> OTHER INFORMATION: n is a, c, g, or t

<400> SEQUENCE: 1007
aactcccagg tttctatatg ccagccaaga ggtgactttg tnaagcagga ctttnctaag      60
ggtagtagtn ctatgancct gctgtgttaa ctcctttnct gcacatncgt ggtancccag     120
ggaagtttgt tttcttctac ctctttatat ggaatatgaa gcatttgcac taaatcatct     180
ctcttgagga aatttagtaa caaccagaac gttttgagaa tgacttgaac agtgtaactg     240
ggtttaataa gtgagtttat tcacttagac atattttctc aaaaataata ctgccttgac     300
agtattattc acagcctgtg ctggttgttg taatgata                             338

<210> SEQ ID NO 1008
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1008

-continued aactcccagg tttctatatg ccagc 25

<210> SEQ ID NO 1009
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1009
tcttctacct ctttatatgg aatat 25

<210> SEQ ID NO 1010
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1010
gcatttgcac taaatcatct ctctt 25

<210> SEQ ID NO 1011
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1011
aaatcatctc tcttgaggaa attta 25

<210> SEQ ID NO 1012
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1012
atctctcttg aggaaattta gtaac 25

<210> SEQ ID NO 1013
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1013
tagtaacaac cagaacgttt tgaga 25

<210> SEQ ID NO 1014
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1014
accagaacgt tttgagaatg acttg 25

<210> SEQ ID NO 1015
<211> LENGTH: 25
<212> TYPE: DNA
<213> ORGANISM: Artificial

```
<220> FEATURE:
<223> OTHER INFORMATION: synthetic oligonucleotide primer

<400> SEQUENCE: 1015
gaatgacttg aacagtgtaa ctggg                                          25

<210> SEQ ID NO 1016
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1016
gagtttattc acttagacat atttt                                          25

<210> SEQ ID NO 1017
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1017
gccttgacag tattattcac agcct                                          25

<210> SEQ ID NO 1018
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1018
gcctgtgctg gttgttgtaa tgata                                          25

<210> SEQ ID NO 1019
<211> LENGTH: 448
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n is a, c, g, or t

<400> SEQUENCE: 1019
gaaagcaatt gtatttgtgc aaagcntaaa caggaaaaca aagtggatga cttggcattt      60
gaagaatgaa aaagccaaac agcactgtca caaccatttc tgccttcagt ctccagtgcc     120 ttttcttc attataaaat ccatagaaat ggcaaggaaa gatataggaa agtttatcac       180
agatacagta gctattacag aaatttggaa ttcagcagat gtttaagtc aaatttcct       240 gtgtaacaga tgaatttgca aagttttgaa aacacagtcc acaaagtaat ttaaaatgtg    300
ataattaaat ttgttttaaa aagcaaatta acacctttta ttttctgtga agataaaaca    360
ataaaagaaa aatgttcata tatccaaacc tatgctggaa gtacacaaaa agacaatttg   420
tatacattac tggcaatagt cttgtttt                                       448

<210> SEQ ID NO 1020
<211> LENGTH: 25
<212> TYPE: DNA
<213> ORGANISM: Artificial
<220> FEATURE:
<223> OTHER INFORMATION: synthetic oligonucleotide primer
```

<400> SEQUENCE: 1020
gaaagcaatt gtatttgtgc aaagc                                              25

<210> SEQ ID NO 1021
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1021
aagtggatga cttggcattt gaaga                                              25

<210> SEQ ID NO 1022
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1022
acagcactgt cacaaccatt tctgc                                              25

<210> SEQ ID NO 1023
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1023
atcacagata cagtagctat tacag                                              25

<210> SEQ ID NO 1024
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1024
tttggaattc agcagatgtt ttaag                                              25

<210> SEQ ID NO 1025
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1025
ctgtgtaaca gatgaatttg caaag                                              25

<210> SEQ ID NO 1026
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1026
gttttgaaaa cacagtccac aaagt                                              25

<210> SEQ ID NO 1027
<211> LENGTH: 25

-continued

<212> TYPE: DNA
<213> ORGANISM: Artificial
<220> FEATURE:
<223> OTHER INFORMATION: synthetic oligonucleotide primer

<400> SEQUENCE: 1027
atgttcatat atccaaacct atgct                                              25

<210> SEQ ID NO 1028
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1028
aaacctatgc tggaagtaca caaaa                                              25

<210> SEQ ID NO 1029
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1029
gacaatttgt atacattact ggcaa                                              25

<210> SEQ ID NO 1030
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1030
acattactgg caatagtctt gtttt                                              25

<210> SEQ ID NO 1031
<211> LENGTH: 482
<212> TYPE: DNA
<213> ORGANISM: Homo sapiens

<400> SEQUENCE: 1031
ctcagaacca ggcggcaggg tcaggatcgg gagaggaacc agatctaagg atagtggggc        60
cctggtctcc gcagtagggg ttgaactata tccaatataa agcattatcc aaggggaccg       120
gattagcccc catgggtgac accaagatgg gagcggggt gggggtgat aagagacaca         180
ggagacagag tcaggtccca gaggcagcaa ggcctacccc caaattgcag tcaggttggg       240
aagtagaatc atggctaggc ccgcggcccc gggtctttct caggctcggt ccctggcacg       300
ccgcggatgt ccggcagcag gcggcagcca gccacgatgt ccagacgctc ggccagcgca       360
caaaggtccc cgcgcgccag gcgcacgctg tgggccgccg ccagccccgc cgcctgggct       420
gccgccagcc tactagccag ggcggccacg tcgcggcctg cacggcggta gacaccgctc       480
ac                                                                     482

<210> SEQ ID NO 1032
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1032
ctcagaacca ggcggcaggg tcagg                                          25

<210> SEQ ID NO 1033
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1033
ggcagggtca ggatcgggag aggaa                                          25

<210> SEQ ID NO 1034
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1034
taaggatagt ggggccctgg tctcc                                          25

<210> SEQ ID NO 1035
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1035
cctggtctcc gcagtagggg ttgaa                                          25

<210> SEQ ID NO 1036
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1036
gtaggggttg aactatatcc aatat                                          25

<210> SEQ ID NO 1037
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1037
taaagcatta tccaagggga ccgga                                          25

<210> SEQ ID NO 1038
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1038
gggtgacacc aagatgggag cgggg                                          25

<210> SEQ ID NO 1039
<211> LENGTH: 25

```
<212> TYPE: DNA
<213> ORGANISM: Artificial
<220> FEATURE:
<223> OTHER INFORMATION: synthetic oligonucleotide primer

<400> SEQUENCE: 1039
ggagacagag tcaggtccca gaggc                                                25

<210> SEQ ID NO 1040
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1040
cctaccccca aattgcagtc aggtt                                                25

<210> SEQ ID NO 1041
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1041
gaagtagaat catggctagg cccgc                                                25

<210> SEQ ID NO 1042
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1042
ctgcacggcg gtagacaccg ctcac                                                25

<210> SEQ ID NO 1043
<211> LENGTH: 223
<212> TYPE: DNA
<213> ORGANISM: Homo sapiens

<400> SEQUENCE: 1043
gtggtccgcg ctctaggaaa agatatgaat ggcctgggtg gccggcgtgc ggcaggcggg          60
acactcgggc tcgctcttgc cgcagatgcg gacggcgcag tccatgcaga agaggttgtg         120
gccgcagggg accagcgcag ccatcacctc gccctcggcg cacaccacgc actctcgcgc         180
cagggccggg gccgaggacg ccgaagggg cttgcggctg ttc                            223

<210> SEQ ID NO 1044
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1044
gtggtccgcg ctctaggaaa agata                                                25

<210> SEQ ID NO 1045
<211> LENGTH: 25
<212> TYPE: DNA
<213> ORGANISM: Artificial
<220> FEATURE:
```

<223> OTHER INFORMATION: synthetic oligonucleotide primer

<400> SEQUENCE: 1045
aaaagatatg aatggcctgg gtggc                                          25

<210> SEQ ID NO 1046
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1046
tatgaatggc ctgggtggcc ggcgt                                          25

<210> SEQ ID NO 1047
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1047
ctcgctcttg ccgcagatgc ggacg                                          25

<210> SEQ ID NO 1048
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1048
gctcttgccg cagatgcgga cggcg                                          25

<210> SEQ ID NO 1049
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1049
tgccgcagat gcggacggcg cagtc                                          25

<210> SEQ ID NO 1050
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1050
acggcgcagt ccatgcagaa gaggt                                          25

<210> SEQ ID NO 1051
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1051
gcagaagagg ttgtggccgc agggg                                          25

```
<210> SEQ ID NO 1052
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1052
gaggacgccg aagggggctt gcggc                                           25

<210> SEQ ID NO 1053
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1053
gacgccgaag ggggcttgcg gctgt                                           25

<210> SEQ ID NO 1054
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1054
cgccgaaggg ggcttgcggc tgttc                                           25

<210> SEQ ID NO 1055
<211> LENGTH: 159
<212> TYPE: DNA
<213> ORGANISM: Homo sapiens

<400> SEQUENCE: 1055
cggccgccta ctactactat acggctgcga gaagacgaca gaaggggcaa gaacgactgg     60
agaaggaaga acaagatagg ctggagagag aggaattgaa agaaaggca gaggaggaaa     120 ggcttcgcct agaagaggaa gcccgaaagc aggaagaag                           159

<210> SEQ ID NO 1056
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1056
cggccgccta ctactactat acggc                                           25

<210> SEQ ID NO 1057
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1057
cctactacta ctatacggct gcgag                                           25

<210> SEQ ID NO 1058
<211> LENGTH: 25
<212> TYPE: DNA
<213> ORGANISM: Artificial
<220> FEATURE:
```

```
<223> OTHER INFORMATION: synthetic oligonucleotide primer

<400> SEQUENCE: 1058
actactatac ggctgcgaga agacg                                              25

<210> SEQ ID NO 1059
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1059
atacggctgc gagaagacga cagaa                                              25

<210> SEQ ID NO 1060
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1060
gacagaaggg gcaagaacga ctgga                                              25

<210> SEQ ID NO 1061
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1061
ggggcaagaa cgactggaga aggaa                                              25

<210> SEQ ID NO 1062
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1062
ggaagaacaa gataggctgg agaga                                              25

<210> SEQ ID NO 1063
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1063
gcagaggagg aaaggcttcg cctag                                              25

<210> SEQ ID NO 1064
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1064
ggaggaaagg cttcgcctag aagag                                              25
```

```
<210> SEQ ID NO 1065
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1065
gcctagaaga ggaagcccga aagca                                              25

<210> SEQ ID NO 1066
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1066
gaggaagccc gaaagcagga agaag                                              25

<210> SEQ ID NO 1067
<211> LENGTH: 456
<212> TYPE: DNA
<213> ORGANISM: Homo sapiens

<400> SEQUENCE: 1067
agctctgaga caccctagga gggcccacac ttctagtaca acaaggctgt cttctcacag         60
cctgtggaaa ctcctgaaga acagcattaa gtgatactcc gaagagatga tgagaagcaa       120
ttggccctcc aagaccatgg tgcgggagtt tgttggaacc agctccagct gactcctctt       180 ccctcccaa gctcctagc tcatcccaaa aggagctcct cccacaagta ccttaatagt         240
cccactccat ttgattctca cagtcctgaa ggggcaggct cctgttgcca ttgtagagat        300
gaaaaaactg aggctcaaaa agaaaattgc cttcctcaac gtcatacagc ttgtcaatgg       360
cagggctggg attcaaaccc aggccaggta tggtggctca cacctttaat tctagcactt       420
tgggaggcca agatgggacg ccaggagttg cttgac                                 456

<210> SEQ ID NO 1068
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1068
agctctgaga caccctagga gggcc                                              25

<210> SEQ ID NO 1069
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1069
ggcccacact tctagtacaa caagg                                              25

<210> SEQ ID NO 1070
<211> LENGTH: 25
<212> TYPE: DNA
<213> ORGANISM: Artificial
<220> FEATURE:
<223> OTHER INFORMATION: synthetic oligonucleotide primer
```

<400> SEQUENCE: 1070
tagtacaaca aggctgtctt ctcac                                    25

<210> SEQ ID NO 1071
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1071
ctcacagcct gtggaaactc ctgaa                                    25

<210> SEQ ID NO 1072
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1072
gatgagaagc aattggccct ccaag                                    25

<210> SEQ ID NO 1073
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1073
gccctccaag accatggtgc gggag                                    25

<210> SEQ ID NO 1074
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1074
ctcctcccac aagtacctta atagt                                    25

<210> SEQ ID NO 1075
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1075
taatagtccc actccatttg attct                                    25

<210> SEQ ID NO 1076
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1076
gattctcaca gtcctgaagg ggcag                                    25

<210> SEQ ID NO 1077
<211> LENGTH: 25

```
<212> TYPE: DNA
<213> ORGANISM: Artificial
<220> FEATURE:
<223> OTHER INFORMATION: synthetic oligonucleotide primer

<400> SEQUENCE: 1077
cttcctcaac gtcatacagc ttgtc                                          25

<210> SEQ ID NO 1078
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1078
gatgggacgc caggagttgc ttgac                                          25

<210> SEQ ID NO 1079
<211> LENGTH: 405
<212> TYPE: DNA
<213> ORGANISM: Homo sapiens

<400> SEQUENCE: 1079
attattttgg tgggcttgat tttatagttt ctcttaaaaa ttgtttggtt gccatccaga    60
gggctctttt atgaagaatc tatataaact actaaaacat ttcttaggac cttttggtg   120 aatttgatca taaaattaaa aagcgtgtat gtgttttata aaggcatacc tctgttaaga   180
aggctggttt tatgtttgcc ttttcttctc tactttgatc accaccctag ctgttccttt   240
ctccagacca ccttactttt caaacttgat tcttgctatc acagctctct gtaacatcag   300
ttaaaatcag ctgcctcaac tctttgagga tgtttgtgca taggacggca ttgtgaaaca   360
tagggaaatg gcagtcttac taacaaaaca ggacctatct ctggc                   405

<210> SEQ ID NO 1080
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1080
attattttgg tgggcttgat tttat                                          25

<210> SEQ ID NO 1081
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1081
ttgtttggtt gccatccaga gggct                                          25

<210> SEQ ID NO 1082
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1082
ggcatacctc tgttaagaag gctgg                                          25
```

<210> SEQ ID NO 1083
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1083
cagaccacct tactttttcaa acttg                                    25

<210> SEQ ID NO 1084
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1084
cttgattctt gctatcacag ctctc                                     25

<210> SEQ ID NO 1085
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1085
cacagctctc tgtaacatca gttaa                                     25

<210> SEQ ID NO 1086
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1086
atcagttaaa atcagctgcc tcaac                                     25

<210> SEQ ID NO 1087
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1087
caactctttg aggatgtttg tgcat                                     25

<210> SEQ ID NO 1088
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1088
gtttgtgcat aggacggcat tgtga                                     25

<210> SEQ ID NO 1089
<211> LENGTH: 25
<212> TYPE: DNA
<213> ORGANISM: Artificial
<220> FEATURE:
<223> OTHER INFORMATION: synthetic oligonucleotide primer

```
<400> SEQUENCE: 1089
catagggaaa tggcagtctt actaa                                            25

<210> SEQ ID NO 1090
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1090
taacaaaaca ggacctatct ctggc                                            25

<210> SEQ ID NO 1091
<211> LENGTH: 269
<212> TYPE: DNA
<213> ORGANISM: Homo sapiens
<220> FEATURE:
<221> NAME/KEY: misc_feature
<222> LOCATION: (93)..(93)
<223> OTHER INFORMATION: n is a, c, g, or t

<400> SEQUENCE: 1091
tttcctgtct tgaataatcc caacaaaacc atttgaatcc tcaagtaaaa atatatttat      60
cacttaaatc agaaacaatg aattcaaaat ggnaaagtag ttaaagtcta aaatgttttt    120
tcccataaac ttagaaagaa ttatcttcta cttccataaa tatattatgt tttataacga    180
tgtattgtgt taccacatac aacaaacctt tatgaactgc tcatataact gtttaattgt    240
tttcaatctc tggctctgaa caattctag                                     269

<210> SEQ ID NO 1092
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1092
tttcctgtct tgaataatcc caaca                                            25

<210> SEQ ID NO 1093
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1093
gaataatccc aacaaaacca tttga                                            25

<210> SEQ ID NO 1094
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1094
caaaaccatt tgaatcctca agtaa                                            25

<210> SEQ ID NO 1095
<211> LENGTH: 25
<212> TYPE: DNA
```

-continued

```
<213> ORGANISM: Artificial
<220> FEATURE:
<223> OTHER INFORMATION: synthetic oligonucleotide primer

<400> SEQUENCE: 1095
gaaagaatta tcttctactt ccata                                    25

<210> SEQ ID NO 1096
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1096
attatcttct acttccataa atata                                    25

<210> SEQ ID NO 1097
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1097
ataacgatgt attgtgttac cacat                                    25

<210> SEQ ID NO 1098
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1098
gttaccacat acaacaaacc tttat                                    25

<210> SEQ ID NO 1099
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1099
caacaaacct ttatgaactg ctcat                                    25

<210> SEQ ID NO 1100
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1100
gaactgctca taaactgtt taatt                                     25

<210> SEQ ID NO 1101
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1101
ttaattgttt tcaatctctg gctct                                    25
```

<210> SEQ ID NO 1102
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1102
aatctctggc tctgaacaat tctag    25

<210> SEQ ID NO 1103
<211> LENGTH: 395
<212> TYPE: DNA
<213> ORGANISM: Homo sapiens

<400> SEQUENCE: 1103
ttcattcaaa catttcttat tatcatttat tgcacatagc atggattaat caaataagtt    60
taaaataaaa taatagacta gagaaaggtg ctttatttta aaaacagaaa caaaagaag    120 gtacgtggat tatctgatgc tacatcacac tctgggagag acttcccttc tttcagagag    180
cctctcattt cttaatgtgg atcattttgc tctttccccc tgataatgct cacttactct    240
ctttcataat ctcccctct ttcacttgtt cttttctttc caatcatcca atgatccatc    300
aaggtacttt ggtgttcagt gctttctcat atggttcaac tcagatcatg tagtctttct    360
cacccaacca attcaactac tgtttcctga gaccc    395

<210> SEQ ID NO 1104
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1104
ttcattcaaa catttcttat tatca    25

<210> SEQ ID NO 1105
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1105
ggtacgtgga ttatctgatg ctaca    25

<210> SEQ ID NO 1106
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1106
atgctacatc acactctggg agaga    25

<210> SEQ ID NO 1107
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1107
ctttcagaga gcctctcatt tctta    25

<210> SEQ ID NO 1108
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1108
cttttctttc caatcatcca atgat    25

<210> SEQ ID NO 1109
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1109
caatgatcca tcaaggtact ttggt    25

<210> SEQ ID NO 1110
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1110
gtactttggt gttcagtgct ttctc    25

<210> SEQ ID NO 1111
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1111
gtgctttctc atatggttca actca    25

<210> SEQ ID NO 1112
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1112
tggttcaact cagatcatgt agtct    25

<210> SEQ ID NO 1113
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1113
ctcacccaac caattcaact actgt    25

<210> SEQ ID NO 1114
<211> LENGTH: 25

```
<212> TYPE: DNA
<213> ORGANISM: Artificial
<220> FEATURE:
<223> OTHER INFORMATION: synthetic oligonucleotide primer

<400> SEQUENCE: 1114
attcaactac tgtttcctga gaccc                                              25

<210> SEQ ID NO 1115
<211> LENGTH: 363
<212> TYPE: DNA
<213> ORGANISM: Homo sapiens
<220> FEATURE:
<221> NAME/KEY: misc_feature
<222> LOCATION: (57)..(57)
<223> OTHER INFORMATION: n is a, c, g, or t
<220> FEATURE:
<221> NAME/KEY: misc_feature
<222> LOCATION: (60)..(60)
<223> OTHER INFORMATION: n is a, c, g, or t
<220> FEATURE:
<221> NAME/KEY: misc_feature
<222> LOCATION: (85)..(86)
<223> OTHER INFORMATION: n is a, c, g, or t
<220> FEATURE:
<221> NAME/KEY: misc_feature
<222> LOCATION: (95)..(95)
<223> OTHER INFORMATION: n is a, c, g, or t
<220> FEATURE:
<221> NAME/KEY: misc_feature
<222> LOCATION: (168)..(168)
<223> OTHER INFORMATION: n is a, c, g, or t
<220> FEATURE:
<221> NAME/KEY: misc_feature
<222> LOCATION: (199)..(199)
<223> OTHER INFORMATION: n is a, c, g, or t
<220> FEATURE:
<221> NAME/KEY: misc_feature
<222> LOCATION: (201)..(202)
<223> OTHER INFORMATION: n is a, c, g, or t
<220> FEATURE:
<221> NAME/KEY: misc_feature
<222> LOCATION: (206)..(206)
<223> OTHER INFORMATION: n is a, c, g, or t

<400> SEQUENCE: 1115
ggggcacgct tttcacaacg tggagatgca gggtcatggg ctgcctgcta ccacgangcn        60 gaagggatg gtgctgggca ccagnncctg ccccngggct gggtttctcc tgggcctggg       120
ccgaggggtg gaggcctgtg ggtgacgtgt tcaagacggc tcagcaancc ccacctgaca       180
gtgtccaggt ggggcctcnt nnccncccc caggctcccc agggagcaca gcctccactc        240
ctacacactg gctactctgc cggaggggga ggccgtgctg gagtgatgcc tggcgcgtgt       300
tgtgtgatgg gagaattggg tatttacagt ttaataacga gatctcgatg ccgtcgatcg       360
gcc                                                                    363

<210> SEQ ID NO 1116
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1116
ggggcacgct tttcacaacg tggag                                              25

<210> SEQ ID NO 1117
<211> LENGTH: 25
<212> TYPE: DNA
```

```
<213> ORGANISM: Artificial
<220> FEATURE:
<223> OTHER INFORMATION: synthetic oligonucleotide primer

<400> SEQUENCE: 1117
gcttttcaca acgtggagat gcagg                                              25

<210> SEQ ID NO 1118
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1118
gagatgcagg gtcatgggct gcctg                                              25

<210> SEQ ID NO 1119
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1119
tgcagggtca tgggctgcct gctac                                              25

<210> SEQ ID NO 1120
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1120
ggcctgtggg tgacgtgttc aagac                                              25

<210> SEQ ID NO 1121
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1121
gtgacgtgtt caagacggct cagca                                              25

<210> SEQ ID NO 1122
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1122
aggccgtgct ggagtgatgc ctggc                                              25

<210> SEQ ID NO 1123
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1123
ctggcgcgtg ttgtgtgatg ggaga                                              25
```

```
<210> SEQ ID NO 1124
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1124
gagaattggg tatttacagt ttaat                                          25

<210> SEQ ID NO 1125
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1125
taacgagatc tcgatgccgt cgatc                                          25

<210> SEQ ID NO 1126
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1126
gagatctcga tgccgtcgat cggcc                                          25

<210> SEQ ID NO 1127
<211> LENGTH: 178
<212> TYPE: DNA
<213> ORGANISM: Homo sapiens

<400> SEQUENCE: 1127
ggcactggga acaggcatgc tcccagctag gaagaagccg gggacataaa gctagcagct    60
gtggtgagga taccagggtg agtgctgagg gtgagggacc tgggcttcct gtttttaatg   120
attaagcctc agcctcaaaa agcttttgac agcctggaca acatggccag accctatc    178

<210> SEQ ID NO 1128
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1128
ggcactggga acaggcatgc tccca                                          25

<210> SEQ ID NO 1129
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1129
gcatgctccc agctaggaag aagcc                                          25

<210> SEQ ID NO 1130
<211> LENGTH: 25
<212> TYPE: DNA
```

```
<213> ORGANISM: Artificial
<220> FEATURE:
<223> OTHER INFORMATION: synthetic oligonucleotide primer

<400> SEQUENCE: 1130
gccggggaca taaagctagc agctg                                              25

<210> SEQ ID NO 1131
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1131
agctagcagc tgtggtgagg atacc                                              25

<210> SEQ ID NO 1132
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1132
gaggatacca gggtgagtgc tgagg                                              25

<210> SEQ ID NO 1133
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1133
gtgctgaggg tgagggacct gggct                                              25

<210> SEQ ID NO 1134
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1134
ctgggcttcc tgtttttaat gatta                                              25

<210> SEQ ID NO 1135
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1135
ttaatgatta agcctcagcc tcaaa                                              25

<210> SEQ ID NO 1136
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1136
aagcctcagc ctcaaaaagc ttttg                                              25
```

<210> SEQ ID NO 1137
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1137
aaaaagcttt tgacagcctg gacaa                                         25

<210> SEQ ID NO 1138
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1138
ctggacaaca tggccagacc ctatc                                         25

<210> SEQ ID NO 1139
<211> LENGTH: 422
<212> TYPE: DNA
<213> ORGANISM: Homo sapiens
<220> FEATURE:
<221> NAME/KEY: misc_feature
<222> LOCATION: (207)..(208)
<223> OTHER INFORMATION: n is a, c, g, or t
<220> FEATURE:
<221> NAME/KEY: misc_feature
<222> LOCATION: (332)..(332)
<223> OTHER INFORMATION: n is a, c, g, or t
<220> FEATURE:
<221> NAME/KEY: misc_feature
<222> LOCATION: (344)..(344)
<223> OTHER INFORMATION: n is a, c, g, or t
<220> FEATURE:
<221> NAME/KEY: misc_feature
<222> LOCATION: (362)..(362)
<223> OTHER INFORMATION: n is a, c, g, or t

<400> SEQUENCE: 1139
ggccccgtat tcattttta tactggaaaa cattttttt gtaattttc tttgcaaaga      60 aatgagcata aaaatgaata ctccaaagaa aaggaattat tatggcaaat taaaagggac  120
acggtactat gatttaatta ctgtcttgtc tttttaaaat gtcatctctt gttttaccct  180
ttttttaaat aaaagcttta aaaacanntc tttgggtatt attctggagg tatgtttctt  240
ttatataaga tttcaagttt aaacatttac aataagtaat aatatttaaa ttcttataac  300
aagtaatgaa atatttggtt tagtaattag cntagtctat tttnaaaaat cattaaaatt  360 tncttttgttt ttaagaatgc catactacaa atgatgttat ttggttttaa tggtgttttg  420
tg                                                                 422

<210> SEQ ID NO 1140
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1140
ggccccgtat tcattttta tactg                                          25

<210> SEQ ID NO 1141

<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1141
aagggacacg gtactatgat ttaat                                              25

<210> SEQ ID NO 1142
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1142
tatgatttaa ttactgtctt gtctt                                              25

<210> SEQ ID NO 1143
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1143
tactgtcttg tctttttaaa atgtc                                              25

<210> SEQ ID NO 1144
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1144
aaaatgtcat ctcttgtttt accct                                              25

<210> SEQ ID NO 1145
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1145
tctttgggta ttattctgga ggtat                                              25

<210> SEQ ID NO 1146
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1146
gtattattct ggaggtatgt ttctt                                              25

<210> SEQ ID NO 1147
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1147

```
tctggaggta tgtttctttt atata                                           25

<210> SEQ ID NO 1148
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1148
tttgttttta agaatgccat actac                                           25

<210> SEQ ID NO 1149
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1149
gaatgccata ctacaaatga tgtta                                           25

<210> SEQ ID NO 1150
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1150
tatttggttt taatggtgtt ttgtg                                           25

<210> SEQ ID NO 1151
<211> LENGTH: 420
<212> TYPE: DNA
<213> ORGANISM: Homo sapiens

<400> SEQUENCE: 1151
ctcttgatct ctcaaccttg tgatctgccc gcctcgacct cccaaagtgc tgggattaca      60
ggcatgagcc actgcgcctg gcctagctac agattttttt acaatgctaa gtattttctg     120
aacagtttga ctgttgccaa ataatttatt caatttttt cccctctatg actcattact      180
taccctgagc aaatcatcta tacgtccctc cttcttttcc aggtcctggg ttttattact     240
ttctaatgct gctaatttca gcattgtgag atcagtctaa atgaaaaaaa gttatttat     300 tatctccatt atatatgttg tttcaagcaa acataaaact agattttact ccaaattcaa     360
aaggtaaaga aaatatatt tgtgtgtata tgtaaagtga atctcaaaaa gtttgtcgac     420

<210> SEQ ID NO 1152
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1152
ctcttgatct ctcaaccttg tgatc                                           25

<210> SEQ ID NO 1153
<211> LENGTH: 25
<212> TYPE: DNA
<213> ORGANISM: Artificial
<220> FEATURE:
```

```
<223> OTHER INFORMATION: synthetic oligonucleotide primer

<400> SEQUENCE: 1153
cgcctggcct agctacagat ttttt                                    25

<210> SEQ ID NO 1154
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1154
tggcctagct acagattttt ttaca                                    25

<210> SEQ ID NO 1155
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1155
tacagatttt tttacaatgc taagt                                    25

<210> SEQ ID NO 1156
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1156
ttctgaacag tttgactgtt gccaa                                    25

<210> SEQ ID NO 1157
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1157
ctctatgact cattacttac cctga                                    25

<210> SEQ ID NO 1158
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1158
atgactcatt acttaccctg agcaa                                    25

<210> SEQ ID NO 1159
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1159
tcattactta ccctgagcaa atcat                                    25
```

```
<210> SEQ ID NO 1160
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1160
aagttatttt attatctcca ttata                                          25

<210> SEQ ID NO 1161
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1161
ctagatttta ctccaaattc aaaag                                          25

<210> SEQ ID NO 1162
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1162
agtgaatctc aaaagtttg tcgac                                           25

<210> SEQ ID NO 1163
<211> LENGTH: 413
<212> TYPE: DNA
<213> ORGANISM: Homo sapiens

<400> SEQUENCE: 1163
gtacacggtc acagttttca tcatactaat ctctcttcaa gaaatcttca aaatttgatt     60
tacttctgaa aatacgtttc acctttctc tcctgttgct attatctatt accatgtcag    120
aacttagtct ccattaaatg ccaagcccac cgttaggcac catgggtaaa aaatgaatag    180
gaaaccatct gtttcatacg gtcttcagtc attttgcgct tttcacaatg tactggtagt    240
agatcacaat ttttttcct ttgtagttac aatagctaga aagtaaatgt tggaatttta    300
aaatatgcag gtatactaga ttttgggaat gtggggatt ggaagcatct agacattgtt    360
tgatttgtga cattcaaaag caggtacgtc ataactcgtt tgcttctatt ttc           413

<210> SEQ ID NO 1164
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1164
gtacacggtc acagttttca tcata                                          25

<210> SEQ ID NO 1165
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1165
```

-continued

| | |
|---|---|
| tttcatcata ctaatctctc ttcaa | 25 |

<210> SEQ ID NO 1166
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1166

| | |
|---|---|
| accatgtcag aacttagtct ccatt | 25 |

<210> SEQ ID NO 1167
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1167

| | |
|---|---|
| gtctccatta aatgccaagc ccacc | 25 |

<210> SEQ ID NO 1168
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1168

| | |
|---|---|
| gcccaccgtt aggcaccatg ggtaa | 25 |

<210> SEQ ID NO 1169
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1169

| | |
|---|---|
| aaaccatctg tttcatacgg tcttc | 25 |

<210> SEQ ID NO 1170
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1170

| | |
|---|---|
| tacggtcttc agtcattttg cgctt | 25 |

<210> SEQ ID NO 1171
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1171

| | |
|---|---|
| tttgcgcttt tcacaatgta ctggt | 25 |

<210> SEQ ID NO 1172
<211> LENGTH: 25
<212> TYPE: DNA
<213> ORGANISM: Artificial

```
-continued

<220> FEATURE:
<223> OTHER INFORMATION: synthetic oligonucleotide primer

<400> SEQUENCE: 1172
ggaagcatct agacattgtt tgatt                                    25

<210> SEQ ID NO 1173
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1173
gcaggtacgt cataactcgt ttgct                                    25

<210> SEQ ID NO 1174
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1174
tcataactcg tttgcttcta ttttc                                    25
```

PREDICTION OF BARE METAL STENT RESTENOSIS

FIELD OF THE INVENTION

The invention generally relates to predicting the probablity of restenosis in patients receiving bare metal stents in native coronary arteries. In the preferred embodiment, the invention provides methods for predicting whether or not a patient is likely to experience restenosis based on the analysis of gene expression profiles of m-RNA-containing components of whole blood, and, based on this prediction, determining whether the patient should receive a bare metal stent or a stent containing anti-restenosis agents.

BACKGROUND OF THE INVENTION

Coronary artery disease is the most prevalent medical problem in the industrialized world. It accounts for over 40% of all deaths in the United States and Western Europe (1). A primary therapy for coronary artery disease is coronary angioplasty with stent implantation (2).

Until recently the success of coronary stenting was limited by the process of restenosis, which occurred in 20-40% of cases (3). There have been reports that risk of developing in-stent restenosis appears to depend upon both clinical and procedural factors such as diabetes, length of lesion and location of lesion (4, 5, 6). The clinical and lesion related risk factors for restenosis, however, are very poorly predictive of restenosis. The most recent approach to prevention of restenosis involves local drug delivery to the vessel wall using drug eluting stents (7, 8). Remarkable success has been achieved in reducing restenosis with the use of stents coated with either Sirolimus or Taxol (9).

Coronary angioplasty with placement of one or more drug eluting stents has become the most common interventional treatment of significant flow limiting coronary artery disease. However, only 2-3 of every 10 patients can be expected to derive an additional benefit beyond that conferred by bare metal stents (10). Bare metal stents are utilized much less frequently compared to drug eluting stents because restenosis is a known problem associated with using bare metal stents. Using a drug-coated stent instead of a bare metal stent is associated with excess costs. Also, although drug-eluting stents would appear to be a significant step forward in the treatment of coronary artery disease, there is concern regarding the long term risk of sub-acute thrombosis associated with drug eluting stents (11). This may occur at an annual rate of 0.2-0.6% and may result in significant excess morbidity and mortality (11). Of note, seventy to eighty percent of patients derive no clinical benefit from drug-eluting stents (10). Therefore, it would be of value to have a test that would be predictive of low risk of restenosis with bare metal stents thereby reducing the indiscriminate use of drug eluting stents with their associated long term risks.

Despite the length of time that restenosis has been an issue and has been the subject of research no current technology exists for reliably determining whether an individual patient is likely to experience restenosis if given a bare metal stent rather than a drug coated stent, i.e., whether the drug coated stent is truly required to prevent restenosis. In addition to the excess costs associated with drug eluting stents, other associated clinical problems may be introduced by indiscriminately using drug coated stents for some patients who might have similar outcomes with a bare metal stent. These include an excess risk of bleeding associated with the need for long term anti-platelet agents in those individuals receiving drug elution stents and the risk of sub-acute stent thrombosis, a particularly severe adverse event associated with 40% mortality rate, in those individuals who may be non-compliant with the prescribed regimen or required to stop anti-platelet agents for other non-related surgical procedures. A method of identifying individual patients who may be equally well treated with a bare metal stent compared to a drug coated stent, from the perspective of whether restenosis is a risk for the patient, would be highly desirable. A gene expression test that accurately predicts bare metal stent restenosis would reduce the need for drug eluting stents and thus reduce long term excess morbidity, costs and mortality associated with drug eluting stents. In light of the vast numbers of patients receiving drug coated stents on a world wide basis, the introduction of simple, rapid and highly predictive gene expression test for prediction of the need for a drug coated stent would have significant beneficial public health consequences.

It has been suggested that restenosis of bare metal stents is due to individual genes. Walter et al (12) reported on 650 consecutive patients receiving non-drug eluting coronary stents and demonstrated a significant association of platelet glycoprotein IIIa gene polymorphism, risk of restenosis and statin therapy. Carriers of the P1A2 allele (A1/A2 heterozygotes) demonstrated a significantly increased restenosis rate, and this difference was largely eliminated by the addition of statin therapy. Walter et al concluded that, "statins interfere with the functional consequence of a genetically determined platelet mediated risk factor". Bauters et al. (13) presented data which supported the involvement of an I/D polymorphism of angiotensin-converting enzyme as a risk factor for coronary restenosis. Their results, however, were not confirmed by Momotte et al (14). de Maat et al. (15) suggested that a common promoter variant of the human stromolysin-1 gene confers a genotype specific response to medication in determining clinical event free survival and the risk for clinical restenosis after angioplasty and, therefore, may serve as a predictor of clinical restenosis. Specifically, patients with the 5A6A or 6A6A variant of the promoter region of this gene had significantly fewer events when treated with the lipid lowering drug pravastatin compared to placebo treated patients. Those with the 5A5A variant did not experience event reduction regardless of treatment assignment. Kastrati et al. (16) demonstrated that the presence of allele 2 of the interleukin receptor antagonist gene is associated with a lower risk of both angiographic and clinical restenosis. A clear gene dose effect was noted as patients homozygous for allele 2 had a lower incidence of in-stent restenosis than heterozygotes. Zohlnhofer et al. (17) demonstrated up-regulation of FK506-binding protein-12 (FKBP12) in neointimal specimens obtained by atherectomy post angioplasty. This is of interest in that FKBP12 is a target (receptor) for Sirolimus, an agent recently found to significantly reduce restenosis when applied to coronary stents. None of the above-mentioned studies of single-genes have been replicated or confirmed.

The expression of an individual gene may not be reliably associated with an outcome. It has been observed that, for the same disease, with similar inclusion and exclusion criteria, and employing the same gene array platform, multiple studies provide dissimilar sets of differentially expressed genes. The reasons for the unreliability of the association between an individual gene and an outcome include: 1) intra-patient and inter-patient variability; 2) small patient sample sizes; 3) low predictive power of most genes; 4) gene microarray platform variance due to their extremely high sensitivity to noise and 5) to bias in sample collection, handling, and pre-processing; 6) variation in processing reagent batch, decay in reagents over time 7) to differences in reading chip wells and 8) in multivariate analysis, the correlation of individual genes.

The prior art has thus far failed to provide a reliable method for assessing the risk of restenosis in individual patients slated for stent placement.

SUMMARY OF THE INVENTION

The invention provides a method of predicting the probability of occurrence of restenosis following placement of a bare metal stent in a native coronary artery of a patient, and methods to predict whether any given patient should receive a bare metal stent or a stent that contains anti-restenosis agents. The invention is based on a heretofore unknown association between overall increased gene activation/up-regulation in the mRNA-containing compartment of whole blood and the likelihood of restenosis. According to the invention, gene expression profiles of the RNA containing compartment of whole blood are used to detect gene activation, and this information is correlated with a probability of the occurrence of restenosis. The ability to predict which patients are at risk for or predisposed to restenosis and which patients are not permits the selective choice of stent type, i.e. bare metal stent vs drug eluting stent: patients with a low risk (less than or equal to a probability output of 50% as determined herein) can receive bare metal stents, thereby decreasing costs and the risk of major adverse clinical events attributable to use of drug eluting stents and the necessary use of long term anti-platelet agents, whereas patients with a high risk (probability output greater than 50% as determined herein) can receive stents that include anti-restenosis agents.

DETAILED DESCRIPTION OF THE

Preferred Embodiments of the Invention

Figure 1:
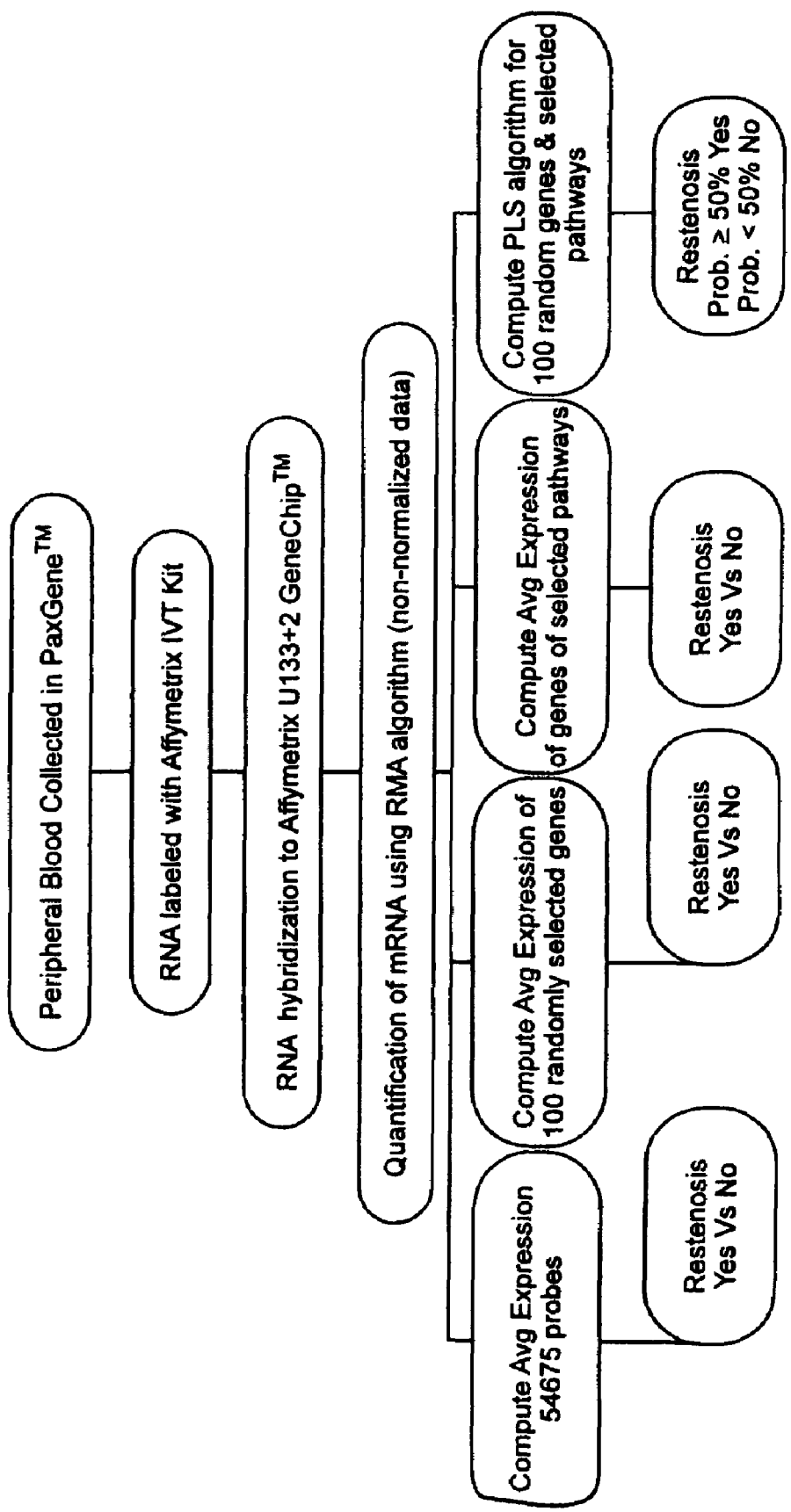
FIG. 1. Schematic representation of the method of the invention.

The present invention is based on the following discoveries:

1) Non-restenosis following native coronary artery stenting with a bare metal stent is a highly predictable event.

2) Expression profiling using MRNA derived from the mRNA containing component of circulating whole blood may be used prospectively to identify individuals who, with a high degree of certainty, will not experience restenosis within 6 months following native coronary artery stenting with a bare metal stent.

3) Increased transcription or decreased inactivation of the components of molecular pathways responsible for multiple cellular functions, including but not limited to T cell function, wound healing, cellular proliferation and migration, prospectively identify patients at high risk for restenosis following bare metal stent implantation who may benefit from the use of drug eluting stents to reduce their probability of restenosis.

4) Subjects who do not exhibit activation of molecular pathways described herein have a high likelihood of non-restenosis and would not be expected to derive benefit from drug eluting stents.

5) Activation of specific molecular pathways as described herein appear to be singular instances of a more generalized phenomena of activation of a plurality of the entire human genome found in the mRNA containing compartment of circulating whole blood, which itself is predictive of restenosis following native coronary artery stenting with bare metal stents.

DEFINITIONS

All scientific and technical terms used herein are understood to have the same meaning as commonly used in the art to which they pertain unless specified otherwise.

The present invention relates to the occurrence of coronary artery restenosis following coronary artery angioplasty with a device referred to as a bare metal stent. "Restenosis" herein means luminal re-narrowing within the confines of the bare metal stent or in the area of the immediately adjacent coronary artery tissue following a percutaneous stenting procedure. Restenosis is defined: i) quantitatively as a narrowing of at least a 50% vessel diameter reduction in the lumen of the stented vessel segment or in the immediate adjacent native vessel relative to a normal appearing non-stented portion of the same human native coronary artery which is located proximally to the stented segment. Restenosis is further defined as a process which fulfills the criteria of i) and; ii) is documented to have occurred within 6 months following placement of a coronary artery bare metal stent.

"Predicting" or "prediction" refers to the likelihood of a prespecified outcome i.e., a probabilistic determination. In this context, a likelihood outcome does not necessarily mean that the prediction will be correct in each instance of each individual for whom a prediction is made.

The phrase "gene expression system" or "gene expression platform" refers to any system, device or means to detect gene expression and is inclusive of diagnostic agents, oligonucleotide sets and/or probe sets used to carry out detection of candidate gene set of interest.

Methods for Determination of Gene Expression Levels

The increased gene activity on which the present invention is based was detected by mRNA expression profiling, i.e. by the elucidation of which genes in a sample were actively producing mRNA. Those skilled in the art will recognize that there are several methods by which gene expression can be detected or measured. Typically, expression of a gene is accompanied by an increase in mRNA transcribed from the gene. If the gene encodes a protein, gene activation is usually also accompanied by increased expression of the protein or peptide translation product from the mRNA. Those of skill in the art will recognize that either of these two entities (mRNA or protein) may be detected as indicators of gene expression. In addition, those skilled in the art will also recognize that nucleic acid sequences in particular are generally interconvertible, e.g. mRNA is readily converted to cDNA which may be converted to cRNA, etc., and any of these molecules may be detected as an indicator of gene expression. Thus, for the purposes of the present invention, gene expression may be assessed by detecting any suitable molecule (i.e. a "target" molecule), so long as the presence of the molecule in a sample is correlated with expression of a gene in a gene set of interest. Further, both the presence and the quantity of a target molecule must be detected/measured. In one embodiment of the invention, the gene expression profile is an mRNA expression profile. In another embodiment of this invention, DNA profiling may be used. In yet another embodiment of this invention, expression at the level of protein products of gene expression may be used.

In the context of the invention, a gene expression profile for a plurality of genes in a gene set of interest is obtained. A "plurality of genes" is at least two and frequently more than two genes. For example, representative gene sets will typically contain a plurality of genes in a range of from two to several hundred, or from two to several thousand, and may include all known human genes. In a preferred embodiment of the invention, the gene set that is analyzed contains one or more of the groups of genes presented in Tables 1-7 of the Examples section below. In another embodiment, the gene set that is analyzed comprises all known human genes the results of which are shown in Table 12a. In another embodiment of this invention, the gene set that is used in the method of the invention may contain any number of genes, so long as the results obtained from an analysis of this gene set is predictive of a probability of restenosis as described herein.

The choice of a particular set of genes for analysis may be based on any of several criteria, including but not limited to commonality of function. In this case, the genes in a gene set of interest may, for example, encode proteins that participate in one or more particular biochemical pathways, or that are expressed in a particular location (e.g. within a certain type of cell or tissue), or that are in some other manner related to one another. Alternatively, genes in a gene set of interest may be chosen simply due to convenience and/or feasibility (e.g. the ready availability of devices for detecting expression of a particular set of genes, or the genes being highly expressed and readily and unambiguously detectable); or selected at random. In the practice of the present invention, any suitable set, group, or category of genes may be analyzed, so long as the results obtained predict either restenosis or non-restenosis to a high degree of reliability, i.e., low false positive rate of predicting restenosis/non-restenosis and possess a high degree of reproducibility. In the context of the invention the phrases "predictive gene set", "candidate gene set" or "molecular signature" may also be used to describe the set of selected genes that are targeted for detection and analysis.

In a preferred embodiment of the invention, the level of gene expression of the genes in a gene set of interest is quantified by determining the mRNA expression profile of the mRNA containing compartment of whole blood, i.e. the intracellular mRNA from whole blood. Such a determination may include both the identification of which genes in the set are expressed and/or the quantification of the mRNA produced from each gene. Those of skill in the art are well-acquainted with the various methods available for establishing a gene expression profile, which include but are not limited to: 1) isolation of mRNA from a sample and separation via gel electrophoresis for subsequent northern hybridization and determination of gene derived mRNA; 2) slot-blots or dot-blots in which mRNA is labeled and hybridized to oligonucleotides derived from a gene set of interest for subsequent quantification of the hybridized product according to standard techniques, and; 3) methods involving: polymerase chain reaction (PCR) and/or reverse transcriptase-PCR (RT-PCR), Fluorescence Resonance Energy Transfer detection, or hybridization to an oligonucleotide array. Additional methods include but are not limited to hybridization to a cDNA array, Taq Man analysis, hybridization to a liquid micro-array, hybridization to a micro-electric array, cDNA sequencing, clone hybridization, cDNA fragment fingerprinting, Serial Analysis of Gene Expression (SAGE) methodology, subtractive hybridization, differential display or screening, and molecular beacon monitoring.

In another preferred embodiment of the invention, DNA microarrays are used to carry out the gene expression profiling. A DNA microarray (also commonly known as gene or genome chip, DNA chip, or gene array) is a collection of microscopic DNA "spots" representing single genes, arrayed on a solid surface. The DNA in a spot of the array usually consists of oligomer probes that are homologous to a target gene. The oligomer probes are typically about 25 to 60 nucleotides in length and are capable of hybridizing with nucleic acids (such as mRNA, cDNA or cRNA) whose sequences are based on (i.e. complementary to) the target gene. Many DNA microarrays of varying styles and designs are known to those of skill in the art, and any suitable DNA microarray may be used in the practice of the present invention. For example, in some microarrays, a single gene may be presented by multiple probes of differing sequences; homologous probes may be paired with non-homologous, non-hybridizing probes to provide negative hybridization controls; etc. As used herein, the phrase "probe set" refers to the probes present in a microarray that represent (i.e. are designed to detect or confirm the presence of) a gene set of interest. Any given gene in a gene set of interest is usually represented by at least one and frequently more than one probe. Thus, the number of probes in a probe set is usually greater than the number of genes in the gene set of interest that the probe set represents.

In one embodiment of the invention, a gene chip such as the Affymetrix U133+2 Genechip® gene chip, which contains 54,675 probe sets and is described as representing in excess of 33,000 genes plus other transcripts, may be used. However, those of skill in the art will recognize that many other alternatives exist or can be developed and used in the same or a similar manner in the practice of the present invention. Examples of alternatives include but are not limited to, for example, bead arrays which are used to simultaneously quantify expression of multiple sequences (e.g. LabMap 100, Luminex, Corp, Austin, Tex.). Electric arrays may be used to quantify the expression of multiple sequences (e.g., e-Sensor, Motorola, Inc. Chicago, Ill.) or various other nanochip technologies may be used (e.g., Nanogen Inc, San Diego, Calif.). Those of skill in the art will recognize that the selection of a suitable microarray may depend in part on the particular candidate (predictive) gene set that is being examined, although all possible gene sets represented on a microarray need not be analyzed or taken into account, even if such data is available. For example, when the Affymetrix U133+2 Genechip® is utilized, the gene expression profile of all genes that are represented on the microarray may be analyzed. Alternatively, data representing only selected subsets of genes of interest (e.g. those belonging to a candidate or predictive gene set as described herein) may be selected for analysis.

In a preferred embodiment of the invention, the sample that is obtained from a patient is "whole blood". However, those of skill in the art will recognize that the practice of the present invention need not be limited to the analysis of whole blood. For example, individual cellular (e.g., lymphocyte, reticulocytes or megakaryocyte) or non-cellular components (e.g., platelets) may be examined with regards to expression profiling. The term leukocyte refers to any nucleated blood cell that is not a nucleated erythrocyte. There are two classes of leukocyte including granulocytes (e.g., neutrophils and basophils) and mononuclear cells (e.g., monocytes and lymphocytes).

In the preferred embodiment of this invention expression profiles are evaluated by detecting mRNA. A multitude of techniques are available for the isolation of m-RNA from whole blood. Any method that allows for isolation of mRNA from cells can be utilized. Peripheral blood is drawn from a subject into one or more sterile tubes containing an anticoagulant such as heparin, EDTA, citrate and or a fixative. In the context of this invention the preferred medium for collection of whole blood is PaxGene™ (Quiagen, Inc). The sample is divided into two portions. One portion is frozen and stored for future use and the other is processed by one of a variety of methods for isolation of RNA. A 8 milliliter sample of whole blood usually yields approximately 5-20 pg of total RNA, which is generally a sufficient quantity for labeling and hybridization to a probe array. Labeled target molecules are prepared from the subjects RNA using standard methods. cDNA may be synthesized from RNA using a poly T primer incorporating a T7 polymerase sequence. cRNA may then be transcribed while incorporating biotinylated nucleotides. In the preferred embodiment of this invention the preferred method is the use of the Affymetrix IVT reaction. The resulting pool of labeled cRNA may be purified and fragmented to allow individual transcripts to hybridize to gene probes representing genes of interest located on e.g., micro-arrays. In some instances the amount of RNA extracted is inadequate for processing and amplification of the RNA may be required. Amplification may be performed by 1) increasing the efficiency of labeling or; 2) by amplifying the RNA sample prior to labeling.

In another embodiment of this invention cDNA may be used for expression profiling. In this embodiment 8 milliliters of whole blood usually yields approximately 5-20 ug of RNA. Labeled target molecules are made from the subjects' sample of RNA using standard methods. cDNA is synthesized from total RNA using a poly T primer and labeled with fluorescent or radioactive nucleotides. The resulting labeled cDNA is hybridized to probes corresponding to known genes or expressed sequence tags and expression data is generated.

Alternatively, in the context of this invention, expression at the level of protein products of gene expression may be performed using proteomics. Proteins are detected in samples of subjects' serum or from whole blood cell or particulate components. Serum may be prepared by centrifugation of whole blood by standard methods. Cellular protein is obtained by standard methods known to those experienced in the art and include but are not limited to Trizol (Invitrogen Life Technologies). Those practiced in the art will recognize that the following methods, among others, may be used for this purpose: 1) Western analysis; 2) mass spectrophotometry; 3) two dimensional gel analysis; 4) chromatographic separation; 5) protein-fusion reporter constructs; 6) calorimetric assays; 7) binding to a protein array and; 8) characterization of polysomal mRNA. One embodiment involves binding of labeled protein expression products to an array of antibodies specific for protein products of a candidate gene set of interest. Details concerning a variety of immunological and/or immunoassay procedures relevant to this invention may be found in standard texts of biochemistry methodology. Alternative approaches use systems for performing spectrometery. Available systems include Ciphergen Biosystems, Inc (Freemont, Calif.). ProteinChip™ arrays approaches also provide arrays for detection of protein expression. Also available are methods which employ affinity reagents such as small molecules and/or antibodies which recognize epitopes of a protein product of interest.

Exemplary Embodiments of the Invention

FIG. 1 illustrates various aspects of the invention. A sample such as a whole blood sample is obtained from a patient in a pre-specified manner e.g., collection in PaxGene™ blood RNA collection tubes. Obtaining a whole blood sample from a patient may be practiced according to usual blood sampling methods known in the art. Using the obtained sample mRNA may be processed according to standard techniques known to those practiced in the art such that labeled target mRNA, cDNA or cRNA is produced. Labeled target is then hybridized to a microarray platform, e.g., to the Affymetric U133+2 GeneChip™ which contains oligonucleotide sequences representative of all known human genes which function as probes to detect homologous cRNA. Target molecules hybridized to probes on the chip are then quantified, at least in part, by standard scanning techniques using a summary measure such as RMA (Robust Multiarray Average) in the case of the Affymetrix U133+2 GeneChip™ (18).

In particular, the mRNA expression profile of a gene set of interest consists of background corrected, log transformed, variance normalized, summarized intensity profiles of the probe sets representing a gene set of interest. The likelihood of the occurrence of restenosis is evaluated by determining the probability output of a trained Partial Least Squares component based regression model derived from all the probe set or gene set intensity profiles of the gene set of interest.

The analysis of the data obtained as described herein has resulted in the development of criteria for establishing two prognosis profiles. The first prognosis profile is that of an individual whose probability output for one or more gene sets of interest is $\leq 50\%$. It has been found that such individuals are unlikely to develop restenosis after stent placement, i.e. individuals fitting this profile have a low probability of restenosis and can safely receive a bare metal stent. The second profile is that of an individual whose probability output is $>50\%$. Such individuals are likely to develop restenosis, i.e. individuals fitting this profile have a high probability of restenosis and should receive a stent that includes anti-restenosis agents.

The invention is further illustrated by the following non-limiting examples.

EXAMPLES

Example 1

Assessment of mRNA Expression in Patients Receiving Bare Metal Stents and Incidence of Restenosis Summary: One hundred twelve (112) non-diabetic patients were enrolled in a prospective clinical trial designed to test the hypothesis that an mRNA expression profile can accurately predict which patients will restenose after bare metal stent placement. Peripheral blood samples were collected prior to coronary angioplasty in all patients. Fifty-six (56) patients were found to have significant coronary artery disease and received at least one bare metal stent. All patients had follow-up angiograms 6 months post stent placement. Twenty-three patients experienced restenosis within 6 months of stent placement. Whole blood mRNA expression profiling was performed using the Affymeytrix U133+2 GeneChip™. Putative molecular pathways and functional molecular families responsible for bare metal stent restenosis were pre-specified prior to analysis. A partial least squares algorithm was used to select components for a logistic regression model that predicted bare metal stent restenosis. The ability of the model to discriminate between patients with and those without restenosis was assessed by the receiver operator characteristic (ROC) and misclassification rate (MR).

The results demonstrated that: 1) restenosis following coronary angioplasty with a bare metal stent can be accurately predicted using mRNA expression profiling of the cellular components of whole blood; 2) biological pathway activation predicts which patients will restenose after placement of a bare metal stent and; 3) generalized transcriptional activation or decreased degradation of the mRNA product of gene transcription of the human genome predicts individual patient risk of restenosis.

Patients

One hundred twelve (112) sequential patients undergoing elective coronary angiography were enrolled. Clinical inclusion criteria for study entry were: 1) age ≧21 years; 2) ability to provide informed consent and; 3) availability for 6 month follow-up angiography. Exclusion criteria were: 1) diabetes mellitus; 2) myocardial infarction within previous 30 days; 3) concurrent infection or inflammatory disease; 4) malignancy; or 5) genetic-based disease process. Angiographic inclusion criteria included: 1) a ≧50% diameter stenosis in a native coronary artery suitable for stenting. Fifty eight (58) patients met clinical as well as angiographic inclusion criteria and received at least one coronary artery bare metal stent in at least one native coronary artery. Six (6) of these fifty-eight patients underwent coronary stent placement in more than a single coronary artery. Two patients refused follow-up angiography. Fifty-six patients were available for analysis. Demographic data were collected on all patients including: age, gender, histories of hypertension, tobacco use and hypercholesterolemia. Laboratory data collected included: Complete blood count with differential leukocyte count, blood urea nitrogen, creatinine and liver chemistry including hepatic transaminase enzyme levels, lipid analysis, high sensitivity C-reactive protein (hsCRP) and homocysteine.

Angiography

All patients underwent coronary angiography according to standard techniques for quantitative coronary angiography. Briefly, 1) the diagnostic coronary catheter of known diameter was utilized as a calibration signal; 2) all images for quantitative analysis were collected in the center of the imaging field in order to minimize "pin cushion" distortion; 3) each coronary artery stenosis of interest was imaged for at least 2 cardiac cycles in order to optimize opportunity for selecting the optimum diastolic image for quantification and; 4) the angiographic view which demonstrated (qualitatively) the greatest degree of stenosis in the opinion of the clinical cardiologist investigator was selected for quantitative analysis. Follow-up angiography, 6 months post stent placement was done according to standard procedures as for initial angiography.

The Sanders Quantitative Coronary Angiographic Analysis System was used for quantitative coronary artery analysis. Pre-procedure angiographic analysis included: 1) Lesion percent diameter stenosis; 2) minimum lumen diameter of the lesion and; 3) minimum lumen diameter of a normal reference segment. Post-procedure angiographic analysis included: 1) Lesion minimum lumen diameter; 2) lesion percent diameter stenosis and; 3) reference segment minimum luminal diameter. Six months post procedure repeat coronary angiography was done to determine the presence or absence of in-stent restenosis. Data collected at that time included 1) percent diameter stenosis of the previously stented lesion (in-stent restenosis); 2) minimum luminal diameter of the in-stent segment; 3) minimum luminal diameter of a normal reference segment and; 4) late lumen loss (defined as post procedure in-stent minimum luminal diameter minus follow-up in-stent minimum luminal diameter). A single angiographic image reader analyzed all the images.

In-stent restenosis was defined in a binary (yes/no) manner with the threshold being a greater than 50% diameter stenosis in the stented segment relative to a normal reference segment. Patients who received stents in more than one coronary vessel at the time of the index procedure were classified as patients with restenosis if at least one of the stented vessels demonstrated greater 50% stenosis in the stented segment at the follow-up coronary angiogram.

mRNA Expression Profiling

Blood samples were collected into PaxGene (PreAnalytix, Inc.) tubes on the day of angiography prior to patient arrival in the cardiac catheterization laboratory. The samples were stored at room temperature for two hours, transferred to −20 degrees C. for two hours and subsequently maintained at −70 degrees C. until shipped frozen to the Core Laboratory (Core Genomics Laboratory, The George Washington University Medical Center, Washington, D.C.) on dry ice. All samples arrived at the Core Laboratory frozen. All sample processing was performed at the Core Laboratory. The samples were stored until there was a sufficient number available for processing and then batch processed. The samples were processed into RNA immediately upon thawing. RNA was purified as specified by the PaxGene manufacturer. The RNA (approximately 8 μg/2.5 ml whole blood) was further purified and concentrated with Affymetrix Blood RNA Concentration Kit. Globin messages were suppressed by peptide-nucleic acid primers annealing to the 3' end of globin messages (globin reduction protocol). The RNA was labeled by reverse transcription with the Affymetrix one-cycle cDNA reaction and an oligo-dT primer incorporating a T7 polymerase sequence. cRNA was transcribed while incorporating biotinylated nucleotides using the Affymetrix UVT reaction. The resulting pool of labeled cRNA was repurified and fragmented to allow an individual transcript to hybridize to the multiple gene probe sets. The labeled probe was hybridized overnight to the Affymetrix U133+2 Genechip®. The hybridized chip was washed, stained with streptavidin-phycoerythrin (SAPE), and amplified with biotinylated anti-SAPE and additional SAPE staining. The array was scanned, deconvolved into gene probe sets, and quality control performed to insure that detection sensitivity and noise were within predetermined limits. Gene probe sets were summarized into transcript levels using, in part, the RMA algorithm (18).

Pathways

Genes and/or gene probe sets were grouped according to pre-specified molecular pathways and functional molecular families. The components of each pathway and family were a set of pre-specified genes. The genes comprising these molecular pathways and functionally related molecules chosen for analysis were derived from the Kyoto Encyclopedia of Genes and Genomics (19) and included:

1) Molecular target of rapamycin (Table 1),

2) Leukocyte trans-endothelial migration (Table 2),

3) TGFβ signaling (Table 3),

4) T cell antigen processing (Table 4),

5) T cell signaling (Table 5),

6) Mitogen activated protein kinase or "MAPK" (Table 6),

7) Cell adhesion molecules (Table 7),

8) A group of 100 probe sets selected in a non-systematic manner (Table 8).

TABLE 1

Pathway 1: Molecular Target of Rapamycin

| Gene Symbol | Probe Set ID | Gene Title |
| --- | --- | --- |
| MAPK1 | 1552263_at | mitogen-activated protein kinase 1 |
| MAPK1 | 1552264_a_at | mitogen-activated protein kinase 1 |
| AVO3 | 1552734_at | TORC2-specific protein AVO3 |
| FLJ39075 | 1553130_at | hypothetical protein FLJ39075 |
| ULK2 | 1554112_a_at | unc-51-like kinase 2 (*C. elegans*) |
| PRKAA1 | 1555177_at | protein kinase, AMP-activated, alpha 1 catalytic subunit |
| RHEB | 1555780_a_at | Ras homolog enriched in brain |
| AKT2 | 1560689_s_at | V-akt murine thymoma viral oncogene homolog 2 |
| MAPK1 | 1562283_at | Mitogen-activated protein kinase 1 |
| RPS6KA3 | 1568448_at | Ribosomal protein S6 kinase, 90 kDa, polypeptide 3 |
| RPS6KA3 | 1568449_at | Ribosomal protein S6 kinase, 90 kDa, polypeptide 3 |
| PIK3R2 | 1568629_s_at | phosphoinositide-3-kinase, regulatory subunit 2 (p85 beta) |
| RPS6 | 200081_s_at | ribosomal protein S6///ribosomal protein S6 |
| HIF1A | 200989_at | hypoxia-inducible factor 1, alpha subunit |
| RPS6 | 201254_x_at | ribosomal protein S6 |
| EIF4E | 201435_s_at | eukaryotic translation initiation factor 4E |
| EIF4E | 201436_at | eukaryotic translation initiation factor 4E |
| EIF4E | 201437_s_at | eukaryotic translation initiation factor 4E |
| RHEB | 201451_x_at | Ras homolog enriched in brain |
| RHEB | 201452_at | Ras homolog enriched in brain |
| RHEB | 201453_x_at | Ras homolog enriched in brain |
| FRAP1 | 202288_at | FK506 binding protein 12-rapamycin associated protein 1 |
| PIK3R3 | 202743_at | phosphoinositide-3-kinase, regulatory subunit 3 (p55, gamma) |
| DDIT4 | 202887_s_at | DNA-damage-inducible transcript 4 |
| RPS6KA1 | 203379_at | ribosomal protein S6 kinase, 90 kDa, polypeptide 1 |
| VEGFB | 203683_s_at | vascular endothelial growth factor B |
| AKT2 | 203808_at | v-akt murine thymoma viral oncogene homolog 2 |
| AKT2 | 203809_s_at | v-akt murine thymoma viral oncogene homolog 2 |
| RPS6KA3 | 203843_at | ribosomal protein S6 kinase, 90 kDa, polypeptide 3 |
| PIK3CD | 203879_at | phosphoinositide-3-kinase, catalytic, delta polypeptide |
| ULK2 | 204062_s_at | unc-51-like kinase 2 (*C. elegans*) |
| ULK2 | 204063_s_at | unc-51-like kinase 2 (*C. elegans*) |
| RPS6KB1 | 204171_at | ribosomal protein S6 kinase, 70 kDa, polypeptide 1 |
| STK11 | 204292_x_at | serine/threonine kinase 11 (Peutz-Jeghers syndrome) |
| PIK3CA | 204369_at | phosphoinositide-3-kinase, catalytic, alpha polypeptide |
| PDPK1 | 204524_at | 3-phosphoinositide dependent protein kinase-1 |
| BRAF | 206044_s_at | v-raf murine sarcoma viral oncogene homolog B1 |
| PIK3CG | 206369_s_at | phosphoinositide-3-kinase, catalytic, gamma polypeptide |
| PIK3CG | 206370_at | phosphoinositide-3-kinase, catalytic, gamma polypeptide |
| INS | 206598_at | insulin |
| FIGF | 206742_at | c-fos induced growth factor (vascular endothelial growth factor D) |
| PIK3R2 | 207105_s_at | phosphoinositide-3-kinase, regulatory subunit 2 (p85 beta) |
| AKT1 | 207163_s_at | v-akt murine thymoma viral oncogene homolog 1 |
| PRKAA2 | 207709_at | protein kinase, AMP-activated, alpha 2 catalytic subunit |
| MAPK1 | 208351_s_at | mitogen-activated protein kinase 1 |
| RPS6 | 209134_s_at | ribosomal protein S6 |
| ULK1 | 209333_at | unc-51-like kinase 1 (*C. elegans*) |
| TSC1 | 209390_at | tuberous sclerosis 1 |
| EIF4E2 | 209393_s_at | eukaryotic translation initiation factor 4E member 2 |
| IGF1 | 209540_at | insulin-like growth factor 1 (somatomedin C) |
| IGF1 | 209541_at | insulin-like growth factor 1 (somatomedin C) |
| IGF1 | 209542_x_at | insulin-like growth factor 1 (somatomedin C) |
| PGF | 209652_s_at | placental growth factor, vascular endothelial growth factor-related protein |
| PRKAA1 | 209799_at | protein kinase, AMP-activated, alpha 1 catalytic subunit |
| VEGFC | 209946_at | vascular endothelial growth factor C |
| VEGF | 210512_s_at | vascular endothelial growth factor |
| VEGF | 210513_s_at | vascular endothelial growth factor |
| PIK3CD | 211230_s_at | phosphoinositide-3-kinase, catalytic, delta polypeptide |
| AKT2 | 211453_s_at | v-akt murine thymoma viral oncogene homolog 2 |
| VEGF | 211527_x_at | vascular endothelial growth factor |
| IGF1 | 211577_s_at | insulin-like growth factor 1 (somatomedin C) |
| RPS6KB1 | 211578_s_at | ribosomal protein S6 kinase, 70 kDa, polypeptide 1 |
| PIK3R3 | 211580_s_at | phosphoinositide-3-kinase, regulatory subunit 3 (p55, gamma) |
| RPS6///LOC392358 | 211690_at | ribosomal protein S6///ribosomal protein S6 |
| EIF4B | 211937_at | eukaryotic translation initiation factor 4B |
| EIF4B | 211938_at | eukaryotic translation initiation factor 4B |
| MAPK3 | 212046_x_at | mitogen-activated protein kinase 3 |
| VEGF | 212171_x_at | vascular endothelial growth factor |
| PIK3R1 | 212239_at | phosphoinositide-3-kinase, regulatory subunit 1 (p85 alpha) |
| PIK3R1 | 212240_s_at | phosphoinositide-3-kinase, regulatory subunit 1 (p85 alpha) |
| PIK3R1 | 212249_at | phosphoinositide-3-kinase, regulatory subunit 1 (p85 alpha) |
| MAPK1 | 212271_at | mitogen-activated protein kinase 1 |
| AKT3 | 212607_at | v-akt murine thymoma viral oncogene homolog 3 (protein kinase B, gamma) |
| AKT3 | 212609_s_at | V-akt murine thymoma viral oncogene homolog 3 (protein kinase B, gamma) |
| PIK3CB | 212688_at | phosphoinositide-3-kinase, catalytic, beta polypeptide |
| PIK3R4 | 212740_at | phosphoinositide-3-kinase, regulatory subunit 4, p150 |
| RHEB | 213404_s_at | Ras homolog enriched in brain |
| RHEB | 213409_s_at | Ras homolog enriched in brain |
| EIF4E2 | 213570_at | eukaryotic translation initiation factor 4E member 2 |
| EIF4E2 | 213571_s_at | eukaryotic translation initiation factor 4E member 2 |
| PRKAA1 | 214917_at | protein kinase, AMP-activated, alpha 1 catalytic subunit |
| ULK2 | 215154_at | Unc-51-like kinase 2 (*C. elegans*) |
| PGF | 215179_x_at | Placental growth factor, vascular endothelial growth factor-related protein |
| FRAP1 | 215381_at | FK506 binding protein 12-rapamycin associated protein 1 |
| TSC2 | 215735_s_at | tuberous sclerosis 2 |
| PIK3R4 | 216436_at | Phosphoinositide-3-kinase, regulatory subunit 4, p150 |

TABLE 1-continued

Pathway 1: Molecular Target of Rapamycin

| Gene Symbol | Probe Set ID | Gene Title |
|---|---|---|
| PIK3R4 | 216752_at | Phosphoinositide-3-kinase, regulatory subunit 4, p150 |
| PIK3CB | 217620_s_at | phosphoinositide-3-kinase, catalytic, beta polypeptide |
| AKT3 | 219393_s_at | v-akt murine thymoma viral oncogene homolog 3 (protein kinase B, gamma) |
| PIK3R5 | 220566_at | phosphoinositide-3-kinase, regulatory subunit 5, p101 |
| GBL | 220587_s_at | G protein beta subunit-like |
| EIF4EBP1 | 221539_at | eukaryotic translation initiation factor 4E binding protein 1 |
| PDPK1 | 221944_at | 3-phosphoinositide dependent protein kinase-1 |
| AKT3 | 222880_at | v-akt murine thymoma viral oncogene homolog 3 (protein kinase B, gamma) |
| AKT3 | 224229_sat | v-akt murine thymoma viral oncogene homolog 3 (protein kinase B, gamma) |
| MAPK1 | 224621_at | mitogen-activated protein kinase 1 |
| PDPK1 | 224986_s_at | 3-phosphoinositide dependent protein kinase-1 |
| AKT2 | 225471_s_at | v-akt murine thymoma viral oncogene homolog 2 |
| raptor | 225715_at | raptor |
| PRKAA1 | 225984_at | protein kinase, AMP-activated, alpha 1 catalytic subunit |
| PRKAA1 | 225985_at | protein kinase, AMP-activated, alpha 1 catalytic subunit |
| AVO3 | 226310_at | TORC2-specific protein AVO3 |
| AVO3 | 226312_at | TORC2-specific protein AVO3 |
| RPS6KA3 | 226335_at | ribosomal protein S6 kinase, 90 kDa, polypeptide 3 |
| BRAF | 226391_at | V-raf murine sarcoma viral oncogene homolog Bi |
| RPS6KB1 | 226660_at | ribosomal protein S6 kinase, 70 kDa, polypeptide 1 |
| EIF4E2 | 226734_at | Eukaryotic translation initiation factor 4E member 2 |
| RHEB | 227633_at | Ras homolog enriched in brain |
| PIK3R5 | 227645_at | phosphoinositide-3-kinase, regulatory subunit 5, p101 |
| PRKAA2 | 227892_at | Protein kinase, AMP-activated, alpha 2 catalytic subunit |
| AVO3 | 228248_at | TORC2-specific protein AVO3 |
| PIK3R2 | 229392_s_at | Phosphoinositide-3-kinase, regulatory subunit 2 (p85 beta) |
| MAPK1 | 229847_at | Mitogen-activated protein kinase 1 |
| STK11 | 231017_at | serine/threonine kinase 11 (Peutz-Jeghers syndrome) |
| STK11 | 231019_x_at | Serine/threonine kinase 11 |
| LOC283874///LOC124216 | 232050_at | Hypothetical protein LOC283874///Hypothetical LOC124216 |
| TSC1 | 233570_at | Tuberous sclerosis 1 |
| RICTOR | 237330_at | Rapamycin-insensitive companion of mTOR |
| EIF4E | 237718_at | eukaryotic translation initiation factor 4E |
| ULK1 | 238042_at | Unc-51-like kinase 1 (*C. elegans*) |
| RPS6 | 238156_at | Ribosomal protein S6 |
| PRKAA2 | 238441_at | Protein kinase, AMP-activated, alpha 2 catalytic subunit |
| PRKAA2 | 238489_at | Protein kinase, AMP-activated, alpha 2 catalytic subunit |
| HIF1A | 238869_at | Hypoxia-inducible factor 1, alpha subunit (basic helix-loop-factor) |
| PRKAA2 | 240349_at | protein kinase, AMP-activated, alpha 2 catalytic subunit |
| AKT3 | 240568_at | V-akt murine thymoma viral oncogene homolog 3 (protein kinase B, gamma) |
| RPS6KA3 | 241460_at | Ribosomal protein S6 kinase, 90 kDa, polypeptide 3 |
| AKT3 | 242876_at | V-akt murine thymoma viral oncogene homolog 3 (protein kinase B, gamma) |
| AKT3 | 242879_x_at | V-akt murine thymoma viral oncogene hom 0109 3 (protein kinase B, gamma) |
| RHEB | 243008_at | Ras homolog enriched in brain |
| BRAF | 243829_at | v-raf murine sarcoma viral oncogene homolog Bi |
| PIK3R1 | 244181_at | Phosphoinositide-3-kinase, regulatory subunit 1 (p85 alpha) |
| EIF4E2 | 244302_at | Eukaryotic translation initiation factor 4E member 2 |
| PDPK1 | 32029_at | 3-phosphoinositide dependent protein kinase-1 |
| STK11 | 41657_at | serine/threonine kinase 11 (Peutz-Jeghers syndrome) |

TABLE 2

Pathway 2: Leukocyte trans-endothelial migration

| Gene Symbol | Probe Set ID | Gene Title |
|---|---|---|
| ITGB1 | 1553530_a_at | integrin, beta 1 (fibronectin receptor, beta polypeptide, antigen CD29 |
| ITGB1 | 1553678_a_at | integrin, beta 1 (fibronectin receptor, beta polypeptide, antigen CD29 |
| RASSF5 | 1554834_a_at | Ras association (RalGDS/AF-6) domain family 5 |
| RAP1A | 1555339_at | RAP1A, member of RAS oncogene family |
| RAP1A | 1555340_x_at | RAP1A, member of RAS oncogene family |
| ITGB2 | 1555349_a_at | integrin, beta 2 (antigen CD18 (p95), lymphocyte function-associated antigen 1 |
| RHOA | 1555814_a_at | ras homolog gene family, member A |
| CDC42 | 1556931_at | Cell division cycle 42 (GTP binding protein, 25kDa) |
| PECAM1 | 1559921_at | platelet/endothelial cell adhesion molecule (CD31 antigen) |
| ROCK2 | 1563329_s_at | Rho-associated, coiled-coil containing protein kinase 2 |
| RAC1 | 1567457_at | Ras-related C3 botulinum toxin substrate 1 (rho family, small GTP binding protein |
| RAC1 | 1567458_s_at | ras-related C3 botulinum toxin substrate 1 (rho family, small GTP binding protein |
| PIK3R2 | 1568629_s_at | phosphoinositide-3-kinase, regulatory subunit 2 (p85 beta) |
| ROCK1 | 1569981_at | Rho-associated, coiled-coil containing protein kinase 1 |

TABLE 2-continued

Pathway 2: Leukocyte trans-endothelial migration

| Gene Symbol | Probe Set ID | Gene Title |
|---|---|---|
| RHOA | 200059_s_at | ras homolog gene family, member A /// ras homolog gene family, member A |
| RAP1B | 200833_s_at | RAP1B, member of RAS oncogene family |
| CD99 | 201028_s_at | CD99 antigen |
| CD99 | 201029_s_at | CD99 antigen |
| GNAI2 | 201040_at | guanine nucleotide binding protein (G protein), alpha inhibiting activity polypeptide 2 |
| GNAI3 | 201179_s_at | guanine nucleotide binding protein (G protein), alpha inhibiting activity polypeptide 3 |
| GNAI3 | 201180_s_at | guanine nucleotide binding protein (G protein), alpha inhibiting activity polypeptide 3 |
| GNAI3 | 201181_at | guanine nucleotide binding protein (G protein), alpha inhibiting activity polypeptide 3 |
| RAP1A | 202362_at | RAP1A, member of RAS oncogene family |
| PIK3R3 | 202743_at | phosphoinositide-3-kinase, regulatory subunit 3 (p55, gamma) |
| ROCK2 | 202762_at | Rho-associated, coiled-coil containing protein kinase 2 |
| ITGB2 | 202803_s_at | integrin, beta 2 (antigen CD18 (p95), lymphocyte function-associated antigen 1 |
| PTK2B | 203110_at | PTK2B protein tyrosine kinase 2 beta |
| PTK2B | 203111_s_at | PTK2B protein tyrosine kinase 2 beta |
| PIK3CD | 203879_at | phosphoinositide-3-kinase, catalytic, delta polypeptide /// phosphoinositide-3-kinase |
| PIK3CA | 204369_at | phosphoinositide-3-kinase, catalytic, alpha polypeptide |
| RHOH | 204951_at | ras homolog gene family, member H |
| VAV2 | 205536_at | vav 2 oncogene |
| VAV2 | 205537_s_at | vav 2 oncogene |
| RAPGEF4 | 205651_x_at | Rap guanine nucleotide exchange factor (GEF) 4 |
| ITGAM | 205785_at | integrant, alpha M (complement component receptor 3, alpha; also known as CD11b (p170), macrophage antigen alpha polypeptide) /// integrin, alpha M (complement component receptor 3, alpha; also known as CD11b (p170), macrophage antigen alpha polypeptide) |
| ITGAM | 205786_s_at | integrin, alpha M (complement component receptor 3, alpha; also known as CD11b (p170), macrophage antigen alpha polypeptide) /// integrin, alpha M (complement component receptor 3, alpha; also known as CD11b (p170), macrophage antigen alpha polypeptide) |
| ITGA4 | 205884_at | integrin, alpha 4 (antigen CD49D, alpha 4 subunit of VLA-4 receptor) |
| ITGA4 | 205885_s_at | integrin, alpha 4 (antigen CD49D, alpha 4 subunit of VLA-4 receptor) |
| VAV1 | 206219_s_at | vav 1 oncogene |
| PIK3CG | 206369_s_at | phosphoinositide-3-kinase, catalytic, gamma polypeptide |
| PIK3CG | 206370_at | phosphoinositide-3-kinase, catalytic, gamma polypeptide |
| TXK | 206828_at | TXK tyrosine kinase |
| PIK3R2 | 207105_s_at | phosphoinositide-3-kinase, regulatory subunit 2 (p85 beta) |
| RAC2 | 207419_s_at | ras-related C3 botulinum toxin substrate 2 (rho family) |
| RAC1 | 208640_at | ras-related C3 botulinum toxin substrate 1 (rho family) |
| RAC1 | 208641_s_at | ras-related C3 botulinum toxin substrate 1 (rho family, small GTP binding protein Rac1) |
| CDC42 | 208727_s_at | cell division cycle 42 (GTP binding protein, 25kDa) |
| CDC42 | 208728_s_at | cell division cycle 42 (GTP binding protein, 25kDa) |
| PECAM1 | 208981_at | platelet/endothelial cell adhesion molecule (CD31 antigen) |
| PECAM1 | 208982_at | Platelet/endothelial cell adhesion molecule (CD31 antigen) |
| PECAM1 | 208983_s_at | platelet/endothelial cell adhesion molecule (CD31 antigen) |
| CXCR4 | 209201_x_at | chemokine (C-X-C motif) receptor 4 |
| GNAI1 | 209576_at | guanine nucleotide binding protein (G protein), alpha inhibiting activity polypeptide 1 |
| RAPGEF3 | 210051_at | Rap guanine nucleotide exchange factor (GEF) 3 |
| CDC42 | 210232_at | cell division cycle 42 (GTP binding protein, 25kDa) |
| PIK3CD | 211230_s_at | phosphoinositide-3-kinase, catalytic, delta polypeptide |
| ITK | 211339_s_at | IL2-inducible T-cell kinase |
| ROCK2 | 211504_x_at | Rho-associated, coiled-coil containing protein kinase 2 |
| PIK3R3 | 211580_s_at | phosphoinositide-3-kinase, regulatory subunit 3 (p55, gamma) |
| CXCR4 | 211919_s_at | chemokine (C-X-C motif) receptor 4 /// chemokine (C-X-C motif) receptor 4 |
| ITGB1 | 211945_s_at | integrin, beta 1 (fibronectin receptor, beta polypeptide, antigen) |
| MYL6 | 212082_s_at | myosin, light polypeptide 6, alkali, smooth muscle and non-muscle |
| PIK3R1 | 212239_at | phosphoinositide-3-kinase, regulatory subunit 1 (p85 alpha) |
| PIK3R1 | 212240_s_at | phosphoinositide-3-kinase, regulatory subunit 1 (p85 alpha) |
| PIK3R1 | 212249_at | phosphoinositide-3-kinase, regulatory subunit 1 (p85 alpha) |
| PIK3CB | 212688_at | phosphoinositide-3-kinase, catalytic, beta polypeptide |
| PIK3R4 | 212740_at | phosphoinositide-3-kinase, regulatory subunit 4, p150 |
| ROCK1 | 213044_at | Rho-associated, coiled-coil containing protein kinase 1 |
| ITGA4 | 213416_at | integrin, alpha 4 (antigen CD49D, alpha 4 subunit of VLA-4 receptor) |
| RAC2 | 213603_s_at | ras-related C3 botulinum toxin substrate 2 (rho family) |
| MYL6 | 214002_at | myosin, light polypeptide 6, alkali, smooth muscle and non-muscle |
| CDC42 | 214230_at | cell division cycle 42 (GTP binding protein, 25kDa) |
| ROCK1 | 214578_s_at | Rho-associated, coiled-coil containing protein kinase 1 |

TABLE 2-continued

Pathway 2: Leukocyte trans-endothelial migration

| Gene Symbol | Probe Set ID | Gene Title |
|---|---|---|
| ITGB1 | 215878_at | integrin, beta 1 (fibronectin receptor, beta polypeptide, antigen CD29) |
| ITGB1 | 215879_at | integrin, beta 1 (fibronectin receptor, beta polypeptide, antigen CD29) |
| RHOH | 216166_at | Ras homolog gene family, member H |
| RHOH | 216168_at | Ras homolog gene family, member H |
| ITGB1 | 216178_x_at | integrin, beta 1 (fibronectin receptor, beta polypeptide, antigen CD29) |
| ITGB1 | 216190_x_at | integrin, beta 1 (fibronectin receptor, beta polypeptide, antigen CD29) |
| PIK3R4 | 216436_at | Phosphoinositide-3-kinase, regulatory subunit 4, p150 |
| ROCK1 | 216621_at | Rho-associated, coiled-coil containing protein kinase 1 |
| ROCK1 | 216625_at | Rho-associated, coiled-coil containing protein kinase 1 |
| PIK3R4 | 216752_at | Phosphoinositide-3-kinase, regulatory subunit 4, p150 |
| CXCR4 | 217028_at | chemokine (C-X-C motif) receptor 4 |
| PIK3CB | 217620_s_at | phosphoinositide-3-kinase, catalytic, beta polypeptide |
| VAV3 | 218806_s_at | vav 3 oncogene |
| VAV3 | 218807_at | vav 3 oncogene |
| PIK3R5 | 220566_at | phosphoinositide-3-kinase, regulatory subunit 5, p101 |
| RASSF5 | 223322_at | Ras association (RaIGDS/AF-6) domain family 5 |
| VAV3 | 224221_s_at | vav 3 oncogene |
| VAV2 | 226063_at | vav 2 oncogene |
| CDC42 | 226400_at | Cell division cycle 42 (GTP binding protein, 25kDa) |
| PIK3R5 | 227645_at | phosphoinositide-3-kinase, regulatory subunit 5, p101 |
| GNAI1 | 227692_at | guanine nucleotide binding protein (G protein), alpha inhibiting activity polypeptide 1 |
| ITGB2 | 229040_at | Homo sapiens, clone IMAGE:5205388, mRNA /// Integrin, beta 2 (antigen CD18) |
| ITGB2 | 229041_s_at | Homo sapiens, clone IMAGE:5205388, mRNA /// Integrin, beta 2 (antigen CD18) |
| PIK3R2 | 229392_s_at | Phosphoinositide-3-kinase, regulatory subunit 2 (p85 beta) |
| CD99 | 230161_at | CD99 antigen |
| ROCK1 | 230239_at | Rho-associated, coiled-coil containing protein kinase 1 |
| RAP1B | 231127_at | RAP1B, member of RAS oncogene family |
| ROCK1 | 235854_x_at | Rho-associated, coiled-coil containing protein kinase 1 |
| RHOH | 236293_at | Ras homolog gene family, member H |
| ITGB2 | 236988_x_at | integrin, beta 2 (antigen CD18 (p95), lymphocyte function-associated antigen 1 |
| RAP1A | 240215_at | RAP1A, member of RAS oncogene family |
| RHOA | 240337_at | Ras homolog gene family, member A |
| RHOA | 241097_at | Ras homolog gene family, member A |
| MYL6 | 241662_x_at | Myosin, light polypeptide 6, alkali, smooth muscle and non-muscle |
| MYL6 | 241664_x_at | Myosin, light polypeptide 6, alkali, smooth muscle and non-muscle |
| RHOH | 242929_at | Ras homolog gene family, member H |
| ITGA4 | 243685_at | Integrin, alpha 4 (antigen CD49D, alpha 4 subunit of VLA-4 receptor) |
| PIK3R1 | 244181_at | Phosphoinositide-3-kinase, regulatory subunit 1 (p85 alpha) |
| ITGA4 | 244599_at | Integrin, alpha 4 (antigen CD49D, alpha 4 subunit of VLA-4 receptor) |

TABLE 3

Pathway 3: Transforming Growth Factor Beta (TGFβ) signaling

| Gene Symbol | Probe Set ID | Gene Title |
|---|---|---|
| MAPK1 | 1552263_at | mitogen-activated protein kinase 1 |
| MAPK1 | 1552264_a_at | mitogen-activated protein kinase 1 |
| ACVR1C | 1552519_at | activin A receptor, type IC |
| SP1 | 1553685_s_at | Sp1 transcription factor |
| ZFYVE16 | 1554638_at | zinc finger, FYVE domain containing 16 |
| RBL1 | 1555003_at | retinoblastoma-like 1 (p107) |
| RBL1 | 1555004_a_at | retinoblastoma-like 1 (p107) |
| ZFYVE16 | 1555011_at | zinc finger, FYVE domain containing 16 |
| TGFB3 | 1555540_at | transforming growth factor, beta 3 |
| RHOA | 1555814_a_at | ras homolog gene family, member A |
| ZFYVE16 | 1555982_at | Zinc finger, FYVE domain containing 16 |
| CREBBP | 1559295_at | CREB binding protein (Rubinstein-Taybi syndrome) |
| RBL1 | 1559307_s_at | retinoblastoma-like 1 (p107) |
| MAPK1 | 1562283_at | Mitogen-activated protein kinase 1 |
| SMAD4 | 1565702_at | SMAD, mothers against DPP homolog 4 (*Drosophila*) |
| SMAD4 | 1565703_at | SMAD, mothers against DPP homolog 4 (*Drosophila*) |
| LTBP1 | 1566267_at | Latent transforming growth factor beta binding protein 1 |
| LTBP1 | 1566268_at | Latent transforming growth factor beta binding protein 1 |
| ROCK1 | 1569981_at | Rho-associated, coiled-coil containing protein kinase 1 |

TABLE 3-continued

Pathway 3: Transforming Growth Factor Beta (TGFβ) signaling

| Gene Symbol | Probe Set ID | Gene Title |
|---|---|---|
| RHOA | 200059_s_at | ras homolog gene family, member A /// ras homolog gene family, member A |
| SKP1A | 200711_s_at | S-phase kinase-associated protein 1A (p19A) |
| SKP1A | 200718_s_at | S-phase kinase-associated protein 1A (p19A) |
| SKP1A | 200719_at | S-phase kinase-associated protein 1A (p19A) |
| THBS1 | 201107_s_at | thrombospondin 1 |
| THBS1 | 201108_s_at | thrombospondin 1 |
| THBS1 | 201109_s_at | thrombospondin 1 |
| THBS1 | 201110_s_at | thrombospondin 1 |
| PPP2CB | 201374_x_at | protein phosphatase 2 (formerly 2A), catalytic subunit, beta isoform |
| PPP2CB | 201375_s_at | protein phosphatase 2 (formerly 2A), catalytic subunit, beta isoform |
| ID2 | 201565_s_at | inhibitor of DNA binding 2, dominant negative helix-loop-helix protein |
| ID2 /// ID2B | 201566_x_at | inhibitor of DNA binding 2, dominant negative helix-loop-helix protein |
| DCN | 201893_x_at | decorin |
| CREBBP | 202160_at | CREB binding protein (Rubinstein-Taybi syndrome) |
| E2F4 | 202248_at | E2F transcription factor 4, p107/p130-binding |
| MYC | 202431_s_at | v-myc myelocytomatosis viral oncogene homolog (avian) |
| SMAD4 | 202526_at | SMAD, mothers against DPP homolog 4 (*Drosophila*) |
| SMAD4 | 202527_s_at | SMAD, mothers against DPP homolog 4 (*Drosophila*) |
| LTBP1 | 202728_s_at | latent transforming growth factor beta binding protein 1 |
| LTBP1 | 202729_s_at | latent transforming growth factor beta binding protein 1 |
| SMAD2 | 203075_at | SMAD, mothers against DPP homolog 2 (*Drosophila*) |
| SMAD2 | 203076_s_at | SMAD, mothers against DPP homolog 2 (*Drosophila*) |
| SMAD2 | 203077_s_at | SMAD, mothers against DPP homolog 2 (*Drosophila*) |
| THBS2 | 203083_at | thrombospondin 2 |
| ZFYVE16 | 203651_at | zinc finger, FYVE domain containing 16 |
| TFDP1 | 204147_s_at | transcription factor Dp-1 |
| RPS6KB1 | 204171_at | ribosomal protein S6 kinase, 70kDa, polypeptide 1 |
| THBS4 | 204776_at | thrombospondin 4 |
| SMAD7 | 204790_at | SMAD, mothers against DPP homolog 7 (*Drosophila*) |
| BMPR1A | 204832_s_at | bone morphogenetic protein receptor, type IA |
| ZFYVE9 | 204893_s_at | zinc finger, FYVE domain containing 9 |
| SMAD5 | 205187_at | SMAD, mothers against DPP homolog 5 (*Drosophila*) |
| SMAD5 | 205188_s_at | SMAD, mothers against DPP homolog 5 (*Drosophila*) |
| ACVR1B | 205209_at | activin A receptor, type IB |
| BMP2 | 205289_at | bone morphogenetic protein 2 |
| BMP2 | 205290_s_at | bone morphogenetic protein 2 |
| RBL1 | 205296_at | retinoblastoma-like 1 (p107) |
| SMAD3 | 205396_at | SMAD, mothers against DPP homolog 3 (*Drosophila*) |
| SMAD3 | 205397_x_at | SMAD, mothers against DPP homolog 3 (*Drosophila*) |
| SMAD3 | 205398_s_at | SMAD, mothers against DPP homolog 3 (*Drosophila*) |
| BMP5 | 205430_at | bone morphogenetic protein 5 |
| BMP5 | 205431_s_at | bone morphogenetic protein 5 |
| SMURF2 | 205596_s_at | SMAD specific E3 ubiquitin protein ligase 2 |
| COMP | 205713_s_at | cartilage oligomeric matrix protein |
| BMP6 | 206176_at | bone morphogenetic protein 6 |
| SMAD9 | 206320_s_at | SMAD, mothers against DPP homolog 9 (*Drosophila*) |
| AMH | 206516_at | anti-Mullerian hormone |
| GDF5 | 206614_at | growth differentiation factors (cartilage-derived morphogenetic protein-1) |
| AMHR2 | 206892_at | anti-Mullerian hormone receptor, type II |
| TGFBR1 | 206943_at | transforming growth factor, beta receptor I (activin A receptor type II-like kinase, 53kDa) |
| SMAD6 | 207069_s_at | SMAD, mothers against DPP homolog 6 (*Drosophila*) |
| TNF | 207113_s_at | tumor necrosis factor (TNF superfamily, member 2) |
| TGFBR2 | 207334_s_at | transforming growth factor, beta receptor II (70/80kDa) |
| CDKN2B | 207530_s_at | cyclin-dependent kinase inhibitor 2B (p15, inhibits CDK4) |
| CUL1 | 207614_s_at | cullin 1 |
| ID3 | 207826_s_at | inhibitor of DNA binding 3, dominant negative helix-loop-helix protein |
| BMP8B | 207865_s_at | bone morphogenetic protein 8b (osteogenic protein 2) |
| BMP8A | 207866_at | bone morphogenetic protein 8a |
| SKP1A | 207974_s_at | S-phase kinase-associated protein 1A (p19A) |
| SMAD1 | 208015_at | SMAD, mothers against DPP homolog 1 (*Drosophila*) |
| ACVR1B | 208218_s_at | activin A receptor, type IB |
| ACVR1B | 208219_at | activin A receptor, type IB |
| ACVR1B | 208222_at | activin A receptor, type IB |
| ACVR1B | 208223_s_at | activin A receptor, type IB |
| MAPK1 | 208351_s_at | mitogen-activated protein kinase 1 |
| ZFYVE9 | 208446_s_at | zinc finger, FYVE domain containing 9 |
| PPP2CA | 208652_at | protein phosphatase 2 (formerly 2A), catalytic subunit, alpha isoform |
| ID1 | 208937_s_at | inhibitor of DNA binding 1, dominant negative helix-loop-helix protein |
| TGFBR2 | 208944_at | transforming growth factor, beta receptor II (70/80kDa) |
| ID4 | 209291_at | inhibitor of DNA binding 4, dominant negative helix-loop-helix protein |
| ID4 | 209292_at | Inhibitor of DNA binding 4, dominant negative helix-loop-helix protein |
| ID4 | 209293_x_at | inhibitor of DNA binding 4, dominant negative helix-loop-helix protein |

TABLE 3-continued

Pathway 3: Transforming Growth Factor Beta (TGFβ) signaling

| Gene Symbol | Probe Set ID | Gene Title |
|---|---|---|
| DCN | 209335_at | decorin |
| THBS3 | 209561_at | thrombospondin 3 |
| BMP7 | 209590_at | Bone morphogenetic protein 7 (osteogenic protein 1) |
| BMP7 | 209591_s_at | bone morphogenetic protein 7 (osteogenic protein 1) |
| TGFB3 | 209747_at | transforming growth factor, beta 3 |
| SMAD6 | 209886_s_at | SMAD, mothers against DPP homolog 6 (*Drosophila*) |
| SMAD6 | 209887_at | SMAD, mothers against DPP homolog 6 (*Drosophila*) |
| TGFB2 | 209908_s_at | Transforming growth factor, beta 2 |
| TGFB2 | 209909_s_at | transforming growth factor, beta 2 |
| BMPR2 | 209920_at | bone morphogenetic protein receptor, type II (serine/threonine kinase) |
| BMPR2 | 210214_s_at | bone morphogenetic protein receptor, type II (serine/threonine kinase) |
| BMPR1B | 210523_at | bone morphogenetic protein receptor, type IB |
| SMAD1 | 210993_s_at | SMAD, mothers against DPP homolog 1 (*Drosophila*) |
| CHRD | 211248_s_at | chordin |
| BMP7 | 211259_s_at | bone morphogenetic protein 7 (osteogenic protein 1) |
| BMP7 | 211260_at | bone morphogenetic protein 7 (osteogenic protein 1) |
| BMP4 | 211518_s_at | bone morphogenetic protein 4 |
| RPS6KB1 | 211578_s_at | ribosomal protein S6 kinase, 70kDa, polypeptide 1 |
| CREBBP | 211808_s_at | CREB binding protein (Rubinstein-Taybi syndrome) |
| DCN | 211813_x_at | decorin |
| DCN | 211896_s_at | decorin |
| MAPK3 | 212046_x_at | mitogen-activated protein kinase 3 |
| MAPK1 | 212271_at | mitogen-activated protein kinase 1 |
| TFDP1 | 212330_at | transcription factor Dp-1 |
| RBL2 | 212331_at | retinoblastoma-like 2 (p130) |
| RBL2 | 212332_at | retinoblastoma-like 2 (p130) |
| SMURF1 | 212666_at | SMAD specific E3 ubiquitin protein ligase1 |
| SMURF1 | 212668_at | SMAD specific E3 ubiquitin protein ligase1 |
| ROCK1 | 213044_at | Rho-associated, coiled-coil containing protein kinase 1 |
| ACVR1B | 213198_at | activin A receptor, type IB |
| SMAD6 | 213565_s_at | SMAD, mothers against DPP homolog 6 (*Drosophila*) |
| BMPR1A | 213578_at | bone morphogenetic protein receptor, type IA |
| ID2 /// ID2B | 213931_at | inhibitor of DNA binding 2, dominant negative helix-loop-helix protein |
| ROCK1 | 214578_s_at | Rho-associated, coiled-coil containing protein kinase 1 |
| SP1 | 214732_at | Sp1 transcription factor |
| BMP6 | 215042_at | bone morphogenetic protein 6 |
| SMURF1 | 215458_s_at | SMAD specific E3 ubiquitin protein ligase 1 |
| SMURF1 | 215589_at | SMAD specific E3 ubiquitin protein ligase 1 |
| PPP2CA | 215628_x_at | Protein phosphatase 2 (formerly 2A), catalytic subunit, alpha isoform |
| THBS1 | 215775_at | Thrombospondin 1 |
| ROCK1 | 216621_at | Rho-associated, coiled-coil containing protein kinase 1 |
| ROCK1 | 216625_at | Rho-associated, coiled-coil containing protein kinase 1 |
| RBX1 | 218117_at | ring-box 1 |
| SMAD3 | 218284_at | SMAD, mothers against DPP homolog 3 (*Drosophila*) |
| TGFB2 | 220406_at | transforming growth factor, beta 2 |
| TGFB2 | 220407_s_at | transforming growth factor, beta 2 |
| E2F5 | 221586_s_at | E2F transcription factor 5, p130-binding |
| BMP8B | 221615_at | bone morphogenetic protein 8b (osteogenic protein 2) |
| CHRD | 221674_s_at | chordin |
| E2F5 | 222051_s_at | E2F transcription factor 5, p130-binding |
| DGAT2 | 224327_s_at | diacylglycerol O-acyltransferase homolog 2 (mouse) |
| MAPK1 | 224621_at | mitogen-activated protein kinase 1 |
| SP1 | 224754_at | Sp1 transcription factor |
| SP1 | 224760_at | Sp1 transcription factor |
| TGFBR1 | 224793_s_at | transforming growth factor, beta receptor I (activin A receptor type II-like kinase, 53kDa) |
| BMPR2 | 225144_at | bone morphogenetic protein receptor, type II (serine/threonine kinase) |
| SMAD5 | 225219_at | SMAD, mothers against DPP homolog 5 (*Drosophila*) |
| SMAD5 | 225223_at | SMAD, mothers against DPP homolog 5 (*Drosophila*) |
| DGAT2 | 226064_s_at | diacylglycerol O-acyltransferase homolog 2 (mouse) |
| SMAD2 | 226563_at | SMAD, mothers against DPP homolog 2 (*Drosophila*) |
| RPS6KB1 | 226660_at | ribosomal protein S6 kinase, 70kDa, polypeptide 1 |
| ID4 | 226933_s_at | Inhibitor of DNA binding 4, dominant negative helix-loop-helix protein |
| BMPR1A | 227273_at | Bone morphogenetic protein receptor, type IA |
| SMURF2 | 227489_at | SMAD specific E3 ubiquitin protein ligase 2 |
| SMAD1 | 227798_at | SMAD, mothers against DPP homolog 1 (*Drosophila*) |
| TGFB2 | 228121_at | Transforming growth factor, beta 2 |
| CREBBP | 228177_at | CREB binding protein (Rubinstein-Taybi syndrome) |
| MAPK1 | 229847_at | Mitogen-activated protein kinase 1 |
| ROCK1 | 230239_at | Rho-associated, coiled-coil containing protein kinase 1 |
| SMURF2 | 230820_at | SMAD specific E3 ubiquitin protein ligase 2 |
| BMPR1A | 230979_at | Bone morphogenetic protein receptor, type IA |
| E2F5 | 231237_x_at | E2F transcription factor 5, p130-binding |
| NOG | 231798_at | Noggin |

TABLE 3-continued

Pathway 3: Transforming Growth Factor Beta (TGFβ) signaling

| Gene Symbol | Probe Set ID | Gene Title |
| --- | --- | --- |
| BMPR2 | 231873_at | bone morphogenetic protein receptor, type II (serine/threonine kinase) |
| SMURF2 | 232020_at | SMAD specific E3 ubiquitin protein ligase 2 |
| DCN | 234104_at | Decorin |
| THBS1 | 235086_at | Thrombospondin 1 |
| BMP8B | 235275_at | Bone morphogenetic protein 8b (osteogenic protein 2) |
| SMAD5 | 235451_at | SMAD, mothers against DPP homolog 5 (*Drosophila*) |
| PPP2CA | 235502_at | Protein phosphatase 2 (formerly 2A), catalytic subunit, alpha isoform |
| SMAD2 | 235598_at | SMAD, mothers against DPP homolog 2 (*Drosophila*) |
| SMAD4 | 235622_at | SMAD, mothers against DPP homolog 4 (*Drosophila*) |
| SMAD4 | 235725_at | SMAD, mothers against DPP homolog 4 (*Drosophila*) |
| ROCK1 | 235854_x_at | Rho-associated, coiled-coil containing protein kinase 1 |
| CREBBP | 235858_at | CREB binding protein (Rubinstein-Taybi syndrome) |
| CDKN2B | 236313_at | cyclin-dependent kinase inhibitor 2B (p15, inhibits CDK4) |
| SMURF1 | 236370_at | SMAD specific E3 ubiquitin protein ligase 1 |
| TGFBR2 | 236419_at | Transforming growth factor, beta receptor II (70/80kDa) |
| TGFBR1 | 236561_at | Transforming growth factor, beta receptor I (activin A receptor type II-like kinase, 53kDa) |
| BMP8B | 237473_at | Bone morphogenetic protein 8b (osteogenic protein 2) |
| SMURF1 | 237723_at | SMAD specific E3 ubiquitin protein ligase 1 |
| SMURF2 | 238391_at | SMAD specific E3 ubiquitin protein ligase 2 |
| BMPR2 | 238393_at | Bone morphogenetic protein receptor, type II (serine/threonine kinase) |
| SMURF2 | 238394_at | SMAD specific E3 ubiquitin protein ligase 2 |
| CUL1 | 238509_at | Cullin 1 |
| BMPR2 | 238516_at | bone morphogenetic protein receptor, type II (serine/threonine kinase) |
| PPP2CA | 238719_at | Protein phosphatase 2 (formerly 2A), catalytic subunit, alpha isoform |
| PPP2CA | 239094_at | Protein phosphatase 2 (formerly 2A), catalytic subunit, alpha isoform |
| SMAD2 | 239271_at | SMAD, mothers against DPP homolog 2 (*Drosophila*) |
| THBS1 | 239336_at | Thrombospondin 1 |
| TGFBR1 | 239605_x_at | Transforming growth factor, beta receptor I (activin A receptor type II-like kinase, 53kDa) |
| BMPR1B | 240331_at | Bone morphogenetic protein receptor, type IB |
| RHOA | 240337_at | Ras homolog gene family, member A |
| DCN | 240556_at | Decorin |
| LTBP1 | 240858_at | Latent transforming growth factor beta binding protein 1 |
| RHOA | 241097_at | Ras homolog gene family, member A |
| BMP6 | 241141_at | Bone morphogenetic protein 6 |
| TFDP1 | 242538_at | Transcription factor Dp-1 |
| DCN | 242605_at | Decorin |
| TFDP1 | 242939_at | transcription factor Dp-1 |
| BMPR1A | 243275_at | Bone morphogenetic protein receptor, type IA |
| CUL1 | 243286_at | Cullin 1 |
| MYC | 244089_at | V-myc myelocytomatosis viral oncogene homolog (avian) |
| TFDP1 | 244550_at | Transcription factor Dp-1 |
| E2F4 | 38707_r_at | E2F transcription factor 4, p107/p130-binding |

TABLE 4

Pathway 4: T cell antigen processing

| Gene Symbol | Probe Set ID | Gene Title |
| --- | --- | --- |
| CD8B1 | 1553562_at | CD8 antigen, beta polypeptide 1 (p37) |
| HLA-DOB | 1554984_a_at | major histocompatibility complex, class II, DO beta |
| TAPBP | 1555565_s_at | TAP binding protein (tapasin) |
| KLRC4 /// KLRK1 | 1555691_a_at | killer cell lectin-like receptor subfamily C, |
| EEF1A1 | 1557120_at | WD repeats and SOF1 domain containing |
| HSPCB | 1557910_at | heat shock 90kDa protein 1, beta |
| NFYC | 1558782_a_at | Nuclear transcription factor Y, gamma |
| NFYC | 1559218_s_at | nuclear transcription factorY, gamma |
| CD74 | 1567627_at | CD74 antigen (invariant polypeptide of major histocompatibility complex |
| CD74 | 1567628_at | CD74 antigen (invariant polypeptide of major histocompatibility complex |
| TRIM24 | 1569316_at | Tripartite motif-containing 24 |
| HSPCB | 200064_at | heat shock 90kDa protein 1, beta /// heat shock 90kDa protein 1, beta |
| CANX | 200068_s_at | calnexin /// calnexin |
| HSPA9B | 200690_at | heat shock 70kDa protein 9B (mortalin-2) |
| HSPA9B | 200691_s_at | heat shock 70kDa protein 9B (mortalin-2) |
| HSPA9B | 200692_s_at | heat shock 70kDa protein 9B (mortalin-2) |
| HSPA1A | 200799_at | heat shock 70kDa protein 1A |
| HSPA1A /// HSPA1B | 200800_s_at | heat shock 70kDa protein 1A /// heat shock 70kDa protein 1B |

TABLE 4-continued

Pathway 4: T cell antigen processing

| Gene Symbol | Probe Set ID | Gene Title |
|---|---|---|
| PSME1 | 200814_at | proteasome (prosome, macropain) activator subunit 1 (PA28 alpha) |
| CTSB | 200838_at | cathepsin B |
| CTSB | 200839_s_at | cathepsin B |
| HLA-E | 200904_at | major histocompatibility complex, class I, E |
| HLA-E | 200905_x_at | major histocompatibility complex, class I, E |
| CALR | 200935_at | calreticulin |
| HLA-DPB1 | 201137_s_at | major histocompatibility complex, class II, DP beta 1 |
| LGMN | 201212_at | legumain |
| IFI30 | 201422_at | interferon, gamma-inducible protein 30 |
| PSME2 | 201762_s_at | proteasome (prosome, macropain) activator subunit 2 (PA28 beta) |
| B2M | 201891_s_at | beta-2-microglobulin |
| CTSL | 202087_s_at | cathepsin L |
| NFYC | 202215_s_at | nuclear transcription factor Y, gamma |
| NFYC | 202216_x_at | nuclear transcription factor Y, gamma |
| TAP1 | 202307_s_at | transporter 1, ATP-binding cassette, sub-family B (MDR/TAP) |
| HSPA1B | 202581_at | heat shock 70kDa protein 1B |
| CTSS | 202901_x_at | cathepsin S |
| CTSS | 202902_s_at | cathepsin S |
| RFX5 | 202963_at | regulatory factor X, 5 (influences HLA class II expression) |
| RFX5 | 202964_s_at | regulatory factor X, 5 (influences HLA class II expression) |
| HLA-DQA1 | 203290_at | major histocompatibility complex, class II, DQ alpha 1 complex. |
| CD4 | 203547_at | CD4 antigen (p55) /// CD4 antigen (p55) |
| HLA-DMB | 203932_at | major histocompatibility complex, class II, DM beta complex. |
| NFYA | 204107_at | nuclear transcription factor Y, alpha |
| NFYA | 204108_at | nuclear transcription factor Y, alpha |
| NFYA | 204109_s_at | nuclear transcription factor Y, alpha |
| CREB1 | 204312_x_at | cAMP responsive element binding protein 1 |
| CREB1 | 204313_s_at | cAMP responsive element binding protein 1 |
| CREB1 | 204314_s_at | cAMP responsive element binding protein 1 |
| TRIM24 | 204391_x_at | tripartite motif-containing 24 |
| HLA-DRB1 | 204670_x_at | major histocompatibility complex, class II, DR beta 1 |
| TAP2 | 204769_s_at | transporter 2, ATP-binding cassette, sub-family B (MDR/TAP) |
| TAP2 | 204770_at | transporter 2, ATP-binding cassette, sub-family B (MDR/TAP) |
| HLA-F | 204806_x_at | major histocompatibility complex, class I, F |
| EEF1A1 | 204892_x_at | eukaryotic translation elongation factor 1 alpha 1 |
| CIITA | 205101_at | class II, major histocompatibility complex, transactivator |
| HLA-DOB | 205671_s_at | major histocompatibility complex, class II, DO beta |
| CD8A | 205758_at | CD8 antigen, alpha polypeptide (p32) /// CD8 antigen, alpha polypeptide (p32) |
| KLRK1 | 205821_at | killer cell lectin-like receptor subfamily K, member 1 |
| HLA-DOA | 206313_at | major histocompatibility complex, class II, DO alpha |
| EEF1A1 | 206559_x_at | eukaryotic translation elongation factor 1 alpha 1 |
| KLRC1 /// KLRC2 | 206785_s_at | killer cell lectin-like receptor subfamily C |
| LTA | 206975_at | lymphotoxin alpha (TNF superfamily, member 1) |
| CCR5 | 206991_s_at | chemokine (C-C motif) receptor 5 |
| KIR3DL2 | 207313_x_at | killer cell immunoglobulin-like receptor, three domains, long cytoplasmic tail, 2 |
| KIR3DL2 | 207314_x_at | killer cell immunoglobulin-like receptor, three domains, long cytoplasmic tail, 2 |
| KLRC3 | 207723_s_at | killer cell lectin-like receptor subfamily C, member 3 |
| KLRD1 | 207795_s_at | killer cell lectin-like receptor subfamily D, member 1 |
| KLRD1 | 207796_x_at | killer cell lectin-like receptor subfamily D, member 1 |
| IFNA8 | 207932_at | interferon, alpha 8 |
| IFNA4 | 207964_x_at | interferon, alpha 4 |
| CD8B1 | 207979_s_at | CD8 antigen, beta polypeptide 1 (p37) |
| KIR2DS3 | 208122_x_at | killer cell immunoglobulin-like receptor, two domains, short cytoplasmic tail, 3 |
| KIR2DL3 | 208179_x_at | killer cell immunoglobulin-like receptor, two domains, long cytoplasmic tail, 3 |
| IFNA14 | 208182_x_at | interferon, alpha 14 |
| KIR2DS1 | 208198_x_at | killer cell immunoglobulin-like receptor, two domains, short cytoplasmic tail, 1 |
| KIR2DS5 | 208203_x_at | killer cell immunoglobulin-like receptor, two domains, short cytoplasmic tail, 5 |
| IFNA10 | 208261_x_at | interferon, alpha 10 |
| HLA-DRB1 | 208306_x_at | Major histocompatibility complex, class II, DR beta 3 |
| IFNA13 | 208344_x_at | interferon, alpha 13 |
| IFNA1 | 208375_at | interferon, alpha 1 |
| KIR2DL4 | 208426_x_at | killer cell immunoglobulin-like receptor, two domains, long cytoplasmic tail, 4 |
| TAP2 | 208428_at | transporter 2, ATP-binding cassette, sub-family B (MDR/TAP) |
| RFXAP | 208492_at | regulatory factor X-associated protein |
| IFNA6 | 208548_at | interferon, alpha 6 |
| PDIA3 | 208612_at | protein disulfide isomerase family A, member 3 |

TABLE 4-continued

Pathway 4: T cell antigen processing

| Gene Symbol | Probe Set ID | Gene Title |
|---|---|---|
| HSPA8 | 208687_x_at | heat shock 70kDa protein 8 |
| HLA-B | 208729_x_at | major histocompatibility complex, class I, B |
| HLA-C | 208812_x_at | major histocompatibility complex, class I, C |
| TAPBP | 208829_at | TAP binding protein (tapasin) |
| CANX | 208852_s_at | calnexin |
| CANX | 208853_s_at | calnexin |
| HLA-DRA | 208894_at | major histocompatibility complex, class II, DR alpha /// class II, DR alpha |
| HLA-B | 209140_x_at | major histocompatibility complex, class I, B |
| HLA-DRB1 | 209312_x_at | major histocompatibility complex, class II, DR beta 1 /// class II, DR beta 1 |
| HLA-DQB1 | 209480_at | Major histocompatibility complex, class II, DQ beta 1 /// class II, DQ beta 1 |
| CD74 | 209619_at | CD74 antigen (invariant polypeptide of major histocompatibility complex class II) |
| HLA-DRB4 | 209728_at | major histocompatibility complex, class II, DR beta 4 /// MHC class II, DR beta 4 |
| HLA-DQB1 | 209823_x_at | major histocompatibility complex, class II, DQ beta 1 |
| HSPA1L | 210189_at | heat shock 70kDa protein 1-like |
| HSPCA | 210211_s_at | heat shock 90kDa protein 1, alpha |
| TAPBP | 210294_at | TAP binding 7protein (tapasin) |
| HSPA8 | 210338_s_at | heat shock 70kDa protein 8 |
| HLA-G | 210514_x_at | HLA-G histocompatibility antigen, class I, G |
| KLRD1 | 210606_x_at | killer cell lectin-like receptor subfamily D, member 1 |
| KLRC4 | 210690_at | killer cell lectin-like receptor subfamily C, member 4 |
| HLA-DQB1 | 210747_at | major histocompatibility complex, class II, DQ beta 1 |
| KIR2DL1 | 210890_x_at | killer cell immunoglobulin-like receptor, two domains, long cytoplasmic tail, 1 |
| CIITA | 210925_at | class II, major histocompatibility complex, transactivator |
| HLA-DRA | 210982_s_at | major histocompatibility complex, class II, DR alpha |
| HLA-DOA | 211142_x_at | major histocompatibility complex, class II, DO alpha |
| IFNA21 | 211145_x_at | interferon, alpha 21 |
| KIR2DL4 | 211242_x_at | killer cell immunoglobulin-like receptor, two domains, long cytoplasmic tail, 4 |
| KIR2DL4 | 211245_x_at | killer cell immunoglobulin-like receptor, two domains, long cytoplasmic tail, 4 |
| NFYC | 211251_x_at | nuclear transcription factor Y, gamma |
| IFNA2 | 211338_at | interferon, alpha 2 |
| KIR3DL1 | 211389_x_at | killer cell immunoglobulin-like receptor, three domains, long cytoplasmic tail, 1 |
| IFNA17 | 211405_x_at | interferon, alpha 17 |
| KIR2DL5A | 211410_x_at | killer cell immunoglobulin-like receptor, two domains, long cytoplasmic tail, 5A |
| HLA-G | 211528_x_at | HLA-G histocompatibility antigen, class I, G |
| HLA-G | 211529_x_at | HLA-G histocompatibility antigen, class I, G |
| HLA-G | 211530_x_at | HLA-G histocompatibility antigen, class I, G |
| KIR2DS2 | 211532_x_at | killer cell immunoglobulin-like receptor, two domains, short cytoplasmic tail, 2 |
| HLA-DQB1 | 211654_x_at | major histocompatibility complex, class II, DQ beta 1 /// MHC class II, DQ beta 1 |
| HLA-DQB1 | 211656_x_at | major histocompatibility complex, class II, DQ beta 1 /// MHC class II, DQ beta 1 |
| KIR3DL1 | 211687_x_at | killer cell immunoglobulin-like receptor, three domains, long cytoplasmic tail. |
| KIR3DL1 /// KIR3DL2 | 211688_x_at | killer cell immunoglobulin-like receptor, three domains, long cytoplasmic tail. |
| NFYC | 211797_s_at | nuclear transcription factor Y, gamma |
| HLA-C | 211799_x_at | major histocompatibility complex, class I, C |
| CIITA | 211884_s_at | class II, major histocompatibility complex, transactivator |
| HLA-B | 211911_x_at | major histocompatibility complex, class I, B /// MHC class I, B |
| HSPA5 | 211936_at | heat shock 70kDa protein 5 (glucose-regulated protein, 78kDa) |
| HSPCA | 211968_s_at | heat shock 90kDa protein 1, alpha |
| HSPCA | 211969_at | heat shock 90kDa protein 1, alpha |
| HLA-DPA1 | 211990_at | major histocompatibility complex, class II, DP alpha 1 |
| HLA-DPA1 | 211991_s_at | major histocompatibility complex, class II, DP alpha 1 |
| HLA-DQA1 /// HLA-DQA2 | 212671_s_at | major histocompatibility complex, class II, DQ alpha 1 /// MHC class II, DQ alpha 2 |
| CALR | 212952_at | Calreticulin |
| CALR | 212953_x_at | calreticulin |
| HLA-DQB1 | 212998_x_at | major histocompatibility complex, class II, DQ beta 1 /// MHC class II, DQ beta 1 |
| HLA-DQB1 | 212999_x_at | Major histocompatibility complex, class II, DO beta 1 /// MHC class II, DQ beta 1 |
| CTSB | 213274_s_at | cathepsin B |
| CTSB | 213275_x_at | cathepsin B |

TABLE 4-continued

Pathway 4: T cell antigen processing

| Gene Symbol | Probe Set ID | Gene Title |
| --- | --- | --- |
| TRIM24 | 213301_x_at | tripartite motif-containing 24 |
| EEF1A1 | 213477_x_at | eukaryotic translation elongation factor 1 alpha 1 |
| HLA-DPA1 | 213537_at | major histocompatibility complex, class II, DP alpha 1 |
| EEF1A1 /// LOC387845 /// LOC389223 /// LOC440595 /// LOC441032 | 213583_x_at | eukaryotic translation elongation factor 1 |
| EEF1A1 | 213614_x_at | eukaryotic translation elongation factor 1 alpha 1 |
| HLA-DQA1 | 213831_at | major histocompatibility complex, class II, DQ alpha 1 |
| HLA-A | 213932_x_at | Major histocompatibility complex, class I, A |
| CALR | 214315_x_at | calreticulin |
| CALR | 214316_x_at | Calreticulin |
| HSPCA | 214328_s_at | heat shock 90kDa protein 1, alpha |
| HSPCB | 214359_s_at | heat shock 90kDa protein 1, beta |
| HLA-C | 214459_x_at | major histocompatibility complex, class I, C |
| CREB1 | 214513_s_at | cAMP responsive element binding protein 1 |
| IFNA5 | 214569_at | interferon, alpha 5 |
| HLA-DRB1 | 215193_x_at | major histocompatibility complex, class II, DR beta 1 |
| HLA-A | 215313_x_at | major histocompatibility complex, class I, A |
| CD8B1 | 215332_s_at | CD8 antigen, beta polypeptide 1 (p37) |
| HLA-DQB2 | 215536_at | major histocompatibility complex, class II, DQ beta 2 |
| HLA-DRB4 | 215666_at | major histocompatibility complex, class II, DR beta 4 |
| HLA-DRB4 | 215669_at | major histocompatibility complex, class II, DR beta 4 |
| NFYA | 215720_s_at | nuclear transcription factor Y, alpha |
| B2M | 216231_s_at | beta-2-microglobulin |
| CD4 | 216424_at | CD4 antigen (p55) |
| HLA-C | 216526_x_at | major histocompatibility complex, class I, C |
| KIR3DL3 | 216676_x_at | killer cell immunoglobulin-like receptor, three domains, long cytoplasmic tail, 3 |
| KIR3DL2 | 216907_x_at | killer cell immunoglobulin-like receptor, three domains, long cytoplasmic tail, 2 |
| HLA-DOA | 216946_at | major histocompatibility complex, class II, DO alpha |
| HLA-DOA | 217001_x_at | major histocompatibility complex, class II, DO alpha |
| KIR2DS1 | 217296_at | Killer cell immunoglobulin-like receptor, two domains, short cytoplasmic tail, 1 |
| KIR3DL2 /// KIR2DL5A /// KIR3DL3 /// KIR3DP1 /// KIR2DL5B | 217318_x_at | killer cell immunoglobulin-like receptor, three domains, long cytoplasmic tail, 2 /// killer cell immunoglobulin-like receptor, two domains, long cytoplasmic tail, 5A /// killer cell immunoglobulin-like receptor, three domains, long cytoplasmic tail, 3 /// killer cell immunoglobulin-like receptor, three domains, pseudogene 1 /// killer cell immunoglobulin-like receptor, two domains, long cytoplasmic tail, 5B |
| HLA-G /// HLA-H | 217436_x_at | HLA-G histocompatibility antigen, class I, G /// major histocompatibility complex, class I, H (pseudogene) |
| HLA-E | 217456_x_at | major histocompatibility complex, class I, E |
| HLA-DMA | 217478_s_at | major histocompatibility complex, class II, DM alpha |
| NFYB | 218127_at | nuclear transcription factor Y, beta |
| NFYB | 218128_at | nuclear transcription factor Y, beta |
| NFYB | 218129_s_at | nuclear transcription factor Y, beta |
| HLA-DRB1 /// HLA-DRB3 /// HLA-DRB4 | 221491_x_at | major histocompatibility complex, class II, DR beta 1 /// major histocompatibility complex, class II, DR beta 1 /// major histocompatibility complex, class II, DR beta 3 /// major histocompatibility complex, class II, DR beta 3 /// major histocompatibility complex, class II, DR beta 4 /// major histocompatibility complex, class II, DR beta 4 |
| HLA-F | 221875_x_at | major histocompatibility complex, class I, F |
| HSPA8 | 221891_x_at | heat shock 70kDa protein 8 |
| HLA-F | 221978_at | major histocompatibility complex, class I, F |
| HSPA8 | 224187_x_at | heat shock 70kDa protein 8 |
| TAP2 | 225973_at | transporter 2, ATP-binding cassette, sub-family B (MDR/TAP) |
| HLA-DOA | 226878_at | major histocompatibility complex, class II, DO alpha |
| PDIA3 | 227033_at | protein disulfide isomerase family A, member 3 |
| EEF1A1 | 227708_at | eukaryotic translation elongation factor 1 alpha 1 |
| CTSB | 227961_at | cathepsin B |
| RFXAP | 229431_at | regulatory factor X-associated protein |
| HSPA5 | 230031_at | heat shock 70kDa protein 5 (glucose-regulated protein, 78kDa) |
| CD8B1 | 230037_at | CD8 antigen, beta polypeptide 1 (p37) |
| HSPA9B | 232200_at | heat shock 70kDa protein 9B (mortalin-2) |
| CTSS | 232617_at | cathepsin S |
| HLA-DQA1 | 236203_at | Major histocompatibility complex, class II, DQ alpha 1 |
| CTSS | 237104_at | Cathepsin S |

TABLE 4-continued

Pathway 4: T cell antigen processing

| Gene Symbol | Probe Set ID | Gene Title |
|---|---|---|
| CANX | 238034_at | calnexin |
| NFYC | 238231_at | Nuclear transcription factor Y, gamma |
| HLA-DRB1 /// HLA-DRB3 | 238900_at | major histocompatibility complex, class II, DR beta 1 /// major histocompatibility complex, class II, DR beta 3 |
| NFYC | 241630_at | Nuclear transcription factor Y, gamma |
| HSPA9B | 241840_at | Heat shock 70kDa protein 9B (mortalin-2) |
| CD74 | 241849_at | CD74 antigen (invariant polypeptide of major histocompatibility complex, class II antigen-associated) |
| KLRK1 | 242873_at | Killer cell lectin-like receptor subfamily K, member 1 |
| CTSB | 243157_at | Cathepsin B |
| CREB1 | 243625_at | CAMP responsive element binding protein 1 |
| NFYB | 244704_at | nuclear transcription factor Y, beta |

TABLE 5

Pathway 5: T cell signaling

| Gene Symbol | Probe Set ID | Gene Title |
|---|---|---|
| PTPRC | 1552480_s_at | protein tyrosine phosphatase, receptor type, C |
| CD8B1 | 1553562_at | CD8 antigen, beta polypeptide 1 (p37) |
| PAK6 | 1555310_a_at | p21(CDKN1A)-activated kinase 6 |
| ZAP70 | 1555613_a_at | zeta-chain (TCR) associated protein kinase 70kDa |
| RHOA | 1555814_a_at | ras homolog gene family, member A |
| CDC42 | 1556931_at | Cell division cycle 42 (GTP binding protein, 25kDa) |
| BCL10 | 1557258_a_at | B-cell CLL/lymphoma 10 |
| PPP3CA | 1557637_at | Protein phosphatase 3 (formerly 2B), catalytic subunit, alpha isoform (calcineurin A alpha) |
| PAK2 | 1559052_s_at | p21 (CDKN1A)-activated kinase 2 |
| FYN | 1559101_at | FYN oncogene related to SRC, FGR, YES |
| KRAS | 1559203_s_at | v-Ki-ras2 Kirsten rat sarcoma viral oncogene homolog |
| KRAS | 1559204_x_at | v-Ki-ras2 Kirsten rat sarcoma viral oncogene homolog |
| PPP3CA | 1560552_a_at | Protein phosphatase 3 (formerly 2B), catalytic subunit, alpha isoform (calcineurin A alpha) |
| AKT2 | 1560689_s_at | V-akt murine thymoma viral oncogene homolog 2 |
| CARD11 | 1562368_at | caspase recruitment domain family, member 11 |
| PPP3R1 | 1565810_at | Protein phosphatase 3 (formerly 2B), regulatory subunit B, 19kDa, alpha isoform |
| PPP3R1 | 1565811_at | Protein phosphatase 3 (formerly 2B), regulatory subunit B, 19kDa, alpha isoform |
| PPP3CA | 1566201_at | Protein phosphatase 3 (formerly 2B), catalytic subunit, alpha isoform (calcineurin A alpha) |
| PPP3CA | 1566202_at | Protein phosphatase 3 (formerly 2B), catalytic subunit, alpha isoform (calcineurin A alpha) |
| PIK3R2 | 1568629_s_at | phosphoinositide-3-kinase, regulatory subunit 2 (p85 beta) |
| PTPRC | 1569830_at | Protein tyrosine phosphatase, receptor type, C |
| NFKB1 | 1570362_at | Nuclear factor of kappa light polypeptide gene enhancer in B-cells 1 (p105) |
| RHOA | 200059_s_at | ras homolog gene family, member A /// ras homolog gene family, member A |
| JUN | 201464_x_at | v-jun sarcoma virus 17 oncogene homolog (avian) |
| JUN | 201465_s_at | v-jun sarcoma virus 17 oncogene homolog (avian) |
| JUN | 201466_s_at | v-jun sarcoma virus 17 oncogene homolog (avian) |
| NFKBIA | 201502_s_at | nuclear factor of kappa light polypeptide gene enhancer in B-cells inhibitor, alpha |
| CDK4 | 202246_s_at | cyclin-dependent kinase 4 |
| PPP3CA | 202425_x_at | protein phosphatase 3 (formerly 2B), catalytic subunit, alpha isoform (calcineurin A alpha) |
| PPP3CA | 202429_s_at | protein phosphatase 3 (formerly 2B), catalytic subunit, alpha isoform (calcineurin A alpha) |
| PPP3CB | 202432_at | protein phosphatase 3 (formerly 2B), catalytic subunit, beta isoform (calcineurin A beta) |
| PPP3CA | 202457_s_at | protein phosphatase 3 (formerly 2B), catalytic subunit, alpha isoform (calcineurin A alpha) |
| NRAS | 202647_s_at | neuroblastoma RAS viral (v-ras) oncogene homolog |
| PIK3R3 | 202743_at | phosphoinositide-3-kinase, regulatory subunit 3 (p55, gamma) |
| PLCG1 | 202789_at | phospholipase C, gamma 1 |
| PAK4 | 203154_s_at | p21(CDKN1A)-activated kinase 4 |
| NCK2 | 203315_at | NCK adaptor protein 2 |
| CD4 | 203547_at | CD4 antigen (p55) /// CD4 antigen (p55) |
| AKT2 | 203808_at | v-akt murine thymoma viral oncogene homolog 2 |
| AKT2 | 203809_s_at | v-akt murine thymoma viral oncogene homolog 2 |

TABLE 5-continued

Pathway 5: T cell signaling

| Gene Symbol | Probe Set ID | Gene Title |
|---|---|---|
| PIK3CD | 203879_at | phosphoinositide-3-kinase, catalytic, delta polypeptide /// phosphoinositide-3-kinase. |
| NFKBIE | 203927_at | nuclear factor of kappa light polypeptide gene enhancer in B-cells inhibitor, epsilon |
| KRAS | 204009_s_at | v-Ki-ras2 Kirsten rat sarcoma viral oncogene homolog |
| KRAS | 204010_s_at | v-Ki-ras2 Kirsten rat sarcoma viral oncogene homolog |
| PIK3CA | 204369_at | phosphoinositide-3-kinase, catalytic, alpha polypeptide |
| PPP3R1 | 204506_at | protein phosphatase 3 (formerly 2B), regulatory subunit B, 19kDa, alpha isoform |
| PPP3R1 | 204507_s_at | protein phosphatase 3 (formerly 2B), regulatory subunit B, 19kDa, alpha isoform |
| NCK1 | 204725_s_at | NCK adaptor protein 1 |
| LCK | 204890_s_at | lymphocyte-specific protein tyrosine kinase |
| LCK | 204891_s_at | lymphocyte-specific protein tyrosine kinase |
| MAP3K8 | 205027_s_at | mitogen-activated protein kinase kinase kinase 8 |
| MAP3K14 | 205192_at | mitogen-activated protein kinase kinase kinase 14 |
| BCL10 | 205263_at | B-cell CLL/lymphoma 10 |
| LCP2 | 205269_at | lymphocyte cytosolic protein 2 (SH2 domain containing leukocyte protein of 76kDa) |
| LCP2 | 205270_s_at | lymphocyte cytosolic protein 2 (SH2 domain containing leukocyte protein of 76kDa) |
| CD3E | 205456_at | CD3E antigen, epsilon polypeptide (TiT3 complex) |
| VAV2 | 205536_at | vav 2 oncogene |
| VAV2 | 205537_s_at | vav 2 oncogene |
| RASGRP1 | 205590_at | RAS guanyl releasing protein 1 (calcium and DAG-regulated) |
| CD8A | 205758_at | CD8 antigen, alpha polypeptide (p32) /// CD8 antigen, alpha polypeptide (p32) |
| NFATC4 | 205897_at | nuclear factor of activated T-cells, cytoplasmic, calcineurin-dependent 4 |
| PAK2 | 205962_at | p21 (CDKN1A)-activated kinase 2 |
| VAV1 | 206219_s_at | vav 1 oncogene |
| TEC | 206301_at | tec protein tyrosine kinase |
| PIK3CG | 206369_s_at | phosphoinositide-3-kinase, catalytic, gamma polypeptide |
| PIK3CG | 206370_at | phosphoinositide-3-kinase, catalytic, gamma polypeptide |
| MRAS | 206538_at | muscle RAS oncogene homolog |
| CD28 | 206545_at | CD28 antigen (Tp44) |
| CBL | 206607_at | Cas-Br-M (murine) ecotropic retroviral transforming sequence |
| PDK1 | 206686_at | pyruvate dehydrogenase kinase, isoenzyme 1 |
| PTPN6 | 206687_s_at | protein tyrosine phosphatase, non-receptor type 6 |
| CD3G | 206804_at | CD3G antigen, gamma polypeptide (TiT3 complex) |
| PPP3CC | 207000_s_at | protein phosphatase 3 (formerly 2B), catalytic subunit, gamma isoform |
| PIK3R2 | 207105_s_at | phosphoinositide-3-kinase, regulatory subunit 2 (p85 beta) |
| TNF | 207113_s_at | tumor necrosis factor (TNF superfamily, member 2) |
| AKT1 | 207163_s_at | v-akt murine thymoma viral oncogene homolog 1 |
| PTPRC | 207238_s_at | protein tyrosine phosphatase, receptor type, C |
| NFATC3 | 207416_s_at | nuclear factor of activated T-cells, cytoplasmic, calcineurin-dependent 3 |
| IL10 | 207433_at | interleukin 10 |
| NFKB2 | 207535_s_at | nuclear factor of kappa light polypeptide gene enhancer in B-cells 2 (p49/p100) |
| IL4 | 207538_at | interleukin 4 |
| IL4 | 207539_s_at | interleukin 4 |
| PDCD1 | 207634_at | programmed cell death 1 |
| IL2 | 207849_at | interleukin 2 |
| CD40LG | 207892_at | CD40 ligand (TNF superfamily, member 5, hyper-IgM syndrome) |
| IL5 | 207952_at | interleukin 5 (colony-stimulating factor, eosinophil) |
| CD8B1 | 207979_s_at | CD8 antigen, beta polypeptide 1 (p37) |
| CHP | 207993_s_at | calcium binding protein P22 |
| NFAT5 | 208003_s_at | nuclear factor of activated T-cells 5, tonicity-responsive |
| NFATC1 | 208196_x_at | nuclear factor of activated T-cells, cytoplasmic, calcineurin-dependent 1 |
| MALT1 | 208309_s_at | mucosa associated lymphoid tissue lymphoma translocation gene 1 |
| CBLB | 208348_s_at | Cas-Br-M (murine) ecotropic retroviral transforming sequence b |
| GRAP2 | 208406_s_at | GRB2-related adaptor protein 2 |
| RRAS2 | 208456_s_at | related RAS viral (r-ras) oncogene homolog 2 |
| CDC42 | 208727_s_at | cell division cycle 42 (GTP binding protein, 25kDa) |
| CDC42 | 208728_s_at | cell division cycle 42 (GTP binding protein, 25kDa) |
| PAK2 | 208875_s_at | p21 (CDKN1A)-activated kinase 2 |
| PAK2 | 208876_s_at | p21 (CDKN1A)-activated kinase 2 |
| PAK2 | 208877_at | p21 (CDKN1A)-activated kinase 2 |
| PAK2 | 208878_s_at | p21 (CDKN1A)-activated kinase 2 |
| FOS | 209189_at | v-fos FBJ murine osteosarcoma viral oncogene homolog |
| NFKB1 | 209239_at | nuclear factor of kappa light polypeptide gene enhancer in B-cells 1 (p105) |
| IKBKB | 209341_s_at | inhibitor of kappa light polypeptide gene enhancer in B-cells, kinase beta |
| IKBKB | 209342_s_at | inhibitor of kappa light polypeptide gene enhancer in B-cells, kinase beta |
| NFKB2 | 209636_at | nuclear factor of kappa light polypeptide gene enhancer in B-cells 2 (p49/p100) |

TABLE 5-continued

Pathway 5: T cell signaling

| Gene Symbol | Probe Set ID | Gene Title |
|---|---|---|
| NFATC1 | 209664_x_at | nuclear factor of activated T-cells, cytoplasmic, calcineurin-dependent 1 |
| CHUK | 209666_s_at | conserved helix-loop-helix ubiquitous kinase |
| CBLB | 209682_at | Cas-Br-M (murine) ecotropic retroviral transforming sequence b |
| PPP3CC | 209697_at | protein phosphatase 3 (formerly 2B), catalytic subunit, gamma isoform (calcineurin A gamma) |
| PPP3CB | 209817_at | protein phosphatase 3 (formerly 2B), catalytic subunit, beta isoform (calcineurin A beta) |
| LAT | 209881_s_at | linker for activation of T cells |
| IKBKG | 209929_s_at | inhibitor of kappa light polypeptide gene enhancer in B-cells, kinase gamma |
| MALT1 | 210017_at | mucosa associated lymphoid tissue lymphoma translocation gene 1 |
| MALT1 | 210018_x_at | mucosa associated lymphoid tissue lymphoma translocation gene 1 |
| CD3Z | 210031_at | CD3Z antigen, zeta polypeptide (TiT3 complex) |
| PRKCQ | 210038_at | protein kinase C, theta |
| PRKCQ | 210039_s_at | protein kinase C, theta |
| FYN | 210105_s_at | FYN oncogene related to SRC, FGR, YES |
| NFATC1 | 210162_s_at | nuclear factor of activated T-cells, cytoplasmic, calcineurin-dependent 1 |
| CSF2 | 210228_at | colony stimulating factor 2 (granulocyte-macrophage) |
| CSF2 | 210229_s_at | colony stimulating factor 2 (granulocyte-macrophage) |
| CDC42 | 210232_at | cell division cycle 42 (GTP binding protein, 25kDa) |
| IFNG | 210354_at | interferon, gamma |
| ICOS | 210439_at | inducible T-cell co-stimulator |
| NFATC3 | 210555_s_at | nuclear factor of activated T-cells, cytoplasmic, calcineurin-dependent 3 |
| NFATC3 | 210556_at | nuclear factor of activated T-cells, cytoplasmic, calcineurin-dependent 3 |
| PAK7 | 210721_s_at | p21(CDKN1A)-activated kinase 7 |
| LAT | 211005_at | linker for activation of T cells |
| IKBKB | 211027_s_at | inhibitor of kappa light polypeptide gene enhancer in B-cells, kinase beta |
| NCK1 | 211063_s_at | NCK adaptor protein 1 /// NCK adaptor protein 1 |
| NFATC1 | 211105_s_at | nuclear factor of activated T-cells, cytoplasmic, calcineurin-dependent 1 |
| PIK3CD | 211230_s_at | phosphoinositide-3-kinase, catalytic, delta polypeptide |
| ITK | 211339_s_at | IL2-inducible T-cell kinase |
| AKT2 | 211453_s_at | v-akt murine thymoma viral oncogene homolog 2 |
| NFKB2 | 211524_at | nuclear factor of kappa light polypeptide gene enhancer in B-cells 2 (p49/p100) |
| PIK3R3 | 211580_s_at | phosphoinositide-3-kinase, regulatory subunit 3 (p55, gamma) |
| SOS2 | 211665_s_at | son of sevenless homolog 2 (Drosophila) /// son of sevenless homolog 2 (Drosophila) |
| CD28 | 211856_x_at | CD28 antigen (Tp44) |
| CD28 | 211861_x_at | CD28 antigen (Tp44) |
| PIK3R1 | 212239_at | phosphoinositide-3-kinase, regulatory subunit 1 (p85 alpha) |
| PIK3R1 | 212240_s_at | phosphoinositide-3-kinase, regulatory subunit 1 (p85 alpha) |
| PIK3R1 | 212249_at | phosphoinositide-3-kinase, regulatory subunit 1 (p85 alpha) |
| FYN | 212486_s_at | FYN oncogene related to SRC, FGR, YES |
| PTPRC | 212587_s_at | protein tyrosine phosphatase, receptor type, C |
| PTPRC | 212588_at | protein tyrosine phosphatase, receptor type, C |
| RRAS2 | 212590_at | related RAS viral (r-ras) oncogene homolog 2 |
| AKT3 | 212607_at | v-akt murine thymoma viral oncogene homolog 3 (protein kinase B, gamma) |
| AKT3 | 212609_s_at | V-akt murine thymoma viral oncogene homolog 3 (protein kinase B, gamma) |
| RRAS | 212647_at | related RAS viral (r-ras) oncogene homolog |
| PIK3CB | 212688_at | phosphoinositide-3-kinase, catalytic, beta polypeptide |
| PIK3R4 | 212740_at | phosphoinositide-3-kinase, regulatory subunit 4, p150 |
| SOS1 | 212777_at | son of sevenless homolog 1 (Drosophila) |
| SOS1 | 212780_at | son of sevenless homolog 1 (Drosophila) |
| HRAS | 212983_at | v-Ha-ras Harvey rat sarcoma viral oncogene homolog |
| NFATC4 | 213345_at | nuclear factor of activated T-cells, cytoplasmic, calcineurin-dependent 4 |
| CD3D | 213539_at | CD3D antigen, delta polypeptide (TiT3 complex) |
| PPP3CC | 213950_s_at | Protein phosphatase 3 (formerly 2B), catalytic subunit, gamma isoform |
| PAK7 | 213990_s_at | p21(CDKN1A)-activated kinase 7 |
| ZAP70 | 214032_at | zeta-chain (TCR) associated protein kinase 70kDa |
| NFKBIB | 214062_x_at | nuclear factor of kappa light polypeptide gene enhancer in B-cells inhibitor, beta |
| PAK3 | 214078_at | P21 (CDKN1A)-activated kinase 3 |
| CDC42 | 214230_at | cell division cycle 42 (GTP binding protein, 25kDa) |
| KRAS | 214352_s_at | v-Ki-ras2 Kirsten rat sarcoma viral oncogene homolog |
| NFKBIB | 214448_x_at | nuclear factor of kappa light polypeptide gene enhancer in B-cells inhibitor, beta |
| PAK3 | 214607_at | p21 (CDKN1A)-activated kinase 3 |
| CHP | 214665_s_at | calcium binding protein P22 |
| GRB2 | 215075_s_at | growth factor receptor-bound protein 2 |
| NFAT5 | 215092_s_at | nuclear factor of activated T-cells 5, tonicity-responsive |
| CD8B1 | 215332_s_at | CD8 antigen, beta polypeptide 1 (p37) |
| FYN | 216033_s_at | FYN oncogene related to SRC, FGR, YES |

TABLE 5-continued

Pathway 5: T cell signaling

| Gene Symbol | Probe Set ID | Gene Title |
|---|---|---|
| CD4 | 216424_at | CD4 antigen (p55) |
| PIK3R4 | 216436_at | Phosphoinositide-3-kinase, regulatory subunit 4, p150 |
| PLCG1 | 216551_x_at | phospholipase C, gamma 1 |
| PIK3R4 | 216752_at | Phosphoinositide-3-kinase, regulatory subunit 4, p150 |
| SOS2 | 217575_s_at | Son of sevenless homolog 2 (*Drosophila*) |
| SOS2 | 217576_x_at | son of sevenless homolog 2 (*Drosophila*) |
| PIK3CB | 217620_s_at | phosphoinositide-3-kinase, catalytic, beta polypeptide |
| SOS2 | 217644_s_at | son of sevenless homolog 2 (*Drosophila*) |
| FYN | 217697_at | FYN oncogene related to SRC, FGR, YES |
| VAV3 | 218806_s_at | vav 3 oncogene |
| VAV3 | 218807_at | vav 3 oncogene |
| AKT3 | 219393_s_at | v-akt murine thymoma viral oncogene homolog 3 (protein kinase B, gamma) |
| PAK6 | 219461_at | p21(CDKN1A)-activated kinase 6 |
| PIK3R5 | 220566_at | phosphoinositide-3-kinase, regulatory subunit 5, p101 |
| CBLC | 220638_s_at | Cas-Br-M (murine) ecotropic retroviral transforming sequence c |
| CTLA4 | 221331_x_at | cytotoxic T-lymphocyte-associated protein 4 |
| AKT3 | 222880_at | v-akt murine thymoma viral oncogene homolog 3 (protein kinase B, gamma) |
| GRB2 | 223049_at | growth factor receptor-bound protein 2 |
| CARD11 | 223514_at | caspase recruitment domain family, member 11 |
| CBLC | 223668_at | Cas-Br-M (murine) ecotropic retroviral transforming sequence c |
| VAV3 | 224221_s_at | vav 3 oncogene |
| AKT3 | 224229_s_at | v-akt murine thymoma viral oncogene homolog 3 (protein kinase B, gamma) |
| NFATC2 | 224542_s_at | nuclear factor of activated T-cells, cytoplasmic, calcineurin-dependent 2 |
| NFAT5 | 224984_at | nuclear factor of activated T-cells 5, tonicity-responsive |
| MRAS | 225185_at | muscle RAS oncogene homolog |
| CBL | 225231_at | Cas-Br-M (murine) ecotropic retroviral transforming sequence |
| CBL | 225234_at | Cas-Br-M (murine) ecotropic retroviral transforming sequence |
| AKT2 | 225471_s_at | v-akt murine thymoma viral oncogene homolog 2 |
| VAV2 | 226063_at | vav 2 oncogene |
| CDG42 | 226400_at | Cell division cycle 42 (GTP binding protein, 25kDa) |
| PDK1 | 226452_at | pyruvate dehydrogenase kinase, isoenzyme 1 |
| NFATC2 | 226991_at | Nuclear factor of activated T-cells, cytoplasmic, calcineurin-dependent 2 |
| SOS1 | 227426_at | Son of sevenless homolog 1 (*Drosophila*) |
| PIK3R5 | 227645_at | phosphoinositide-3-kinase, regulatory subunit 5, p101 |
| CBLB | 227900_at | Cas-Br-M (murine) ecotropic retroviral transforming sequence b |
| NFKBIB | 228388_at | nuclear factor of kappa light polypeptide gene enhancer in B-cells inhibitor, beta |
| NFATC2 | 228442_at | Nuclear factor of activated T-cells, cytoplasmic, calcineurin-dependent 2 |
| GRB2 | 228572_at | growth factor receptor-bound protein 2 |
| CBL | 229010_at | Cas-Br-M (murine) ecotropic retroviral transforming sequence |
| NFATC3 | 229223_at | Nuclear factor of activated T-cells, cytoplasmic, calcineurin-dependent 3 |
| SOS1 | 229261_at | Son of sevenless homolog 1 (*Drosophila*) |
| PIK3R2 | 229392_s_at | Phosphoinositide-3-kinase, regulatory subunit 2 (p85 beta) |
| PPP3CA | 229606_at | Protein phosphatase 3 (formerly 2B), catalytic subunit, alpha isoform (calcineurin A alpha) |
| NCK1 | 229895_s_at | NCK adaptor protein 1 |
| CD8B1 | 230037_at | CD8 antigen, beta polypeptide 1 (p37) |
| SOS1 | 230337_at | son of sevenless homolog 1 (*Drosophila*) |
| PPP3R2 | 231304_at | protein phosphatase 3 (formerly 2B), regulatory subunit B, 19kDa, beta isoform |
| NFKBIA | 231699_at | Nuclear factor of kappa light polypeptide gene enhancer in B-cells inhibitor, alpha |
| CTLA4 | 231794_at | cytotoxic T-lymphocyte-associated protein 4 |
| NFATC2 | 231801_at | nuclear factor of activated T-cells, cytoplasmic, calcineurin-dependent 2 |
| NFATC2 | 233706_at | Nuclear factor of activated T-cells, cytoplasmic, calcineurin-dependent 2 |
| NFATC2 | 233708_at | Nuclear factor of activated T-cells, cytoplasmic, calcineurin-dependent 2 |
| RASGRP1 | 233926_at | RAS guanyl releasing protein 1 (calcium and DAG-regulated) |
| CBLB | 234112_at | Cas-Br-M (murine) ecotropic retroviral transforming sequence b |
| CTLA4 | 234362_s_at | cytotoxic T-lymphocyte-associated protein 4 |
| NCK2 | 234595_at | NCK adaptor protein 2 |
| NCK2 | 234705_at | NCK adaptor protein 2 |
| CTLA4 | 234895_at | cytotoxic T-lymphocyte-associated protein 4 |
| MAP3K8 | 235421_at | Mitogen-activated protein kinase kinase kinase 8 |
| NFATC4 | 236270_at | nuclear factor of activated T-cells, cytoplasmic, calcineurin-dependent 4 |
| PAK3 | 236277_at | P21 (CDKN1A)-activated kinase 3 |
| PAK2 | 236283_x_at | p21 (CDKN1A)-activated kinase 2 |
| CTLA4 | 236341_at | cytotoxic T-lymphocyte-associated protein 4 |
| PPP3CA | 236545_at | Protein phosphatase 3 (formerly 2B), catalytic subunit, alpha isoform (calcineurin A alpha) |
| PRKCQ | 237542_at | Protein kinase C, theta |
| SOS2 | 238830_at | Son of sevenless homolog 2 (*Drosophila*) |

TABLE 5-continued

Pathway 5: T cell signaling

| Gene Symbol | Probe Set ID | Gene Title |
|---|---|---|
| PAK6 | 239470_at | P21 (CDKN1A)-activated kinase 6 |
| NFKB1 | 239876_at | Nuclear factor of kappa light polypeptide gene enhancer in B-cells 1 (p105) |
| RHOA | 240337_at | Ras homolog gene family, member A |
| AKT3 | 240568_at | V-akt murine thymoma viral oncogene homolog 3 (protein kinase B, gamma) |
| RHOA | 241097_at | Ras homolog gene family, member A |
| PPP3R1 | 241786_at | Protein phosphatase 3 (formerly 2B), regulatory subunit B, 19kDa, alpha isoform |
| SOS1 | 242018_at | Son of sevenless homolog 1 (Drosophila) |
| SOS1 | 242682_at | Son of sevenless homolog 1 (Drosophila) |
| AKT3 | 242876_at | V-akt murine thymoma viral oncogene homolog 3 (protein kinase B, gamma) |
| AKT3 | 242879_x_at | V-akt murine thymoma viral oncogene homolog 3 (protein kinase B, gamma) |
| FYN | 243006_at | FYN oncogene related to SRC, FGR, YES |
| CBL | 243475_at | Cas-Br-M (murine) ecotropic retroviral transforming sequence |
| PIK3R1 | 244181_at | Phosphoinositide-3-kinase, regulatory subunit 1 (p85 alpha) |
| LCP2 | 244251_at | Lymphocyte cytosolic protein 2 (SH2 domain containing leukocyte protein of 76kDa) |
| PAK2 | 244268_x_at | p21 (CDKN1A)-activated kinase 2 |
| LCP2 | 244556_at | Lymphocyte cytosolic protein 2 (SH2 domain containing leukocyte protein of 76kDa) |
| LCP2 | 244578_at | lymphocyte cytosolic protein 2 (SH2 domain containing leukocyte protein of 76kDa) |
| PPP3R2 | 244782_at | protein phosphatase 3 (formerly 2B), regulatory subunit B, 19kDa, beta isoform |
| PPP3CC | 32540_at | Protein phosphatase 3 (formerly 2B), catalytic subunit, gamma isoform |
| PPP3CC | 32541_at | protein phosphatase 3 (formerly 2B), catalytic subunit, gamma isoform |
| PAK4 | 33814_at | p21(CDKN1A)-activated kinase 4 |
| IKBKG | 36004_at | inhibitor of kappa light polypeptide gene enhancer in B-cells, kinase gamma |

TABLE 6

Pathway 6: Mitogen activated protein kinase

| Gene Symbol | Probe Set ID | Gene Title |
|---|---|---|
| MAPK1 | 1552263_at | mitogen-activated protein kinase 1 |
| MAPK1 | 1552264_a_at | mitogen-activated protein kinase 1 |
| ACVR1C | 1552519_at | activin A receptor, type IC |
| CACNG5 | 1552602_at | calcium channel, voltage-dependent, gamma subunit 5 |
| MAP3K6 | 1552631_a_at | mitogen-activated protein kinase kinase kinase 6 |
| CASP1 /// COP1 | 1552703_s_at | caspase 1, apoptosis-related cysteine peptidase (interleukin 1, beta, convertase) |
| FGF1 | 1552721_a_at | fibroblast growth factor 1 (acidic) |
| CACNG6 | 1552863_a_at | calcium channel, voltage-dependent, gamma subunit 6 |
| FGF4 | 1552982_a_at | fibroblast growth factor 4 (heparin secretory transforming protein 1) |
| CASP8 | 1553306_at | caspase 8, apoptosis-related cysteine peptidase |
| RPS6KA5 | 1554319_at | ribosomal protein S6 kinase, 90kDa, polypeptide 5 |
| FGF7 /// FLJ30435 | 1554741_s_at | fibroblast growth factor 7 (keratinocyte growth factor) |
| PDGFRA | 1554828_at | platelet-derived growth factor receptor, alpha polypeptide |
| PTPN7 | 1554860_at | protein tyrosine phosphatase, non-receptor type 7 |
| FGFR4 | 1554961_at | fibroblast growth factor receptor 4 |
| FGFR4 | 1554962_a_at | fibroblast growth factor receptor 4 |
| RASGRF1 | 1554992_at | Ras protein-specific guanine nucleotide-releasing factor 1 |
| CACNB2 | 1555098_a_at | calcium channel, voltage-dependent, beta 2 subunit |
| FGF7 | 1555102_at | fibroblast growth factor 7 (keratinocyte growth factor) |
| FGF7 | 1555103_s_at | fibroblast growth factor 7 (keratinocyte growth factor) |
| ATF2 | 1555146_at | activating transcription factor 2 |
| GNG12 | 1555240_s_at | guanine nucleotide binding protein (G protein), gamma 12 |
| ZAK | 1555259_at | Hypothetical protein LOC339751 |
| RAP1A | 1555339_at | RAP1A, member of RAS oncogene family |
| RAP1A | 1555340_x_at | RAP1A, member of RAS oncogene family |
| DUSP16 | 1555399_a_at | dual specificity phosphatase 16 |
| TGFB3 | 1555540_at | transforming growth factor, beta 3 |
| CAGNA1D | 1555993_at | Calcium channel, voltage-dependent, L type, alpha 1D subunit |
| RASGRF2 | 1556128_a_at | Ras protein-specific guanine nucleotide-releasing factor 2 |
| MAPK12 | 1556340_at | Mitogen-activated protein kinase 12 |
| MAPK12 | 1556341_s_at | Mitogen-activated protein kinase 12 |

TABLE 6-continued

Pathway 6: Mitogen activated protein kinase

| Gene Symbol | Probe Set ID | Gene Title |
|---|---|---|
| NLK | 1556568_a_at | Nemo-like kinase |
| CDC42 | 1556931_at | Cell division cycle 42 (GTP binding protein, 25kDa) |
| EEF1A1 | 1557120_at | WD repeats and SOF1 domain containing |
| DUSP16 | 1557343_at | Dual specificity phosphatase 16 |
| PPP3CA | 1557637_at | Protein phosphatase 3 (formerly 2B), catalytic subunit, alpha isoform |
| RAF1 | 1557675_at | V-raf-1 murine leukemia viral oncogene homolog 1 |
| PRKCB1 | 1557811_a_at | Protein kinase C, beta 1 |
| DUSP16 | 1558739_at | Dual specificity phosphatase 16 |
| DUSP16 | 1558740_s_at | Dual specificity phosphatase 16 |
| PAK2 | 1559052_s_at | p21 (CDKN1A)-activated kinase 2 |
| KRAS | 1559203_s_at | v-Ki-ras2 Kirsten rat sarcoma viral oncogene homolog |
| KRAS | 1559204_x_at | v-Ki-ras2 Kirsten rat sarcoma viral oncogene homolog |
| CACNB2 | 1559419_at | calcium channel, voltage-dependent, beta 2 subunit |
| CACNB2 | 1559420_x_at | calcium channel, voltage-dependent, beta 2 subunit |
| ARRB2 | 1559436_x_at | Arrestin, beta 2 |
| FGFR1 | 1559449_a_at | Fibroblast growth factor receptor 1 (fms-related tyrosine kinase 2, Pfeiffer syndrome) |
| CACNA1G | 1559948_at | Calcium channel, voltage-dependent, alpha 1G subunit |
| MAX | 1560012_at | MYC associated factor X |
| PRKCA | 1560074_at | protein kinase C, alpha |
| STK4 | 1560214_at | Serine/threonine kinase 4 |
| PPP3CA | 1560552_a_at | Protein phosphatase 3 (formerly 2B), catalytic subunit, alpha isoform |
| AKT2 | 1560689_s_at | V-akt murine thymoma viral oncogene homolog 2 |
| FGFR2 | 1560859_at | Fibroblast growth factor receptor 2 (bacteria-expressed kinase. |
| MAP4K4 | 1560868_s_at | Mitogen-activated protein kinase kinase kinase kinase 4 |
| FLNB | 1561834_a_at | Filamin B, beta (actin binding protein 278) |
| MAPK1 | 1562283_at | Mitogen-activated protein kinase 1 |
| FGF12 | 1562794_at | Fibroblast growth factor 12 |
| DUSP16 | 1563505_at | Dual specificity phosphatase 16 |
| RUNX1T1 | 1564642_at | runt-related transcription factor 1; translocated to, 1 (cyclin D-related) |
| BDNF | 1565265_at | Brain-derived neurotrophic factor opposite strand |
| EGFR | 1565483_at | epidermal growth factor receptor (erythroblastic leukemia viral oncogene homolog) |
| EGFR | 1565484_x_at | epidermal growth factor receptor (erythroblastic leukemia viral oncogene homolog) |
| FUS | 1565715_at | Fusion (involved in t(12;16) in malignant liposarcoma) |
| FUS | 1565717_s_at | fusion (involved in t(12;16) in malignant liposarcoma) |
| PAK1 | 1565772_at | p21/Cdc42/Rac1-activated kinase 1 (STE20 homolog, yeast) |
| PPP3R1 | 1565810_at | Protein phosphatase 3 (formerly 2B), regulatory subunit B, 19kDa, alpha isoform |
| PPP3R1 | 1565811_at | Protein phosphatase 3 (formerly 2B), regulatory subunit B, 19kDa, alpha isoform |
| MAP3K7IP2 | 1565888_at | Mitogen-activated protein kinase kinase kinase 7 interacting protein 2 |
| MAP3K7IP2 | 1565889_at | Mitogen-activated protein kinase kinase kinase 7 interacting protein 2 |
| PPP3CA | 1566201_at | Protein phosphatase 3 (formerly 2B), catalytic subunit, alpha isoform |
| PPP3CA | 1566202_at | Protein phosphatase 3 (formerly 2B), catalytic subunit, alpha isoform |
| MAPK10 | 1566596_at | Mitogen-activated protein kinase 10 |
| MAPK10 | 1566597_at | Mitogen-activated protein kinase 10 |
| TPM3 | 1567105_at | tropomyosin 3 |
| TPM3 /// TPM4 | 1567107_s_at | tropomyosin 3 /// tropomyosin 4 |
| BDNF | 1567359_at | Brain-derived neurotrophic factor opposite strand |
| RAC1 | 1567457_at | Ras-related C3 botulinum toxin substrate 1 (rho family, small GTP binding protein) |
| RAC1 | 1567458_s_at | ras-related C3 botulinum toxin substrate 1 (rho family, small GTP binding protein) |
| BDNF | 1567575_at | Brain-derived neurotrophic factor opposite strand |
| BDNF | 1567576_at | Brain-derived neurotrophic factor opposite strand |
| RPS6KA3 | 1568448_at | Ribosomal protein S6 kinase, 90kDa, polypeptide 3 |
| RPS6KA3 | 1568449_at | Ribosomal protein S6 kinase, 90kDa, polypeptide 3 |
| TRIM24 | 1569316_at | Tripartite motif-containing 24 |
| NLK | 1569540_at | Nemo-like kinase |
| STK4 | 1569791_at | serine/threonine kinase 4 |
| RUNX1 | 1570350_at | runt-related transcription factor 1 (acute myeloid leukemia 1; aml1 oncogene) |
| NFKB1 | 1570362_at | Nuclear factor of kappa light polypeptide gene enhancer in B-cells 1 (p105) |
| MAP3K4 | 1570439_at | Mitogen-activated protein kinase kinase kinase 4 |
| HSPA9B | 200690_at | heat shock 70kDa protein 9B (mortalin-2) |
| HSPA9B | 200691_s_at | heat shock 70kDa protein 9B (mortalin-2) |
| HSPA9B | 200692_s_at | heat shock 70kDa protein 9B (mortalin-2) |
| ATF4 | 200779_at | activating transcription factor 4 (tax-responsive enhancer element B67) |
| STMN1 | 200783_s_at | stathmin 1/oncoprotein 18 |
| HSPA1A | 200799_at | heat shock 70kDa protein 1A |

TABLE 6-continued

Pathway 6: Mitogen activated protein kinase

| Gene Symbol | Probe Set ID | Gene Title |
|---|---|---|
| HSPA1A /// HSPA1B | 200800_s_at | heat shock 70kDa protein 1A /// heat shock 70kDa protein 1B |
| RAP1B | 200833_s_at | RAP1B, member of RAS oncogene family |
| FLNA | 200859_x_at | filamin A, alpha (actin binding protein 280) |
| FUS | 200959_at | fusion (involved in t(12; 16) in malignant liposarcoma) |
| DUSP1 | 201041_s_at | dual specificity phosphatase 1 |
| DUSP1 | 201044_x_at | dual specificity phosphatase 1 |
| RAF1 | 201244_s_at | v-raf-1 murine leukemia viral oncogene homolog 1 |
| MAPKAPK2 | 201460_at | mitogen-activated protein kinase-activated protein kinase 2 |
| MAPKAPK2 | 201461_s_at | mitogen-activated protein kinase-activated protein kinase 2 |
| JUN | 201464_x_at | v-jun sarcoma virus 17 oncogene homolog (avian) |
| JUN | 201465_s_at | v-jun sarcoma virus 17 oncogene homolog (avian) |
| JUN | 201466_s_at | v-jun sarcoma virus 17 oncogene homolog (avian) |
| DUSP3 | 201536_at | dual specificity phosphatase 3 (vaccinia virus phosphatase VH1-related) |
| DUSP3 | 201537_s_at | dual specificity phosphatase 3 (vaccinia virus phosphatase VH1-related) |
| DUSP3 | 201538_s_at | dual specificity phosphatase 3 (vaccinia virus phosphatase VH1-related) |
| CD14 | 201743_at | CD14 antigen /// CD14 antigen |
| TP53 | 201746_at | tumor protein p53 (Li-Fraumeni syndrome) |
| DAXX | 201763_s_at | death-associated protein 6 |
| HSPB1 | 201841_s_at | heat shock 27kDa protein 1 |
| CDC25B | 201853_s_at | cell division cycle 25B |
| PPP5C | 201979_s_at | protein phosphatase 5, catalytic subunit |
| EGFR | 201983_s_at | epidermal growth factor receptor (erythroblastic leukemia viral oncogene homolog) |
| EGFR | 201984_s_at | epidermal growth factor receptor (erythroblastic leukemia viral oncogene homolog) |
| CRK | 202224_at | v-crk sarcoma virus CT10 oncogene homolog (avian) |
| CRK | 202225_at | V-crk sarcoma virus CT10 oncogene homolog (avian) |
| CRK | 202226_at | v-crk sarcoma virus CT10 oncogene homolog (avian) |
| PDGFRB | 202273_at | platelet-derived growth factor receptor, beta polypeptide |
| NR4A1 | 202340_x_at | nuclear receptor subfamily 4, group A, member 1 |
| RAP1A | 202362_at | RAP1A, member of RAS oncogene family |
| SRF | 202400_s_at | serum response factor (c-fos serum response element-binding transcription factor) |
| SRF | 202401_s_at | serum response factor (c-fos serum response element-binding transcription factor) |
| MAP2K2 | 202424_at | mitogen-activated protein kinase kinase 2 |
| PPP3CA | 202425_x_at | protein phosphatase 3 (formerly 2B), catalytic subunit, alpha isoform |
| PPP3CA | 202429_s_at | protein phosphatase 3 (formerly 2B), catalytic subunit, alpha isoform |
| MYC | 202431_s_at | v-myc myelocytomatosis viral oncogene homolog (avian) |
| PPP3CB | 202432_at | protein phosphatase 3 (formerly 2B), catalytic subunit, beta isoform |
| PPP3CA | 202457_s_at | protein phosphatase 3 (formerly 2B), catalytic subunit, alpha isoform |
| MAPK14 | 202530_at | mitogen-activated protein kinase 14 |
| HSPA1B | 202581_at | heat shock 70kDa protein 1B |
| NRAS | 202647_s_at | neuroblastoma RAS viral (v-ras) oncogene homolog |
| MAP2K1 | 202670_at | mitogen-activated protein kinase kinase 1 |
| RASA1 | 202677_at | RAS p21 protein activator (GTPase activating protein) 1 |
| PRKACB | 202741_at | protein kinase, cAMP-dependent, catalytic, beta |
| PRKACB | 202742_s_at | protein kinase, cAMP-dependent, catalytic, beta |
| CASP3 | 202763_at | caspase 3, apoptosis-related cysteine peptidase |
| PRKACA | 202801_at | protein kinase, cAMP-dependent, catalytic, alpha |
| IL1R1 | 202948_at | interleukin 1 receptor, type I |
| TGFB1 | 203084_at | transforming growth factor, beta 1 (Camurati-Engelmann disease) |
| TGFB1 | 203085_s_at | transforming growth factor, beta 1 (Camurati-Engelmann disease) |
| PDGFRA | 203131_at | platelet-derived growth factor receptor, alpha polypeptide |
| MAPK9 | 203218_at | mitogen-activated protein kinase 9 |
| MAP2K4 | 203265_s_at | mitogen-activated protein kinase kinase 4 |
| MAP2K4 | 203266_s_at | mitogen-activated protein kinase kinase 4 |
| DUSP14 | 203367_at | dual specificity phosphatase 14 |
| RPS6KA1 | 203379_at | ribosomal protein S6 kinase, 90kDa, polypeptide 1 |
| ARRB2 | 203388_at | arrestin, beta 2 |
| MAP3K3 | 203514_at | mitogen-activated protein kinase kinase kinase 3 |
| ELK1 | 203617_x_at | ELK1, member of ETS oncogene family |
| FGFR2 | 203638_s_at | fibroblast growth factor receptor 2 (bacteria-expressed kinase) |
| FGFR2 | 203639_s_at | fibroblast growth factor receptor 2 (bacteria-expressed kinase) |
| PLA2G2A | 203649_s_at | phospholipase A2, group IIA (platelets, synovial fluid) |
| GADD45A | 203725_at | growth arrest and DNA-damage-inducible, alpha |
| JUND | 203751_x_at | jun D proto-oncogene |
| JUND | 203752_s_at | jun D proto-oncogene |
| AKT2 | 203808_at | v-akt murine thymoma viral oncogene homolog 2 |
| AKT2 | 203809_s_at | v-akt murine thymoma viral oncogene homolog 2 |
| MAP3K5 | 203836_s_at | mitogen-activated protein kinase kinase kinase 5 |
| MAP3K5 | 203837_at | mitogen-activated protein kinase kinase kinase 5 |
| RPS6KA3 | 203843_at | ribosomal protein S6 kinase, 90kDa, polypeptide 3 |
| MAP3K7IP1 | 203901_at | mitogen-activated protein kinase kinase kinase 7 interacting protein 1 |

TABLE 6-continued

Pathway 6: Mitogen activated protein kinase

| Gene Symbol | Probe Set ID | Gene Title |
| --- | --- | --- |
| MAPT | 203928_x_at | microtubule-associated protein tau |
| MAPT | 203929_s_at | microtubule-associated protein tau |
| MAPT | 203930_s_at | microtubule-associated protein tau |
| PPM1A | 203966_s_at | protein phosphatase 1A (formerly 2C), magnesium-dependent, alpha isoform |
| CASP9 | 203984_s_at | caspase 9, apoptosis-related cysteine peptidase |
| KRAS | 204009_s_at | v-Ki-ras2 Kirsten rat sarcoma viral oncogene homolog |
| KRAS | 204010_s_at | v-Ki-ras2 Kirsten rat sarcoma viral oncogene homolog |
| DUSP4 | 204014_at | dual specificity phosphatase 4 |
| DUSP4 | 204015_s_at | dual specificity phosphatase 4 |
| PRKX /// PRKY | 204060_s_at | protein kinase, X-linked /// protein kinase, Y-linked |
| PRKX | 204061_at | protein kinase, X-linked |
| STK3 | 204068_at | serine/threonine kinase 3 (STE20 homolog, yeast) |
| MAP3K4 | 204089_x_at | mitogen-activated protein kinase kinase kinase 4 |
| GADD45G | 204121_at | growth arrest and DNA-damage-inducible, gamma |
| PDGFB | 204200_s_at | platelet-derived growth factor beta polypeptide (simian sarcoma viral oncogene) |
| NF1 | 204323_x_at | neurofibromin 1 (neurofibromatosis, von Recklinghausen disease, Watson disease) |
| NF1 | 204325_s_at | neurofibromin 1 (neurofibromatosis, von Recklinghausen disease, Watson disease) |
| FGFR3 | 204379_s_at | fibroblast growth factor receptor 3 (achondroplasia, thanatophoric dwarfism) |
| FGFR3 | 204380_s_at | fibroblast growth factor receptor 3 (achondroplasia, thanatophoric dwarfism) |
| TRIM24 | 204391_x_at | tripartite motif-containing 24 |
| TRAF2 | 204413_at | TNF receptor-associated factor 2 |
| FGF2 | 204421_s_at | fibroblast growth factor 2 (basic) |
| FGF2 | 204422_s_at | fibroblast growth factor 2 (basic) |
| PPP3R1 | 204506_at | protein phosphatase 3 (formerly 2B), regulatory subunit B, 19kDa, alpha isoform |
| PPP3R1 | 204507_s_at | protein phosphatase 3 (formerly 2B), regulatory subunit B, 19kDa, alpha isoform |
| IKBKE | 204549_at | inhibitor of kappa light polypeptide gene enhancer in B-cells, kinase epsilon |
| FGFR4 | 204579_at | fibroblast growth factor receptor 4 |
| RPS6KA4 | 204632_at | ribosomal protein S6 kinase, 90kDa, polypeptide 4 |
| RPS6KA5 | 204633_s_at | ribosomal protein S6 kinase, 90kDa, polypeptide 5 |
| RPS6KAS | 204635_at | ribosomal protein S6 kinase, 90kDa, polypeptide 5 |
| PLA2G6 | 204691_x_at | phospholipase A2, group VI (cytosolic, calcium-independent) |
| MAP2K5 | 204756_at | mitogen-activated protein kinase kinase 5 |
| FAS | 204780_s_at | Fas (TNF receptor superfamily, member 6) |
| FAS | 204781_s_at | Fas (TNF receptor superfamily, member 6) |
| DUSP2 | 204794_at | dual specificity phosphatase 2 |
| MAPK10 | 204813_at | mitogen-activated protein kinase 10 |
| PTPN7 | 204852_s_at | protein tyrosine phosphatase, non-receptor type 7 |
| TAOK2 | 204877_s_at | TAO kinase 2 |
| TAOK2 | 204878_s_at | TAO kinase 2 |
| EEF1A1 | 204892_x_at | eukaryotic translation elongation factor 1 alpha 1 |
| MAP4K2 | 204936_at | mitogen-activated protein kinase kinase kinase kinase 2 |
| TAOK2 | 204986_s_at | TAO kinase 2 |
| MAP3K8 | 205027_s_at | mitogen-activated protein kinase kinase kinase 8 |
| IL1B | 205067_at | interleukin 1, beta |
| FGF13 | 205110_s_at | fibroblast growth factor 13 |
| FGF1 | 205117_at | fibroblast growth factor 1 (acidic) |
| MAP3K14 | 205192_at | mitogen-activated protein kinase kinase kinase 14 |
| ACVR1B | 205209_at | activin A receptor, type IB |
| IL1R2 | 205403_at | interleukin 1 receptor, type II |
| STK4 | 205411_at | serine/threonine kinase 4 |
| ATF2 | 205446_s_at | activating transcription factor 2 |
| MAP3K12 | 205447_s_at | mitogen-activated protein kinase kinase kinase 12 |
| MAP3K12 | 205448_s_at | mitogen-activated protein kinase kinase kinase 12 |
| CASP10 | 205467_at | caspase 10, apoptosis-related cysteine peptidase |
| RUNX1T1 | 205528_s_at | runt-related transcription factor 1; translocated to, 1 (cyclin D-related) |
| RUNX1T1 | 205529_s_at | runt-related transcription factor 1; translocated to, 1 (cyclin D-related) |
| TRAF6 | 205558_at | TNF receptor-associated factor 6 |
| RASGRP1 | 205590_at | RAS guanyl releasing protein 1 (calcium and DAG-regulated) |
| MAP2K6 | 205698_s_at | mitogen-activated protein kinase kinase 6 |
| MAP2K6 | 205699_at | mitogen-activated protein kinase kinase 6 |
| DUSP9 | 205777_at | dual specificity phosphatase 9 |
| FGF7 | 205782_at | fibroblast growth factor 7 (keratinocyte growth factor) |
| RASGRP3 | 205801_s_at | RAS guanyl releasing protein 3 (calcium and DAG-regulated) |
| HSPB2 | 205824_at | heat shock 27kDa protein 2 |
| CACNA1H | 205845_at | calcium channel, voltage-dependent, alpha 1H subunit |

TABLE 6-continued

Pathway 6: Mitogen activated protein kinase

| Gene Symbol | Probe Set ID | Gene Title |
|---|---|---|
| NFATC4 | 205897_at | nuclear factor of activated T-cells, cytoplasmic, calcineurin-dependent 4 |
| PAK2 | 205962_at | p21 (CDKN1A)-activated kinase 2 |
| ELK4 | 205994_at | ELK4, ETS-domain protein (SRF accessory protein 1) |
| CASP1 | 206011_at | caspase 1, apoptosis-related cysteine peptidase (interleukin 1, beta, convertase) |
| MAPK11 | 206040_s_at | mitogen-activated protein kinase 11 |
| BRAF | 206044_s_at | v-raf murine sarcoma viral oncogene homolog B1 |
| PTPRR | 206084_at | protein tyrosine phosphatase, receptor type, R |
| RAC3 | 206103_at | ras-related C3 botulinum toxin substrate 3 (rho family) |
| MAPK12 | 206106_at | mitogen-activated protein kinase 12 |
| PLA2G5 | 206178_at | phospholipase A2, group V |
| CRKL | 206184_at | v-crk sarcoma virus CT10 oncogene homolog (avian)-like |
| MAP3K13 | 206249_at | mitogen-activated protein kinase kinase kinase 13 |
| EGF | 206254_at | epidermal growth factor (beta-urogastrone) |
| PRKCG | 206270_at | protein kinase C, gamma |
| PRKY | 206279_at | protein kinase, Y-linked |
| MAP4K1 | 206296_x_at | mitogen-activated protein kinase kinase kinase 1 |
| PLA2G1B | 206311_s_at | phospholipase A2, group IB (pancreas) |
| MAP3K10 | 206362_x_at | mitogen-activated protein kinase kinase kinase 10 |
| DUSP8 | 206374_at | dual specificity phosphatase 8 |
| BDNF | 206382_s_at | brain-derived neurotrophic factor |
| CACNG3 | 206384_at | calcium channel, voltage-dependent, gamma subunit 3 |
| CAGNA1A | 206399_x_at | calcium channel, voltage-dependent, P/Q type, alpha 1A subunit |
| MAPT | 206401_s_at | microtubule-associated protein tau |
| FGF9 | 206404_at | fibroblast growth factor 9 (glia-activating factor) |
| MRAS | 206538_at | muscle RAS oncogene homolog |
| EEF1A1 | 206559_x_at | eukaryotic translation elongation factor 1 alpha 1 |
| MAP4K4 | 206571_s_at | mitogen-activated protein kinase kinase kinase kinase 4 |
| CACNG1 | 206612_at | calcium channel, voltage-dependent, gamma subunit 1 |
| RASA2 | 206636_at | RAS p21 protein activator 2 |
| NTF3 | 206706_at | neurotrophin 3 |
| FGF4 | 206783_at | fibroblast growth factor 4 (heparin secretory transforming protein 1) |
| NGFB | 206814_at | nerve growth factor, beta polypeptide |
| MAP3K7 | 206853_s_at | Mitogen-activated protein kinase kinase kinase 7 |
| MAP3K7 | 206854_s_at | mitogen-activated protein kinase kinase kinase 7 |
| ELK4 | 206919_at | ELK4, ETS-domain protein (SRF accessory protein 1) |
| PRKCA | 206923_at | protein kinase C, alpha |
| TGFBR1 | 206943_at | transforming growth factor, beta receptor I (activin A receptor type II-like kinase) |
| FGF18 | 206986_at | fibroblast growth factor 18 |
| FGF18 | 206987_x_at | fibroblast growth factor 18 |
| CCR5 | 206991_s_at | chemokine (C-C motif) receptor 5 |
| CACNB1 | 206996_x_at | calcium channel, voltage-dependent, beta 1 subunit |
| PPP3CC | 207000_s_at | protein phosphatase 3 (formerly 2B), catalytic subunit, gamma isoform |
| CACNA2D1 | 207050_at | calcium channel, voltage-dependent, alpha 2/delta subunit 1 |
| TNF | 207113_s_at | tumor necrosis factor (TNF superfamily, member 2) |
| NTRK2 | 207152_at | neurotrophic tyrosine kinase, receptor, type 2 |
| CACNA1B | 207162_s_at | calcium channel, voltage-dependent, L type, alpha 1B subunit |
| CASP7 | 207181_s_at | caspase 7, apoptosis-related cysteine peptidase |
| PLA2G10 | 207222_at | phospholipase A2, group X |
| PRKACG | 207228_at | protein kinase, cAMP-dependent, catalytic, gamma |
| MAPK7 | 207292_s_at | mitogen-activated protein kinase 7 |
| TGFBR2 | 207334_s_at | transforming growth factor, beta receptor II (70/80kDa) |
| RAC2 | 207419_s_at | ras-related C3 botulinum toxin substrate 2 (rho family, Rac 2) |
| CASP5 | 207500_at | caspase 5, apoptosis-related cysteine peptidase |
| FGF12 | 207501_s_at | fibroblast growth factor 12 |
| NFKB2 | 207535_s_at | nuclear factor of kappa light polypeptide gene enhancer in B-cells 2 (p49/p100) |
| GADD45B | 207574_s_at | growth arrest and DNA-damage-inducible, beta |
| TNFRSF1A | 207643_s_at | tumor necrosis factor receptor superfamily, member 1A |
| MAP2K3 | 207667_s_at | mitogen-activated protein kinase kinase 3 |
| CASP8 | 207686_s_at | caspase 8, apoptosis-related cysteine peptidase |
| CACNB4 | 207693_at | calcium channel, voltage-dependent, beta 4 subunit |
| CACNB2 | 207776s_at | calcium channel, voltage-dependent, beta 2 subunit |
| FGFR1 | 207822_at | fibroblast growth factor receptor 1 (fms-related tyrosine kinase 2, Pfeiffer syndrome) |
| CAGNA1G | 207869_s_at | calcium channel, voltage-dependent, alpha 1G subunit |
| FLNC | 207876_s_at | filamin C, gamma (actin binding protein 280) |
| FGFR1 | 207937_x_at | fibroblast growth factor receptor 1 (fms-related tyrosine kinase 2, Pfeiffer syndrome) |
| MEF2C | 207968_s_at | MADS box transcription enhancer factor 2, polypeptide C (myocyte enhancer 20) |
| CHP | 207993_s_at | calcium binding protein P22 |
| CAGNA1D | 207998_s_at | calcium channel, voltage-dependent, L type, alpha 1D subunit |
| CASP2 | 208050_s_at | caspase 2, apoptosis-related cysteine peptidase |

TABLE 6-continued

Pathway 6: Mitogen activated protein kinase

| Gene Symbol | Probe Set ID | Gene Title |
|---|---|---|
| RUNX1 | 208129_x_at | runt-related transcription factor 1 (acute myeloid leukemia 1; aml1 oncogene) |
| IL1A | 208200_at | interleukin 1, alpha |
| RASGRP2 | 208206_s_at | RAS guanyl releasing protein 2 (calcium and DAG-regulated) |
| ACVR1B | 208218_s_at | activin A receptor, type IB |
| ACVR1B | 208219_at | activin A receptor, type IB |
| ACVR1B | 208222_at | activin A receptor, type IB |
| ACVR1B | 208223_s_at | activin A receptor, type IB |
| FGFR2 | 208225_at | fibroblast growth factor receptor 2 (bacteria-expressed kinase) |
| FGFR2 | 208228_s_at | fibroblast growth factor receptor 2 (bacteria-expressed kinase) |
| FGFR2 | 208229_at | fibroblast growth factor receptor 2 (bacteria-expressed kinase) |
| FGFR2 | 208234_x_at | fibroblast growth factor receptor 2 (bacteria-expressed kinase) |
| FGF1 | 208240_s_at | fibroblast growth factor 1 (acidic) |
| CACNA1I | 208299_at | calcium channel, voltage-dependent, alpha 1I subunit |
| MAPK1 | 208351_s_at | mitogen-activated protein kinase 1 |
| CACNA1F | 208377_s_at | calcium channel, voltage-dependent, alpha 1F subunit |
| FGF5 | 208378_x_at | fibroblast growth factor 5 |
| MAX | 208403_x_at | MYC associated factor X |
| FGF6 | 208417_at | fibroblast growth factor 6 |
| MDS1 | 208434_at | myelodysplasia syndrome 1 |
| FGF8 | 208449_s_at | fibroblast growth factor 8 (androgen-induced) |
| RRAS2 | 208456_s_at | related RAS viral (r-ras) oncogene homolog 2 |
| NTRK1 | 208605_s_at | neurotrophic tyrosine kinase, receptor, type 1 |
| FLNB | 208613_s_at | filamin B, beta (actin binding protein 278) |
| FLNB | 208614_s_at | filamin B, beta (actin binding protein 278) |
| RAC1 | 208640_at | ras-related C3 botulinum toxin substrate 1 (rho family) |
| RAC1 | 208641_s_at | ras-related C3 botulinum toxin substrate 1 (rho family) |
| HSPA8 | 208687_x_at | heat shock 70kDa protein 8 |
| CDC42 | 208727_s_at | cell division cycle 42 (GTP binding protein, 25kDa) |
| CDC42 | 208728_s_at | cell division cycle 42 (GTP binding protein, 25kDa) |
| PAK2 | 208875_s_at | p21 (CDKN1A)-activated kinase 2 |
| PAK2 | 208876_s_at | p21 (CDKN1A)-activated kinase 2 |
| PAK2 | 208877_at | p21 (CDKN1A)-activated kinase 2 |
| PAK2 | 208878_s_at | p21 (CDKN1A)-activated kinase 2 |
| DUSP6 | 208891_at | dual specificity phosphatase 6 |
| DUSP6 | 208892_s_at | dual specificity phosphatase 6 |
| DUSP6 | 208893_s_at | dual specificity phosphatase 6 |
| TGFBR2 | 208944_at | transforming growth factor, beta receptor II (70/80kDa) |
| FOS | 209189_at | v-fos FBJ murine osteosarcoma viral oncogene homolog |
| MEF2C | 209199_s_at | MADS box transcription enhancer factor 2, polypeptide C (myocyte enhancer 2C) |
| MEF2C | 209200_at | MADS box transcription enhancer factor 2, polypeptide C (myocyte enhancer 2C) |
| NFKB1 | 209239_at | nuclear factor of kappa light polypeptide gene enhancer in B-cells 1 (p105) |
| MINK1 | 209241_x_at | misshapen-like kinase 1 (zebrafish) |
| PPM1B | 209296_at | protein phosphatase 1B (formerly 2C), magnesium-dependent, beta isoform |
| GADD45B | 209304_x_at | growth arrest and DNA-damage-inducible, beta |
| GADD45B | 209305_s_at | growth arrest and DNA-damage-inducible, beta |
| CASP4 | 209310_s_at | caspase 4, apoptosis-related cysteine peptidase |
| MAX | 209331_s_at | MYC associated factor X |
| MAX | 209332_s_at | MYC associated factor X |
| IKBKB | 209341_s_at | inhibitor of kappa light polypeptide gene enhancer in B-cells, kinase beta |
| IKBKB | 209342_s_at | inhibitor of kappa light polypeptide gene enhancer in B-cells, kinase beta |
| RUNX1 | 209359_x_at | runt-related transcription factor 1 (acute myeloid leukemia 1; amlI oncogene) |
| RUNX1 | 209360_s_at | runt-related transcription factor 1 (acute myeloid leukemia 1; amlI oncogene) |
| DDIT3 | 209383_at | DNA-damage-inducible transcript 3 |
| DUSP5 | 209457_at | dual specificity phosphatase 5 |
| MKNK1 | 209467_s_at | MAP kinase interacting serine/threonine kinase 1 |
| CACNB3 | 209530_at | calcium channel, voltage-dependent, beta 3 subunit |
| PAK1 | 209615_s_at | p21/Cdc42/Rac1-activated kinase 1 (STE20 homolog, yeast) |
| NFKB2 | 209636_at | nuclear factor of kappa light polypeptide gene enhancer in B-cells 2 (p49/p100) |
| CHUK | 209666_s_at | conserved helix-loop-helix ubiquitous kinase |
| PRKCB1 | 209685_s_at | protein kinase C, beta 1 |
| PPP3CC | 209697_at | protein phosphatase 3 (formerly 2B), catalytic subunit, gamma isoform |
| TGFB3 | 209747_at | transforming growth factor, beta 3 |
| CASP6 | 209790_s_at | caspase 6, apoptosis-related cysteine peptidase |
| CASP2 | 209811_at | caspase 2, apoptosis-related cysteine peptidase (neural precursor cell expressed) |

TABLE 6-continued

Pathway 6: Mitogen activated protein kinase

| Gene Symbol | Probe Set ID | Gene Title |
| --- | --- | --- |
| CASP2 | 209812_x_at | caspase 2, apoptosis-related cysteine peptidase (neural precursor cell expressed) |
| PPP3CB | 209817_at | protein phosphatase 3 (formerly 2B), catalytic subunit, beta isoform |
| TGFB2 | 209908_s_at | Transforming growth factor, beta 2 |
| TGFB2 | 209909_s_at | transforming growth factor, beta 2 |
| IKBKG | 209929_s_at | inhibitor of kappa light polypeptide gene enhancer in B-cells, kinase gamma |
| MAP2K7 | 209951_s_at | mitogen-activated protein kinase kinase 7 |
| MAP2K7 | 209952_s_at | mitogen-activated protein kinase kinase 7 |
| CASP1 | 209970_x_at | caspase 1, apoptosis-related cysteine peptidase (interleukin 1, beta, convertase) |
| MAPK13 | 210058_at | mitogen-activated protein kinase 13 |
| MAPK13 | 210059_s_at | mitogen-activated protein kinase 13 |
| CACNA1D | 210108_at | calcium channel, voltage-dependent, L type, alpha 1D subunit |
| IL1A | 210118_s_at | interleukin 1, alpha |
| PLA2G4A | 210145_at | phospholipase A2, group IVA (cytosolic, calcium-dependent) |
| CACNB1 | 210185_at | calcium channel, voltage-dependent, beta 1 subunit |
| HSPA1L | 210189_at | heat shock 70kDa protein 1-like |
| NR4A1 | 210226_at | nuclear receptor subfamily 4, group A, member 1 |
| CDC42 | 210232_at | cell division cycle 42 (GTP binding protein, 25kDa) |
| MAP3K7IP2 | 210284_s_at | mitogen-activated protein kinase kinase kinase 7 interacting protein 2 |
| FGF5 | 210310_s_at | fibroblast growth factor 5 |
| FGF5 | 210311_at | fibroblast growth factor 5 |
| HSPA8 | 210338_s_at | heat shock 70kDa protein 8 |
| RUNX1 | 210365_at | runt-related transcription factor 1 (acute myeloid leukemia 1; aml1 oncogene) |
| ELK1 | 210376_x_at | ELK1, member of ETS oncogene family |
| CAGNA1G | 210380_s_at | calcium channel, voltage-dependent, alpha 1G subunit |
| PPM1A | 210407_at | protein phosphatase 1A (formerly 2C), magnesium-dependent, alpha isoform |
| MAPK14 | 210449_x_at | mitogen-activated protein kinase 14 |
| MAPK8 | 210477_x_at | mitogen-activated protein kinase 8 |
| MAP2K5 | 210482_x_at | mitogen-activated protein kinase kinase 5 |
| RASGRF1 | 210550_s_at | Ras protein-specific guanine nucleotide-releasing factor 1 |
| MAPK9 | 210570_x_at | mitogen-activated protein kinase 9 |
| RASA1 | 210621_s_at | RAS p21 protein activator (GTPase activating protein) 1 |
| NF1 | 210631_at | neurofibromin 1 (neurofibromatosis, von Recklinghausen disease, Watson disease) |
| PLA2G6 | 210647_x_at | phospholipase A2, group VI (cytosolic, calcium-independent) |
| MAPK8 | 210671_x_at | mitogen-activated protein kinase 8 |
| PTPRR | 210675_s_at | protein tyrosine phosphatase, receptor type, R |
| CASP10 | 210708_x_at | caspase 10, apoptosis-related cysteine peptidase |
| MAX | 210734_x_at | MYC associated factor X |
| CAGNA1A | 210770_s_at | calcium channel, voltage-dependent, P/Q type, alpha 1A subunit |
| CASP9 | 210775_x_at | caspase 9, apoptosis-related cysteine peptidase |
| RUNX1 | 210805_x_at | runt-related transcription factor 1 (acute myeloid leukemia 1; aml1 oncogene) |
| ELK1 | 210850_s_at | ELK1, member of ETS oncogene family |
| FASLG | 210865_at | Fas ligand (TNF superfamily, member 6) |
| CASP10 | 210955_at | caspase 10, apoptosis-related cysteine peptidase |
| CACNB1 | 210967_x_at | calcium channel, voltage-dependent, beta 1 subunit |
| FGFR1 | 210973_s_at | fibroblast growth factor receptor 1 (fms-related tyrosine kinase 2, Pfeiffer syndrome) |
| EGFR | 210984_x_at | epidermal growth factor receptor (erythroblastic leukemia viral oncogene homolog) |
| IKBKB | 211027_s_at | inhibitor of kappa light polypeptide gene enhancer in B-cells, kinase beta cells) |
| FGF18 | 211029_x_at | fibroblast growth factor 18 /// fibrobiast growth factor 18 |
| STK3 | 211078_s_at | serine/threonine kinase 3 (STE20 homolog, yeast) |
| MAP3K13 | 211083_s_at | mitogen-activated protein kinase kinase kinase |
| STK4 | 211085_s_at | serine/threonine kinase 4 /// serine/threonine kinase 4 |
| MAPK14 | 211087_x_at | mitogen-activated protein kinase 14 /// mitogen-activated protein kinase 14 |
| NF1 | 211094_s_at | neurofibromin 1 (neurofibromatosis, von Recklinghausen disease, Watson disease) |
| NF1 | 211095_at | neurofibromin 1 (neurofibromatosis, von Recklinghausen disease, Watson disease) |
| CASP2 | 211140_s_at | caspase 2, apoptosis-related cysteine peptidase |
| NR4A1 | 211143_x_at | nuclear receptor subfamily 4, group A, member 1 |
| RUNX1 | 211179_at | runt-related transcription factor 1 (acute myeloid leukemia 1; aml1 oncogene) |
| RUNX1 | 211180_x_at | runt-related transcription factor 1 (acute myeloid leukemia 1; aml1 oncogene) |
| RUNX1 | 211181_x_at | runt-related transcription factor 1 (acute myeloid leukemia 1; aml1 oncogene) |

TABLE 6-continued

Pathway 6: Mitogen activated protein kinase

| Gene Symbol | Probe Set ID | Gene Title |
| --- | --- | --- |
| RUNX1 | 211182_x_at | runt-related transcription factor 1 (acute myeloid leukemia 1; aml1 oncogene) |
| FGFR4 | 211237_s_at | fibroblast growth factor receptor 4 |
| TP53 | 211300_s_at | tumor protein p53 (Li-Fraumeni syndrome) |
| CACNA1G | 211314_at | calcium channel, voltage-dependent, alpha 1G subunit |
| CACNA1G | 211315_s_at | calcium channel, voltage-dependent, alpha 1G subunit |
| FASLG | 211333_s_at | Fas ligand (TNF superfamily, member 6) |
| CASP1 | 211366_x_at | caspase 1, apoptosis-related cysteine peptidase (interleukin 1, beta, convertase) |
| CASP1 | 211367_s_at | caspase 1, apoptosis-related cysteine peptidase (interleukin 1, beta, convertase) |
| CASP1 | 211368_s_at | caspase 1, apoptosis-related cysteine peptidase (interleukin 1, beta, convertase) |
| MAP2K5 | 211370_s_at | mitogen-activated protein kinase kinase 5 |
| MAP2K5 | 211371_at | mitogen-activated protein kinase kinase 5 |
| IL1R2 | 211372_s_at | interleukin 1 receptor, type II |
| FGFR2 | 211398_at | fibroblast growth factor receptor 2 (bacteria-expressed kinase) |
| FGFR2 | 211399_at | fibroblast growth factor receptor 2 (bacteria-expressed kinase) |
| FGFR2 | 211400_at | fibroblast growth factor receptor 2 (bacteria-expressed kinase) |
| FGFR2 | 211401_s_at | fibroblast growth factor receptor 2 (bacteria-expressed kinase) |
| MAP3K4 | 211437_at | Mitogen-activated protein kinase kinase kinase |
| AKT2 | 211453_s_at | v-akt murine thymoma viral oncogene homolog 2 |
| CASP6 | 211464_x_at | caspase 6, apoptosis-related cysteine peptidase |
| FGF18 | 211485_s_at | fibroblast growth factor 18 |
| MAPK11 | 211499_s_at | mitogen-activated protein kinase 11 |
| MAPK11 | 211500_at | mitogen-activated protein kinase 11 |
| NFKB2 | 211524_at | nuclear factor of kappa light polypeptide gene enhancer in B-cells 2 (p49/p100) |
| PDGFRA | 211533_at | platelet-derived growth factor receptor, alpha polypeptide |
| FGFR1 | 211535_s_at | fibroblast growth factor receptor 1 (fms-related tyrosine kinase 2, Pfeiffer syndrome) |
| MAP3K7 | 211536_x_at | mitogen-activated protein kinase kinase kinase 7 |
| MAP3K7 | 211537_x_at | mitogen-activated protein kinase kinase kinase 7 |
| EGFR | 211550_at | epidermal growth factor receptor (erythroblastic leukemia viral oncogene homolog) |
| EGFR | 211551_at | epidermal growth factor receptor (erythroblastic leukemia viral oncogene homolog) |
| MAPK14 | 211561_x_at | mitogen-activated protein kinase 14 |
| EGFR | 211607_x_at | epidermal growth factor receptor (erythroblastic leukemia viral oncogene homolog) |
| RUNX1 | 211620_x_at | runt-related transcription factor 1 (acute myeloid leukemia 1; aml1 oncogene) |
| SOS2 | 211665_s_at | son of sevenless homolog 2 (Drosophila) /// son of seveniess homolog 2 |
| CAGNA1G | 211802_x_at | calcium channel, voltage-dependent, alpha 1G subunit |
| CAGNA1I | 211830_s_at | calcium channel, voltage-dependent, alpha 1I subunit |
| CASP10 | 211888_x_at | caspase 10, apoptosis-related cysteine peptidase |
| NF1 | 211914_x_at | neurofibromin 1 (neurofibromatosis, von Recklinghausen disease, Watson disease) |
| HSPA5 | 211936_at | heat shock 70kDa protein 5 (glucose-regulated protein, 78kDa) |
| MAPK3 | 212046_x_at | mitogen-activated protein kinase 3 |
| CRKL | 212180_at | v-crk sarcoma virus CT10 oncogene homolog (avian)-like |
| MAP3K7IP2 | 212184_s_at | mitogen-activated protein kinase kinase kinase 7 interacting protein 2 |
| MAPK1 | 212271_at | mitogen-activated protein kinase 1 |
| GNG12 | 212294_at | guanine nucleotide binding protein (G protein), gamma 12 |
| RRAS2 | 212590_at | related RAS viral (r-ras) oncogene homolog 2 |
| AKT3 | 212607_at | v-akt murine thymoma viral oncogene homolog 3 (protein kinase B, gamma) |
| AKT3 | 212609_s_at | V-akt murine thymoma viral oncogene homolog 3 (protein kinase B, gamma) |
| RRAS | 212647_at | related RAS viral (r-ras) oncogene homolog |
| NF1 | 212676_at | Neurofibromin 1 (neurofibromatosis, von Recklinghausen disease, Watson disease) |
| NF1 | 212678_at | Neurofibromin 1 (neurofibromatosis, von Recklinghausen disease, Watson disease) |
| SOS1 | 212777_at | son of sevenless homolog 1 (Drosophila) |
| SOS1 | 212780_at | son of sevenless homolog 1 (Drosophila) |
| MAPKAPK5 | 212871_at | mitogen-activated protein kinase-activated protein kinase 5 |
| HRAS | 212983_at | v-Ha-ras Harvey rat sarcoma viral oncogene homolog |
| ATF2 | 212984_at | Activating transcription factor 2 |
| MAPK8IP1 | 213013_at | mitogen-activated protein kinase 8 interacting protein 1 |
| MAPK8IP1 | 213014_at | mitogen-activated protein kinase 8 interacting protein 1 |
| PRKCA | 213093_at | protein kinase C, alpha |
| MAPK8IP3 | 213177_at | mitogen-activated protein kinase 8 interacting protein 3 |
| MAPK8IP3 | 213178_s_at | mitogen-activated protein kinase 8 interacting protein 3 |

TABLE 6-continued

Pathway 6: Mitogen activated protein kinase

| Gene Symbol | Probe Set ID | Gene Title |
| --- | --- | --- |
| ACVR1B | 213198_at | activin A receptor, type 1B |
| PPM1B | 213225_at | protein phosphatase 1B (formerly 2C), magnesium-dependent, beta isoform |
| TRIM24 | 213301_x_at | tripartite motif-containing 24 |
| NFATC4 | 213345_at | nuclear factor of activated T-cells, cytoplasmic, calcineurin-dependent 4 |
| CASP8 | 213373_s_at | caspase 8, apoptosis-related cysteine peptidase |
| EEF1A1 | 213477_x_at | eukaryotic translation elongation factor 1 alpha 1 |
| MAP2K2 | 213487_at | Mitogen-activated protein kinase kinase 2 |
| MAP2K2 | 213490_s_at | mitogen-activated protein kinase kinase 2 |
| GADD45B | 213560_at | Growth arrest and DNA-damage-inducible, beta |
| EEF1A1 /// LOC387845 /// LOC389223 /// LOC440595 /// LOC441032 | 213583_x_at | eukaryotic translation elongation factor 1 alpha |
| CASP4 | 213596_at | caspase 4, apoptosis-related cysteine peptidase |
| RAC2 | 213603_s_at | ras-related C3 botulinum toxin substrate 2 (rho family, small GTP binding Rac2) |
| EEF1A1 | 213614_x_at | eukaryotic translation elongation factor 1 alpha 1 |
| CACNB2 | 213714_at | calcium channel, voltage-dependent, beta 2 subunit |
| FLNA | 213746_s_at | filamin A, alpha (actin binding protein 280) |
| DUSP7 | 213848_at | Dual specificity phosphatase 7 |
| PPP3CC | 213950_s_at | Protein phosphatase 3 (formerly 2B), catalytic subunit, gamma isoform |
| MAX | 214108_at | MYC associated factor X |
| MAP4K1 | 214219_x_at | mitogen-activated protein kinase kinase kinase kinase 1 |
| CDC42 | 214230_at | cell division cycle 42 (GTP binding protein, 25kDa) |
| MINK1 | 214246_x_at | misshapen-like kinase 1 (zebrafish) |
| FGF18 | 214284_s_at | Fibroblast growth factor 18 |
| JUND | 214326_x_at | jun D proto-oncogene |
| MAP4K1 | 214339_s_at | mitogen-activated protein kinase kinase kinase kinase 1 |
| KRAS | 214352_s_at | v-Ki-ras2 Kirsten rat sarcoma viral oncogene homolog |
| TPM3 | 214365_at | tropomyosin 3 |
| RASGRP2 | 214367_at | RAS guanyl releasing protein 2 (calcium and DAG-regulated) |
| RASGRP2 | 214368_at | RAS guanyl releasing protein 2 (calcium and DAG-regulated) |
| RASGRP2 | 214369_s_at | RAS guanyl releasing protein 2 (calcium and DAG-regulated) |
| IKBKE | 214398_s_at | inhibitor of kappa light polypeptide gene enhancer in B-cells, kinase epsilon |
| CACNG2 | 214495_at | calcium channel, voltage-dependent, gamma subunit 2 |
| FGF3 | 214571_at | fibroblast growth factor 3 (murine mammary tumor virus integration site oncogene) |
| FGF12 | 214589_at | fibroblast growth factor 12 |
| MAP2K1 | 214592_s_at | Mitogen-activated protein kinase kinase 1 |
| MINK1 | 214625_s_at | misshapen-like kinase 1 (zebrafish) |
| CHP | 214665_s_at | calcium binding protein P22 |
| NTRK2 | 214680_at | neurotrophic tyrosine kinase, receptor, type 2 |
| FLNA | 214752_x_at | filamin A, alpha (actin binding protein 280) |
| MAP3K1 | 214786_at | mitogen-activated protein kinase kinase kinase 1 |
| DUSP7 | 214793_at | dual specificity phosphatase 7 |
| CACNA1A | 214933_at | calcium channel, voltage-dependent, P/Q type, alpha 1A subunit |
| MAPKAPK2 | 215050_x_at | mitogen-activated protein kinase-activated protein kinase 2 |
| GRB2 | 215075_s_at | growth factor receptor-bound protein 2 |
| PRKCA | 215194_at | protein kinase C, alpha |
| PRKCA | 215195_at | protein kinase C, alpha |
| PDGFRA | 215305_at | platelet-derived growth factor receptor, alpha polypeptide |
| CACNB2 | 215365_at | calcium channel, voltage-dependent, beta 2 subunit |
| FGFR1 | 215404_x_at | fibroblast growth factor receptor 1 (fms-related tyrosine kinase 2, Pfeiffer syndrome) |
| MAP2K3 | 215498_s_at | mitogen-activated protein kinase kinase 3 /// mitogen-activated protein kinase kinase 3 |
| MAP2K3 | 215499_at | mitogen-activated protein kinase kinase 3 /// mitogen-activated protein kinase kinase 3 |
| DUSP10 | 215501_s_at | dual specificity phosphatase 10 |
| IL1R1 | 215561_s_at | interleukin 1 receptor, type I |
| RASGRF1 | 215688_at | Ras protein-specific guanine nucleotide-releasing factor 1 |
| PPP5C | 215705_at | protein phosphatase 5, catalytic subunit |
| FAS | 215719_x_at | Fas (TNF receptor superfamily, member 6) |
| FUS | 215744_at | fusion (involved in t(12; 16) in malignant liposarcoma) |
| EVI1 | 215851_at | ecotropic viral integration site 1 |
| PLA2G5 | 215870_s_at | phospholipase A2, group V |
| PLA2G5 | 215871_at | phospholipase A2, group V |
| MINK1 | 215909_x_at | misshapen-like kinase 1 (zebrafish) |
| PLA2G6 | 215938_s_at | phospholipase A2, group VI (cytosolic, calcium-independent) |
| DAXX | 216038_x_at | death-associated protein 6 |
| PDGFB | 216055_at | Platelet-derived growth factor beta polypeptide (simian sarcoma viral oncogene) |

TABLE 6-continued

Pathway 6: Mitogen activated protein kinase

| Gene Symbol | Probe Set ID | Gene Title |
|---|---|---|
| PDGFB | 216061_x_at | platelet-derived growth factor beta polypeptide (simian sarcoma viral oncogene) |
| NF1 | 216115_at | Neurofibromin 1 (neurofibromatosis, von Recklinghausen disease, Watson disease) |
| MAPK8IP3 | 216137_s_at | Mitogen-activated protein kinase 8 interacting protein 3 |
| MAPK8IP3 | 216139_s_at | mitogen-activated protein kinase 8 interacting protein 3 |
| MAP3K4 | 216199_s_at | mitogen-activated protein kinase kinase kinase 4 |
| MAP2K7 | 216206_x_at | mitogen-activated protein kinase kinase 7 |
| PRKACA | 216234_s_at | protein kinase, cAMP-dependent, catalytic, alpha |
| FAS | 216252_x_at | Fas (TNF receptor superfamily, member 6) |
| MAP2K5 | 216435_at | Mitogen-activated protein kinase kinase 5 |
| MAP2K5 | 216765_at | Mitogen-activated protein kinase kinase 5 |
| RUNX1T1 | 216831_s_at | runt-related transcription factor 1; translocated to, 1 (cyclin D-related) |
| RUNX1T1 | 216832_at | runt-related transcription factor 1; translocated to, 1 (cyclin D-related) |
| PDGFB | 217112_at | platelet-derived growth factor beta polypeptide (simian sarcoma viral oncogene) |
| STMN1 | 217253_at | Stathmin 1/oncoprotein 18 |
| STMN1 | 217257_at | Stathmin 1/oncoprotein 18 |
| RUNX1 | 217263_x_at | runt-related transcription factor 1 (acute myeloid leukemia 1; aml1 oncogene) |
| FUS | 217370_x_at | fusion (involved in t(12;16) in malignant liposarcoma) |
| CAGNA1S | 217515_s_at | calcium channel, voltage-dependent, L type, alpha 1S subunit |
| SOS2 | 217575_s_at | Son of sevenless homolog 2 (*Drosophila*) |
| SOS2 | 217576_x_at | son of sevenless homolog 2 (*Drosophila*) |
| SOS2 | 217644_s_at | son of sevenless homolog 2 (*Drosophila*) |
| STMN1 | 217714_x_at | stathmin 1/oncoprotein 18 |
| TFG | 217839_at | TRK-fused gene |
| MAP2K1IP1 | 217971_at | mitogen-activated protein kinase kinase 1 interacting protein 1 |
| MAP4K4 | 218181_s_at | mitogen-activated protein kinase kinase kinase 4 |
| MKNK2 | 218205_s_at | MAP kinase interacting serine/threonine kinase 2 |
| SITPEC | 218225_at | signaling intermediate in Toll pathway, evolutionarily conserved |
| MAP4K3 | 218311_at | mitogen-activated protein kinase kinase kinase 3 |
| NLK | 218318_s_at | nemo like kinase |
| ARRB1 | 218832_x_at | arrestin, beta 1 |
| ZAK | 218833_at | sterile alpha motif and leucine zipper containing kinase AZK |
| MAP3K6 | 219278_at | mitogen-activated protein kinase kinase kinase 6 |
| AKT3 | 219393_s_at | v-akt murine thymoma viral oncogene homolog 3 (protein kinase B, gamma) |
| FGF20 | 220394_at | fibroblast growth factor 20 |
| TGFB2 | 220406_at | transforming growth factor, beta 2 |
| TGFB2 | 220407_s_at | transforming growth factor, beta 2 |
| PLA2G2D | 220423_at | phospholipase A2, group IID |
| PLA2G3 | 220780_at | phospholipase A2, group III |
| PLA2G12A | 221027_s_at | phospholipase A2, group XIIA /// phospholipase A2, group XIIA |
| FGF23 | 221166_at | fibroblast growth factor 23 |
| FGF14 | 221310_at | fibroblast growth factor 14 |
| FGF22 | 221315_s_at | fibroblast growth factor 22 |
| MOS | 221367_at | v-mos Moloney murine sarcoma viral oncogene homolog |
| FGF16 | 221374_at | fibroblast growth factor 16 |
| FGF17 | 221376_at | fibroblast growth factor 17 |
| PLA2G2E | 221389_at | phospholipase A2, group IIE |
| CACNG5 | 221401_at | calcium channel, voltage-dependent, gamma subunit 5 |
| FGF21 | 221433_at | fibroblast growth factor 21 |
| DUSP10 | 221563_at | dual specificity phosphatase 10 |
| CACNG4 | 221585_at | calcium channel, voltage-dependent, gamma subunit 4 |
| CACNA1I | 221631_at | calcium channel, voltage-dependent, alpha 1I subunit |
| MAP3K2 | 221695_s_at | mitogen-activated protein kinase kinase kinase 2 |
| GNA12 | 221737_at | guanine nucleotide binding protein (G protein) alpha 12 |
| NTRK2 | 221795_at | neurotrophic tyrosine kinase, receptor, type 2 |
| NTRK2 | 221796_at | neurotrophic tyrosine kinase, receptor, type 2 |
| TFG | 221871_s_at | TRK-fused gene |
| EVI1 | 221884_at | ecotropic viral integration site 1 |
| HSPA8 | 221891_x_at | heat shock 70kDa protein 8 |
| FGFR3 | 222006_at | Fibroblast growth factor receptor 3 (achondroplasia, thanatophoric dwarfism) |
| FGFR1 | 222164_at | Fibroblast growth factor receptor 1 (fms-related tyrosine kinase 2, Pfeiffer syndrome) |
| MAP4K4 | 222547_at | mitogen-activated protein kinase kinase kinase 4 |
| MAP4K4 | 222548_s_at | mitogen-activated protein kinase kinase kinase 4 |
| NLK | 222589_at | nemo like kinase |
| NLK | 222590_s_at | nemo like kinase |
| ARRB1 | 222756_s_at | arrestin, beta 1 |
| ZAK | 222757_s_at | sterile alpha motif and leucine zipper containing kinase AZK |
| GNG12 | 222834_s_at | guanine nucleotide binding protein (G protein), gamma 12 |

TABLE 6-continued

| | Pathway 6: Mitogen activated protein kinase | |
|---|---|---|
| Gene Symbol | Probe Set ID | Gene Title |
| AKT3 | 222880_at | v-akt murine thymoma viral oncogene homolog 3 (protein kinase B, gamma) |
| ARRB1 | 222912_at | arrestin, beta 1 |
| CACNA1H | 222960_at | calcium channel, voltage-dependent, alpha 1H subunit |
| TPM3 | 222976_s_at | tropomyosin 3 |
| GRB2 | 223049_at | growth factor receptor-bound protein 2 |
| MKNK2 | 223199_at | MAP kinase interacting serine/threonine kinase 2 |
| PLA2G12A | 223373_s_at | phospholipase A2, group XIIA |
| ZAK | 223519_at | sterile alpha motif and leucine zipper containing kinase AZK |
| STK4 | 223746_at | serine/threonine kinase 4 |
| MAP2K5 | 224114_at | Mitogen-activated protein kinase kinase 5 |
| CACNG7 | 224137_at | calcium channel, voltage-dependent, gamma subunit 7 |
| TPM3 | 224164_at | tropomyosin 3 |
| HSPA8 | 224187_x_at | heat shock 70kDa protein 8 |
| AKT3 | 224229_s_at | v-akt murine thymoma viral oncogene homolog 3 (protein kinase B, gamma) |
| CAGNG6 | 224291_at | calcium channel, voltage-dependent, gamma subunit 6 |
| DUSP16 | 224336_s_at | dual specificity phosphatase 16 /// dual specificity phosphatase 16 |
| NFATC2 | 224542_s_at | nuclear factor of activated T-cells, cytoplasmic, calcineurin-dependent 2 |
| MAPK1 | 224621_at | mitogen-activated protein kinase 1 |
| GNA12 | 224681_at | guanine nucleotide binding protein (G protein) alpha 12 |
| TGFBR1 | 224793_s_at | transforming growth factor, beta receptor I (activin A receptor type II-like kinase) |
| DUSP16 | 224832_at | dual specificity phosphatase 16 |
| EGFR | 224999_at | Epidermal growth factor receptor (erythroblastic leukemia viral oncogene homolog) |
| MRAS | 225185_at | muscle RAS oncogene homolog |
| PRKCA | 225225_at | Homo sapiens, clone IMAGE:4103364, mRNA /// Protein kinase C, alpha |
| PRKCA | 225332_at | Homo sapiens, clone IMAGE:4103364, mRNA /// Protein kinase C, alpha |
| STK4 | 225364_at | serine/threonine kinase 4 |
| MAPT | 225379_at | microtubule-associated protein tau |
| AKT2 | 225471_s_at | v-akt murine thymoma viral oncogene homolog 2 |
| ZAK | 225662_at | sterile alpha motif and leucine zipper containing kinase AZK |
| ZAK | 225665_at | sterile alpha motif and leucine zipper containing kinase AZK |
| MAPK9 | 225781_at | Mitogen-activated protein kinase 9 |
| MAP3K1 | 225927_at | mitogen-activated protein kinase kinase kinase 1 |
| MAP2K7 | 226023_at | mitogen-activated protein kinase kinase 7 |
| CASP2 | 226032_at | caspase 2, apoptosis-related cysteine peptidase (neural precursor cell expressed) |
| DUSP4 | 226034_at | Dual specificity phosphatase 4 |
| CASP2 | 226036_x_at | caspase 2, apoptosis-related cysteine peptidase (neural precursor cell expressed) |
| MAPK8 | 226046_at | mitogen-activated protein kinase 8 |
| MAPK8 | 226048_at | mitogen-activated protein kinase 8 |
| MAP2K7 | 226053_at | mitogen-activated protein kinase kinase 7 |
| RPS6KA3 | 226335_at | ribosomal protein S6 kinase, 90kDa, polypeptide 3 |
| BRAF | 226391_at | V-raf murine sarcoma viral oncogene homolog B1 |
| RASA2 | 226392_at | RAS p21 protein activator 2 |
| CDC42 | 226400_at | Cell division cycle 42 (GTP binding protein, 25kDa) |
| EVI1 | 226420_at | ecotropic viral integration site 1 |
| MAP3K2 | 226441_at | Mitogen-activated protein kinase kinase kinase 2 |
| PAK1 | 226507_at | p21/Cdc42/Rac1-activated kinase 1 (STE20 homolog, yeast) |
| DUSP1 | 226578_s_at | Dual specificity phosphatase 1 |
| FGFR1 | 226705_at | Fibroblast growth factor receptor 1 (fms-related tyrosine kinase 2, Pfeiffer syndrome) |
| MAP3K2 | 226979_at | mitogen-activated protein kinase kinase kinase 2 |
| NFATC2 | 226991_at | Nuclear factor of activated T-cells, cytoplasmic, calcineurin-dependent 2 |
| MAP3K2 | 227073_at | Mitogen-activated protein kinase kinase kinase 2 |
| MAP3K3 | 227131_at | mitogen-activated protein kinase kinase kinase 3 |
| FGF11 | 227271_at | fibroblast growth factor 11 |
| SOS1 | 227426_at | Son of sevenless homolog 1 (*Drosophila*) |
| MAP2K1IP1 | 227562_at | Mitogen-activated protein kinase kinase 1 interacting protein 1 |
| CACNA2D1 | 227623_at | Calcium channel, voltage-dependent, alpha 2/delta subunit 1 |
| EEF1A1 | 227708_at | eukaryotic translation elongation factor 1 alpha 1 |
| PPM1A | 227728_at | Protein phosphatase 1A (formerly 2C), magnesium-dependent, alpha isoform |
| PRKCB1 | 227817_at | Protein kinase C, beta 1 |
| RASGRF2 | 228109_at | Ras protein-specific guanine nucleotide-releasing factor 2 |
| TGFB2 | 228121_at | Transforming growth factor, beta 2 |
| NFATC2 | 228442_at | Nuclear factor of activated T-cells, cytoplasmic, calcineurin-dependent 2 |
| CAGNA1D | 228560_at | Calcium channel, voltage-dependent, L type, alpha 1D subunit |

TABLE 6-continued

Pathway 6: Mitogen activated protein kinase

| Gene Symbol | Probe Set ID | Gene Title |
|---|---|---|
| GRB2 | 228572_at | growth factor receptor-bound protein 2 |
| RUNX1T1 | 228827_at | Runt-related transcription factor 1; translocated to, 1 (cyclin D-related) |
| PPM1A | 229027_at | Protein phosphatase 1A (formerly 2C), magnesium-dependent, alpha isoform |
| JUND | 229117_s_at | Jun D proto-oncogene |
| SOS1 | 229261_at | Son of sevenless homolog 1 (*Drosophila*) |
| NTRK2 | 229463_at | neurotrophic tyrosine kinase, receptor, type 2 |
| PPP3CA | 229606_at | Protein phosphatase 3 (formerly 2B), catalytic subunit, alpha isoform |
| MAPK8 | 229664_at | Mitogen-activated protein kinase 8 |
| MAPK1 | 229847_at | Mitogen-activated protein kinase 1 |
| MAP3K6 | 229960_at | mitogen-activated protein kinase kinase kinase 6 |
| HSPA5 | 230031_at | heat shock 70kDa protein 5 (glucose-regulated protein, 78kDa) |
| PAK1 | 230100_x_at | p21/Cdc42/Rac1-activated kinase 1 (STE20 homolog, yeast) |
| MAPK8IP3 | 230162_s_at | Mitogen-activated protein kinase 8 interacting protein 3 |
| FGF14 | 230288_at | Fibroblast growth factor 14 |
| SOS1 | 230337_at | son of sevenless homolog 1 (*Drosophila*) |
| PRKCB1 | 230437_s_at | Protein kinase C, beta 1 |
| RPS6KA4 | 230544_at | Ribosomal protein S6 kinase, 90kDa, polypeptide 4 |
| ELK4 | 230549_at | ELK4, ETS-domain protein (SRF accessory protein 1) |
| RASA2 | 230669_at | RAS p21 protein activator 2 |
| FGFR2 | 230842_at | Fibroblast growth factor receptor 2 (bacteria-expressed kinase) |
| FGF7 | 230918_at | Fibroblast growth factor 7 (keratinocyte growth factor) |
| FUS | 231108_at | Fusion (involved in t(12; 16) in malignant liposarcoma) |
| RAP1B | 231127_at | RAP1B, member of RAS oncogene family |
| CASP8 | 231218_at | Caspase 8, apoptosis-related cysteine peptidase |
| PPP3R2 | 231304_at | protein phosphatase 3 (formerly 2B), regulatory subunit B, 19kDa, beta isoform |
| RASGRP4 | 231328_s_at | RAS guanyl releasing protein 4 |
| PPM1A | 231370_at | Protein phosphatase 1A (formerly 2C), magnesium-dependent, alpha isoform |
| FGF18 | 231382_at | Fibroblast growth factor 18 |
| FGF14 | 231523_at | fibroblast growth factor 14 |
| CASP14 | 231722_at | caspase 14, apoptosis-related cysteine peptidase |
| CACNG4 | 231737_at | calcium channel, voltage-dependent, gamma subunit 4 |
| FGF10 | 231762_at | fibroblast growth factor 10 |
| NTF5 | 231785_at | neurotrophin 5 (neurotrophin 4/5) |
| NFATC2 | 231801_at | nuclear factor of activated T-cells, cytoplasmic, calcineurin-dependent 2 |
| FGF11 | 231803_at | fibroblast orowth factor 11 |
| MAPK8IP | 3232085_at | mitogen-activated protein kinase 8 interacting protein 3 |
| HSPA9B | 232200_at | heat shock 70kDa protein 9B (mortalin-2) |
| EGFR | 232541_at | Epidermal growth factor receptor (erythroblastic leukemia viral oncogene homolog |
| PPM1B | 232580_x_at | Protein phosphatase 1B (formerly 2C), magnesium-dependent, beta isoform |
| MAX | 233283_at | MYC associated factor X |
| PTPN5 | 233470_at | Protein tyrosine phosphatase, non-receptor type 5 (striatum-enriched) |
| PTPN5 | 233471_at | protein tyrosine phosphatase, non-receptor type 5 (striatum-enriched) |
| MEF2C | 233522_at | MADS box transcription enhancer factor 2, polypeptide C |
| MAP3K7IP1 | 233679_at | Mitogen-activated protein kinase kinase kinase 7 interacting protein 1 |
| NFATC2 | 233706_at | Nuclear factor of activated T-cells, cytoplasmic, calcineurin-dependent 2 |
| NFATC2 | 233708_at | Nuclear factor of activated T-cells, cytoplasmic, calcineurin-dependent 2 |
| STK3 | 233779_x_at | Serine/threonine kinase 3 (STE20 homolog, yeast) |
| RASGRP1 | 233926_at | RAS guanyl releasing protein 1 (calcium and DAG-regulated) |
| MAP3K7IP2 | 233957_at | Mitogen-activated protein kinase kinase kinase 7 interacting protein 2 |
| IL1R1 | 234516_at | Interleukin 1 receptor, type I |
| IL1R1 | 234523_at | Interleukin 1 receptor, type I |
| CACNG8 | 234750_at | calcium channel, voltage-dependent, gamma subunit 8 |
| CACNG8 | 234756_at | calcium channel, voltage-dependent, gamma subunit 8 |
| MAP3K2 | 235011_at | Mitogen-activated protein kinase kinase 2 |
| PPM1A | 235344_at | Protein phosphatase 1A (formerly 2C), magnesium-dependent, alpha isoform |
| MAP3K8 | 235421_at | Mitogen-activated protein kinase kinase kinase 8 |
| MAP3K7IP1 | 235480_at | Mitogen-activated protein kinase kinase kinase 7 interacting protein 1 |
| MAP2K5 | 235601_at | Mitogen-activated protein kinase kinase 5 |
| STMN1 | 235669_at | Stathmin 1/oncoprotein 18 |
| PRKACB | 235780_at | protein kinase, cAMP-dependent, catalytic, beta |
| CACNA1B | 235781_at | calcium channel, voltage-dependent, L type, alpha 1B subunit |
| MAP3K7IP1 | 235827_at | mitogen-activated protein kinase kinase kinase 7 interacting protein 1 |

TABLE 6-continued

Pathway 6: Mitogen activated protein kinase

| Gene Symbol | Probe Set ID | Gene Title |
|---|---|---|
| NTRK2 | 236095_at | neurotrophic tyrosine kinase, receptor, type 2 |
| RUNX1 | 236114_at | Runt-related transcription factor 1 (acute myeloid leukemia 1; aml1 oncogene) |
| PRKCG | 236195_x_at | protein kinase C, gamma |
| STK4 | 236259_at | serine/threonine kinase 4 |
| NFATC4 | 236270_at | nuclear factor of activated T-cells, cytoplasm ic, calcineurin-dependent 4 |
| PAK2 | 236283_x_at | p21 (CDKN1A)-activated kinase 2 |
| MEF2C | 236395_at | MADS box transcription enhancer factor 2, polypeptide C |
| TGFBR2 | 236419_at | Transforming growth factor, beta receptor II (70/80kDa) |
| PTPN5 | 236456_at | protein tyrosine phosphatase, non-receptor type 5 (striatum-enriched) |
| DUSP16 | 236511_at | Dual specificity phosphatase 16 |
| PPP3CA | 236545_at | Protein phosphatase 3 (formerly 2B), catalytic subunit, alpha isoform i |
| TGFBR1 | 236561_at | Transforming growth factor, beta receptor I (activin A receptor type II-like kinase) |
| CASP3 | 236729_at | Caspase 3, apoptosis-related cysteine peptidase |
| ZAK | 237133_at | Hypothetical protein LOC339751 |
| MDS1 | 237269_at | Myelodysplasia syndrome 1 |
| MAPK10 | 237413_at | Mitogen-activated protein kinase 10 |
| ZAK | 237548_at | Hypothetical protein LOC339751 |
| CACNB2 | 237698_at | Calcium channel, voltage-dependent, beta 2 subunit |
| PLA2G6 | 237726_at | Phospholipase A2, group VI (cytosolic, calcium-independent) |
| MAP2K2 | 237878_at | Mitogen-activated protein kinase kinase 2 |
| EGFR | 237938_at | Epidermal growth factor receptor (erythroblastic leukemia viral oncogene homolog) |
| TPM3 | 238079_at | Tropomyosin 3 |
| RASA1 | 238243_at | RAS p21 protein activator (GTPase activating protein) 1 |
| MDS1 | 238370_x_at | Myelodysplasia syndrome 1 |
| MDS1 | 238375_at | Myelodysplasia syndrome 1 |
| DUSP8 | 238594_x_at | Dual specificity phosphatase 8 |
| ZAK | 238613_at | sterile alpha motif and leucine zipper containing kinase AZK |
| NLK | 238624_at | Nemo-like kinase |
| MAP4K4 | 238769_at | Mitogen-activated protein kinase kinase kinase kinase 4 |
| SOS2 | 238830_at | Son of sevenless homolog 2 (*Drosophila*) |
| RASA1 | 239301_at | RAS p21 protein activator (GTPase activating protein) 1 |
| BDNF | 239367_at | brain-derived neurotrophic factor |
| TFG | 239385_at | TRK-fused gene |
| TGFBR1 | 239605_x_at | Transforming growth factor, beta receptor I (activin A receptor type Il-like kinase) |
| NFKB1 | 239876_at | Nuclear factor of kappa light polypeptide gene enhancer in B-cells 1 (p105) |
| MEF2C | 239938_x_at | MADS box transcription enhancer factor 2, polypeptide C |
| MEF2C | 239966_at | MADS box transcription enhancer factor 2, polypeptide C |
| FGF12 | 240067_at | Fibroblast growth factor 12 |
| RAP1A | 240215_at | RAP1A, member of RAS oncogene family |
| FGF2 | 240243_at | Fibroblast growth factor 2 (basic) |
| AKT3 | 240568_at | V-akt murine thymoma viral oncogene homolog 3 (protein kinase B, gamma) |
| RASGRP4 | 240862_at | RAS guanyl releasing protein 4 |
| FGFR2 | 240913_at | fibroblast growth factor receptor 2 (bacteria-expressed kinase) |
| FGF12 | 241323_at | Fibroblast growth factor 12 |
| CASP4 | 241340_at | Caspase 4, apoptosis-related cysteine peptidase |
| RPS6KA3 | 241460_at | Ribosomal protein S6 kinase, 90kDa, polypeptide 3 |
| MDS1 | 241628_at | Myelodysplasia syndrome 1 |
| MDS1 | 241635_at | Myelodysplasia syndrome 1 |
| FGFR1 | 241724_x_at | Fibroblast growth factor receptor 1 (fms-related tyrosine kinase 2, Pfeiffer syndrome) |
| PPP3R1 | 241786_at | Protein phosphatase 3 (formerly 2B), regulatory subunit B, 19kDa, alpha isoform) |
| HSPA9B | 241840_at | Heat shock 70kDa protein 9B (mortalin-2) |
| TNFRSF1A | 241944_x_at | Tumor necrosis factor receptor superfamily, member 1A |
| SOS1 | 242018_at | Son of sevenless homolog 1 (*Drosophila*) |
| RAF1 | 242425_at | V-raf-1 murine leukemia viral oncogene homolog 1 |
| MAP3K5 | 242461_at | Mitogen-activated protein kinase kinase kinase 5 |
| SOS1 | 242682_at | Son of sevenless homolog 1 (*Drosophila*) |
| AKT3 | 242876_at | V-akt murine thymoma viral oncogene homolog 3 (protein kinase B, gamma) |
| AKT3 | 242879_x_at | V-akt murine thymoma viral oncogene homolog 3 (protein kinase B, gamma) |
| MAP3K1 | 243030_at | Mitogen-activated protein kinase kinase kinase 1 |
| CACNB4 | 243244_at | Calcium channel, voltage-dependent, beta 4 subunit |
| MKNK1 | 243256_at | MAP kinase interacting serine/threonine kinase 1 |
| EVI1 | 243277_x_at | Ecotropic viral integration site 1 |
| EGFR | 243327_at | Epidermal growth factor receptor (erythroblastic leukemia viral oncogene homolog) |

TABLE 6-continued

Pathway 6: Mitogen activated protein kinase

| Gene Symbol | Probe Set ID | Gene Title |
| --- | --- | --- |
| CACNA1D | 243334_at | Calcium channel, voltage-dependent, L type, alpha 10 subunit |
| MAP3K7IP2 | 243557_at | Mitogen-activated protein kinase kinase kinase 7 interacting protein 2 |
| BRAF | 243829_at | v-raf murine sarcoma viral oncogene homolog Bi |
| STK4 | 243981_at | serine/threonine kinase 4 |
| MYC | 244089_at | V-myc myelocytomatosis viral oncogene homolog (avian) |
| MEF2C | 244230_at | MADS box transcription enhancer factor 2, polypeptide C |
| PAK2 | 244268_x_at | p21 (CDKN1A)-activated kinase 2 |
| MAP2K5 | 244298_at | Mitogen-activated protein kinase kinase 5 |
| RAF1 | 244373_at | V-raf-1 murine leukemia viral oncogene homolog 1 |
| RUNX1T1 | 244420_at | Runt-related transcription factor 1; translocated to, 1 (cyclin D-related) |
| BDNF | 244503_at | Brain-derived neurotrophic factor opposite strand |
| TFG | 244614_at | TRK-fused gene |
| PPP3R2 | 244782_at | protein phosphatase 3 (formerly 2B), regulatory subunit B, 19kDa, beta isoform |
| MAP4K4 | 244846_at | Mitogen-activated protein kinase kinase kinase kinase 4 |
| PPP3CC | 32540_at | Protein phosphatase 3 (formerly 2B), catalytic subunit, gamma isoform |
| PPP3CC | 32541_at | protein phosphatase 3 (formerly 2B), catalytic subunit, gamma isoform |
| CASP2 | 34449_at | caspase 2, apoptosis-related cysteine peptidase (neural precursor cell expressed) |
| CACNB3 | 34726_at | calcium channel, voltage-dependent, beta 3 subunit |
| MAPK7 | 35617_at | mitogen-activated protein kinase 7 |
| IKBKG | 36004_at | inhibitor of kappa light polypeptide gene enhancer in B-cells, kinase gamma |
| IL1B | 39402_at | interleukin 1, beta |
| CACNG4 | 62987_r_at | calcium channel, voltage-dependent, gamma subunit 4 |

TABLE 7

Pathway 7: Cell adhesion molecules

| Gene Symbol | Probe Set ID | Gene Title |
| --- | --- | --- |
| ITGAL | 1554240_a_at | integrin, alpha L (antigen CD11A (p180), lymphocyte function-associated antigen 1; alpha polypeptide) |
| CD80 | 1554519_at | CD80 antigen (CD28 antigen ligand 1, B7-1 antigen) |
| HLA-DOB | 1554984_a_at | major histocompatibility complex, class II, DO beta |
| ITGB2 | 1555349_a_at | integrin, beta 2 (antigen CD18 (p95), lymphocyte function-associated antigen 1; macrophage antigen 1 (mac-1) beta subunit) |
| CD80 | 1555689_at | CD80 antigen (CD28 antigen ligand 1, B7-1 antigen) |
| ALCAM | 1563958_at | Activated leukocyte cell adhesion molecule |
| ALCAM | 1569362_at | Activated leukocyte cell adhesion molecule |
| HLA-E | 200904_at | major histocompatibility complex, class I, E |
| HLA-E | 200905_x_at | major histocompatibility complex, class I, E |
| HLA-DPB1 | 201137_s_at | major histocompatibility complex, class II, DP beta 1 |
| ALCAM | 201951_at | activated leukocyte cell adhesion molecule |
| ALCAM | 201952_at | activated leukocyte cell adhesion molecule |
| ICAM1 | 202637_s_at | intercellular adhesion molecule 1 (CD54), human rhinovirus receptor |
| ICAM1 | 202638_s_at | intercellular adhesion molecule 1 (CD54), human rhinovirus receptor |
| ITGB2 | 202803_s_at | integrin, beta 2 (antigen CD18 (p95), lymphocyte function-associated antigen 1; macrophage antigen 1 (mac-1) beta subunit) |
| HLA-DQA1 | 203290_at | major histocompatibility complex, class II, DQ alpha 1 /// major histocompatibility complex, class II, DQ alpha 1 |
| HLA-DMB | 203932_at | major histocompatibility complex, class II, DM beta /// major histocompatibility complex, class II, DM beta |
| CD22 /// MAG | 204581_at | CD22 antigen /// myelin associated glycoprotein |
| HLA-DRB1 | 204670_x_at | major histocompatibility complex, class II, DR beta 1 |
| ICAM2 | 204683_at | intercellular adhesion molecule 2 |
| HLA-F | 204806_x_at | major histocompatibility complex, class I, F |
| ICAM3 | 204949_at | intercellular adhesion molecule 3 |
| CD40 | 205153_s_at | CD40 antigen (TNF receptor superfamily member 5) |
| CD58 | 205173_x_at | CD58 antigen, (lymphocyte function-associated antigen 3) |
| HLA-DOB | 205671_s_at | major histocompatibility complex, class II, DO beta |
| CD86 | 205685_at | CD86 antigen (CD28 antigen ligand 2, B7-2 antigen) |
| CD86 | 205686_s_at | CD86 antigen (CD28 antigen ligand 2, B7-2 antigen) |
| HLA-DOA | 206313_at | major histocompatibility complex, class II, DO alpha |
| CD80 | 207176_s_at | CD80 antigen (CD28 antigen ligand 1, B7-1 antigen) |
| HLA-DRB5 | 208306_x_at | Major histocompatibility complex, class II, DR beta 3 |
| HLA-B | 208729_x_at | major histocompatibility complex, class I, B |
| HLA-C | 208812_x_at | major histocompatibility complex, class I, C |

TABLE 7-continued

Pathway 7: Cell adhesion molecules

| Gene Symbol | Probe Set ID | Gene Title |
|---|---|---|
| HLA-DRA | 208894_at | major histocompatibility complex, class II, DR alpha /// major histocompatibility complex, class II, DR alpha |
| HLA-B | 209140_x_at | major histocompatibility complex, class I, B |
| HLA-DRB1 | 209312_x_at | major histocompatibility complex, class II, DR beta 1 /// major histocompatibility complex, class II, DR beta 1 |
| HLA-DQB1 | 209480_at | Major histocompatibility complex, class II, DQ beta 1 /// Major histocompatibility complex, class II, DQ beta 1 |
| HLA-DRB4 | 209728_at | major histocompatibility complex, class II, DR beta 4 /// major histocompatibility complex, class II, DR beta 4 |
| HLA-DQB1 | 209823_x_at | major histocompatibility complex, class II, DQ beta 1 |
| HLA-G | 210514_x_at | HLA-G histocompatibility antigen, class I, G |
| HLA-DQB1 | 210747_at | major histocompatibility complex, class II, DQ beta 1 |
| CD86 | 210895_s_at | CD86 antigen (CD28 antigen ligand 2, B7-2 antigen) |
| HLA-DRA | 210982_s_at | major histocompatibility complex, class II, DR alpha |
| HLA-DOA | 211142_x_at | major histocompatibility complex, class II, DO alpha |
| ICOSLG | 211197_s_at | inducible T-cell co-stimulator ligand |
| ICOSLG | 211198_s_at | inducible T-cell co-stimulator ligand |
| ICOSLG | 211199_s_at | inducible T-cell co-stimulator ligand |
| HLA-G | 211528_x_at | HLA-G histocompatibility antigen, class I, G |
| HLA-G | 211529_x_at | HLA-G histocompatibility antigen, class I, G |
| HLA-G | 211530_x_at | HLA-G histocompatibility antigen, class I, G |
| HLA-DQB1 | 211654_x_at | major histocompatibility complex, class II, DQ beta 1 /// major histocompatibility complex, class II, DQ beta 1 |
| HLA-DQB1 | 211656_x_at | major histocompatibility complex, class II, DQ beta 1 /// major histocompatibility complex, class II, DQ beta 1 |
| CD58 | 211744_s_at | CD58 antigen, (lymphocyte function-associated antigen 3) /// CD58 antigen, (lymphocyte function-associated antigen 3) |
| HLA-C | 211799_x_at | major histocompatibility complex, class I, C |
| HLA-B | 211911_x_at | major histocompatibility complex, class I, B /// major histocompatibility complex, class I, B |
| HLA-DPA1 | 211990_at | major histocompatibility complex, class II, DP alpha 1 |
| HLA-DPA1 | 211991_s_at | major histocompatibility complex, class II, DP alpha 1 |
| HLA-DQA1 /// HLA-DQA2 | 212671_s_at | major histocompatibility complex, class II, DQ alpha 1 /// major histocompatibility complex, class II, DQ alpha 2 |
| HLA-DQB1 | 212998_x_at | major histocompatibility complex, class II, DQ beta 1 /// major histocompatibility complex, class II, DQ beta 1 |
| HLA-DQB1 | 212999_x_at | Major histocompatibility complex, class II, DQ beta 1 /// Major histocompatibility complex, class II, DQ beta 1 |
| ICOSLG | 213450_s_at | inducible T-cell co-stimulator ligand |
| ITGAL | 213475_s_at | integrin, alpha L (antigen CD11A (p180), lymphocyte function-associated antigen 1; alpha polypeptide) |
| HLA-DPA1 | 213537_at | major histocompatibility complex, class II, DP alpha 1 |
| ICAM2 | 213620_s_at | intercellular adhesion molecule 2 |
| HLA-DQA1 | 213831_at | major histocompatibility complex, class II, DQ alpha 1 |
| HLA-A | 213932_x_at | Major histocompatibility complex, class I, A |
| HLA-C | 214459_x_at | major histocompatibility complex, class I, C |
| HLA-DRB1 | 215193_x_at | major histocompatibility complex, class II, DR beta 1 |
| HLA-A | 215313_x_at | major histocompatibility complex, class I, A |
| CD40 | 215346_at | CD40 antigen (TNF receptor superfamily member 5) |
| ICAM1 | 215485_s_at | intercellular adhesion molecule 1 (CD54), human rhinovirus receptor |
| HLA-DQB2 | 215536_at | major histocompatibility complex, class II, DQ beta 2 |
| HLA-DRB4 | 215666_at | major histocompatibility complex, class II, DR beta 4 |
| HLA-DRB4 | 215669_at | major histocompatibility complex, class II, DR beta 4 |
| CD58 | 216322_at | CD58 antigen, (lymphocyte function-associated antigen 3) |
| HLA-C | 216526_x_at | major histocompatibility complex, class I, C |
| CD58 | 216942_s_at | CD58 antigen, (lymphocyte function-associated antigen 3) |
| HLA-DOA | 216946_at | major histocompatibility complex, class II, DO alpha |
| HLA-DOA | 217001_x_at | major histocompatibility complex, class II, DO alpha |
| CD22 /// MAG | 217422_s_at | CD22 antigen /// myelin associated glycoprotein |
| HLA-G /// HLA-H | 217436_x_at | HLA-G histocompatibility antigen, class I, G /// major histocompatibility complex, class I, H (pseudogene) |
| HLA-E | 217456_x_at | major histocompatibility complex, class I, E |
| HLA-DMA | 217478_s_at | major histocompatibility complex, class II, DM alpha |
| SN | 219519_s_at | Sialoadhesin /// Sialoadhesin |
| PDCD1LG2 | 220049_s_at | programmed cell death 1 ligand 2 |
| HLA-DRB1 | 221491_x_at | major histocompatibility complex, class II, DR beta 1 /// major histocompatibility complex, class II, DR beta 1 |
| HLA-F | 221875_x_at | major histocompatibility complex, class I, F |
| HLA-F | 221978_at | major histocompatibility complex, class I, F |
| CD58 | 222061_at | CD58 antigen, (lymphocyte function-associated antigen 3) |
| CD40 | 222292_at | CD40 antigen (TNF receptor superfamily member 5) |
| CD274 | 223834_at | CD274 antigen |
| PDCD1LG2 | 224399_at | programmed cell death 1 ligand 2 /// programmed cell death 1 ligand 2 |
| HLA-DOA | 226878_at | major histocompatibility complex, class II, DO alpha |
| PDCD1LG1 | 227458_at | CD274 antigen |
| ICOSLG | 228976_at | inducible T-cell co-stimulator ligand |
| ICAM3 | 229859_at | Intercellular adhesion molecule 3 |
| CD58 | 234128_at | CD58 antigen, (lymphocyte function-associated antigen 3) |
| HLA-DQA1 | 236203_at | Major histocompatibility complex, class II, DQ alpha 1 |
| ICAM3 | 236567_at | Intercellular adhesion molecule 3 |

TABLE 7-continued

Pathway 7: Cell adhesion molecules

| Gene Symbol | Probe Set ID | Gene Title |
|---|---|---|
| ITGB2 | 236988_x_at | integrin, beta 2 (antigen CD18 (p95), lymphocyte function-associated antigen 1; macrophage antigen 1 (mac-1) beta subunit) |
| HLA-DRB1 /// HLA-DRB3 | 238900_at | major histocompatibility complex, class II, DR beta 1 /// major histocompatibility complex, class II, DR beta 3 |
| ALCAM | 240655_at | Activated leukocyte cell adhesion molecule |
| CD58 | 243931_at | CD58 antigen, (lymphocyte function-associated antigen 3) |
| CD40 | 35150_at | CD40 antigen (TNF receptor superfamily member 5) |
| SN | 44673_at | Sialoadhesin |

TABLE 8

Probe set identification of 100 randomly selected gene probe sets

| Probe Set ID | Gene Symbol | Gene Title |
|---|---|---|
| 1570227_at | — | CDNA clone IMAGE:4857625, with apparent retained intron |
| 1570330_at | — | *Homo sapiens*, clone IMAGE:4151631, mRNA |
| 201148_s_at | TIMP3 | TIMP metallopeptidase inhibitor 3 (Sorsby fundus dystrophy, pseudoinflammatory) |
| 201159_s_at | NMT1 | N-myristoyltransferase 1 |
| 201280_s_at | DAB2 | disabled homolog 2, mitogen-responsive phosphoprotein (*Drosophila*) |
| 202495_at | TBCC | tubulin folding cofactor C |
| 202905_x_at | NBN | nibrin |
| 203249_at | EZH1 | enhancer of zeste homolog 1 (*Drosophila*) |
| 205300_s_at | U1SNRNPBP | U11/U12 snRNP 35K |
| 205440_s_at | NPY1R | neuropeptide Y receptor Y1 |
| 205515_at | PRSS12 | protease, serine, 12 (neurotrypsin, motopsin) |
| 205529_s_at | RUNX1T1 | runt-related transcription factor 1; translocated to, 1 (cyclin D-related) |
| 205533_s_at | CDH6 | cadherin 6, type 2, K-cadherin (fetal kidney) |
| 205626_s_at | CALB1 | calbindin 1, 28 kDa |
| 205651_x_at | RAPGEF4 | Rap guanine nucleotide exchange factor (GEF) 4 |
| 205709_s_at | CDS1 | CDP-diacylglycerol synthase (phosphatidate cytidylyltransferase) 1 |
| 205729_at | OSMR | oncostatin M receptor |
| 205760_s_at | OGG1 | 8-oxoguanine DNA glycosylase |
| 205789_at | CD1D | CD1d molecule |
| 206114_at | EPHA4 | EPH receptor A4 |
| 206855_s_at | HYAL2 | hyaluronoglucosaminidase 2 |
| 206929_s_at | NFIC | nuclear factor I/C (CCAAT-binding transcription factor) |
| 207087_x_at | ANK1 | ankyrin 1, erythrocytic |
| 207270_x_at | CD300C | CD300c molecule |
| 207319_s_at | CDC2L5 | cell division cycle 2-like 5 (cholinesterase-related cell division controller) |
| 207428_x_at | CDC2L1 /// LOC728642 | cell division cycle 2-like 1 (PITSLRE proteins) proteins) |
| 207618_s_at | BCS1L | BCS1-like (yeast) |
| 207856_s_at | FLJ41352 /// SMPD4 | sphingomyelin phosphodiesterase 4, neutral membrane |
| 209117_at | WBP2 | WW domain binding protein 2 |

TABLE 8-continued

Probe set identification of 100 randomly selected gene probe sets

| Probe Set ID | Gene Symbol | Gene Title |
|---|---|---|
| 209375_at | XPC | xeroderma pigmentosum, complementation group C |
| 210061_at | ZNF589 | zinc finger protein 589 |
| 210063_at | SARDH | sarcosine dehydrogenase |
| 210124_x_at | SEMA4F | sema domain, immunoglobulin domain (Ig,) |
| 210157_at | C19orf2 | chromosome 19 open reading frame 2 |
| 210200_at | WWP2 | WW domain containing E3 ubiquitin protein ligase 2 |
| 210220_at | FZD2 | frizzled homolog 2 (*Drosophila*) |
| 210234_at | GRM4 | glutamate receptor, metabotropic 4 |
| 210417_s_at | PIK4CB | phosphatidylinositol 4-kinase, catalytic, beta polypeptide |
| 210616_s_at | SEC31A | SEC31 homolog A (*S. cerevisiae*) |
| 214400_at | INSL3 | insulin-like 3 (Leydig cell) |
| 214475_x_at | CAPN3 | calpain 3, (p94) |
| 214570_x_at | DKFZp434K191 /// DKFZP434P211 /// LOC646074 /// LOC651452 /// LOC727983 /// LOC728418 /// LOC728451 /// POM121L1 | POM121 membrane glycoprotein-like 1 (rat) /// POM121-like protein |
| 214674_at | USP19 | ubiquitin specific peptidase 19 |
| 219350_s_at | DIABLO | diablo homolog (*Drosophila*) |
| 221007_s_at | FIP1L1 | FIP1 like 1 (*S. cerevisiae*) |
| 221515_s_at | LCMT1 | leucine carboxyl methyl-transferase 1 |
| 221522_at | ANKRD27 | ankyrin repeat domain 27 (VPS9 domain) |
| 221808_at | RAB9A | RAB9A, member RAS oncogene family |
| 221871_s_at | TFG | TRK-fused gene |
| 221887_s_at | DFNB31 | deafness, autosomal recessive 31 |
| 221941_at | PAOX | polyamine oxidase (exo-N4-amino) |
| 221945_at | FBXO41 | F-box protein 41 |
| 222042_x_at | RKHD1 | Ring finger and KH domain containing 1 |
| 222108_at | AMIGO2 | adhesion molecule with Ig-like domain 2 |
| 222727_s_at | SLC24A6 | solute carrier family 24 (sodium/potassium/calcium exchanger), member 6 |
| 223203_at | LOC727866 /// TMEM29 | transmembrane protein 29 /// similar to transmembrane protein 29 |
| 224898_at | WDR26 | WD repeat domain 26 |
| 225716_at | — | Full-length cDNA clone CS0DK008YI09 of HeLa cells Cot 25-normalized of *Homo sapiens* (human) |
| 225852_at | ANKRD17 | ankyrin repeat domain 17 |
| 230576_at | BLOC1S3 | Biogenesis of lysosome-related organelles complex-1, subunit 3 |
| 230629_s_at | EP400 | E1A binding protein p400 |
| 230632_at | — | Full-length cDNA clone CS0DI051YA02 of Placenta Cot 25-normalized of *Homo sapiens* (human) |
| 230640_at | — | Transcribed locus |
| 230651_at | — | Transcribed locus |
| 232096_x_at | — | CDNA: FLJ22140 fis, clone HEP20977 |
| 232433_at | KIAA1683 | KIAA1683 |
| 232522_at | — | CDNA: FLJ21484 fis, clone COL05256 |
| 232649_at | GLDN | gliomedin |
| 232841_at | — | CDNA: FLJ23097 fis, clone LNG07418 |
| 233236_at | TSPAN16 | tetraspanin 16 |
| 233266_at | — | CDNA FLJ13844 fis, clone THYRO1000805 |

TABLE 8-continued

Probe set identification of 100 randomly selected gene probe sets

| Probe Set ID | Gene Symbol | Gene Title |
|---|---|---|
| 240117_at | FBN3 | fibrillin 3 |
| 240224_at | — | Transcribed locus |
| 240277_at | SLC30A7 | Solute carrier family 30 (zinc transporter), member 7 |
| 240280_at | UFSP1 | inactive Ufm1-specific protease 1 |
| 240452_at | GSPT1 | G1 to S phase transition 1 |
| 240617_at | — | — |
| 240630_at | — | Transcribed locus |
| 240780_at | — | — |
| 241485_at | MYT1L | myelin transcription factor 1-like |
| 241532_at | — | Transcribed locus |
| 241566_at | — | — |
| 241643_at | TLK1 | Tousled-like kinase 1 |
| 241674_s_at | — | Transcribed locus |
| 241677_x_at | — | — |
| 241708_at | DOCK1 | dedicator of cytokinesis 1 |
| 241737_x_at | — | Transcribed locus |
| 241760_x_at | — | — |
| 241861_at | SYCP3 | Synaptonemal complex protein 3 |
| 241864_x_at | — | Transcribed locus, moderately similar to XP_517655.1 similar to KIAA0825 protein [*Pan troglodytes*] |
| 241873_at | — | *Homo sapiens*, clone IMAGE:5209126, mRNA |
| 241874_at | LOC492311 | similar to bovine IgA regulatory protein |
| 241887_at | — | CDNA FLJ41537 fis, clone BRTHA2017985 |
| 241919_x_at | WDR31 | WD repeat domain 31 |
| 244659_at | TRIP12 | Thyroid hormone receptor interactor 12 |
| 244740_at | MGC9913 | Hypothetical protein MGC9913 |
| 244862_at | — | — |
| 31637_s_at | NR1D1 /// THRA | thyroid hormone receptor, alpha (erythroblastic leukemia viral (v-erb-a) oncogene homolog, avian) /// nuclear receptor subfamily 1, group D, member 1 |
| 37005_at | NBL1 | neuroblastoma, suppression of tumorigenicity 1 |
| 48808_at | DHFR | dihydrofolate reductase |

Statistical Analysis

Each pre-specified pathway was assessed in the following manner: A partial least squares (PLS) regression algorithm was used to reduce the data (20, 21, 22). This supervised learning algorithm reduces the independent variables (gene probe sets) to PLS components that are mutually uncorrelated and associated with the binary dependent study variable (restenosis vs. no restenosis). The components of the PLS analysis became the independent variables for logistic regression (SAS, Cary, N.C.). The receiver operating characteristic (ROC) was used to evaluate the predictive accuracy (discrimination) of the logistic regression model. In addition, the misclassification rate (MR), defined as false positives+false negatives/ all was also determined. The Wilcoxon test was also used to test for differences in Pathway expression between the patients who restenosed and those that did not, with significance set at the 0.05 level (one-sided) (SAS, Cary, N.C.).

Results

The demographic characteristics and clinical laboratory data of patients with and without restenosis were similar as shown in Tables 9 and 10. Of note, there was no significant difference in hsCRP (high sensitivity C-reactive protein) in patients who developed restenosis compared to those without restenosis.

TABLE 9

Clinical Variables

| Variable | No Restenosis Group | Restenosis Group |
|---|---|---|
| Age (yrs) | 61 ± 2.0 | 64 ± 2.3 |
| Gender (M) (%) | 82 | 74 |
| Hx of Hypertension (%) | 68 | 57 |
| Hx of ↑ Lipids (%) | 55 | 67 |
| Hx of Smoking (%) | 74 | 67 |
| Hx of Stable Angina (%) | 16 | 10 |
| Hx Unstable Angina (%) | 63 | 76 |

TABLE 10

Laboratory Values

| Variable | No Restenosis Group | Restenosis Group |
|---|---|---|
| Hematocrit (%) | 42.6 ± 0.6 | 43 ± 0.6 |
| Platelets (#/ml × 1000) | 226 ± 15 | 232 ± 14 |
| WBC (#/ml × 1000) | 7.5 ± 0.4 | 7.9 ± 0.4 |
| Neutrophils (%) | 63.7 ± 1.6 | 64.3 ± 2.0 |
| Lymphocytes (%) | 26.3 ± 1.3 | 27 ± 1.9 |
| Monocytes (%) | 6.8 ± 0.4 | 6.0 ± 0.5 |
| Eosinophils (%) | 2.6 ± 0.3 | 2.2 ± 0.3 |
| hsCRP (mg %) | 2.2 ± 0.3 | 2.2 ± 0.3 |

Numbers represent Values ± SEM.

The angiographic characteristics of coronary lesions in each group prior to stent placement, immediately following stent placement and at 6 month follow-up angiography are shown in Table 11.

TABLE 11

Angiographic Data

| Vessel Stented | No Restenosis Group | Restenosis Group |
|---|---|---|
| Left ant. descending (%) | 58 | 44 |
| Left circumflex (%) | 21 | 21 |
| Right coronary (%) | 21 | 35 |
| **Vessel Diameter (mm) | 3.0 ± 0.1 | 2.7 ± 0.1 |
| Stent Diameter (mm) | 3.0 ± 0.1 | 3.0 ± 0.1 |
| Lesion Length (mm) | 11.5 ± 0.8 | 13 ± 1.2 |
| Stent Length (mm) | 19 ± 0.9 | 19 ± 1.0 |
| Post stent MLD (mm) | 2.7 ± 0.1 | 2.5 ± 0.1 |
| Acute Gain (mm) | 1.8 ± 0.1 | 1.7 ± 0.1 |
| Late Loss (mm) | 0.8 ± 0.1 | 1.7 ± 0.1 |

Numbers represent values ± SEM;
**p ≦ 0.05;
MLD = minimum luminal diameter of stented vessel segment;
Acute Gain = immediate post stent MLD minus pre stent MLD;
Late Loss = Post stent MLD minus 6 month follow-up MLD.

Coronary lesions in this study were relatively discrete with lesion length being <20 mm in the majority of instances. Stent length was <23 mm in most instances. There was a significant difference in the reference diameter of the vessel chosen for intervention between those patients with and without restenosis (Table 11). Patients with restenosis had, on average, vessel sizes 0.3 mm smaller than those patients without restenosis. There was no difference in the frequency of the particular vessel stented, lesion length, stent length, or minimum lesion diameter post stenting between patients with and without restenosis. Acute gain was similar in each group immediately post stent placement. Late loss was significantly greater in patients with restenosis vs those without restenosis. The binary rate of restenosis 6 months following stent placement was 41%.

Figure 2:
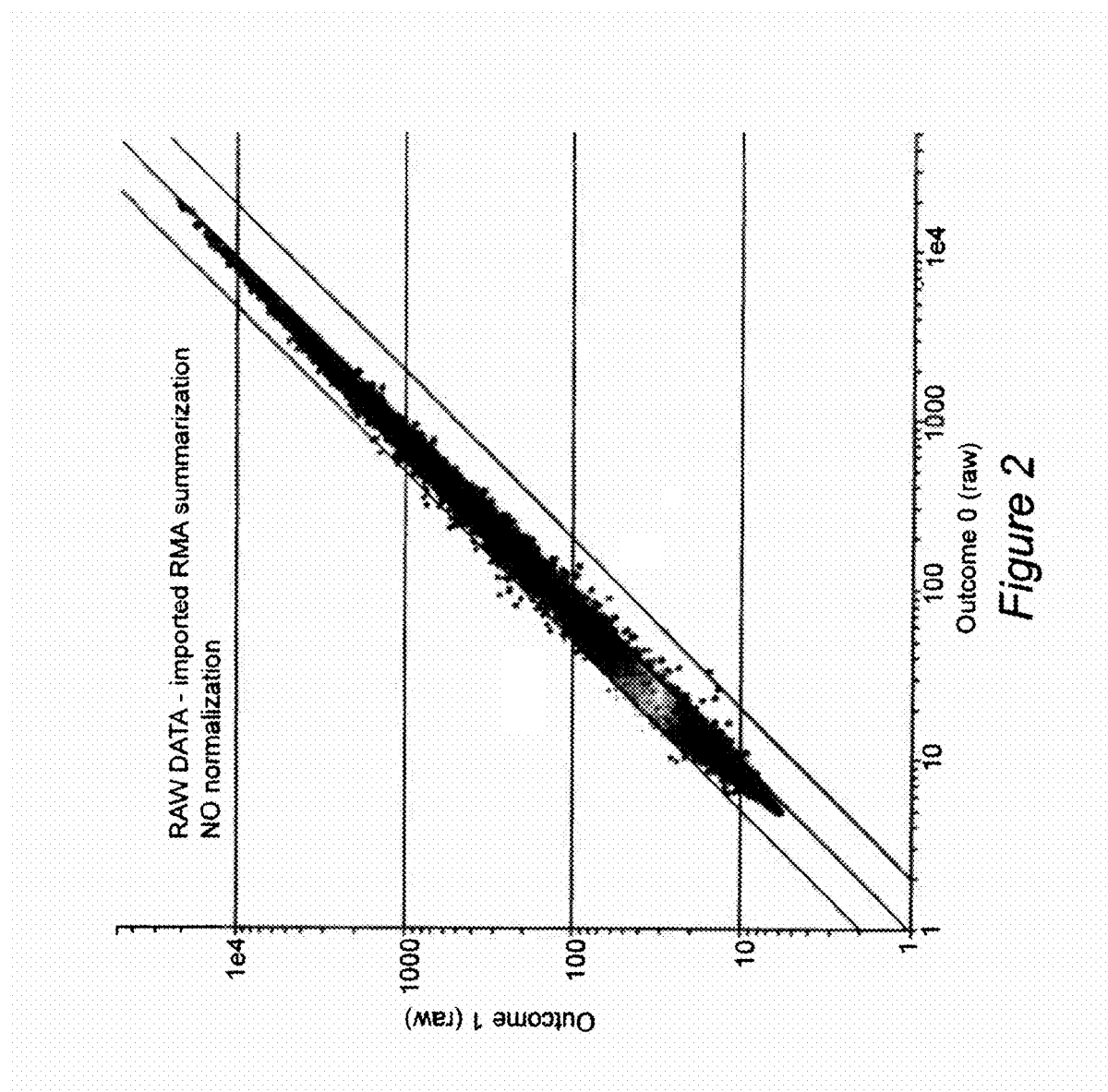
FIG. 2. Results of mRNA expression profiling demonstrating difference between non-restenosis (x-axis) and restenosis (y-axis) patients.

Patients with documented angiographic restenosis within six months after receiving a bare metal stent exhibited, on average, a greater extent of mRNA expression at study enrollment compared to those patients without restenosis (Table 12A). FIG. 2, demonstrates that this phenomena is a result of an apparent increase in mRNA expression in the great majority of probe sets/genes examined. All pre-specified molecular pathways and functional molecular families were significantly over expressed (activated) in those patients with restenosis compared to those patients without restenosis. These data are shown in Table 12C. Of note, a sample of 100 probe sets (Table 12B) selected in a non-systematic manner also demonstrated increased mRNA expression at the time of enrollment in those patients with subsequent restenosis compared to those without restenosis.

TABLE 12. Predictive Accuracy:

TABLE 12A 54,675 probe sets.

| Analysis set | Number of probe sets | Cases + RS Mean (SD) | Controls − RS Mean (SD) |
|---|---|---|---|
| All probes | 54,675 | 200 (68) | 166 (75) |

TABLE 12B

Set of 100 probe sets selected in a non-systematic manner from a set of probes corresponding to a set of named genes.

| Analysis set | Number of probe sets | PLS ROC | PLS-MCR | Cases + RS Mean (SD) | Controls − RS Mean (SD) |
|---|---|---|---|---|---|
| Pathway 100 | 100 | .893 | .17 | 115 (47) | 92 (47) |

TABLE 12C

Pre-specified Pathways

| Analysis set | Number of probe sets | PLS ROC | PLS-MCR | Cases + RS Mean (SD) | Controls − RS Mean (SD) |
|---|---|---|---|---|---|
| Pathway 1 | 135 | .893 | .17 | 360 (113) | 295 (136) |
| Pathway 2 | 112 | .952 | .07 | 865 (284) | 720 (304) |
| Pathway 3 | 206 | .760 | .30 | 233 (76) | 195 (83) |
| Pathway 4 | 204 | .942 | .07 | 1937 (560) | 1641 (642) |
| Pathway 5 | 258 | .857 | .15 | 353 (116) | 289 (134) |
| Pathway 6 | 821 | .942 | .09 | 357 (112) | 297 (122) |
| Pathway 7 | 105 | .956 | .04 | 2460 (742) | 2081 (816) |

+RS = Restenosis group;
−RS = No restenosis group.
PLS ROC = Partial Least Square Receiver Operating Characteristic;
PLS-MCR = Partial Least Square Misclassification Rate.

Discussion

In order to carry out the studies described herein, several molecular pathways were pre-specified and tested for their ability to be predictive of bare metal stent restenosis. The results showed that each of these pathways was significantly activated in patients who experienced restenosis compared to those who did not. Thus, activation of any one of these pathways was an independent and highly accurate predictor or molecular signature of coronary restenosis following placement of a bare metal stent. The data presented herein also imply that a more generalized phenomenon, i.e., a pre-existing generalized genome activation within the mRNA-containing compartment of circulating whole blood appears to be a characteristic associated with those patients who experience restenosis following placement of a coronary artery stent. This interpretation is supported by the finding that a group of 100 genes selected in a non-systematic manner were also highly predictive of restenosis. This finding suggests that restenosis is a complex process involving multiple molecular mechanisms and is associated with either a pre-existing, general transcriptional activation of the genome and/or decreased degradation of the mRNA in the mRNA containing compartment of circulating whole blood. This is consistent with a large number of reports, each of which has identified a diverse assortment of genes up-regulated in response to coronary angioplasty and purported to be related to the restenosis process.

The following conclusions may be drawn from the experimental results presented herein:

I. Non-restenosis following coronary artery stenting with a bare metal stent is a highly predictable event.

II. Expression profiling using mRNA derived from the mRNA containing compartment of circulating whole blood may be used to identify patients who, with a high degree of certainty, will not experience restenosis within 6 months following coronary stenting with bare metal stents.

III. Increased transcription or decreased inactivation/degradation of the mRNA representative of molecular pathways responsible for multiple cellular functions, including but not limited to, T cell function, wound healing, cellular proliferation and migration, identify patients at high risk for restenosis who may benefit from the use of drug eluting stents to reduce their probability of restenosis.

IV. Subjects who do not exhibit activation of the molecular pathways described herein have a high likelihood of non-restenosis and would not be expected to derive any benefit from drug eluting stents.

V. Activated specific molecular pathways appear to be singular instances of a more generalized phenomena of transcriptional activation of a significant proportion of the whole genome of cells derived from whole blood, which itself is predictive of restenosis.

VI. Application of these expression profiling algorithms correctly predicted non-restenosis in 75-80% of cases that did not restenose and would be expected to significantly reduce the use of drug eluting stents and their potential excess morbidity, mortality and cost.

In summary, these results demonstrate that non-restenosis (or alternatively, the risk of restenosis) following coronary angioplasty with a bare metal stent can be accurately predicted using mRNA expression profiling of samples derived from whole blood. Further, biological pathway activation predicts which patients will restenose after placement of a bare metal stent. Finally, generalized transcriptional activation and/or decreased degradation of the products of the transcriptional process play a role in restenosis. These findings can be employed in the development of methods to predict which patients will not restenose and can therefore be offered a bare metal stent with a low risk for subsequent restenosis.

Conversely, patients with a high risk of restenosis can be identified and offered a stent that includes anti-restenosis agents.

Example 2

Methods for Predicting a Patient's Propensity for Restenosis

Based on the data in Tables 12A, 12B and 12C above, the patient may be predicted to be a good candidate for a bare metal stent (one not likely to have restenosis within six months) according to the following three exemplary methods:

I a) In a first embodiment, the invention provides a method for predicting a patient's propensity for bare metal stent restenosis, comprising the steps of: ai) obtaining a whole blood sample from a patient deemed to be in need of a stent; aii) measuring total mRNA from a volume of blood obtained from said blood sample using a gene probe substrate having at least a plurality of gene probes that hybridize to at least a plurality of mRNA sequences; aiii) computing an average mRNA value for said predetermined volume of blood from said total mRNA and said plurality of genes; aiv) classifying said patient as having a prognosis selected from a group consisting of a first prognosis and a second prognosis on the basis of a mRNA expression profile comprising the nucleic acid levels of expression of all genes and expressed sequence tags expressed on the Affymetrix U133+2 GeneChip™; av) determining the similarity between said patients profile and first prognosis profile comprising the average nucleic acid expression of the genes and expressed sequence tags expressed on the Affymetrix U133+2 GeneChip™ and; avi) determining the similarity of said patient expression profile and second prognosis profile comprising the average nucleic acid levels of expression of all genes and expressed sequence tags expressed on the Affymetrix U133+2 GeneChip™ and; avii) classifying said patient as having first prognosis if said patient average mRNA expression of all genes and expressed sequence tags present on the Affymetrix U133+2 GeneChip™ is closer to the average mRNA expression of the first prognosis profile compared to the second prognosis profile and; aviii) classifying said patient as having second prognosis if said patient average mRNA expression of all genes and expressed sequence tags present on the Affymetrix U133+2 GeneChip™ is closer to the average mRNA expression of the second prognosis profile as compared to the first prognosis profile.

b) The invention in another embodiment provides a method of predicting a patient's propensity for bare metal stent restenosis, comprising: (bi) from the patient who is deemed to need a coronary artery stent, taking a blood sample; (bii) from the sample, measuring the amount of mRNA present using a gene probe substrate having at least a plurality of gene probes that hybridize to at least a plurality of mRNA sequences corresponding to those genes and probe sets comprising as described herein each of the seven genomic pathways and one set of 100 non-systematically chosen genes listed in Tables 12B and 12C; biii) classifying said patient as having a prognosis selected from a group consisting of a first prognosis and a second prognosis on the basis of a mRNA expression profile comprising the nucleic acid levels of expression of any or all of the seven genomic pathways and one set of 100 non-systematically chosen genes listed in Tables 12B and 12C by a method comprising one of the following; biv) determining the similarity between said patients expression profile and first prognosis profile comprising the average nucleic acid levels of expression of the genes comprising any or all of the seven genomic pathways and set of 100 non-systematically chosen genes listed in Tables 12B and 12c and; bv) determining the similarity between said patients expression profile and second prognosis profile comprising the average nucleic acid levels of expression of the genes comprising any or all of the seven genomic pathways and set of 100 non-systematically chosen genes listed in Table 12B and 12C and; bvi) classifying said patient as having first prognosis if said patient average mRNA expression of genes present in any or all of seven genomic pathways and set of 100 non-systematically chosen genes listed in Tables 12B and 12c is closer to the average mRNA expression of the first prognosis profile compared to the second prognosis profile and; bvii) classifying said patient as having second prognosis if said patient average mRNA expression of genes present in any or all of seven genomic pathways and set of 100 non-systematically chosen genes listed in Tables 12B and 12C is closer to the average mRNA expression of the second prognosis profile as compared to the first prognosis profile.

c) The invention, in another embodiment, provides a method for predicting a patient's propensity for bare metal stent restenosis, comprising the steps of: ci) obtaining whole blood sample from a patient deemed to be in need of a coronary artery stent; cii) from the sample, measure the amount of mRNA present using a gene probe substrate having at least a plurality of genes that hybridize to at least a plurality of mRNA sequences comprising the seven genomic pathways and set of 100 non-systematically chosen genes listed in Tables 12B and 12C; ciii) classifying said patient as having a prognosis selected from a group consisting of a first prognosis and a second prognosis on the basis of nucleic acid levels of expression of any or all of the seven genomic pathways or 100 non-systematically chosen genes listed in Tables 12B and 12C by a method comprising one of the following; civ) determining the similarity between said patients expression profile and first prognosis profile as embodied in the probability output of a trained Partial Least Squares component based regression model derived from any or all of the seven genomic pathways or 100 non-systematically chosen genes listed in Tables 12B or 12C and; cv) determining the similarity between said patients mRNA expression profile and a second prognosis profile as embodied in the probability output of a Partial Least Squares component based regression model derived from any or all of the seven genomic pathways or 100 non-systematically chosen genes listed in Tables 12B and 12C and; cvi) classifying said patient as having first prognosis if said patients Partial Least Squares component based regression model probability output is <50% and; cvii) classifying said patient as having second prognosis if said patients Partial Least Squares component based regression model probability output is >50%.

II. Detailed Algorthims based on methodologies set forth in I above include the following a) The method of 1a, wherein said patient average mRNA expression profile comprises the average of log transformed, background corrected, variance normalized, summarized intensity profiles of all probe sets present on the Affymetrix U133+2 Gene Chip™ b). The method in 1avii, wherein first prognosis comprises the average mRNA expression profile of log transformed, background corrected, variance normalized, summarized probe set intensity profiles of all probe sets (n=54,675) present on the Affymetrix U133+2 GeneChip™ referred to as Controls (non-restenosis) in Table 12A.

c) The method in 1avii, wherein the first prognosis value is 166.

d) The method in 1aviii, wherein second prognosis comprises average mRNA expression profile of log transformed, background corrected, variance normalized, summarized probe set intensity profiles of all probe sets (n=54,675) present on the Affymetrix U133+2 GeneChip™ referred to as Cases (restenosis) in Table 12A.

e) The method in 1aviii, wherein the second prognosis value is 200.

f) The method of 1b, wherein said patient average mRNA expression profile comprises the average of log transformed, background corrected, variance normalized, summarized intensity profiles of all probe sets present on the Affymetrix U133+2 Gene Chip™ which correspond to all of the probe sets or genes listed in each or any of the seven genomic pathways or 100 non-systematically chosen genes in Tables 12B and 12C.

g) The method in 1bvii, wherein first prognosis comprises the average mRNA expression profile of log transformed, background corrected, variance normalized, summarized probe set intensity profiles of all probe sets present on the Affymetrix U133+2 GeneChip™ which correspond to all of the probe sets or genes listed in each or any of the seven genomic pathways or 100 non-systematically chosen genes referred to as Controls (non-restenosis) in Tables 12B and 12C.

h) The method in 1bvii, wherein the first prognosis value for each of the genomic pathways listed in Tables 12B and 12C are as follows: Pathway 100: 92; Pathway 1: 295; Pathway 2: 720; Pathway 3: 195; Pathway 4: 1641; Pathway 5: 289; Pathway 6: 297; Pathway 7: 2081.

i) The method in 1bviii, wherein second prognosis comprises average mRNA expression profile of log transformed, background corrected, variance normalized, summarized probe set intensity profiles of all probe sets present on the Affymetrix U133+2 GeneChip™ which correspond to all of the probe sets or genes listed in any or all of the seven genomic pathways or 100 non-systematically chosen genes referred to as Cases (restenosis) in Tables 12B and 12C.

j) The method in 1bvii, wherein the second prognosis value for each of the genomic pathways listed in Tables 12B and 12C are as follows: Pathway 100: 115; Pathway 1: 360; Pathway 2: 865; Pathway 3: 233; Pathway 4: 1937; Pathway 5: 353; Pathway 6: 357; Pathway 7: 2460.

k) The method of 1c, wherein said patient mRNA expression profile comprises log transformed, background corrected, variance normalized, summarized intensity profiles of all probe sets present on the Affymetrix U133+2 Gene Chip™ which correspond to all of the probe sets or genes comprising each or any of the seven genomic pathways or 100 non-systematically chosen genes listed in Tables 12B and 12C.

l) The method in 1cvii, wherein first prognosis (no restenosis) comprises the probability output of a trained Partial Least Squares component based regression model derived from all of the probe sets or gene intensity profiles from any or all of the seven genomic pathways or 100 random genes listed in Tables 12B and 12C where the probability output is $\leq 50\%$ and where the regression model using Partial Least Squares derived components is formulated as follows for each pathway: Pathway 100: Probability=$\beta_1(X)+\beta_2(Y)$ . . . ; Pathway 1: Probability=$\beta_1(X)+\beta_2(Y)$ . . . ; Pathway 2: Probability=$\beta_1(X)+\beta_2(Y)$ . . . ; Pathway 3: Probability=$\beta_1(X)+\beta_2(Y)$ . . . ; Pathway 4: Probability=$\beta_1(X)+\beta_2(Y)$ . . . ; Pathway 5: Probability=$\beta_1(X)+\beta_2(Y)$ . . . ; Pathway 6: Probability=$\beta_1(X)+\beta_2(Y)$ . . . ; Pathway 7: Probability=$\beta_1(X)+\beta_2(Y)$ . . . ;

m) The method in 1cvii, wherein second prognosis (restenosis) comprises the probability output of a trained Partial Least Squares component based regression model derived from all of the probe sets or gene intensity profiles from any or all of the genomic pathways listed in Tables 12B and 12C where the probability output is >50% and where the predictive regression model using Partial Least Squares derived components is formulated as follows for each pathway: Pathway 100: Probability=$\beta_1(X)+\beta_2(Y)$ . . . ; Pathway 1: Probability=$\beta_1(X)+\beta_2(Y)$ . . . ; Pathway 2: Probability=$\beta_1(X)+\beta_2(Y)$ . . . ; Pathway 3: Probability=$\beta_1(X)+\beta_2(Y)$ . . . ; Pathway 4: Probability=$\beta_1(X)+\beta_2(Y)$ . . . ; Pathway 5: Proboility=$\beta_1(X)+\beta_2(Y)$ . . . ; Pathway 6: Probability=$\beta_1(X)+\beta_2(Y)$ . . . ; Pathway 7: Probability=$\beta_1(X)+\beta_2(Y)$ . . . ;

The following is a list of the sequences of the genes and probes referred to in Table 8. HG-U133_PLUS_2 is the Affymetrix Genechip used. In the list below, the probeset identifier (e.g. 214475_X_AT) is followed by the cDNA sequence which is interrogated by the probeset, which is followed by the sequences of the probeset. Probe X and Probe Y indicate the physical positions of the probe within the array. The Probe Interrogation Position defines the position of the probe within the full length cDNA. The target strandedness of all probes was antisense.

```
>HG-U133_PLUS_2:214475_X_AT
SEQ ID NO:1
agaaggtccttaacacagtcgtgaacaaacacaaggacctgaagacacacgggttcacac
tggagtcctgccgtagcatgatngcgctcatggatacagatggctctggaaagctcaacc
tgcaggagttccaccacctctggaacaagattaaggcctggcagaaaattttcaaanact
atgacacagaccagtccggcaccatcaacagctacgagatgcgaaatgcagtcaacgacg
caggattccacctcaacaaccagctctatgacatcattaccatngcggtacgcagacaaa
cacatgaacatcgactttgacagtttcatctgctngcttcgttaggcntggagggcatgt
tcagagcttttcatgcatttgacaaggnnngagatggtatcatcaagctcaacgttctgg
agtggctgcagctcaccatgtatnnctgaaccaggctggcctcatccaaagccatgcagg
atcactcaggat
```

Cluster Members
Consensus/Exemplar

-continued

BLASTn GenBank NR
Probe Info

| Probe Sequence(5'-3') | Probe X | Probe Y | Probe Interrogation Position | SEQ ID NO: |
|---|---|---|---|---|
| AGAAGGTCCTTAACACAGTCGTGAA | 509 | 127 | 2243 | 2 |
| GACACACGGGTTCACACTGGAGTCC | 893 | 599 | 2286 | 3 |
| GATGGCTCTGGAAAGCTCAACCTGC | 716 | 665 | 2341 | 4 |
| AAAGCTCAACCTGCAGGAGTTCCAC | 1152 | 211 | 2352 | 5 |
| TGCAGTCAACGACGCAGGATTCCAC | 489 | 959 | 2469 | 6 |
| ACCTCAACAACCAGCTCTATGACAT | 46 | 155 | 2492 | 7 |
| GAACATCGACTTTGACAGTTTCATC | 376 | 581 | 2548 | 8 |
| GGAGGGCATGTTCAGAGCTTTTCAT | 725 | 845 | 2592 | 9 |
| GGTATCATCAAGCTCAACGTTCTGG | 269 | 827 | 2638 | 10 |
| CAACGTTCTGGAGTGGCTGCAGCTC | 629 | 301 | 2652 | 11 |
| AAAGCCATGCAGGATCACTCAGGAT | 499 | 213 | 2710 | 12 |

>HG-U133_PLUS_2:207428_X_AT
SEQ ID NO:13
cacggccgtggacatgtggtcagtgggttgcatcttcggggagctgctgactcagaagcc
tctgttccccgggaagtcagaaatcgatcagatcaacaaggtgttcaaggatctggggac
ccctagtgagaaaatctggcccggctacagcgagctcccagcagtcaagaagatgacctt
cagcgagcacccctacaacaacctccgcaagcgcttcggggctctgctctcagaccaggg
cttcgacctcatgaacaagttcctgacctacttcccgggaggaggatcagcgctgagga
cggcctcaagcatgagtatttccgcgagaccccctccccatcgaccctccatgttccc
cacgtggcccgccaagagcgagcagcagcgtgtgaagcggggcaccagcccgaggccccc
tgagggaggcctgggctacagccagctgggtgacgac Cluster Members
Consensus/Exemplar
BLASTn GenBank NR
Probe Info

| Probe Sequence(5'-3') | Probe X | Probe Y | Probe Interrogation Position | SEQ ID NO: |
|---|---|---|---|---|
| CACGGCCGTGGACATGTGGTCAGTG | 937 | 315 | 1971 | 14 |
| AGCTGCTGACTCAGAAGCCTCTGTT | 999 | 139 | 2012 | 15 |
| GCCTCTGTTCCCCGGGAAGTCAGAA | 641 | 477 | 2028 | 16 |
| GGTGTTCAAGGATCTGGGGACCCCT | 744 | 817 | 2070 | 17 |
| CGAGCTCCCAGCAGTCAAGAAGATG | 663 | 415 | 2121 | 18 |
| GGCTTCGACCTCATGAACAAGTTCC | 360 | 879 | 2209 | 19 |
| TGACCTACTTCCCCGGGAGGAGGAT | 860 | 941 | 2234 | 20 |
| GAGGATCAGCGCTGAGGACGGCCTC | 107 | 659 | 2253 | 21 |
| CAAGCATGAGTATTTCCGCGAGACC | 187 | 299 | 2277 | 22 |
| GAGCAGCAGCGTGTGAAGCGGGGCA | 690 | 631 | 2350 | 23 |
| GGGCTACAGCCAGCTGGGTGACGAC | 284 | 795 | 2403 | 24 |

>HG-U133_PLUS_2:210616_S_AT
SEQ ID NO:25
gcgtacagcaacctcttggtcaaacaggcatgccaccatctttttcaaagcccaatattg
aaggtgccccaggggctcctattggaaataccttccagcatgtgcagtctttgccaacaa
aaaaaattaccaagaaacctattccagatgagcacctcattctaaagaccacatttgagg
atcttattcagcgctgcctttcttcagcaacagaccctcaaaccaagaggaagctagatg
atgccagcaaacgtttggagtttctgtatgataaacttagggaacagacactttcaccaa
caatcaccagtggtttacacaacattgcaaggagcattgaaactcgaaactactcagaag
gattgaccatgcatacccacatagttagcaccagcaacttcagtgagacctctgctttca
tgccagttctcaaagttgttctcacccaggccaataagctgggtgtctaaaaggacagct
tctcttccactcaatattgccatt Cluster Members
Consensus/Exemplar
BLASTn GenBank NR
Probe Info

| Probe Sequence(5'-3') | Probe X | Probe Y | Probe Interrogation Position | SEQ ID NO: |
|---|---|---|---|---|
| GCGTACAGCAACCTCTTGGTCAAAC | 935 | 491 | 3584 | 26 |
| TGAAGGTGCCCCAGGGGCTCCTATT | 995 | 951 | 3642 | 27 |
| TTGAGGATCTTATTCAGCGCTGCCT | 675 | 1153 | 3758 | 28 |
| GCTGCCTTTCTTCAGCAACAGACCC | 1026 | 503 | 3776 | 29 |
| AACAGACACTTTCACCAACAATCAC | 757 | 229 | 3866 | 30 |
| AGAAGGATTGACCATGCATACCCAC | 1152 | 127 | 3939 | 31 |
| CATACCCACATAGTTAGCACCAGCA | 262 | 351 | 3955 | 32 |
| GCACCAGCAACTTCAGTGAGACCTC | 1118 | 535 | 3971 | 33 |
| TTCAGTGAGACCTCTGCTTTCATGC | 867 | 1129 | 3982 | 34 |

| | | | | |
|---|---|---|---|---|
| GCCAGTTCTCAAAGTTGTTCTCACC | 1134 | 471 | 4005 | 35 |
| TTCTCTTCCACTCAATATTGCCATT | 488 | 1135 | 4063 | 36 |

>HG-U133_PLUS_2:223203_AT
SEQ ID NO:37
agtgccaggacctgtgtaccgggacacgtgggagtcctcccagcatgatgcttgactgac
ccgaggaaggtcctcatgtttcgtgcctgtcattctcggatggctgtgaggcattccttg
gcaagggacgctgcgtaccagcggtcctcaccgcatctcacatggctcctgtgatgcatg
ttgtcgctttcccaccgggatctccatctctcttccttcctgctgtcagtaagagatc
acatgtctgtgtagtgtgaatgccttgtcgctgtcctgtgcttttgcaccattgagttga
ctgcctctgagaagcagcactaggcctgttgaaatgcaatgtgctgccctgagatccagt
ttcaagaatgggcaggtaaacgcagtgtgggaaaggaatgtggaatgagaacttggtggt
tcaccgctgtactatttgtgtaaatgtttacgtatgtgataagctacatgtatgtaaatg
ttgcaatacccctaacagtcgagtagtagtctcccttacaggaattttttgacggggttcc
tcatca Cluster Members
Consensus/Exemplar
BLASTn GenBank NR
Probe Info

| Probe Sequence(5'-3') | Probe X | Probe Y | Probe Interrogation Position | SEQ ID NO: |
|---|---|---|---|---|
| AGTGCCAGGACCTGTGTACCGGGAC | 139 | 95 | 685 | 38 |
| AGTCCTCCCAGCATGATGCTTGACT | 281 | 97 | 717 | 39 |
| TGCCTGTCATTCTCGGATGGCTGTG | 307 | 971 | 768 | 40 |
| GGCTGTGAGGCATTCCTTGGCAAGG | 1071 | 883 | 786 | 41 |
| TGGCTCCTGTGATGCATGTTGTCGC | 150 | 897 | 847 | 42 |
| GTAGTGTGAATGCCTTGTCGCTGTC | 979 | 727 | 935 | 43 |
| GCACCATTGAGTTGACTGCCTCTGA | 156 | 537 | 970 | 44 |
| GCTGCCCTGAGATCCAGTTTCAAGA | 668 | 503 | 1027 | 45 |
| GTGGTTCACCGCTGTACTATTTGTG | 606 | 787 | 1100 | 46 |
| TCGAGTAGTAGTCTCCCTTACAGGA | 551 | 993 | 1183 | 47 |
| GAATTTTTGACGGGGTTCCTCATCA | 450 | 547 | 1206 | 48 |

>HG-U133_PLUS_2:205300_S_AT
SEQ ID NO:49
ggacttggtcacaggttttttcaaagggctacgccttcatcgaatacaaggaggagcgtgc
cgtgatcaaagcttaccgagatgctgatggcctggttattgaccagcatgagatatttgt
ggactacgagctggaaaggactctcaaagggtggatccctcggcgacttggaggcggtct
tgggggaaaaaaggagtctgggcaactgagatttgggggacgggaccggccttttcgaaa
acctattaacttgccagttgttaaaaacgacctctatagagagggaaaacgggaaaggcg
ggagcgatctcgatcccgagaaagacactgggactcgaggacaagggatcgagaccatga
caggggccgggagaagagatggcaagaaagagagccgaccagggtgtgcccgacaatga
ctgggagagagagagggacttcagagatgacaggatcaaggggagggagaagaaggaaag
aggcaagtagaggcccaacagcagaaccccaaagtgaagttacagtggaaatgagtggag
ggggattgtctttcaacgcagcgtgagt Cluster Members
Consensus/Exemplar
BLASTn GenBank NR
Probe Info

| Probe Sequence(5'-3') | Probe X | Probe Y | Probe Interrogation Position | SEQ ID NO: |
|---|---|---|---|---|
| GGACTTGGTCACAGGTTTTTCAAAG | 780 | 855 | 324 | 50 |
| TTCAAAGGGCTACGCCTTCATCGAA | 76 | 1127 | 342 | 51 |
| AAGGAGGAGCGTGCCGTGATCAAAG | 187 | 267 | 370 | 52 |
| GCTTACCGAGATGCTGATGGCCTGG | 960 | 515 | 394 | 53 |
| CTCAAAGGGTGGATCCCTCGGCGAC | 1043 | 373 | 466 | 54 |
| GGAAAGGCGGGAGCGATCTCGATCC | 265 | 859 | 615 | 55 |
| AGGGATCGAGACCATGACAGGGGCC | 219 | 89 | 667 | 56 |
| AAGAGAGCCGACCAGGGTGTGGCCC | 953 | 253 | 711 | 57 |
| GGGTGTGGCCCGACAATGACTGGGA | 225 | 809 | 725 | 58 |
| AAGTAGAGGCCCAACAGCAGAACCC | 1083 | 257 | 808 | 59 |
| GATTGTCTTTCAACGCAGCGTGAGT | 129 | 695 | 867 | 60 |

>HG-U133_PLUS_2:207618_S_AT
SEQ ID NO:61
tggactgctcaatgccttggatggtgtggcttccaccgaggcccgcatcgtgttcatgac
caccaaccacgttgacaggctggaccctgccctgatacgcccggggcgagtggacctgaa
ggagtacgtgggctactgctcacactggcagctgacccagatgttccagaggttctatcc
agggcaggccacttcctttagctgagaactttgcagaacatgtccttcgagctacaaacca
gatcagtcctgcccaggtgcagggatacttcatgctgtataaaaatgaccctgtagggc -continued aattcacaatgctgagtctctgaggaggtgatcaggctgggctcagctcagctctcctcc
tctagctcaataaacat Cluster Members
Consensus/Exemplar
BLASTn GenBank NR
Probe Info

| Probe Sequence(5'-3') | Probe X | Probe Y | Probe Interrogation Position | SEQ ID NO: |
|---|---|---|---|---|
| TGGACTGCTCAATGCCTTGGATGGT | 204 | 901 | 1055 | 62 |
| CTTGGATGGTGTGGCTTCCACCGAG | 573 | 355 | 1070 | 63 |
| TCGTGTTCATGACCACCAACCACGT | 267 | 995 | 1102 | 64 |
| CCAACCACGTTGACAGGCTGGACCC | 773 | 465 | 1117 | 65 |
| GCCCTGATACGCCCGGGGCGAGTGG | 1148 | 485 | 1143 | 66 |
| GAAGGAGTACGTGGGCTACTGCTCA | 31 | 561 | 1172 | 67 |
| CTGGCAGCTGACCCAGATGTTCCAG | 693 | 407 | 1199 | 68 |
| TGTTCCAGAGGTTCTATCCAGGGCA | 998 | 931 | 1216 | 69 |
| GCACCTTCCTTAGCTGAGAACTTTG | 418 | 531 | 1242 | 70 |
| GAACATGTCCTTCGAGCTACAAACC | 281 | 581 | 1269 | 71 |
| TCTCCTCCTCTAGCTCAATAAACAT | 931 | 1003 | 1407 | 72 |

HG-U133_PLUS_2:219350_S_AT
SEQ ID NO:73
catgactgtctgtgcaccgagaagaggcggcaggtcctgccctggccaatcaggcgagac
gcctttgtgagctgtgagtgcctcctgtggtctcaggcttgcgctggacctggttcttag
cccttgggcactgcaccctgtttaacatttcaccccactctgtacagctgctcttaccca
tttttttacctcacacccaaagcattttgcctacctgggtcagagagaggagtcctttt
tgtcatgcccttaagttcagcaactgtttaacctgttttcagtcttatttacgtcgtcaa
aaatgatttagtacttgttccctctgttgggatgccagttgtggcaggggaggggaacc
tgtccagtttgtacgatttctttgtatgtatttctgatgtgttctctgatctgccccac
tgtcctgtgaggacagctgaggccaaggagtgaaaaacctattactactaagagaagggg
tgcagagtgtttacctggtgctctcaacaggac Cluster Members
Consensus/Exemplar
BLASTn GenBank NR
Probe Info

| Probe Sequence(5'-3') | Probe X | Probe Y | Probe Interrogation Position | SEQ ID NO: |
|---|---|---|---|---|
| CATGACTGTCTGTGCACCGAGAAGA | 328 | 345 | 826 | 74 |
| TGCCCTGGCCAATCAGGCGAGACGC | 178 | 969 | 863 | 75 |
| CGAGACGCCTTTGTGAGCTGTGAGT | 576 | 415 | 880 | 76 |
| CTGCACCCTGTTTAACATTTCACCC | 372 | 395 | 956 | 77 |
| ACCTCACACCCAAAGCATTTTGCCT | 513 | 153 | 1014 | 78 |
| GCATTTTGCCTACCTGGGTCAGAGA | 74 | 521 | 1028 | 79 |
| TCCTTTTTGTCATGCCCTTAAGTTC | 147 | 981 | 1059 | 80 |
| GTTTTCAGTCTTATTTACGTCGTCA | 843 | 711 | 1100 | 81 |
| GTACTTGTTCCCTCTGTTGGGATGC | 424 | 735 | 1136 | 82 |
| TTTCTGATGTGTTCTCTGATCTGCC | 831 | 1097 | 1216 | 83 |
| GTTTACCTGGTGCTCTCAACAGGAC | 464 | 715 | 1314 | 84 |

>HG-U133_PLUS_2:207856_S_AT
SEQ ID NO:85
ccagctgttccaagactgggccgtagaattccatgtttcaggagcctaagaccctcccag
agcccaggggcttcaccgcagaccccaagccattgagcacatcacccaaagcagtggcca
acatcgcggaccccgtgccttgtcacagatgggtgctggtcctcaggcgttggggacac
tgctgggtcgatggggtcggattctgccagtttctgctctgcagccaaagatggtcagaa
gcattgtcacttcagtaacatcaagtgctcaaagacatggcaaccgttcagtgactta
agtattcaaaatatacaactacagattctctgacagaaaccagcacgggtcttcacctt
cattcacccacaggcgacacgcgagggagaacagcatctcagtggtgatttccaaacca
agcctttgt Cluster Members
Consensus/Exemplar
BLASTn GenBank NR
Probe Info

| Probe Sequence(5'-3') | Probe X | Probe Y | Probe Interrogation Position | SEQ ID NO: |
|---|---|---|---|---|
| CCAGCTGTTCCAAGACTGGGCCGTA | 375 | 459 | 2792 | 86 |
| GGGCCGTAGAATTCCATGTTTCAGG | 724 | 791 | 2809 | 87 |
| CAAAGCAGTGGCCAACATCGCGGAC | 790 | 305 | 2898 | 88 |
| GTGCCTTGTCACAGATGGGTGCTGG | 1154 | 761 | 2927 | 89 |
| GGTCCTCAGGCGTTGGGGACACTGC | 221 | 823 | 2950 | 90 |

-continued

| | | | |
|---|---|---|---|
| TGGGTCGATGGGGTCGGATTCTGCC | 816 | 909 | 2975 | 91 |
| TCTGCTCTGCAGCCAAAGATGGTCA | 348 | 1001 | 3004 | 92 |
| AAGCATTGTCACTTCAGTAACATCA | 482 | 249 | 3030 | 93 |
| GACATGGCAACCGTTCAGTGGTACT | 749 | 605 | 3065 | 94 |
| GAACAGCATCTCAGTGGTGATTTCC | 1019 | 581 | 3181 | 95 |
| GGTGATTTCCAAACCAAGCCTTTGT | 954 | 817 | 3196 | 96 |

>HG-U133_PLUS_2:210417_S_AT
SEQ ID NO: 97
atcgtggagatcatgcagcaaggttctcagcttccttgcttccatggctccagcaccatt
cgaaacctcaaagagaggttccacatgagcatgactgaggagcagctgcagctgctggtg
gagcagatggtggatggcagtatgcggtctatcaccaccaaactctatgacggcttccag
tacctcaccaacggcatcatgtgacacgctcctcagcccaggagtggtgggggtccagg
gcaccctccctagagggcccttgtttgagaaaccccaaaccaggaaaccccacctaccca
accatccacccaagggaaatggaaggcaagaaacacgaaggatcatgtggtaactgcgag
agcttgctgaggggtgggagagccagctgtgggtccagacttgttggggcttccctgcc
cctcctggtctgtgtcagtattaccaccagactgactccaggactcactgccctccagaa
aacagaggtgacaaatgtgagggacactggggccttctctcctccttgtagggtctctca
gag Cluster Members
Consensus/Exemplar
BLASTn GenBank NR
Probe Info

| Probe Sequence(5'-3') | Probe X | Probe Y | Probe Interrogation Position | SEQ ID NO: |
|---|---|---|---|---|
| ATCGTGGAGATCATGCAGCAAGGTT | 525 | 47 | 2504 | 98 |
| GCAAGGTTCTCAGCTTCCTTGCTTC | 604 | 545 | 2521 | 99 |
| AAGAGAGGTTCCACATGAGCATGAC | 420 | 255 | 2574 | 100 |
| ATGGCAGTATGCGGTCTATCACCAC | 1097 | 69 | 2637 | 101 |
| TCACCACCAAACTCTATGACGGCTT | 1027 | 999 | 2655 | 102 |
| GTACCTCACCAACGGCATCATGTGA | 864 | 731 | 2683 | 103 |
| CACCAACGGCATCATGTGACACGCT | 816 | 321 | 2689 | 104 |
| GAAGGATCATGTGGTAACTGCGAGA | 255 | 561 | 2840 | 105 |
| CCAGCTGTGGGTCCAGACTTGTTG | 328 | 461 | 2886 | 106 |
| CACTGCCCTCCAGAAAACAGAGGTG | 208 | 315 | 2969 | 107 |
| TTCTCCTTGTAGGGGTCTCTCAGAG | 830 | 1135 | 3022 | 108 |

>HG-U133_PLUS_2:210234_AT
SEQ ID NO: 109
cccgtgggcacccacggacgtggcttggtgctgagatagcagagcccccagccatcactg
ctggcagcctgggcaaaccgggtgagcaacaggaggacgaggggccgggcggtgccagg
ctaccacaagaacctgcgtcttggaccattgcccctcccggcccaaaccacaggggctc
aggtcgtgtgggcccagtgctagatctctccctcccttcgtctctgtgctgttgg
cgacccctctgtctgtctccagccctgtctttctgttctcttatctctttgtttcaccttt
ttccctctctggcgctccccggctgcttgtactcttggccttttctgtgtctcctttctgg
ctcttgcctccgcctctctctcatcctctttgtcctcagctcctcctgctttcttggg
tcccaccagtgtcacttttctgccgttttctttcctgttctcctctgcttcattctcgtc
cagccattgctccctctccctgccacccttccccagttcaccaaaccttacatgtt Cluster Members
Consensus/Exemplar
BLASTn GenBank NR
Probe Info

| Probe Sequence(5'-3') | Probe X | Probe Y | Probe Interrogation Position | SEQ ID NO: |
|---|---|---|---|---|
| CCCGTGGGCACCCACGGACGTGGCT | 784 | 429 | 2873 | 110 |
| ACGGACGTGGCTTGGTGCTGAGATA | 310 | 165 | 2886 | 111 |
| TGGTGCTGAGATAGCAGAGCCCCCA | 1154 | 907 | 2898 | 112 |
| CAGCCTGGGCAAACCGGGTGAGCAA | 334 | 323 | 2937 | 113 |
| GGCAAACCGGGTGAGCAACAGGAGG | 255 | 867 | 2944 | 114 |
| AGCAACAGGAGGACGAGGGGCCGGG | 702 | 129 | 2957 | 115 |
| GTGCCAGGCTACCACAAGAACCTGC | 915 | 761 | 2985 | 116 |
| ACCACAAGAACCTGCGTCTTGGACC | 494 | 135 | 2995 | 117 |
| CGGCCCCAAACCACAGGGGCTCAGG | 176 | 405 | 3031 | 118 |
| CAGGGGCTCAGGTCGTGTGGGCCCC | 164 | 339 | 3044 | 119 |
| CCCAGTTCACCAAACCTTACATGTT | 339 | 423 | 3385 | 120 |

>HG-U133_PLUS_2:221515_S_AT
SEQ ID NO: 121
gcaaacctcctgaagtgggcagcaacagttttgagagagccatgttcataaactacgaa
caggtgaacatgggtgatcggtttgggcagatcatgattgaaaacctgcggagacgccag
tgtgacctggcggagtggagacctgcaagtcattagagtcacagaaagaacggctcctg
tcgaatgggtgggaaacagcatcggccgtcgacgatgatggagttgtacaacaggttacct
cgagctgaagtgagcaggatagaatcacttgaattcctggatgaaatggagctgctggag -continued

```
cagctcatgcggcattactgcctttgctgggcaaccaaaggaggaaatgagcttgggctg
aaggagataacttattaatctgtcgaaggcttatgccgagccagaagccgaagccacttg
ccctcctggaggagacctgcaagctccctgagcggtgggcgggcctcgtccgcaggtctc
atcccacactcttgagaagccttggtcactacagtggtcgcacatgttcctcttcctgtt
cctgttgacatgtcgttgtt
```

Cluster Members
Consensus/Exemplar
BLASTn GenBank NR
Probe Info

| Probe Sequence(5'-3') | Probe X | Probe Y | Probe Interrogation Position | SEQ ID NO: |
|---|---|---|---|---|
| GCAAACCTCCTGAAGTGGGCAGCCA | 972 | 541 | 765 | 122 |
| GAACATGGGTGATCGGTTTGGGCAG | 1 | 577 | 830 | 123 |
| GAAAACCTGCGGAGACGCCAGTGTG | 229 | 583 | 864 | 124 |
| AAAGAACGGCTCCTGTCGAATGGGT | 981 | 209 | 930 | 125 |
| CAGCATCGGCCGTCGACATGATGGA | 37 | 325 | 961 | 126 |
| GGAGTTGTACAACAGGTTACCTCGA | 946 | 815 | 983 | 127 |
| CATTACTGCCTTTGCTGGGCAACCA | 29 | 353 | 1077 | 128 |
| GTCTCATCCCACACTCTTGAGAAGC | 628 | 751 | 1240 | 129 |
| AGCCTTGGTCACTACAGTGGTCGCA | 248 | 147 | 1262 | 130 |
| ACTACAGTGGTCGCACATGTTCCTC | 796 | 173 | 1272 | 131 |
| CTGTTCCTGTTGACATGTCGTTGTT | 937 | 399 | 1300 | 132 |

>HG-U133_PLUS_2:210220_AT
SEQ ID NO: 133
```
caagaccgaaaagctggagcggctcatggtgcgcatcggcgtcttctccgtgctctacac
agtgcccgccaccatcgtcatcgcttgctacttctacgagcaggccttccgcgagcactg
ggagcgctcgtgggtgagccagcactgcaagagcctggccatcccgtgcccggcgcacta
cacgccgcgcatgtcgcccgacttcacggtctacatgatcaaatacctcatgacgctcat
cgtgggcatcacgtcgggcttctggatctggtcgggcaagacgctgcactcgtggaggaa
gttctacactcgcctcaccaacagccgacacggtgagaccaccgtgtg
```

Cluster Members
Consensus/Exemplar
BLASTn GenBank NR
Probe Info

| Probe Sequence(5'-3') | Probe X | Probe Y | Probe Interrogation Position | SEQ ID NO: |
|---|---|---|---|---|
| CAAGACCGAAAAGCTGGAGCGGCTC | 206 | 299 | 1494 | 134 |
| GTGAGCCAGCACTGCAAGAGCCTGG | 737 | 771 | 1627 | 135 |
| GAGCCAGCACTGCAAGAGCCTGGCC | 42 | 625 | 1629 | 136 |
| CCCGACTTCACGGTCTACATGATCA | 712 | 429 | 1690 | 137 |
| CACGGTCTACATGATCAAATACCTC | 1033 | 315 | 1698 | 138 |
| GATCAAATACCTCATGACGCTCATC | 1068 | 679 | 1710 | 139 |
| CAAATACCTCATGACGCTCATCGTG | 229 | 307 | 1713 | 140 |
| CAAGACGCTGCACTCGTGGAGGAAG | 247 | 299 | 1770 | 141 |
| GCTGCACTCGTGGAGGAAGTTCTAC | 760 | 501 | 1776 | 142 |
| CAACAGCCGACACGGTGAGACCACC | 338 | 303 | 1812 | 143 |
| GCCGACACGGTGAGACCACCGTGTG | 274 | 481 | 1817 | 144 |

>HG-U133_PLUS_2:210157_AT
SEQ ID NO: 145
```
aaagcattctgcattagtactaaaataagccatcaatgccagtccaccctctctattcat
ggctaaatatttaaaggttatttatagcttctttaatgaattcttcttaaacaaagtgaa
attatgtcctagaaaagtagaagctattcgtaactagagcagtgcaactttaaagtttta
tgaatatgtattttaatgacaaggggcgagcttgcatcccactagttaatggataatt
caaaccgaggactgattttgaaagatcacctaaaaatgtagatttgttctttagtaaatt
tagatcaactatgcatatattttgtaggtaaatctttcagtccatgccccaaccctcacc
aaaaccaaagcagaaattacacacacaaagatgctcccgttaggaattgctattcacatg
aggctttctgtgctagatttttttctcagaaacaaactttactgtaggactattgtggtg
ttcttaac
```

Cluster Members
Consensus/Exemplar
BLASTn GenBank NR
Probe Info

| Probe Sequence(5'-3') | Probe X | Probe Y | Probe Interrogation Position | SEQ ID NO: |
|---|---|---|---|---|
| AAAGCATTCTGCATTAGTACTAAAA | 766 | 211 | 2628 | 146 |
| AAATAAGCCATCAATGCCAGTCCAC | 1121 | 199 | 2650 | 147 |
| CCACCCTCTCTATTCATGGCTAAAT | 683 | 463 | 2671 | 148 |
| GACAAGGGGCGAGCTTGCATCCCC | 158 | 599 | 2825 | 149 |

-continued

| | | | |
|---|---|---|---|
| GCTTGCATCCCCACTAGTTAATGGA | 2 | 513 | 2838 | 150 |
| TAGGTAAATCTTTCAGTCCATGCCC | 933 | 1073 | 2952 | 151 |
| ACACACAAAGATGCTCCCGTTAGGA | 419 | 193 | 3008 | 152 |
| GATGCTCCCGTTAGGAATTGCTATT | 64 | 675 | 3017 | 153 |
| ATTGCTATTCACATGAGGCTTTCTG | 834 | 5 | 3033 | 154 |
| AGGCTTTCTGTGCTAGATTTTTTTC | 343 | 75 | 3048 | 155 |
| GTAGGACTATTGTGGTGTTCTTAAC | 360 | 725 | 3091 | 156 |

HG-U133_PLUS_2:221007_S_AT
SEQ ID NO: 157
gacagagagcgagaccgtgatcgggacagagaaagagaacgcaccagagagagagagg
gagcgtgatcacagtcctacaccaagtgttttcaacagcgatgaagaacgatacagatac
agggaatatgcagaaagaggttatgagcgtcacagagcaagtcgagaaaaagaagaacg
catagagaaagacgacacagggagaaagaggaaaccagacataagtcttctcgaagtaat
agtagacgtc Cluster Members
Consensus/Exemplar
BLASTn GenBank NR
Probe Info

| Probe Sequence(5'-3') | Probe X | Probe Y | Probe Interrogation Position | SEQ ID NO: |
|---|---|---|---|---|
| GACAGAGAGCGAGACCGTGATCGGG | 678 | 603 | 1359 | 158 |
| GAGCGAGACCGTGATCGGGACAGAG | 1160 | 625 | 1365 | 159 |
| GACCGTGATCGGGACAGAGAAAGAG | 157 | 621 | 1371 | 160 |
| GAGAAAGAGAACGCACCAGAGAGAG | 1129 | 635 | 1387 | 161 |
| GAGGGAGCGTGATCACAGTCCTACA | 406 | 655 | 1415 | 162 |
| GTGTTTTCAACAGCGATGAAGAACG | 808 | 721 | 1444 | 163 |
| GAAGAACGATACAGATACAGGGAAT | 238 | 569 | 1461 | 164 |
| GCAGAAAGAGGTTATGAGCGTCACA | 891 | 531 | 1488 | 165 |
| TGAGCGTCACAGAGCAAGTCGAGAA | 871 | 943 | 1502 | 166 |
| GAAACCAGACATAAGTCTTCTCGAA | 51 | 591 | 1569 | 167 |
| TCTTCTCGAAGTAATAGTAGACGTC | 675 | 1013 | 1584 | 168 |

>HG-U133_PLUS_2:221941_AT
SEQ ID NO: 169
ctcacccaagtgctccggagagtgacaggaaacccacggctccccgcgcccaagagcgtc
ctgcggtctcgctggcacancnccccgtacactaggggtcctacagctacgtggccgtg
ggcagtactgggggcgacctggacctgctggctcagncccctccctgcagacggcgccggc
gcccagctccagatcctgtttgcgggggaagccacacatcgcacgttttactccacgacg
cacggggctctgctgtcgggatggagggaggccgaccgcctcctcagtctgtgggccccg
caggtgcagcagcccaggccnaggctctagctnggcccagcctactctgttccaccgtg
tcgggggtaggctgggaccntcatttcttctgacagatttcagtctggcttgaaatttgg
ggatgttaatgagggtcctctggttttggtaaccagggccaccttctcagttcttgtgt
ctgttattggagtctggccagggttgacttgagctgagacaccagatgctcacggagatg
ctggacacat Cluster Members
Consensus/Exemplar
BLASTn GenBank NR
Probe Info

| Probe Sequence(5'-3') | Probe X | Probe Y | Probe Interrogation Position | SEQ ID NO: |
|---|---|---|---|---|
| CTCACCCAAGTGCTCCGGAGAGTGA | 635 | 377 | 1296 | 170 |
| GAGAGTGACAGGAAACCCACGGCTC | 1083 | 641 | 1313 | 171 |
| ACTAGGGGGTCCTACAGCTACGTGG | 215 | 175 | 1386 | 172 |
| AGCTACGTGGCCGTGGGCAGTACTG | 637 | 137 | 1401 | 173 |
| GTTTGCGGGGGAAGCCACACATCGC | 402 | 717 | 1493 | 174 |
| GGCTCTGCTGTCGGGATGGAGGGAG | 27 | 883 | 1541 | 175 |
| TTCCACCCGTGTCGGGGGTAGGCTG | 868 | 1141 | 1645 | 176 |
| CACCTTCTCAGTTCTTGTGTCTGTT | 58 | 321 | 1756 | 177 |
| GTCTGGCCAGGGTTGACTTGAGCTG | 677 | 755 | 1787 | 178 |
| GAGCTGAGACACCAGATGCTCACGG | 204 | 629 | 1806 | 179 |
| ATGCTCACGGAGATGCTGGACACAT | 1044 | 53 | 1821 | 180 |

>HG-U133_PLUS_2:207087_X_AT
SEQ ID NO: 181
gcctacagccggacctgatagagggcaggaaggggcgcagatagtgaagcgggccagcc
tgaaaaggggaaacagtgaccccgagccgctctccttggagtagcctctcggaggatc
acacctcgacacccaaccctgaaccccacacactctctgccatgcacacaggaggagag
ctggacctgagggccaccgcagcggtgcacacattcctctgggctgacggcatgacctct
gtaagggactcctgctagtcccctcttggcatgaatgactgactgtagacgcatgacctc
caggcttcaatcctgcctcttgcaatgacagctgatctgtcggaaccaggacacaaaagc -continued agcaagaagcggggagagagagggatagaaaacaagcgcaggagagcctgcgaacgcaaa
agtgaatgagggcttttgtggctgggg Cluster Members
Consensus/Exemplar
BLASTn GenBank NR
Probe Info

| Probe Sequence(5'-3') | Probe X | Probe Y | Probe Interrogation Position | SEQ ID NO: |
|---|---|---|---|---|
| GCCTACAGCCGGACCTGATAGAGGG | 87 | 479 | 651 | 182 |
| AGATAGTGAAGCGGGCCAGCCTGAA | 1126 | 105 | 690 | 183 |
| TCTCCTTGGAGTAGCCTCTCGGGAG | 286 | 1003 | 742 | 184 |
| CTCTCGGGAGGATCACACCTCGACA | 18 | 383 | 757 | 185 |
| CTCTCTGCCATGCACACAGGAGGAG | 171 | 383 | 804 | 186 |
| GCATGACCTCTGTAAGGGACTCCTG | 1116 | 523 | 880 | 187 |
| CTAGTCCCCTCTTGGCATGAATGAC | 366 | 371 | 905 | 188 |
| TGACTGACTGTAGACGCATGACCTC | 354 | 947 | 926 | 189 |
| AATCCTGCCTCTTGCAATGACAGCT | 982 | 277 | 959 | 190 |
| ACAGCTGATCTGTCGGAACCAGGAC | 443 | 189 | 978 | 191 |
| GAATGAGGGCTTTTGTGGCTGGGG | 600 | 557 | 1074 | 192 |

>HG-U133_PLUS_2:205651_X_AT
SEQ ID NO:193
atgtaatttagggaggactggtctgtaatttctgaatgtatatagaataatatttatgtt
tacaatgtaacttttcaaaatttacaaatcaggattatatacataagaattccactaaga
aatgccaagattcttaaatttgccagcgttaaagtagaaaataacatttcagaagagcac
aatatgcataaaacatttttcaaaattgaaatattttcctgggcattaaaaacctttact
attggctacaaaatttattgtacctgatgaaaacatattttctggacttaaatgttattac
aaatatcttaattttcagtaattgttttgcactttcaaagattgtaaatagttcattcaa
tcaatggtatagagttatttatttgctacataatagatactgtgccaaataattctttt
tatttattttatttagtacgtaattttgaagtacatttttcctgttttcacaattagac
tacatttaatgtgtaggaattgtatgtatgtatatcttctgtaaataacatctagtatct
tcact Cluster Members
Consensus/Exemplar
BLASTn GenBank NR
Probe Info

| Probe Sequence(5'-3') | Probe X | Probe Y | Probe Interrogation Position | SEQ ID NO: |
|---|---|---|---|---|
| ATGTAATTTAGGGAGGACTGGTCTG | 708 | 53 | 3716 | 194 |
| GGACTGGTCTGTAATTTCTGAATGT | 540 | 855 | 3730 | 195 |
| AGAATTCCACTAAGAAATGCCAAGA | 95 | 129 | 3821 | 196 |
| GATTCTTAAATTTGCCAGCGTTAAA | 1028 | 691 | 3844 | 197 |
| TTGAAATATTTTCCTGGGCATTAAA | 254 | 1149 | 3921 | 198 |
| GCATTAAAAACCTTTACTATTGGCT | 892 | 519 | 3938 | 199 |
| TTCAGTAATTGTTTTGCACTTTCAA | 901 | 1129 | 4029 | 200 |
| GCTACATAATAGATACTGTGCCAAA | 293 | 511 | 4100 | 201 |
| GTACATTTTTTCCTGTTTTCACAAT | 517 | 735 | 4166 | 202 |
| TCCTGTTTTCACAATTAGACTACAT | 251 | 985 | 4176 | 203 |
| GTAAATAACATCTAGTATCTTCACT | 87 | 737 | 4236 | 204 |

HG-U133_PLUS_2:31637_S_AT
SEQ ID NO: 205
catgggcatgggagacctgctcagtgccatgtnnnnnnnnnnnnnnnnnnnnnnnnnnnn
nnnnnnnnnnnnnnnnnnnnnnnnnnnnnnnnnnnnnnnnnnnnnnnnnnnnnnnnnnn
nnnnnnnnnnnnnnnnnnnnnnnnnnnnnnnnnnnnnnnnnnnnnnnnnnnnnnnnnnn
nnnnnnnnnnnnnnnnnnnnnnnnnnnnnnnnnnnnnnnnnnnnnnnnnnnnnnnnnnn
nnnnnnnnnnnnnnnnnnnnnnnnnnnnnnnnnnnnnnnnnnnnnnnnnnnnnnnnnnn
nnnnnnnnnnnnnnnnnnnnnnnnnnnnnnnnnnnnnnnnnnnnnnnnnnnnnnnnnnn
nnnnnnnnnnnnnnnnnnnnnnnnnnnnnnnnnnnnnnnnnnnnnnnnnnnnnnnnnnn
nnnnnnnnnnnnnnnnnnnnnnnnnnnnnnnnnnnnnnnnnnnnaatcttatt
atattgttataaaatattccaagatgagcctctggcccctgagccttcttgtaaatacc
tgcctccctcccccatcaccgaacttcccctcctcccctatttaaaccactctgtctccc
ccacaaccctcccctggccctctgatttgttctgttcctgtctcaa Cluster Members
Consensus/Exemplar
Group Members
BLASTn GenBank NR
Note: "n"'s represent regions that are not probed by the probe sequences.

-continued

| Probe Sequence(5'-3') | Probe X | Probe Y | Probe Interrogation Position | SEQ ID NO: |
|---|---|---|---|---|
| CATGGGCATGGGAGACCTGCTCAGT | 827 | 343 | 1744 | 206 |
| TCTGGCCCCCTGAGCCTTCTTGTAA | 345 | 997 | 2194 | 207 |
| GCCCCCTGAGCCTTCTTGTAAATAC | 889 | 485 | 2198 | 208 |
| CCCTGAGCCTTCTTGTAAATACCTG | 711 | 427 | 2201 | 209 |
| CCTGAGCCTTCTTGTAAATACCTGC | 525 | 441 | 2202 | 210 |
| CTGAGCCTTCTTGTAAATACCTGCC | 881 | 395 | 2203 | 211 |
| TCCCCTGGCCCTCTGATTTGTTCTG | 23 | 989 | 2293 | 212 |
| CCCCTGGCCCTCTGATTTGTTCTGT | 688 | 431 | 2294 | 213 |
| CCCTGGCCCTCTGATTTGTTCTGTT | 703 | 429 | 2295 | 214 |
| CCTGGCCCTCTGATTTGTTCTGTTC | 173 | 439 | 2296 | 215 |
| CTGGCCCTCTGATTTGTTCTGTTCC | 1013 | 407 | 2297 | 216 |
| TGGCCCTCTGATTTGTTCTGTTCCT | 614 | 895 | 2298 | 217 |
| GGCCCTCTGATTTGTTCTGTTCCTG | 159 | 889 | 2299 | 218 |
| GCCCTCTGATTTGTTCTGTTCCTGT | 751 | 487 | 2300 | 219 |
| CCCTCTGATTTGTTCTGTTCCTGTC | 173 | 427 | 2301 | 220 |
| CTGATTTGTTCTGTTCCTGTCTCAA | 367 | 399 | 2305 | 221 |

>HG-U133_PLUS_2:206855_S_AT
SEQ ID NO: 222
ccccagctgcgacctgtgggggagctcagttgggccgacattgaccacctgcagacacac
ttccgctgccagtgctacttgggctggagtggtgagcaatgccagtgggaccataggcag
gcagctggaggtgccaacgaggcctgggctgggtcccacctccagtctgctggctctg
gcagccctggcctttacctggaccttgtaggggtctcctgcctagctgcctagcaagctg
gcctctacacaagggctctcttaggcatgtaggaccctgcagggggtggtcaaactggag
tctggagtgcagagcccccaggaaacccaggagggcatccataccagtctcgcacccccct
gttctaaggggagggaagtccctgggaggcccttctctccctgccagaggggaagga
gggtacagctgggctggggaggacctgaccctactcccttgccctagatagtttat Cluster Members
Consensus/Exemplar
BLASTn GenBank NR
Probe Info

| Probe Sequence(5'-3') | Probe X | Probe Y | Probe Interrogation Position | SEQ ID NO: |
|---|---|---|---|---|
| CCCCAGCTGCGACCTGTGGGGGAGC | 962 | 433 | 1325 | 223 |
| AGCTCAGTTGGGCCGACATTGACCA | 991 | 137 | 1347 | 224 |
| GGGCTGGAGTGGTGAGCAATGCCAG | 516 | 793 | 1405 | 225 |
| GGTGAGCAATGCCAGTGGGACCATA | 559 | 819 | 1415 | 226 |
| GCAATGCCAGTGGGACCATAGGCAG | 414 | 547 | 1420 | 227 |
| ACCTGGACCTTGTAGGGGTCTCCTG | 171 | 155 | 1520 | 228 |
| CACAAGGGCTCTCTTAGGCATGTAG | 563 | 307 | 1572 | 229 |
| GGCTCTCTTAGGCATGTAGGACCCT | 36 | 883 | 1578 | 230 |
| TTAGGCATGTAGGACCCTGCAGGGG | 743 | 1117 | 1585 | 231 |
| GCATGTAGGACCCTGCAGGGGTGG | 580 | 519 | 1589 | 232 |
| TACTCCCTTGCCCTAGATAGTTTAT | 713 | 1055 | 1776 | 233 |

>HG-U133_PLUS_2:221887_S_AT
SEQ ID NO: 234
ggaactggtgctgtactgggtacacagtaggcgcccaggacaagtgggttgcaagacagg
aagaaaggaaaaggaagggcagagtgctggtttctccaggttgggttgggggcactgctg
tccccctccagctaggacccagcccatccccagatgcctgagcctttgtccaaagtgag
gtcactcgagaattcatggacacggcccccagtcaggggcatcttgcaagacctttagt
gccacaaataagcatcgagcacctccccattcacaccccattcctcctggctccttatc
ccccatggtgtttattatttatttccctcccatgccctggggaccccaaggccccagc
ttccctctgcaccccagcctatcccagaggccttgcaggtgaccagcagtgtcattgta Cluster Members
Consensus/Exemplar
BLASTn GenBank NR
Probe Info

| Probe Sequence(5'-3') | Probe X | Probe Y | Probe Interrogation Position | SEQ ID NO: |
|---|---|---|---|---|
| GGAACTGGTGCTGTACTGGGTACAC | 444 | 863 | 2384 | 235 |
| TGGGTACACAGTAGGCGCCCAGGAC | 858 | 911 | 2400 | 236 |
| GGAAGGGCAGAGTGCTGGTTTCTCC | 656 | 867 | 2456 | 237 |
| GCTGGTTTCTCCAGGTTGGGTTGGG | 659 | 483 | 2469 | 238 |
| ATGCCTGAGCCTTTGTCCAAAGTGA | 512 | 53 | 2538 | 239 |
| GTGAGGTCACTCGAGAATTCATGGA | 804 | 773 | 2559 | 240 |
| AGTCAGGGGCATCTTGCAAGACCT | 673 | 97 | 2594 | 241 |
| ATCTTGCAAGACCTTTAGTGCCACA | 580 | 41 | 2605 | 242 |
| CACAAATAAGCATCGAGCACCTCCC | 372 | 307 | 2626 | 243 |

-continued

| | | | |
|---|---|---|---|
| TCCTTATCCCCCATGGTGTTTATTA | 800 | 979 | 2676 | 244 |
| GCAGGTGACCAGCAGTGTCATTGTA | 639 | 527 | 2779 | 245 |

>HG-U133_PLUS_2:222727_S_AT
SEQ ID NO: 246
gggcttgtatgtgttctatgtggtcactgtgattctctgcacctggatctaccaacggca
acggagaggatctctgttctgccccatgccagttactccagagatcctctcagactccga
ggaggaccgggtatcttctaataccaacagctatgactacggtgatgagtaccggccgct
gttcttctaccaggagaccacggctcagatcctggtccgggccctcaatcccctggatta
catgaagtggagaaggaaatcagcatactggaaagccctcaaggtgttcaagctgcctgt
ggagttcctgctgctcctcacagtcccgtcgtggacccggacaaggatgaccagaactg
gaaacggcccctcaactgtctgcatctggttatcagcccctggttgtggtcctgaccct
gcagtcggggacctatggtgtctatgagataggcggcctcgttcccgtctgggtcgtggt
ggtgatcgcaggcacagccttggcttcagtgacctttttgccacatctga Cluster Members
Consensus/Exemplar
BLASTn GenBank NR
Probe Info

| Probe Sequence(5'-3') | Probe X | Probe Y | Probe Interrogation Position | SEQ ID NO: |
|---|---|---|---|---|
| GGGCTTGTATGTGTTCTATGTGGTC | 606 | 795 | 947 | 247 |
| AGTTACTCCAGAGATCCTCTCAGAC | 329 | 103 | 1037 | 248 |
| GACTCCGAGGAGGACCGGGTATCTT | 690 | 611 | 1059 | 249 |
| TACGGTGATGAGTACCGGCCGCTGT | 848 | 1057 | 1104 | 250 |
| TTCTACCAGGAGACCACGGCTCAGA | 607 | 1131 | 1131 | 251 |
| CCCTCAAGGTGTTCAAGCTGCCTGT | 1030 | 425 | 1222 | 252 |
| ACTGTCTGCATCTGGTTATCAGCCC | 557 | 167 | 1321 | 253 |
| ACCCTGCAGTCGGGGACCTATGGTG | 354 | 159 | 1362 | 254 |
| CTATGAGATAGGCGGCCTCGTTCCC | 276 | 369 | 1388 | 255 |
| GTCGTGGTGGTGATCGCAGGCACAG | 1031 | 755 | 1419 | 256 |
| CAGTGACCTTTTTTGCCACATCTGA | 386 | 335 | 1453 | 257 |

>HG-U133_PLUS_2:205529_S_AT
SEQ ID NO: 258
gaagtaagagactcagcctgcagttaattagcattctggcagttttgacatcagccagct
gccctaaataacccttcaacgtttcttcacttttgcaagttccacagagtaagacattgg
gtctattccagctcattcatttttatattgaaaaaaataattttaaaaatggtggcttcag
ctccagccccttccaaaattttttcaaccccaccctgtttggattttaattaaaaacta
gtagttctcttggtgttaaaacacttctgtcctgtgaggtttcccaatggtgttttctt
gtaaatgtgttggacaaatgtgaagatgcattgtagtttaaccatatgcccacatttagt
ctctttattcctagttggtgagaaacctgtatctttctatgctgcttttatatctgtatg
t Cluster Members
Consensus/Exemplar
BLASTn GenBank NR
Probe Info

| Probe Sequence(5'-3') | Probe X | Probe Y | Probe Interrogation Position | SEQ ID NO: |
|---|---|---|---|---|
| GAAGTAAGAGACTCAGCCTGCAGTT | 1133 | 563 | 2983 | 259 |
| GCCTGCAGTTAATTAGCATTCTGGC | 404 | 481 | 2998 | 260 |
| CCTTCAACGTTTCTTCACTTTTGCA | 227 | 437 | 3055 | 261 |
| GACATTGGGTCTATTCCAGCTCATT | 1082 | 607 | 3095 | 262 |
| GTGTTAAAACACTTCTGTCCTGTGA | 142 | 777 | 3235 | 263 |
| TGAGGTTTCCCAATGGTGTTTTTCT | 306 | 939 | 3257 | 264 |
| GTGAAGATGCATTGTAGTTTAACCA | 1116 | 767 | 3302 | 265 |
| TAACCATATGCCCACATTTAGTCTC | 651 | 1041 | 3321 | 266 |
| GCCCACATTTAGTCTCTTTATTCCT | 753 | 489 | 3330 | 267 |
| AAACCTGTATCTTTCTATGCTGCTT | 614 | 215 | 3365 | 268 |
| CTATGCTGCTTTTATATCTGTATGT | 886 | 369 | 3379 | 269 |

>HG-U133_PLUS_2:205760_S_AT
SEQ ID NO: 270
cctggccagtcaaagtagtctctcccctggccacagtaattggtcatgtgatgcaagcca
gcttactagcactttgagaatgagtctcctgttgagctggtaggatgtaagctggagct
aatggcgatcatctttgccaccgcctggggagagcctgcttgggaatgaaattaacacaa
aggaagtccaacctgagaaatggccaaatatatttcctgataacattatgtggccctctg
gatccagccatgcctgaggtctaccctgggcttttggattatgtgtacagttggttcat
cccttttctgctaattcgagtcatggctaatttaacacccttagaaccttaaagaacc
atcagcatcacccgggaactttttagaaatgcaaaatctctactgctttggatcctggg -continued

```
tcaaaaaaagaaaaaaaaagaaatgcaaaactttaggccctgccccagatttactaaa
tcaatctgcagtttaacaaaatcctcaggtgatttgtatgctcat
```

Cluster Members
Consensus/Exemplar
BLASTn GenBank NR
Probe Info

| Probe Sequence(5'-3') | Probe X | Probe Y | Probe Interrogation Position | SEQ ID NO: |
|---|---|---|---|---|
| CCTGGCCAGTCAAAGTAGTCTCTCC | 1046 | 437 | 1521 | 271 |
| CTCCCCTGGCCACAGTAATTGGTCA | 636 | 387 | 1542 | 272 |
| AATTGGTCATGTGATGCAAGCCAGC | 1071 | 291 | 1558 | 273 |
| GCAAGCCAGCTTACTAGCACTTTGA | 303 | 545 | 1573 | 274 |
| GCTAATGGCGATCATCTTTGCCACC | 865 | 509 | 1638 | 275 |
| CCTGGGCTTTTGGATTATGTGTACA | 805 | 439 | 1786 | 276 |
| TGTACAGTTGGTTCATCCCTTTTTC | 89 | 925 | 1805 | 277 |
| ATCCCTTTTTCTGCTAATTCGAGTC | 143 | 49 | 1819 | 278 |
| ATGCAAAATCTCTACTGCTTTGGAT | 1 | 57 | 1910 | 279 |
| CCCTGCCCCAGATTTACTAAATCAA | 909 | 427 | 1980 | 280 |
| ATCCTCAGGTGATTTGTATGCTCAT | 623 | 49 | 2021 | 281 |

>HG-U133_PLUS_2:230629_S_AT
SEQ ID NO: 282
```
gtggaaggtggctgctgcgaagaagctcgttagaactgtggtgcgccatcacgaggagaa
gcagctccgtgaagaaaggggggaagaaggaagagcagagcagactgaggcggatagccgc
ctccacggcccgggagatagagtgcntttggtcgaatattgaacaggttgtgg
```

Cluster Members
Consensus/Exemplar
BLASTn GenBank NR
Probe Info

| Probe Sequence(5'-3') | Probe X | Probe Y | Probe Interrogation Position | SEQ ID NO: |
|---|---|---|---|---|
| GTGGAAGGTGGCTGCTGCGAAGAAG | 387 | 789 | 283 | 283 |
| GAAGGTGGCTGCTGCGAAGAAGCTC | 569 | 561 | 286 | 284 |
| GTGGCTGCTGCGAAGAAGCTCGTTA | 211 | 791 | 290 | 285 |
| GGCTGCTGCGAAGAAGCTCGTTAGA | 1122 | 881 | 292 | 286 |
| GAAGCTCGTTAGAACTGTGGTGCGC | 554 | 571 | 304 | 287 |
| GCTCGTTAGAACTGTGGTGCGCCAT | 759 | 505 | 307 | 288 |
| TTAGAACTGTGGTGCGCCATCACGA | 706 | 1115 | 312 | 289 |
| GTGGTGCGCCATCACGAGGAGAAGC | 955 | 785 | 320 | 290 |
| TGCGCCATCACGAGGAGAAGCAGCT | 873 | 967 | 324 | 291 |
| CCTCCACGGCCCGGGAGATAGAGTG | 512 | 443 | 402 | 292 |
| TGGTCGAATATTGAACAGGTTGTGG | 175 | 907 | 431 | 293 |

>HG-U133_PLUS_2:241919_X_AT
SEQ ID NO: 294
```
gcccagaattacaggagttagcacaccnagctcntacagataagaaaacattgaaattca
agattaaggccaaaaatatctcacttgcaattttaatattttcatttggatttatataa
atgaaacatatatatgtttttggaatggccagagtgaggcaaaggggatccctgaaataac
attagaacatacaggaaaaacgaggcnggcagatcactttaggtcaggagttcaagacca
gcctgtacgcgtgcctgtagtcccagctactcgggaggctgagatgggagaatcactt
gaacctggggaggcagagtttgcagtgagctgagantntnccactgcactccagtctgtgt
gacagaatgagaccttgtcttgaaacaaacacaaaaacaaaaaaccacatacaggaaaca
agagagggatggagtcaactgtgccccagacattaagcgcccttcagtgaggaggggcaa
agtgctcaggcctgcctgtgtggcccacaggagtcagaactcg
```

Cluster Members
Consensus/Exemplar
BLASTn GenBank NR
Probe Info

| Probe Sequence(5'-3') | Probe X | Probe Y | Probe Interrogation Position | SEQ ID NO: |
|---|---|---|---|---|
| GCCCAGAATTACAGGAGTTAGCACA | 1122 | 485 | 1019 | 295 |
| AGGCCAAAAATATCTCACTTGCAAT | 450 | 71 | 1086 | 296 |
| GAGTGAGGCAAAGGGGATCCCTGAA | 50 | 653 | 1169 | 297 |
| CTGCACTCCAGTCTGTGTGACAGAA | 688 | 395 | 1361 | 298 |
| GAGACCTTGTCTTGAAACAAACACA | 555 | 639 | 1387 | 299 |
| GAGGGATGGAGTCAACTGTGCCCCA | 542 | 655 | 1442 | 300 |
| TCAACTGTGCCCCAGACATTAAGCG | 1064 | 1027 | 1453 | 301 |
| GACATTAAGCGCCCTTCAGTGAGGA | 352 | 607 | 1467 | 302 |
| GAGGAGGGGCAAAGTGCTCAGGCCT | 794 | 659 | 1487 | 303 |

-continued

| | | | | |
|---|---|---|---|---|
| AAAGTGCTCAGGCCTGCCTGTGTGG | 630 | 207 | 1497 | 304 |
| TGTGGCCCACAGGAGTCAGAACTCG | 314 | 915 | 1517 | 305 |

>HG-U133_PLUS_2:206114_AT
SEQ ID NO:306
gcaaccccaacagcttgaagaggacagggacggagagctccagacctaacactgccttgt
tggatccaagctcccctgaattctctgctgtggtatcagtgggcgattggctccaggcca
ttaaaatggaccggtataaggataacttcacagctgctggttataccacactagaggctg
tggtgcacgtgaaccaggaggacctggcaagaattggtatcacagccatcacgcaccaga
ataagattttgagcagtgtccaggcaatgcgaacccaaatgcagcagatgcacggcagaa
tggttcccgtctgagccagtactgaataaactcaaaactcttgaaattagtttacctcat
ccatgcactttaatt Cluster Members
Consensus/Exemplar
BLASTn GenBank NR
Probe Info

| Probe Sequence(5'-3') | Probe X | Probe Y | Probe Interrogation Position | SEQ ID NO: |
|---|---|---|---|---|
| GCAACCCCAACAGCTTGAAGAGGAC | 320 | 543 | 2693 | 307 |
| TCCAGACCTAACACTGCCTTGTTGG | 458 | 977 | 2731 | 308 |
| CCCTGAATTCTCTGCTGTGGTATCA | 1140 | 427 | 2766 | 309 |
| TATCAGTGGGCGATTGGCTCCAGGC | 918 | 1081 | 2786 | 310 |
| ACAGCTGCTGGTTATACCACACTAG | 726 | 189 | 2842 | 311 |
| GGTGCACGTGAACCAGGAGGACCTG | 787 | 819 | 2874 | 312 |
| CAGCCATCACGCACCAGAATAAGAT | 1013 | 321 | 2915 | 313 |
| GCAGTGTCCAGGCAATGCGAACCCA | 216 | 529 | 2945 | 314 |
| TGCACGGCAGAATGGTTCCCGTCTG | 485 | 957 | 2981 | 315 |
| TTCCCGTCTGAGCCAGTACTGAATA | 302 | 1141 | 2996 | 316 |
| TTTACCTCATCCATGCACTTTAATT | 1017 | 1103 | 3043 | 317 |

>HG-U133_PLUS_2:202905_X_AT
SEQ ID NO: 318
agcgccccagtgaacactacaacatacgtagctgacacagaatcagagcaagcagataca
tgggatttgagtgaaaggccaaaagaaatcaaagtctccaaaatggaacaaaaattcaga
atgctttcacaagangcacccactgtaaaggagtcctgcaaaacaagctctaataataat
agtatggtatcaaatactttggctaagatgagaatcccaaactatcagcttttcaccaact
aaattgccaagtataaataaaagtaaagatagggcttctcagcagcagcagaccaactcc
atcagaaactactttcagccgtctaccaaaaaaagggaaagggatgaagaaaatcaagaa
atgtcttcatgcaaatcagcaagaatagaaacgtcttgttctcttttagaacaaacacaa
cctgctacaccctcattgtggaaaaataaggagcagcatctatctgagaatgagcctgtg
gacacaaactcagacaataacttatttacagatacagatttaaaatctattgtgaaaaat
tctgccagtaaatctcatgct Cluster Members
Consensus/Exemplar
BLASTn GenBank NR

| Probe Sequence(5'-3') | Probe X | Probe Y | Probe Interrogation Position | SEQ ID NO: |
|---|---|---|---|---|
| AGCGCCCCAGTGAACACTACAACAT | 753 | 143 | 1213 | 319 |
| GCACCCACTGTAAAGGAGTCCTGCA | 514 | 537 | 1348 | 320 |
| GAATCCCAAACTATCAGCTTTCACC | 153 | 547 | 1424 | 321 |
| AGCTTTCACCAACTAAATTGCCAAG | 987 | 133 | 1439 | 322 |
| AAGATAGGGCTTCTCAGCAGCAGCA | 716 | 257 | 1478 | 323 |
| GCAGACCAACTCCATCAGAAACTAC | 247 | 531 | 1500 | 324 |
| TCAGAAACTACTTTCAGCCGTCTAC | 470 | 1019 | 1514 | 325 |
| TAGAAACGTCTTGTTCTCTTTTAGA | 152 | 1065 | 1598 | 326 |
| TAGAACAAACACAACCTGCTACACC | 95 | 1067 | 1619 | 327 |
| CCTGCTACACCCTCATTGTGGAAAA | 587 | 441 | 1633 | 328 |
| AAATTCTGCCAGTAAATCTCATGCT | 689 | 197 | 1749 | 329 |

>HG-U133_PLUS_2:210063_AT
SEQ ID NO: 330
gccattgactccctgagcattgagaaaggctaccggcactggcacgcggacctgcggcca
gacgacagcccctggaggcaggcctggccttcacctgcaagctcaagtcgccggtgccc
ttcctggggaggcagggccctggagcagcagcgggccgcaggcctccgccggcgcctggtg
tgcttcaccatggaggacaaagtacccatgtttggctggaggccatctggagaacgcc
caagtggtgggccatgtccggagggctgacttgggttcgccatcgacaagaccatcgcc
tacggttacatccatgaccccagcggtgggccggtctcgctggactttgtgaagagcggg
gactatgccctggagagaatggggggtgacctatggtgccc Cluster Members
Consensus/Exemplar
BLASTn GenBank NR
Probe Info -continued

| Probe Sequence(5'-3') | Probe X | Probe Y | Probe Interrogation Position | SEQ ID NO: |
|---|---|---|---|---|
| GCCATTGACTCCCTGAGCATTGAGA | 101 | 475 | 2341 | 331 |
| TTGAGAAAGGCTACCGGCACTGGCA | 361 | 1153 | 2360 | 332 |
| CACCTGCAAGCTCAAGTCGCCGGTG | 489 | 317 | 2433 | 333 |
| CGCCTGGTGTGCTTCACCATGGAGG | 960 | 419 | 2512 | 334 |
| AAGTACCCATGTTTGGCCTGGAGGC | 448 | 257 | 2540 | 335 |
| GCCTGGAGGCCATCTGGAGGAACGG | 734 | 481 | 2555 | 336 |
| CTGGAGGAACGGCCAAGTGGTGGGC | 416 | 401 | 2568 | 337 |
| TTTGGGTTCGCCATCGACAAGACCA | 457 | 1087 | 2611 | 338 |
| CGGTCTCGCTGGACTTTGTGAAGAG | 84 | 411 | 2672 | 339 |
| TGAAGAGCGGGGACTATGCCCTGGA | 954 | 951 | 2690 | 340 |
| AGAATGGGGGTGACCTATGGTGCCC | 1157 | 127 | 2716 | 341 |

>HG-U133_PLUS_2:209117_AT
SEQ ID NO: 342
cacttcagaccagccaggtgtcttcccgggccctgccagaccctgctcacattccctctg
ctggtctgtgctggtctcagaaggccaccgcgcccgcattccactcagccagggtccagc
tgcagccccgccacccttccttccctccctgtcctgggtcatgttgttgccaccctgt
gtgacttttgaagctgtaaaatgagcttccagggcttgggtggcgtcggggcagggccgc
cgaggctgggaggaagcccttctgccttttgctggtgtttctggaatttgctttccctca
cctctcacttccttctagaaggagcttcctgactggaaccagagaatgcatgtctgtcca
cttg Cluster Members
Consensus/Exemplar
BLASTn GenBank NR
Probe Info

| Probe Sequence(5'-3') | Probe X | Probe Y | Probe Interrogation Position | SEQ ID NO: |
|---|---|---|---|---|
| CACTTCAGACCAGCCAGGTGTCTTC | 478 | 311 | 1227 | 343 |
| GCTGGTCTGTGCTGGTCTCAGAAGG | 479 | 497 | 1286 | 344 |
| TTCCCTGTCCTGGGTCATGTTGTTG | 75 | 1143 | 1373 | 345 |
| CACCCTGTGTGACTTTTGAAGCTGT | 87 | 319 | 1399 | 346 |
| GTGTGACTTTTGAAGCTGTAAAATG | 756 | 781 | 1405 | 347 |
| AAATGAGCTTCCAGGGCTTGGGTGG | 893 | 203 | 1425 | 348 |
| CTTTTGCTGGTGTTTCTGGAATTTG | 351 | 365 | 1492 | 349 |
| GCTGGTGTTTCTGGAATTTGCTTTC | 280 | 497 | 1497 | 350 |
| ACCTCTCACTTCCTTCTAGAAGGAG | 763 | 155 | 1526 | 351 |
| GCTTCCTGACTGGAACCAGAGAATG | 947 | 517 | 1550 | 352 |
| CAGAGAATGCATGTCTGTCCACTTG | 316 | 329 | 1566 | 353 |

>HG-U133_PLUS_2:201280_S_AT
SEQ ID NO: 354
aatccttattgttcagagttgtttggggttctgtttcagagcataaaacctaaaggtta
tagtagaacaaggcaccttcttaaaagaaatcttgcttcagaccatcagttacagagaat
ttcctaaagtaaaattgaagcaactacaacttctccttagacactttggaatctaaccac
ttaaggaccttttaaagagatagcttctcttctttctgaagatcaatttctcccaaggc
caagattgtccttttctcccatttcttgctagctattgcaaatgagggaagaacattatt
catctctcctccccttttttttctgattcttttttcagtcagttttgctcctgggttcaa
gtagtattaccacccttcacaagcaacagactc Cluster Members
Consensus/Exemplar
BLASTn GenBank NR
Probe Info

| Probe Sequence(5'-3') | Probe X | Probe Y | Probe Interrogation Position | SEQ ID NO: |
|---|---|---|---|---|
| AATCCTTATTGTTCAGAGTTGTTTG | 47 | 279 | 2855 | 355 |
| GAAATCTTGCTTCAGACCATCAGTT | 1005 | 595 | 2941 | 356 |
| GACCATCAGTTACAGAGAATTTCCT | 897 | 621 | 2955 | 357 |
| AACTACAACTTCTCCTTAGACACTT | 1088 | 233 | 2996 | 358 |
| GACACTTTGGAATCTAACCACTTAA | 863 | 599 | 3014 | 359 |
| CTGAAGATCAATTTCTCCCAAGGCC | 523 | 395 | 3071 | 360 |
| CTCCCAAGGCCAAGATTGTCCTTTT | 496 | 385 | 3085 | 361 |
| CTCCCATTTCTTGCTAGCTATTGCA | 185 | 387 | 3110 | 362 |
| GAAGAACATTATTCATCTCTCCTCC | 191 | 569 | 3142 | 363 |
| TTTTTTCAGTCAGTTTTGCTCCTGG | 725 | 1107 | 3184 | 364 |
| CCACCCTTTCACAAGCAACAGACTC | 685 | 463 | 3224 | 365 |

>HG-U133_PLUS_2:225852_AT
SEQ ID NO: 366
gctgcctctggtggatatgcggaggtgggccgagttcttttggataaaggtgctgatgtt -continued

```
aatgccntccagttccctcctcaagagatacagctttaaccatagcagcagataaaggg
cattacaaattctgtgagcttcttattggcaggggagctcatattgatgtacgtaacaag
aaggggaacactccattgtggctagcagcaaatggtggacacctcgatgtggttcagtta
ctggtgcaagcaggtgcagatgtggatgcagcagataaccgcaagataactcctcttatg
gcagcatttagaaagggtcatgtgaaggtggtgcgctacttagtcaaagaagtcaatcag
tttccatcagattctgaatgtatgagatacatagcaaccatcactgat
```

Cluster Members
Consensus/Exemplar
BLASTn GenBank NR
Note: "n"'s represent regions that are not probed by the probe sequences.
Probe Info

| Probe Sequence(5'-3') | Probe X | Probe Y | Probe Interrogation Position | SEQ ID NO: |
|---|---|---|---|---|
| GCTGCCTCTGGTGGATATGCGGAGG | 1109 | 503 | 4082 | 367 |
| GAGGTGGGCCGAGTTCTTTTGGATA | 1077 | 655 | 4103 | 368 |
| AGTTCCCTCCTCAAGAGATACAGCT | 383 | 105 | 4153 | 369 |
| TGTGAGCTTCTTATTGGCAGGGGAG | 703 | 917 | 4214 | 370 |
| GGAACACTCCATTGTGGCTAGCAGC | 104 | 863 | 4266 | 371 |
| GTGGACACCTCGATGTGGTTCAGTT | 270 | 789 | 4296 | 372 |
| GCAGATAACCGCAAGATAACTCCTC | 158 | 531 | 4352 | 373 |
| AGATAACTCCTCTTATGGCAGCATT | 1062 | 107 | 4365 | 374 |
| GAAGGTGGTGCGCTACTTAGTCAAA | 949 | 537 | 4405 | 375 |
| AGAAGTCAATCAGTTTCCATCAGAT | 591 | 127 | 4429 | 376 |
| GAGATACATAGCAACCATCACTGAT | 299 | 645 | 4465 | 377 |

>HG-U133_PLUS_2:207319_S_AT
SEQ ID NO: 378
```
taagccgaatatgtgggagtccatgtcctgcagtgtggcctgatgtaatcaaactaccat
atttcaacaccatgaaaccaaagaagcaatatcgtcgaaagttaagagaagaatttgttt
ttattcctgcagctgcgctagacttatttgattacatgcttgccttggatcctagtaagc
gctgcactgctgaacaggctcttcagtgcgagttcctccgagatgtggaaccctcaaaat
gcctccaccagatctccctttatggcaagattgtcatgagttatggagtaaaaagcgaag
aagacagaagcagatgggcatgactgatgtttccaccattaaagcccccaggaaggactt
gtctctgggcttggatgacagcagaaccaacacacccagggtgtgctgccatcttcaca
gctgaaatctcagggcagctcaaatgtggcacc
```

Cluster Members
Consensus/Exemplar
BLASTn GenBank NR
Probe Info

| Probe Sequence(5'-3') | Probe X | Probe Y | Probe Interrogation Position | SEQ ID NO: |
|---|---|---|---|---|
| TAAGCCGAATATGTGGGAGTCCATG | 868 | 1039 | 1718 | 379 |
| GCAGTGTGGCCTGATGTAATCAAAC | 625 | 527 | 1747 | 380 |
| TCAAACTACCATATTTCAACACCAT | 1142 | 1029 | 1766 | 381 |
| TTCCTGCAGCTGCGCTAGACTTATT | 823 | 1143 | 1841 | 382 |
| GCGCTAGACTTATTTGATTACATGC | 26 | 491 | 1852 | 383 |
| TGCCTTGGATCCTAGTAAGCGCTGC | 754 | 971 | 1878 | 384 |
| TAAGCGCTGCACTGCTGAACAGGCT | 280 | 1041 | 1893 | 385 |
| GAACAGGCTCTTCAGTGCGAGTTCC | 494 | 581 | 1909 | 386 |
| CACCAGATCTCCCTTTATGGCAAGA | 923 | 319 | 1963 | 387 |
| TGGATGACAGCAGAACCAACACACC | 15 | 905 | 2089 | 388 |
| CTCAGGGCAGCTCAAATGTGGCACC | 1158 | 377 | 2146 | 389 |

>HG-U133_PLUS_2:224898_AT
SEQ ID NO:390
```
gcagctaggtgagtttgttttccgggtctgtcttaactggcagcttcctgtacatactgg
tacttatttgctgtaaacgtctgtttcatacatttgccatgcagtgactgtgctcgaaag
gtgaaatcaatggtaaagaagcctaggattttatggtatgagaaactgatcgcaggattt
tctgatccatagctattaattgaaaacttctgatagtgctgtaggctctatagtaggctt
aagagtgagtcttatactatgaagccagccacaagatactaacaaatgtataaattgaaa
agtaccaatactttttgcacatagatcaaaatagagtgggagaatttgggctccaaaaatc
aggttagtaggctcatttccatgtgcttaa
```

Cluster Members
Consensus/Exemplar
BLASTn GenBank NR
Probe Info

| Probe Sequence(5'-3') | Probe X | Probe Y | Probe Interrogation Position | SEQ ID NO: |
|---|---|---|---|---|
| GCAGCTAGGTGAGTTTGTTTTCCGG | 592 | 533 | 1780 | 391 |
| TTTTCCGGGTCTGTCTTAACTGGCA | 221 | 1109 | 1797 | 392 |

-continued

| | | | |
|---|---|---|---|
| TAACTGGCAGCTTCCTGTACATACT | 886 | 1041 | 1813 | 393 |
| GGTACTTATTTGCTGTAAACGTCTG | 611 | 827 | 1838 | 394 |
| TTTGCCATGCAGTGACTGTGCTCGA | 683 | 1095 | 1872 | 395 |
| GATTTTCTGATCCATAGCTATTAAT | 608 | 689 | 1955 | 396 |
| AACTTCTGATAGTGCTGTAGGCTCT | 875 | 233 | 1984 | 397 |
| GCTGTAGGCTCTATAGTAGGCTTAA | 628 | 497 | 1997 | 398 |
| GAGTCTTATACTATGAAGCCAGCCA | 919 | 649 | 2026 | 399 |
| GAAGCCAGCCACAAGATACTAACAA | 598 | 573 | 2040 | 400 |
| AGTAGGCTCATTTCCATGTGCTTAA | 810 | 101 | 2145 | 401 |

>HG-U133_PLUS_2:202495_AT
SEQ ID NO: 402
gttgacgattttaactggctggcccgggatatggcctccccaaactggagtattcttcct
gaagaggagcgaaatatccagtgggactaagcagttgtcactctgttcttcactcctacc
aaatactttccacgttggactttccccttatgggtctcgaagtttacttattgtcaca
ctgtgtatgttttcagcattttaaggctagagattgtaatgggctcctacttgtaattc
cattaaattcgtaacaggtataacactaaagcattttgtcatttcgtcatgcctttga
gactgagtcttactccgtccccagcgtggtggcgcgctgggattacaggcgcgcgccac
cacgcgaactcgtattttagtagagacgggtttcgccatgttgtccgggctgctctcg
aactcctgacctcaggtgatcacccgcttcagcttcccaaagtgctggcattacaggcg
tgagccaccacgccagggctttatttatttat Cluster Members
Consensus/Exemplar
BLASTn GenBank NR
Probe Info

| Probe Sequence(5'-3') | Probe X | Probe Y | Probe Interrogation Position | SEQ ID NO: |
|---|---|---|---|---|
| GTTGACGATTTTAACTGGCTGGCCC | 13 | 699 | 987 | 403 |
| AACTGGCTGGCCCGGGATATGGCCT | 699 | 239 | 999 | 404 |
| ATGGCCTCCCCAAACTGGAGTATTC | 665 | 71 | 1017 | 405 |
| GACTAAGCAGTTGTCACTCTGTTCT | 588 | 611 | 1071 | 406 |
| CTCCTACCAAATACTTTCCACGTTG | 534 | 389 | 1099 | 407 |
| GAAGTTTACTTATTGTCACACTGTG | 547 | 565 | 1147 | 408 |
| GGGCTCCTACTTGTAATTTCCATTA | 400 | 793 | 1207 | 409 |
| TTTGCTATTTTCGTCATGCCTTTGA | 304 | 1095 | 1262 | 410 |
| CCCCCAGCGTGGTGGCGCGCTGGGA | 160 | 431 | 1305 | 411 |
| CCACCACGCGAACTCGTATTTTTAG | 407 | 461 | 1343 | 412 |
| CCACGCCAGGGCTTTATTTATTTAT | 718 | 463 | 1474 | 413 |

>HG-U133_PLUS_2:210061_AT
SEQ ID NO: 414
gtcacgtgtcagaggacacactcgggagaaaccttcatggagtgagagtaaggtgttggc
tggaagtggcccttaagagatacttggagtcaaatctatccactgtacgcccaccccac
tcttgttctaagagctttggggacagtcttttgacccccttacattcctttagatgtgaag
atgacagagatctaacttctgagagcagag Cluster Members
Consensus/Exemplar
BLASTn GenBank NR
Probe Info

| Probe Sequence(5'-3') | Probe X | Probe Y | Probe Interrogation Position | SEQ ID NO: |
|---|---|---|---|---|
| GTCACGTGTCAGAGGACACACTCGG | 981 | 743 | 2511 | 415 |
| CACACTCGGGAGAAACCTTCATGGA | 999 | 307 | 2527 | 416 |
| TCGGGAGAAACCTTCATGGAGTGAG | 863 | 995 | 2532 | 417 |
| CATGGAGTGAGAGTAAGGTGTTGGC | 162 | 343 | 2546 | 418 |
| TGGCTGGAAGTGGCCCCTTAAGAGA | 250 | 883 | 2567 | 419 |
| GTGGCCCCTTAAGAGATACTTGGAG | 809 | 789 | 2576 | 420 |
| GAGATACTTGGAGTCAAATCTATCC | 687 | 643 | 2588 | 421 |
| GAGTCAAATCTATCCACTGTACGCC | 365 | 649 | 2598 | 422 |
| CCACCCCACTCTTGTTCTAAGAGCT | 527 | 463 | 2622 | 423 |
| TGACCCCTTACATTCCTTTAGATGT | 620 | 945 | 2662 | 424 |
| AGAGATCTAACTTCTGAGAGCAGAG | 1120 | 113 | 2696 | 425 |

>HG-U133_PLUS_2:201159_S_AT
SEQ ID NO: 426
tgcagggtttggcttgtgggctgcttgctgctcatctgatttttgtcccagtagtccctg
cgttcttcattcaacccttctgggacttcagctcagagagcaccatcccggggtcagg
gcctccccacaggagccctgcagtgtggtagcgccatggctgtctcaaaccaagcaaagg
aaggaccctgaggccttcacgctaaccatcctcgagcaactgctgttggaaggcctccct
gggcctggcccccaccctctgccaccagtcctcccagctgccatgtttcaaagacgacc
tttacctcctgcctttggattgactctgcatttgaccacggactccagtctgtgtgtagg
gagagagctgagtaggaggcctccactccggatcgaggcctgtataggggctcgttttccc -continued

```
acacatgcctatttctgaagaggcttctgtcttatttgaaggccagcccacacccagcta
ctttaacaccaggtttatggaaaatgtcaggccttcccca
```

Cluster Members
Consensus/Exemplar
BLASTn GenBank NR
Probe Info

| Probe Sequence(5'-3') | Probe X | Probe Y | Probe Interrogation Position | SEQ ID NO: |
|---|---|---|---|---|
| TGCAGGGTTTGGCTTGTGGGCTGCT | 548 | 959 | 3799 | 427 |
| GCTGCTCATCTGATTTTTGTCCCAG | 573 | 503 | 3825 | 428 |
| CCCTTCTGGGACTTCAGCTCAGAGA | 786 | 425 | 3874 | 429 |
| GAGCAACTGCTGTTGGAAGGCCTCC | 761 | 633 | 4012 | 430 |
| AGCTGCCATGTTTCAAAGACGACCT | 945 | 139 | 4075 | 431 |
| ACCACGGACTCCAGTCTGTGTGTAG | 538 | 149 | 4133 | 432 |
| GAGAGCTGAGTAGGAGGCCTCCACT | 95 | 641 | 4161 | 433 |
| CACTCCGGATCGAGGCCTGTATAGG | 456 | 313 | 4182 | 434 |
| TGTCTTATTTGAAGGCCAGCCCACA | 320 | 923 | 4246 | 435 |
| ACACCCAGCTACTTTAACACCAGGT | 439 | 191 | 4268 | 436 |
| TATGGAAAATGTCAGGCCTTCCCCA | 436 | 1075 | 4294 | 437 |

>HG-U133_PLUS_2:206929_S_AT
SEQ ID NO:438
```
ccacgagtagcagccgcaactggacggaggacatggaaggaggcatctcgtcccggtga
agaagacagagatggacaagtcaccattcaacagcccgtcccccaggactctcccgcc
tctccagcttcacccagcaccaccggcccgtcatcgccgtgcacagcgggatcgccgga
gcccacacccgtcctccgctctgcatttccctacgacgtccatcctaccccagacggcct
ccacctacttcccccacacggccatccgctacccacctcatctcaaccccaggacccgc
tcaaagatcttgtctcgctggcctgcgacccagccagccagcaacctggaccgtcctggt
atctgggatagcaaaggtcttcttccctcgccccttctccatcgtcccaggaatcccagg
gggcagcacagccggccccggcccacgttttcggtggaaaattagagtgaacaagaaca
cccctgccgactccagcccggccaaaaagacaaaacacatagacgcacacactcagg
```

Cluster Members
Consensus/Exemplar
BLASTn GenBank NR
Probe Info

| Probe Sequence(5'-3') | Probe X | Probe Y | Probe Interrogation Position | SEQ ID NO: |
|---|---|---|---|---|
| CCACGAGTAGCAGCCGCAACTGGAC | 581 | 463 | 953 | 439 |
| GTAGCAGCCGCAACTGGACGGAGGA | 661 | 729 | 959 | 440 |
| GCAACTGGACGGAGGACATGGAAGG | 569 | 543 | 968 | 441 |
| ACATGGAAGGAGGCATCTCGTCCCC | 596 | 183 | 983 | 442 |
| GCATCTCGTCCCCGGTGAAGAAGAC | 357 | 523 | 995 | 443 |
| TCTCGTCCCCGGTGAAGAAGACAGA | 1115 | 1003 | 998 | 444 |
| TGGACAAGTCACCATTCAACAGCCC | 121 | 901 | 1025 | 445 |
| GTCCTGGTATCTGGGATAGCAAAGG | 225 | 759 | 1305 | 446 |
| CTGGGATAGCAAAGGTCTTCTTCCC | 881 | 403 | 1315 | 447 |
| TAGAGTGAACAAGAACACCCCTGCC | 113 | 1069 | 1416 | 448 |
| AAACACATAGACGCACACACTCAGG | 480 | 219 | 1466 | 449 |

>HG-U133_PLUS_2:222108_AT
SEQ ID NO: 450
```
tattcagccaaaattaccgttttagaccagaatgaatagactacactgataaaatgtact
ggataatgccacatcctatatggtgttatagaaatagtgcaaggaaagtacatttgtttg
cctgtcttttcattttgtacattcttcccattctgtattcttgtacaaaagatctcattg
aaaatttaaagtcatcataatttgttgccataaatatgtaagtgtcaataccaaaatgtc
tgagtaacttcttaaatccctgttctagcaaactaatattggttcatgtgcttgtgtata
tgtaaatcttaaattatgtgaactattaaatagaccctactgtactgtgctttggacatt
tgaattaatgtaaatatatgtaatctgtgacttgatattttgttttatttggctatttaa
aancataaatctaaaatgtcttatgttatcagattatgctattttgtataaagcacnnnn
nnnnncaannnnnnnncnaaannanaaantcactggaccgacgttttaacaacg
```

Cluster Members
Consensus/Exemplar
BLASTn GenBank NR
Note: "n"'s represent regions that are not probed by the probe sequences.
Probe Info

| Probe Sequence(5'-3') | Probe X | Probe Y | Probe Interrogation Position | SEQ ID NO: |
|---|---|---|---|---|
| TATTCAGCCAAAATTACCGTTTTAG | 171 | 1083 | 2070 | 451 |
| AATGCCACATCCTATATGGTGTTAT | 856 | 277 | 2134 | 452 |

-continued

| | | | |
|---|---|---|---|
| GAAAGTACATTTGTTTGCCTGTCTT | 139 | 593 | 2173 | 453 |
| TTCATTTTGTACATTCTTCCCATTC | 613 | 1131 | 2198 | 454 |
| AAGTCATCATAATTTGTTGCCATAA | 373 | 261 | 2258 | 455 |
| GAGTAACTTCTTAAATCCCTGTTCT | 115 | 649 | 2311 | 456 |
| AAATCCCTGTTCTAGCAAACTAATA | 382 | 203 | 2323 | 457 |
| ATATTGGTTCATGTGCTTGTGTATA | 1044 | 21 | 2345 | 458 |
| AATAGACCCTACTGTACTGTGCTTT | 709 | 283 | 2398 | 459 |
| ACTGTACTGTGCTTTGGACATTTGA | 443 | 167 | 2408 | 460 |
| TCACTGGACCGACGTTTTAACAACG | 886 | 1025 | 2579 | 461 |

>HG-U133_PLUS_2:214674_AT
SEQ ID NO: 462
cttcccggatttggcaggagctggaggctgaggaggagccggtgcctgagggtctgggc
ccctgggtccctgggggccccaagactgggtgggccccctaccacgtggccctaccacac
cagatgagggctgcctccggtactttgtcctgggcaccgtggcggctttggtggccctcg
tgctcaacgtgttctatcctctggtatcccagagtcgctggagatgagctcgcctgcagg
cagctgctgtgagctggcctacctgcctgccccaggccatgcctgcctttgttgtgggga
acacctctgggctttgggcctcagcttatgcatctggtgggagagggtggggaggttgtg
gcccctgcaggggcagagtatcctagggtgtgtatccatctggctgtctgtccattcatc
ctgctgctctgaccccttggcctcaggcttggccctgcccaagctacttcctgtacttaaa
ag Cluster Members
Consensus/Exemplar
BLASTn GenBank NR
Probe Info

| Probe Sequence(5'-3') | Probe X | Probe Y | Probe Interrogation Position | SEQ ID NO: |
|---|---|---|---|---|
| CTTCCCGGATTTGGCAGGAGCTGGA | 92 | 361 | 4113 | 463 |
| TGTTCTATCCTCTGGTATCCCAGAG | 385 | 931 | 4302 | 464 |
| TCTGGTATCCCAGAGTCGCTGGAGA | 741 | 997 | 4312 | 465 |
| AGAGTCGCTGGAGATGAGCTCGCCT | 905 | 113 | 4323 | 466 |
| GCCTCAGCTTATGCATCTGGTGGGA | 433 | 479 | 4430 | 467 |
| TCAGCTTATGCATCTGGTGGGAGAG | 1136 | 1023 | 4433 | 468 |
| GCCCCTGCAGGGGCAGAGTATCCTA | 522 | 485 | 4473 | 469 |
| GGGGCAGAGTATCCTAGGGTGTGTA | 1057 | 813 | 4482 | 470 |
| GAGTATCCTAGGGTGTGTATCCATC | 625 | 647 | 4488 | 471 |
| CTAGGGTGTGTATCCATCTGGCTGT | 249 | 371 | 4495 | 472 |
| CCAAGCTACTTCCTGTACTTAAAAG | 410 | 467 | 4570 | 473 |

>HG-U133_PLUS_2:214400_AT
SEQ ID NO: 474
ccggaggcgaccgtgagttgctacagtggctggagagacgacatctgctccatgggctgg
tggccgacagtaatctcacgctgggacc Cluster Members
Consensus/Exemplar
BLASTn GenBank NR
Probe Info

| Probe Sequence(5'-3') | Probe X | Probe Y | Probe Interrogation Position | SEQ ID NO: |
|---|---|---|---|---|
| CCGGAGGCGACCGTGAGTTGCTACA | 758 | 437 | 1327 | 475 |
| GCGACCGTGAGTTGCTACAGTGGCT | 1074 | 491 | 1333 | 476 |
| GACCGTGAGTTGCTACAGTGGCTGG | 375 | 621 | 1335 | 477 |
| CGTGAGTTGCTACAGTGGCTGGAGA | 1155 | 411 | 1338 | 478 |
| GCTGGAGAGACGACATCTGCTCCAT | 205 | 497 | 1355 | 479 |
| GGAGAGACGACATCTGCTCCATGGG | 32 | 849 | 1358 | 480 |
| CCATGGGCTGGTGGCCGACAGTAAT | 20 | 455 | 1376 | 481 |
| ATGGGCTGGTGGCCGACAGTAATCT | 196 | 67 | 1378 | 482 |
| CTGGTGGCCGACAGTAATCTCACGC | 966 | 403 | 1383 | 483 |
| GCCGACAGTAATCTCACGCTGGGAC | 847 | 483 | 1389 | 484 |
| CCGACAGTAATCTCACGCTGGGACC | 946 | 431 | 1390 | 485 |

>HG-U133_PLUS_2:233236_AT
SEQ ID NO: 486
gttacagccacatcgtgggtgcagcagggtgtaggcgattccaaagagcagatgattcaa
attcgtgtgcgatgggtacagagagatacgcttggctccagacccacgcgtctccctgtt
tccctctcttgtggtgggggcacagtagccttcgtgtgtcttcctctagcacagacccct
gagctgagggtaggnnnnatgaaggcagcacgagggacgctccacctcccactctatcc
tcaagaacctcggccaatgaacgggccactcttgctagttggggtactgatcacttcctg
tcctctctgtgaggttggagatgtggccttggaacacaccttcgtgaccccaggagttg
ctgtaaatccatcggaagtgtgtcctgtgacggacgcgatgtgtctccnnncgtcatcca -continued ccagaaggtaactggagattttgtgtgttgccttgacagacccctgagggctggtgactt
cattttatt Cluster Members
Consensus/Exemplar
BLASTn GenBank NR
Note: "n"'s represent regions that are not probed by the probe
sequences.
Probe Info

| Probe Sequence(5'-3') | Probe X | Probe Y | Probe Interrogation Position | SEQ ID NO: |
|---|---|---|---|---|
| GTTACAGCCACATCGTGGGTGCAGC | 819 | 707 | 34 | 487 |
| GGTGCAGCAGGGTGTAGGCGATTCC | 39 | 821 | 51 | 488 |
| CAGAGAGATACGCTTGGCTCCAGAC | 873 | 329 | 112 | 489 |
| GCACAGACCCCTGAGCTGAGGGTAG | 1123 | 539 | 202 | 490 |
| ATGAAGGCAGCACGAGGGACGCTCC | 202 | 57 | 232 | 491 |
| GAACCTCGGCCAATGAACGGGCCAC | 1111 | 573 | 278 | 492 |
| GGCCACTCTTGCTAGTTGGGGTACT | 485 | 893 | 297 | 493 |
| TTCCTGTCCTCTCTGTGAGGTTGGA | 776 | 1143 | 328 | 494 |
| CTGGAGATTTTGTGTGTTGCCTTGA | 630 | 405 | 465 | 495 |
| CCTTGACAGACCCCTGAGGGCTGGT | 1148 | 451 | 484 | 496 |
| GAGGGCTGGTGACTTCATTTTTATT | 1094 | 653 | 499 | 497 |

>HG-U133_PLUS_2:241708_AT
SEQ ID NO: 498
gacgatcagtcagtacatctggagagacaggaggacctggaggactgctgtcagctgctc
agccacatcctggaggtgctgtacaggaaggacgtggggccaacccagaggcacgtccag
attatcatggagaaacttctccggaccgtgaaccgaaccgtcatttccatgggacgagat
tctgaactcattgtaagtgcttggtgacatatgtttggatatttaactggggctgacagc
atccttctccaactgctgtttgaacatagcttattatactgcaatgtagtgagcagttga
gatacagcttggtatataaaatgtcctcattttccaaatgaatgtcaaagttgaagggta
agcaaaccaactttaaagatggaaacatttggctcttgttttctcattacttacttatag
caaaagacatgtattttctgctgagtcgtcattcttctggcagttttctccatagtgttta
cactta Cluster Members
Consensus/Exemplar
BLASTn GenBank NR
Probe Info

| Probe Sequence(5'-3') | Probe X | Probe Y | Probe Interrogation Position | SEQ ID NO: |
|---|---|---|---|---|
| GACGATCAGTCAGTACATCTGGAGA | 832 | 617 | 22 | 499 |
| GAACTCATTGTAAGTGCTTGGTGAC | 249 | 579 | 205 | 500 |
| TAACTGGGGCTGACAGCATCCTTCT | 514 | 1043 | 245 | 501 |
| CTCCAACTGCTGTTTGAACATAGCT | 241 | 391 | 268 | 502 |
| GAACATAGCTTATTATACTGCAATG | 321 | 581 | 283 | 503 |
| GTGAGCAGTTGAGATACAGCTTGGT | 879 | 771 | 310 | 504 |
| AGCTTGGTATATAAAATGTCCTCAT | 1030 | 135 | 327 | 505 |
| ATGGAAACATTTGGCTCTTGTTTTC | 203 | 71 | 400 | 506 |
| TTCTCATTACTTACTTATAGCAAAA | 891 | 1135 | 422 | 507 |
| ACATGTATTTTCTGCTGAGTCGTCA | 721 | 183 | 448 | 508 |
| AGTTTCTCCATAGTGTTTACACTTA | 237 | 103 | 483 | 509 |

>HG-U133_PLUS_2:241708_AT
SEQ ID NO: 510
ctggaagactgttgtggcctctcagttctctttgagtctgactgactgtggccagtccct
ggactggtagctgctggaggccttcttgtttctccagtccctggaagctgagctctatgt
gtatttgatgacattgtcagctcttaccaaacgtcaagacctcttcctgcttgaccactc
gcacatggctctaggcttctcctgctgagtcctggtcttggcctgtgaatgtgcctcgtt
catccctggtgcttgagcccctcaagctccagtcaatgatccagtccttccccttgaag
ttttctgctctactttccttggcagcagcctgtgaactactcaaaagagtcccccttgggt
ttggaattatcagtggctttgccactagtaaatgtgtgatcttcggcaagtaacctaacc
tagggacatcagtttactcatctgcgaagtggggataataaaacctacctcagggttgct
tcaagga Cluster Members
Consensus/Exemplar
BLASTn GenBank NR
Probe Info

| Probe Sequence(5'-3') | Probe X | Probe Y | Probe Interrogation Position | SEQ ID NO: |
|---|---|---|---|---|
| CTGGAAGACTGTTGTGGCCTCTCAG | 305 | 407 | 3754 | 511 |
| GCCTCTCAGTTCTCTTTGAGTCTGA | 779 | 479 | 3770 | 512 |

-continued

| | | | |
|---|---|---|---|
| TCCCTGGACTGGTAGCTGCTGGAGG | 299 | 989 | 3809 | 513 |
| GCTGGAGGCCTTCTTGTTTCTCCAG | 225 | 497 | 3826 | 514 |
| GACATTGTCAGCTCTTACCAAACGT | 201 | 607 | 3883 | 515 |
| GGTCTTGGCCTGTGAATGTGCCTCG | 23 | 825 | 3967 | 516 |
| AAGCTCCAGTCAATGATCCAGTCCT | 102 | 247 | 4017 | 517 |
| TTGAAGTTTTCTGCTCTACTTTCCT | 846 | 1151 | 4048 | 518 |
| CTTTCCTTGGCAGCAGCCTGTGAAC | 596 | 367 | 4066 | 519 |
| GGGACATCAGTTTACTCATCTGCGA | 880 | 799 | 4176 | 520 |
| ACCTACCTCAGGGTTGCTTCAAGGA | 73 | 155 | 4216 | 521 |

>HG-U133_PLUS_2:209375_AT
SEQ ID NO:522
aactgaggcagcatgcacggaggcggggtcaggggagacgaggccaagctgaggaggtgc
tgcaggtcccgtctggctccagcccttgtcagattcacccagggtgaagccttcaaagct
ttttgctaccaaagcccactcacccttgagctacagaacactttgctaggagatactct
tctgcctcctagacctgttctttccatctttagaaacatcagttttttgtatggaagccac
cgggagatttctggatggtggtgcatccgtgaatgcgctgatcgtttcttccagttagag
tcttcatctgtccgacaagttcactcgcctcggttgcggacctaggaccatttctctgca
ggccacttaccttcccctgagtcaggcttactaatgctgccctcactgcctctttgcagt
aggggagagagcagagaagtacaggtcatctgctgggatctagtttc Cluster Members
Consensus/Exemplar
BLASTn GenBank NR
Probe Info

| Probe Sequence(5'-3') | Probe X | Probe Y | Probe Interrogation Position | SEQ ID NO: |
|---|---|---|---|---|
| AACTGAGGCAGCATGCACGGAGGCG | 999 | 237 | 3055 | 523 |
| AGGGGAGACGAGGCCAAGCTGAGGA | 623 | 87 | 3085 | 524 |
| AGCCCTTGTCAGATTCACCCAGGGT | 250 | 145 | 3135 | 525 |
| TTGCTAGGAGATACTCTTCTGCCTC | 935 | 1149 | 3218 | 526 |
| GGAAGCCACCGGGAGATTTCTGGAT | 1128 | 863 | 3286 | 527 |
| TGAATGCGCTGATCGTTTCTTCCAG | 654 | 953 | 3324 | 528 |
| CCAGTTAGAGTCTTCATCTGTCCGA | 906 | 457 | 3345 | 529 |
| TCATCTGTCCGACAAGTTCACTCGC | 787 | 1017 | 3358 | 530 |
| TCAGGCTTACTAATGCTGCCCTCAC | 1045 | 1019 | 3436 | 531 |
| CCCTCACTGCCTCTTTGCAGTAGGG | 932 | 425 | 3454 | 532 |
| GGTCATCTGCTGGGATCTAGTTTTC 7 | 96 | 823 | 3498 | 533 |

>HG-U133_PLUS_2:205709_S_AT
SEQ ID NO: 534
atcctacaacccaccttgaaggtataactggatccagagagggaaggactgacaagaagg
aattattcagaaaaacactgacagatgttttataaattgtacagaaaaatagttaaaaat
gcaataggttgaagttttccagatatgtttctctctgaaattactgtgaatatttaacaa
acacttacttgatctatgttatgaaataagtagcaaattgccagcaaaatgtcttgtacc
ttttctaaagtgtattttctgatgtgaacttccttccccttacttgctaggtttcaataa
tttaaaagagtcaaacactataaatgagtaagttgacgatgttttaagattgcacctggc
agtgtgcctttttgcaacaaatatttacctggcagtgtgcctttttgcaacaaatattta
ctttgcacttggagctgcttttaattttagcaaaatgttttatgcaaggcacaataggaa
gtcagtctcctgcacttcctcctcatgtagtctggagtactttctaaagggc Cluster Members
Consensus/Exemplar
BLASTn GenBank NR
Probe Info

| Probe Sequence(5'-3') | Probe X | Probe Y | Probe Interrogation Position | SEQ ID NO: |
|---|---|---|---|---|
| ATCCTACAACCCACCTTGAAGGTAT | 844 | 47 | 1806 | 535 |
| ACCTTGAAGGTATAACTGGATCCAG | 766 | 143 | 1818 | 536 |
| GATATGTTTCTCTCTGAAATTACTG | 973 | 685 | 1947 | 537 |
| TAACAAACACTTACTTGATCTATGT | 207 | 1045 | 1980 | 538 |
| GCAAAATGTCTTGTACCTTTTCTAA | 842 | 541 | 2029 | 539 |
| GTTTTAAGATTGCACCTGGCAGTGT | 205 | 713 | 2146 | 540 |
| GCACTTGGAGCTGCTTTTAATTTTA | 1114 | 537 | 2230 | 541 |
| GCAAAATGTTTTATGCAAGGCACAA | 906 | 541 | 2255 | 542 |
| GGCACAATAGGAAGTCAGTTCTCCT | 625 | 871 | 2273 | 543 |
| CACTTCCTCCTCATGTAGTCTGGAG | 78 | 313 | 2299 | 544 |
| TAGTCTGGAGTACTTTCTAAAGGGC | 585 | 1063 | 2314 | 545 |

>HG-U133_PLUS_2:207270_X_AT
SEQ ID NO: 546
tggctccgagactttcatgatcccattgtcgaggttgaggtgtccgtgttcccggccggg
acgaccacagcctcagcccccagagctccatgggcacctcaggtcctcccacgaagctg
cccgtgcacacctggcccagcgtgaccagaaaggacagccccgaacccagcccacccct
ggctccctgttcagcaatgtccgcttcctgctcctggtcctcttggagctgcccctgctc -continued

```
ctgagcatgctgggtgccgtcctctgggtgaacagacctcagagaagctctagaagcagg
cagaattggcccaagggtgagaaccagtagcatctgctgtccatcaaggccctgtgctgc
aacagagcccctctggggactggaatgacctcctgaccatcaaggcctgcaacagagccc
ctctggggactggaatgacctcctgaccactccctcccgggctgctctctccaacatct
cctggaatcctttgtgagcctc
```

Cluster Members
Consensus/Exemplar
BLASTn GenBank NR
Probe Info

| Probe Sequence(5'-3') | Probe X | Probe Y | Probe Interrogation Position | SEQ ID NO: |
|---|---|---|---|---|
| TGGCTCCGAGACTTTCATGATCCCA | 151 | 897 | 597 | 547 |
| ATGATCCCATTGTCGAGGTTGAGGT | 279 | 61 | 613 | 548 |
| CCAGCGTGACCAGAAAGGACAGCCC | 160 | 461 | 733 | 549 |
| CGTCCTCTGGGTGAACAGACCTCAG | 496 | 413 | 854 | 550 |
| GGCCCAAGGGTGAGAACCAGTAGCA | 589 | 887 | 904 | 551 |
| GAACCAGTAGCATCTGCTGTCCATC | 361 | 575 | 917 | 552 |
| TCAAGGCCCTGTGCTGCAACAGAGC | 524 | 1031 | 940 | 553 |
| ACAGAGCCCCTCTGGGGACTGGAAT | 1053 | 185 | 958 | 554 |
| TGACCATCAAGGCCTGCAACAGAGC | 437 | 945 | 990 | 555 |
| CAGAGCCCCTCTGGGGACTGGAAT | 909 | 329 | 1009 | 556 |
| TCTCCTGGAATCCTTTGTGAGCCTC | 1055 | 1003 | 1074 | 557 |

>HG-U133_PLUS_2:205789_AT
SEQ ID NO: 558
```
gtcatgaggcagctttcatcacacccttttaacatttatctaaaagaatttaaattctttt
ttcaaaaattacactacaagtttataagcccaaatggctctgtgaaatcagaagtgcaaa
ggtgtgcaaacttgtatctgaagacctaccagggacaagcaggtaagagctgatgtgagt
gtgtgtgatgggatctgtaaggaactggaacacacatgtcctatccaaaggaatcagctg
cagctgcttgttgtcaagtataaagtcaggacctggcttggctttaaccgttttcaaga
aaactggaaatctggattttcagcgaacatgcctgatttttaaaaggttgactcaagtttt
tacaaaatactatgtgggacacctcaaatacatacctactgactgatgacaaacccagga
gtttgtgtctttataaaaagtttgccctggatgtcatat
```

Cluster Members
Consensus/Exemplar
BLASTn GenBank NR
Probe Info

| Probe Sequence(5'-3') | Probe X | Probe Y | Probe Interrogation Position | SEQ ID NO: |
|---|---|---|---|---|
| GTCATGAGGCAGCTTTCATCACACC | 165 | 747 | 1323 | 559 |
| TCATCACACCCTTTTAACATTTATC | 348 | 1017 | 1338 | 560 |
| AAAGGTGTGCAAACTTGTATCTGAA | 785 | 207 | 1440 | 561 |
| GTATCTGAAGACCTACCAGGGACAA | 1027 | 723 | 1456 | 562 |
| GGAACACACATGTCCTATCCAAAGG | 1042 | 861 | 1529 | 563 |
| CTATCCAAAGGAATCAGCTGCAGCT | 1145 | 369 | 1543 | 564 |
| TAAAGTCAGGACCTGGCTTGGCTTT | 442 | 1047 | 1583 | 565 |
| TCTGGATTTTCAGCGAACATGCCTG | 2 | 997 | 1633 | 566 |
| GGACACCTCAAATACATACCTACTG | 1063 | 857 | 1699 | 567 |
| ACTGACTGATGACAAACCCAGGAGT | 417 | 167 | 1720 | 568 |
| AAAAGTTTGCCCTGGATGTCATAT | 764 | 219 | 1760 | 569 |

>HG-U133_PLUS_2:221522_AT
SEQ ID NO: 570
```
gatattcggttactacacgtgcacctgtagcagtatttctagaaacatcccttttttgttg
agaacctcccttgaatgtctgtcacactcacacctgacgggatggttactggattagaga
gtagatttggcacatcttttcttagtcttttgattcaaattcaaaacttaacagcacaaa
ccaggtcagagttactttcggttagaatttattgccatttattccttttataaatttct
atagattatactgttatttttatgttattggcctagagctacacgtatatgggtttgtcc
tgagtccgttttcaaatgaccttgtgataggaaatggttttgtccatgttcttgg
```

Cluster Members
Consensus/Exemplar
BLASTn GenBank NR
Probe Info

| Probe Sequence(5'-3') | Probe X | Probe Y | Probe Interrogation Position | SEQ ID NO: |
|---|---|---|---|---|
| GATATTCGGTTACTACACGTGCACC | 1094 | 685 | 3949 | 571 |
| ACACGTGCACCTGTAGCAGTATTTC | 1118 | 189 | 3963 | 572 |
| TTGAGAACCTCCTTTGAATGTCTGT | 1026 | 1151 | 4006 | 573 |
| CACACTCACACCTGACGGGATGGTT | 693 | 307 | 4031 | 574 |
| GGCACATCTTTTCTTAGTCTTTTGA | 964 | 869 | 4077 | 575 |

-continued

| | | | | |
|---|---|---|---|---|
| AACTTAACAGCACAAACCAGGTCAG | 496 | 231 | 4113 | 576 |
| CCAGGTCAGAGTTACTTTCGGTTAG | 851 | 455 | 4129 | 577 |
| GTTATTGGCCTAGAGCTACACGTAT | 712 | 711 | 4212 | 578 |
| GTATATGGGTTTGTCCTGAGTCCGT | 167 | 711 | 4233 | 579 |
| CTGAGTCCGTTTTCAAATGACCTTG | 574 | 393 | 4248 | 580 |
| GAAATGGTTTTGTCCATGTTCTTGG | 47 | 595 | 4280 | 581 |

>HG-U133_PLUS_2:221522_AT
SEQ ID NO: 582
cacactggagggcacacacgtaccccgcacccagcaactcctgacagaaagctcctccca
cccaaatgggccaggccccagcatgatcctgaaatctgcatccgccgtggtttgtattca
ttgtgcatatcagggatacccctcaagctggactgtgggttccaaattactcatagaggag
aaaaccagagaaagatgaagaggaggagttaggtctatttgaaatgccaggggctcgctg
tgaggaataggtaaaaaaaaacttttcaccagcctttgagagactagactgaccccaccc
ttccttcagtgagcagaatcactgtggtcagtctcctgtcccagcttcagttcatgaata
ctcctgttcctccagtttcccatcctttgtccctgctgtccccacttttaaagatgggt
ctcaaccccctcccaccacgtcatgatggatgggcaaggtggtggggactaggggagcc
tggtatacatgcggcttcattgcc Cluster Members
Consensus/Exemplar
BLASTn GenBank NR
Probe Info

| Probe Sequence(5'-3') | Probe X | Probe Y | Probe Interrogation Position | SEQ ID NO: |
|---|---|---|---|---|
| CACACTGGAGGGCACACACGTACCC | 307 | 309 | 4047 | 583 |
| CAACTCCTGACAGAAAGCTCCTCCC | 1034 | 301 | 4081 | 584 |
| GCATGATCCTGAAATCTGCATCCGC | 50 | 525 | 4127 | 585 |
| TGCATCCGCCGTGGTTTGTATTCAT | 1137 | 959 | 4143 | 586 |
| GCCAGGGGCTCGCTGTGAGGAATAG | 636 | 473 | 4272 | 587 |
| AAAACTTTTCACCAGCCTTTGAGAG | 618 | 221 | 4304 | 588 |
| TTTGAGAGACTAGACTGACCCCACC | 953 | 1093 | 4321 | 589 |
| ACCCTTCCTTCAGTGAGCAGAATCA | 985 | 159 | 4343 | 590 |
| GCAGAATCACTGTGGTCAGTCTCCT | 1064 | 531 | 4359 | 591 |
| CAGTTCATGAATACTCCTGTTCCTC | 488 | 333 | 4394 | 592 |
| CTGGTATACATGCGGCTTCATTGCC | 1039 | 405 | 4526 | 593 |

>HG-U133_PLUS_2:221808_AT
SEQ ID NO: 594
ataagcgaacggcaggtgtctacagaagaagcccaagcttggtgcagggacaacggcgac
tatccttatttgaaacaagtgcaaaagatgccacaaatgtggcagcagcctttgaggaa
gcggttcgaagagttcttgctaccgaggataggtcagatcatttgattcagacagacaca
gtcaatcttcaccgaaagcccaagcctagctcatcttgctgttgattgttagattgttga
tgcattctaaccaactcacacatatacacaaaatcaacatggggatggagaagagaatta
gcgtttgcagcagtgtatcatctactaataaaattaaactaatgttgctgcttcattagt
tggtgggagaagggacacatccactcttggaggaatatatttactcaataatggcacctt
aca Cluster Members
Consensus/Exemplar
BLASTn GenBank NR
Probe Info

| Probe Sequence(5'-3') | Probe X | Probe Y | Probe Interrogation Position | SEQ ID NO: |
|---|---|---|---|---|
| ATAAGCGAACGGCAGGTGTCTACAG | 2 | 35 | 637 | 595 |
| CAAGCTTGGTGCAGGGACAACGGCG | 354 | 299 | 670 | 596 |
| GACAACGGCGACTATCCTTATTTTG | 644 | 597 | 685 | 597 |
| GGAAGCGGTTCGAAGAGTTCTTGCT | 274 | 865 | 753 | 598 |
| GAGTTCTTGCTACCGAGGATAGGTC | 817 | 645 | 767 | 599 |
| CACAGTCAATCTTCACCGAAAGCCC | 1156 | 309 | 813 | 600 |
| GATGCATTCTAACCAACTCACACAT | 757 | 673 | 875 | 601 |
| GCGTTTGCAGCAGTGTATCATCTAC | 493 | 493 | 937 | 602 |
| GTTGCTGCTTCATTAGTTGGTGGGA | 320 | 701 | 980 | 603 |
| AGAAGGGACACATCCACTCTTGGAG | 968 | 127 | 1004 | 604 |
| ATTTACTCAATAATGGCACCTTACA | 930 | 17 | 1035 | 605 |

>HG-U133_PLUS_2:205533_S_AT
SEQ ID NO: 606
ctgccatccttgactttgaactaatgataaagtaatgatctcaaactatgacagaaaagt
aatgtaaaatccatccaatctattatttctctaattatgcaattagcctcatagttatta
tccagaggacccaactgaactgaactaatcctctggcagattcaaatcgtttatttcac
acgctgttctaatggcacttatcattagaatcttaccttgtgcagtcatcagaaattcca
gcgtactataatgaaaacatccttgttttgaaaacctaaaagacaggctctgtatatata
tatacttaagaatatgctgacttcacttattagtcttagggatttattttcaattaatat
taattttctacaaataattttagtgtcatttccatttggggatattgtcatatcagcaca -continued tattttctgtttggaa Cluster Members
Consensus/Exemplar
BLASTn GenBank NR
Probe Info

| Probe Sequence(5'-3') | Probe X | Probe Y | Probe Interrogation Position | SEQ ID NO: |
|---|---|---|---|---|
| CTGCCATCCTTGACTTTGAACTAAT | 703 | 391 | 3828 | 607 |
| AAAATCCATCCAATCTATTATTTCT | 156 | 225 | 3893 | 608 |
| ATGCAATTAGCCTCATAGTTATTAT | 1000 | 55 | 3924 | 609 |
| AGAGGACCCAACTGAACTGAACTAA | 3 | 113 | 3951 | 610 |
| TGAACTAATCCTTCTGGCAGATTCA | 521 | 951 | 3968 | 611 |
| AATCGTTTATTTCACACGCTGTTCT | 134 | 279 | 3993 | 612 |
| CACGCTGTTCTAATGGCACTTATCA | 436 | 317 | 4007 | 613 |
| CATTAGAATCTTACCTTGTGCAGTC | 772 | 353 | 4030 | 614 |
| CTTGTGCAGTCATCAGAAATTCCAG | 584 | 355 | 4044 | 615 |
| TTAGTGTCATTTCCATTTGGGGATA | 26 | 1119 | 4207 | 616 |
| ATCAGCACATATTTTCTGTTTGGAA | 353 | 39 | 4239 | 617 |

>HG-U133_PLUS_2:205729_AT
SEQ ID NO: 618
ggagacttgagcttgacctaaggatatgcattaaccactctacagactcccactcagtac
tgtacagggtggctgtggtcctagaagttcagttttttactgaggaaatatttccattaac
agcaattattatattgaaggctttaataaaggccacaggagacattactatagcatagat
tgtcaaatgtaaatttactgagcgtgttttataaaaaactcacaggtgtttgaggccaaa
acagattttagacttaccttgaacggataagaatctatagttcactgacacagtaaaatt
aactctgtgggtggggcgggggcatagctctaatctaatatataaaatgtgtgatgaa
tcaacaagatttccacaattcttctgtcaagcttactacagtgaaagaatgggattggca
agtaacttctgacttactgtcagttgtacttctgctccatagacatcagtattctgccat
cattttttgatgactacctcagaacataaaaaggaacgtatatcacacaattccagtcaca
gttttttggttcctctt Cluster Members
Consensus/Exemplar
BLASTn GenBank NR
Probe Info

| Probe Sequence(5'-3') | Probe X | Probe Y | Probe Interrogation Position | SEQ ID NO: |
|---|---|---|---|---|
| GGAGACTTGAGCTTGACCTAAGGAT | 105 | 849 | 3583 | 619 |
| ATGCATTAACCACTCTACAGACTCC | 476 | 55 | 3608 | 620 |
| GGCTGTGGTCCTAGAAGTTCAGTTT | 700 | 885 | 3653 | 621 |
| AGGCCACAGGAGACATTACTATAGC | 1162 | 71 | 3732 | 622 |
| CGGGGGGCATAGCTCTAATCTAATA | 1147 | 409 | 3900 | 623 |
| GATTTCCACAATTCTTCTGTCAAGC | 838 | 687 | 3950 | 624 |
| GGCAAGTAACTTCTGACTTACTGTC | 381 | 871 | 3999 | 625 |
| TACTGTCAGTTGTACTTCTGCTCCA | 1007 | 1057 | 4017 | 626 |
| GACATCAGTATTCTGCCATCATTTT | 508 | 607 | 4044 | 627 |
| ACGTATATCACATAATTCCAGTCAC | 788 | 163 | 4097 | 628 |
| CCAGTCACAGTTTTTGGTTCCTCTT | 403 | 457 | 4114 | 629 |

>HG-U133_PLUS_2:240280_AT
SEQ ID NO:630
ggactggccgccgtacaggcggccctggaggacatgggcgacaagcccccggcttccgg
ggctcccgggactggatcggctgcgtggaggccagcctctgcctcgctcacttcggaggg
ccccaggacgcctctgccacgtaccccggggagtggggctgcacggggagctggagaggc
tttactcgcacattcgcacggggtgggggcccagtcatggttgggggggacgcagatgcc
aggtccaaggccttgctgggagntctgcngtngnggtcaggcacggaagcctatgtcctg
gtattggaccctcactactggggcactccaaaaagcccagtgaactacaggctgctggg
tgggtgggctggcaanaggtnagtgcagcctttgaccccaactccttctacaacctgtgc
ttgaccagccttagctcccaacagcagcagcgcaccttggactgaggacgaagttacaga
actgagattctcgggtcccagac Cluster Members
Consensus/Exemplar
BLASTn GenBank NR
Note: "n"'s represent regions that are not probed by the probe sequences.
Probe Info

| Probe Sequence(5'-3') | Probe X | Probe Y | Probe Interrogation Position | SEQ ID NO: |
|---|---|---|---|---|
| GGACTGGCCGCCGTACAGGCGGCCC | 276 | 855 | 352 | 631 |
| TACAGGCGGCCCTGGAGGACATGGG | 751 | 1051 | 365 | 632 |

-continued

| | | | |
|---|---|---|---|
| TGGAGGACATGGGCGACAAGCCCCC | 895 | 903 | 377 | 633 |
| GCTGGAGAGGCTTTACTCGCACATT | 1161 | 495 | 521 | 634 |
| CAGGCACGGAAGCCTATGTCCTGGT | 133 | 341 | 629 | 635 |
| TGTCCTGGTATTGGACCCTCACTAC | 688 | 917 | 645 | 636 |
| CTCACTACTGGGGCACTCCAAAAAG | 177 | 377 | 662 | 637 |
| GTGAACTACAGGCTGCTGGGTGGGT | 423 | 769 | 692 | 638 |
| TTCTACAACCTGTGCTTGACCAGCC | 82 | 1135 | 757 | 639 |
| CAGCGCACCTTGGACTGAGGACGAA | 979 | 323 | 799 | 640 |
| GAACTGAGATTCTCGGGTCCCAGAC | 406 | 577 | 830 | 641 |

>HG-U133_PLUS_2:205626_S_AT
SEQ ID NO: 642
gtattctgtggattctatatttcatattgagatcagcattcaaaatagttctatttctat
ctgcaaatagtttcaaatgagtttaaaaaaataacatctgaaaagaaatgctaatgtaat
catttatcttatctagcaagaagattctaaaacattctttaacatacatctaagtcagtt
tcacatatttgtagctagaatatcctatactggttatagttgatatgtaacagttggtga
ttttagatttctttgattgtgaaacagggagctatgagagatgtgtccatgtgaaattta
cagttactgcctaggagttaatgatcgttctgggtcagcttgaatgtccccattctataa
attcaacacttattttctgaattcataaaaataaccaaaaaatgtgagctataatgtttc
cctcaagaacaaacagaaacgagatttgccaaaaactaaaattcaacaaatgatgttgag
tgggagattggctttgcctttagcgtgtaaatggaagcactgccattagactgaatt Cluster Members
Consensus/Exemplar
BLASTn GenBank NR
Probe Info

| Probe Sequence(5'-3') | Probe X | Probe Y | Probe Interrogation Position | SEQ ID NO: |
|---|---|---|---|---|
| GTATTCTGTGGATTCTATATTTCAT | 342 | 721 | 1971 | 643 |
| CATACATCTAAGTCAGTTTCACATA | 870 | 349 | 2133 | 644 |
| GTAGCTAGAATATCCTATACTGGTT | 1017 | 729 | 2161 | 645 |
| GGAGCTATGAGAGATGTGTCCATGT | 599 | 851 | 2238 | 646 |
| GCCTAGGAGTTAATGATCGTTCTGG | 709 | 477 | 2279 | 647 |
| GATCGTTCTGGGTCAGCTTGAATGT | 493 | 673 | 2293 | 648 |
| AATGTCCCCATTCTATAAATTCAAC | 415 | 271 | 2313 | 649 |
| GAGCTATAATGTTTCCCTCAAGAAC | 1162 | 629 | 2376 | 650 |
| TGAGTGGGAGATTGGCTTTGCCTTT | 911 | 939 | 2447 | 651 |
| GATTGGCTTTGCCTTTAGCGTGTAA | 820 | 695 | 2456 | 652 |
| GGAAGCACTGCCNTTAGACTGAATT | 709 | 865 | 2483 | 653 |

>HG-U133_PLUS_2:48808_AT
SEQ ID NO: 654
gttaggcaatcattctagggcagaaagaagtacaggatnggaagagcataatacactgtt
tttctcaacaaggagncagtatgtacacagtcataatgatgtgactgcttagcccctaaa
tatggtaactactctgggacaatatgggagg Cluster Members
Consensus/Exemplar
BLASTn GenBank NR
Note: "n"'s represent regions that are not probed by the probe
sequences.
Probe Info

| Probe Sequence(5'-3') | Probe X | Probe Y | Probe Interrogation Position | SEQ ID NO: |
|---|---|---|---|---|
| GTTAGGCAATCATTCTAGGGCAGAA | 904 | 709 | 812 | 655 |
| GGCAATCATTCTAGGGCAGAAAGAA | 7 | 871 | 816 | 656 |
| TCATTCTAGGGCAGAAAGAAGTACA | 238 | 1015 | 821 | 657 |
| CATTCTAGGGCAGAAAGAAGTACAG | 5 | 351 | 822 | 658 |
| ATACACTGTTTTTCTCAACAAGGAG | 1084 | 31 | 862 | 659 |
| TACACAGTCATAATGATGTGACTGC | 683 | 1051 | 895 | 660 |
| ACACAGTCATAATGATGTGACTGCT | 508 | 193 | 896 | 661 |
| CATAATGATGTGACTGCTTAGCCCC | 897 | 349 | 903 | 662 |
| ATAATGATGTGACTGCTTAGCCCCT | 963 | 35 | 904 | 663 |
| TAATGATGTGACTGCTTAGCCCCTA | 598 | 1037 | 905 | 664 |
| GATGTGACTGCTTAGCCCCTAAATA | 130 | 669 | 909 | 665 |
| ATGTGACTGCTTAGCCCCTAAATAT | 927 | 65 | 910 | 666 |
| AATATGGTAACTACTCTGGGACAAT | 373 | 285 | 930 | 667 |
| ATGGTAACTACTCTGGGACAATATG | 956 | 57 | 933 | 668 |
| TGGTAACTACTCTGGGACAATATGG | 1039 | 905 | 934 | 669 |
| AACTACTCTGGGACAATATGGGAGG | 1049 | 233 | 938 | 670 |

>HG-U133_PLUS_2:210200_AT
SEQ ID NO: 671
agagtgcttcttattccggcagggcttcgtgagaatgccaccaagttatccaaaaccaaag
gatgagagaggcttccaagagagggaagactgtccaagttcaaggagaaggggtttggtt

```
ccctgtctgccagggacagaaagttctttccacatgtgtctcctggtcccgagagctttc
aaaaggggatgtattctgctccaagaaagaatcacctcccagtaaagtagccatgaaggg
ctcctgtataaaatatgcacacttccctgccctgagtttgtggagggaaaggctgtcgg
aagtagggactcttaggagagcccgtgtgccctgtttggttcagctgtcaggcgtgtgcc
acacacatcccacctcatcttctggtcccataattctccatggatgggctgcttttagct
ccagttttccagtagaatgcttgagttttccttttttccgtacctcctggaggatgaaac
tcataacctgtcatcatcagtactcactgtgttttccactttga
```

Cluster Members
Consensus/Exemplar
BLASTn GenBank NR
Probe Info

| Probe Sequence(5'-3') | Probe X | Probe Y | Probe Interrogation Position | SEQ ID NO: |
|---|---|---|---|---|
| AGAGTGCTTCTTATTCGGCAGGGCT | 364 | 113 | 1334 | 672 |
| GCAGGGCTTCGTGAGAATGCCACCA | 1052 | 527 | 1351 | 673 |
| GAGAAGGGGTTTGGTTCCCTGTCTG | 158 | 633 | 1438 | 674 |
| GCTCCAAGAAAGAATCACCTCCCAG | 168 | 505 | 1531 | 675 |
| ATCACCTCCCAGTAAAGTAGCCATG | 421 | 37 | 1544 | 676 |
| AGGGACTCTTAGGAGAGCCCGTGTG | 374 | 89 | 1638 | 677 |
| TTGGTTCAGCTGTCAGGCGTGTGCC | 802 | 1161 | 1669 | 678 |
| ATCTTCTGGTCCCATAATTCTCCAT | 1094 | 41 | 1710 | 679 |
| CCATGGATGGGCTGCTTTTAGCTCC | 1013 | 455 | 1731 | 680 |
| TTTTTTCCGTACCTCCTGGAGGATG | 925 | 1105 | 1785 | 681 |
| GTACTCACTGTGTTTTCCACTTTGA | 995 | 733 | 1833 | 682 |

>HG-U133_PLUS_2:241874_AT
SEQ ID NO:683
```
actacactagtctgtttctttgccctggtctcaagtctctaagacgctggtgtgtattat
gtgggctaagttcatgtgttatcctaaggcacaagagttgaggaatgggtgagcttggtg
tcagagcactgtgtggttggagggtggacttctgtgatgctgtgtggggatgaaattggccc
tcttttagcataagttggggagtgtgcactggctggaggcttccagaggcttccagccat
gaggtgtgagctgaaaccaattttcctctttccttatagcatgttgagaaaatctgttg
ggttttcagcagtcagggaaggccggagttctgctttaatctgggtaactgaggctaata
tgagcaagactttggttaattaactgggttctcagatgccacagactccgtgagaagtca
ccattattttcaatggttgtgatagaatttcccccagtagccattattttaag
```

Cluster Members
Consensus/Exemplar
BLASTn GenBank NR
Probe Info

| Probe Sequence(5'-3') | Probe X | Probe Y | Probe Interrogation Position | SEQ ID NO: |
|---|---|---|---|---|
| ACTACACTAGTCTGTTTCTTTGCCC | 820 | 163 | 158 | 684 |
| TGCCCTGGTCTCAAGTCTCTAAGAC | 680 | 969 | 178 | 685 |
| GACGCTGGTGTGTATTATGTGGGCT | 305 | 619 | 200 | 686 |
| TGGGTGAGCTTGGTGTCAGAGCACT | 581 | 911 | 263 | 687 |
| GGAGGGTGGACTCTTGTGATGCTGT | 428 | 845 | 296 | 688 |
| GATGAAATTGGCCCTCTTTTAGCAT | 259 | 671 | 324 | 689 |
| TTCCTCTTTCCTTATAGCATGTTGA | 121 | 1145 | 421 | 690 |
| GGGTTTTCAGCAGTCAGGGAAGGCC | 1096 | 805 | 457 | 691 |
| GAAGGCCGGAGTTCTGCTTTAATCT | 166 | 559 | 475 | 692 |
| GCCACAGACTCCGTGAGAAGTCACC | 605 | 469 | 555 | 693 |
| TTCCCCCAGTAGCCATTATTTTAAG | 83 | 1143 | 606 | 694 |

>HG-U133_PLUS_2:205515_AT
SEQ ID NO: 695
```
taccccctgctgcttttgagaaatttgtgaacattttcagaggcctcagtgtagtggaag
tgataatccttaaatgaacattttctaccctaatttcactggagtgacttattctaagcc
tcatctatcccctacctatttctcaaaatcattctatgctgattttacaaaagatcattt
ttacatttgaactgagaaccccttttaattgaatcagtggtgtctgaaatcatattaaat
acccacatttgacataaatgcggtaccctttactacactcatgagtggcatatttatgct
taggtcttttcaaaagacttgacaagaaatcttcatattctctgtagcctttgtcaagtg
aggaaatcagtggttaaagaattccactataaactttaggcctgaataggagtagtaaa
gcctcaaggacatctgcctgtcacaatatattctca
```

Cluster Members
Consensus/Exemplar
BLASTn GenBank NR
Probe Info

| Probe Sequence(5'-3') | Probe X | Probe Y | Probe Interrogation Position | SEQ ID NO: |
|---|---|---|---|---|
| TACCCCCTGCTGCTTTTGAGAAATT | 364 | 1061 | 2810 | 696 |
| GTGAACATTTTCAGAGGCCTCAGTG | 2 | 769 | 2836 | 697 |

-continued

| | | | |
|---|---|---|---|
| GAACATTTTCTACCCTAATTTCACT | 211 | 581 | 2885 | 698 |
| GGAGTGACTTATTCTAAGCCTCATC | 1034 | 845 | 2910 | 699 |
| TGAACTGAGAACCCCTTTTAATTGA | 647 | 951 | 2997 | 700 |
| GACATAAATGCGGTACCCTTTACTA | 808 | 605 | 3060 | 701 |
| GTACCCTTTACTACACTCATGAGTG | 599 | 733 | 3072 | 702 |
| GCATATTTATGCTTAGGTCTTTTCA | 501 | 521 | 3097 | 703 |
| AAATCTTCATATTCTCTGTAGCCTT | 857 | 201 | 3136 | 704 |
| TAAAGCCTCAAGGACATCTGCCTGT | 701 | 1047 | 3226 | 705 |
| ATCTGCCTGTCACAATATATTCTCA | 748 | 45 | 3241 | 706 |

>HG-U133_PLUS_2:221945_AT
SEQ ID NO: 707
caaaaccttgggacctcagcagtcccaaggctgccctgacaatcaggcaggctccccacc
gtgaggccaagcctcctctgccactgccagcatggcccaagggaggcttggccttgggct
tgccagcctcagctctgccctgacaagggtcttgtatccagggcagaggcctgaggtgac
ccaggcttgctttgtggctgatgccagcaggcttggttctagtgggcaccactggtgggc
aacctccataactggcccttaggcccctaccttcctacacagtaggctataatgggcctg
agtgagagggtagcttcccagccccaagcacaggcagaggggtggagagcaatttttgg
ttttattttgtttctgaagtggtgcctgtacctccagncccaggggccttccctggc
cacacttctctgccccacccangcatcgccatcccagcactttgctccatgtcacccgta
agatgccctttgctgaatgtacctgagtgtatgtatttaaaaggactcacatgggcatca
gagaatttatggctctgtatccaat Cluster Members
Consensus/Exemplar
BLASTn GenBank NR
Note: "n"'s represent regions that are not probed by the probe
sequences.
Probe Info

| Probe Sequence(5'-3') | Probe X | Probe Y | Probe Interrogation Position | SEQ ID NO: |
|---|---|---|---|---|
| CAAAACCTTGGGACCTCAGCAGTCC | 462 | 303 | 13 | 708 |
| TGCCCTGACAATCAGGCAGGCTCCC | 441 | 969 | 44 | 709 |
| GCATGGCCCAAGGGAGGCTTGGCCT | 87 | 525 | 102 | 710 |
| TGCCCTGACAAGGGTCTTGTATCCA | 123 | 969 | 148 | 711 |
| GGTCTTGTATCCAGGGCAGAGGCCT | 432 | 823 | 160 | 712 |
| GAGGCCTGAGGTGACCCAGGCTTGC | 1074 | 663 | 178 | 713 |
| CCAGGCTTGCTTTGTGGCTGATGCC | 385 | 457 | 193 | 714 |
| GCTTTGTGGCTGATGCCAGCAGGCT | 778 | 513 | 201 | 715 |
| TTTCTGAAGTGGTGCCTGTACCTCC | 686 | 1093 | 384 | 716 |
| AGATGCCCTTTGCTGAATGTACCTG | 40 | 109 | 493 | 717 |
| GAGAATTTATGGCTCTGTATCCAAT | 371 | 633 | 553 | 718 |

HG-U133_PLUS_2:205440_S_AT
SEQ ID NO: 719
cagactgttcagtgtttgtcaagcttctggtctaatatgtactcgaaagactttccgctt
acaatttgtagaaacacaaatatcgttttccatacagcagtgcctatatagtgactgatt
ttaactttcaatgtccatctttcaaaggaagtaacaccaaggtacaatgttaaaggaata
ttcacttttacctagcagggaaaaatacacaaaaactgcagatacttcatatagcccattt
taacttgtataaactgtgtgacttgtggcgtcttataaataatgcactgtaaagattact
gaatagttgtgtcatgttaatgtgcctaatttcatgtatcttgtaatcatgattgagcct
cagaatcatttggagaaactatattttaaagaacaagacatacttcaatgtattatacag
ataaagtattacatgtgtttgattttaaaagggcggacattttattaaaatcaatattgt
ttttgcttttttctgaggagtctctttcagtttca Cluster Members
Consensus/Exemplar
BLASTn GenBank NR
Probe Info

| Probe Sequence(5'-3') | Probe X | Probe Y | Probe Interrogation Position | SEQ ID NO: |
|---|---|---|---|---|
| CAGACTGTTCAGTGTTTGTCAAGCT | 348 | 329 | 2218 | 720 |
| GTGTTTGTCAAGCTTCTGGTCTAAT | 391 | 777 | 2229 | 721 |
| AGCTTCTGGTCTAATATGTACTCGA | 25 | 137 | 2239 | 722 |
| GAAAGACTTTCCGCTTACAATTTGT | 323 | 569 | 2262 | 723 |
| ATATCGTTTTCCATACAGCAGTGCC | 128 | 25 | 2297 | 724 |
| TTAACTTTCAATGTCCATCTTTCAA | 255 | 1123 | 2338 | 725 |
| GATACTTCATATAGCCCATTTTAAC | 625 | 683 | 2437 | 726 |
| TGTGTGACTTGTGGCGTCTTATAAA | 1035 | 915 | 2472 | 727 |
| GTTGTGTCATGTTAATGTGCCTAAT | 697 | 697 | 2523 | 728 |
| TGTGCCTAATTTCATGTATCTTGTA | 162 | 921 | 2538 | 729 |
| TTCTGAGGAGTCTCTTTCAGTTTCA | 1144 | 1137 | 2707 | 730 |

>HG-U133_PLUS_2:244740_AT
SEQ ID NO: 731

-continued

```
aaagacactgtgtacaacgttggacactgtgcaggatgatgccacttcatcttggatgct
aatctgccatgttgacttctgattaaccccaggcccaggaatgcctcaagatttctactt
tacttactgttgcttgtgtaagccaagacaaccttgatgttatcataaacatgtacttac
ctaagtcctgtcctttggcaaattatgggctatgagacacagcattcttgcctttccctg
aggggtcaatttcagcgatcctacacattcc
```

Cluster Members
Consensus/Exemplar
BLASTn GenBank NR
Probe Info

| Probe Sequence(5'-3') | Probe X | Probe Y | Probe Interrogation Position | SEQ ID NO: |
|---|---|---|---|---|
| AAAGACACTGTGTACAACGTTGGAC | 284 | 211 | 319 | 732 |
| GACACTGTGTACAACGTTGGACACT | 479 | 601 | 322 | 733 |
| CTGTGTACAACGTTGGACACTGTGC | 1157 | 401 | 326 | 734 |
| GGCAAATTATGGGCTATGAGACACA | 942 | 871 | 515 | 735 |
| GGCTATGAGACACAGCATTCTTGCC | 157 | 881 | 526 | 736 |
| TGAGACACAGCATTCTTGCCTTTCC | 759 | 941 | 531 | 737 |
| TGCCTTTCCCTGAGGGGTCAATTTC | 1100 | 969 | 547 | 738 |
| CTTTCCCTGAGGGGTCAATTTCAGC | 1036 | 365 | 550 | 739 |
| GAGGGGTCAATTTCAGCGATCCTAC | 1138 | 653 | 558 | 740 |
| GTCAATTTCAGCGATCCTACACATT | 1031 | 741 | 563 | 741 |
| CAATTTCAGCGATCCTACACATTCC | 347 | 293 | 565 | 742 |

>HG-U133_PLUS_2:230632_AT
SEQ ID NO: 743
```
aaggcgccgtcaagtcaaataaataaatgccctacaacaccaacccaggactgagatctg
catgctggaatgacggtggtggtggtggctttcagtattccccaggttttgtccggagca
ccggcacgccctctcttgaagtccgctctccgcacagtggttagacgggaagatccggag
ctgtccagtgtcttgggtaatgcacggcatcgcctgatgtctgacgctagaacaccacgt
aaagtcaagcagagggaagtgaatgcgccctaggcccctgcaggccaccaagaagagcta
gagggagttggtgcaatcctagagatgccggcaggtgcaccaatctgtggcacacgtacg
ctctccaatggaagacaactcaagaccacaccaa
```

Cluster Members
Consensus/Exemplar
BLASTn GenBank NR
Probe Info

| Probe Sequence(5'-3') | Probe X | Probe Y | Probe Interrogation Position | SEQ ID NO: |
|---|---|---|---|---|
| AAGGCGCCGTCAAGTCAAATAAATA | 344 | 269 | 31 | 744 |
| CTACAACACCAACCCAGGACTGAGA | 110 | 375 | 62 | 745 |
| ACACCAACCCAGGACTGAGATCTGC | 206 | 189 | 67 | 746 |
| GGACTGAGATCTGCATGCTGGAATG | 420 | 855 | 78 | 747 |
| TGCTGGAATGACGGTGGTGGTGGTG | 999 | 965 | 93 | 748 |
| CCAGGTTTTGTCCGGAGCACCGGCA | 227 | 457 | 132 | 749 |
| CGCTCTCCGCACAGTGGTTAGACGG | 94 | 419 | 174 | 750 |
| GCTAGAGGGAGTTGGTGCAATCCTA | 798 | 511 | 327 | 751 |
| ACACGTACGCTCTCCAATGGAAGAC | 359 | 189 | 382 | 752 |
| GTACGCTCTCCAATGGAAGACAACT | 729 | 733 | 386 | 753 |
| GGAAGACAACTCAAGACCACACCAA | 906 | 865 | 400 | 754 |

>HG-U133_PLUS_2:232096_X_AT
SEQ ID NO: 755
```
tggggagagtcttacaatgaataactcagaaaaaagttttcaaaataatcctagattgta
agatatctacgaccattatccatagccatatctttaaaaaaaaaaaaanaaannnanaaa
anaanaaacaaggngtttctttacccaggncangtgagcactaaagcttccngtcntaat
gaggaggcagtgggggcnanttngctttngagactnggagtcccagtattacngggagtg
ccctgacccctcaggtagggactngtcnnnnctccagaagacctaaggtacagtcagagc
tgagccacgcctttgtccatgaagagaatgggggttgaaagtggagactgaggccgaggcg
ggtggatcacgaggtcaggagatccagaccatcctatcctggctaatacagtgaaaccct
g
```

Cluster Members
Consensus/Exemplar
Group Members
BLASTn GenBank NR
Note: "n"'s represent regions that are not probed by the probe sequences.
Probe Info

| Probe Sequence(5'-3') | Probe X | Probe Y | Probe Interrogation Position | SEQ ID NO: |
|---|---|---|---|---|
| TGGGGAGAGTCTTACAATGAATAAC | 665 | 907 | 3428 | 756 |
| GATTGTAAGATATCTACGACCATTA | 1054 | 693 | 3481 | 757 |

| -continued | | | |
|---|---|---|---|
| ATCTACGACCATTATCCATAGCCAT | 938 | 41 | 3492 | 758 |
| GACCATTATCCATAGCCATATCTTT | 334 | 623 | 3498 | 759 |
| GAAGACCTAAGGTACAGTCAGAGCT | 870 | 565 | 3704 | 760 |
| GGTACAGTCAGAGCTGAGCCACGCC | 487 | 827 | 3714 | 761 |
| CCACGCCTTTGTCCATGAAGAAT | 686 | 463 | 3732 | 762 |
| GAGAATGGGGTTGAAAGTGGAGACT | 428 | 633 | 3751 | 763 |
| AAAGTGGAGACTGAGGCCGAGGCGG | 991 | 207 | 3764 | 764 |
| TCAGGAGATCCAGACCATCCTATCC | 136 | 1021 | 3802 | 765 |
| TCCTGGCTAATACAGTGAAACCCTG | 243 | 985 | 3824 | 766 |

>HG-U133_PLUS_2:232841_AT
SEQ ID NO:767
ctgtccgaagcggcaagtgcgtccactaccactcatgctggagaggacaggccgcctgtc
ttctgtggccagggacacaggcttggggcccaccctcagacctctgagaactgcctgcca
gcccccgatgcagaaccctt gantagncaagcctcagtttctccacaccccactcctctt
tctcctctcctcagccttacagctggagggcaggggctggggaagggg ntcaccccaat
gccctggactgggcccacagctccccggctgcttgcttccttctcctgacggccggct
ccttcccacttcagcctcctctgtgggcaccgaggcccaggagcttcaaaagtcagacca
agactgtccttggtcccacaggggcagaggtgagatctgtgcgtgcccctctccacact
cacggggacagggcgtgagatctttgcgccccctccccatgatctccctttccagatttt
caaa Cluster Members
Consensus/Exemplar
BLASTn GenBank NR
Note: "n"'s represent regions that are not probed by the probe
sequences.
Probe Info

| Probe Sequence(5'-3') | Probe X | Probe Y | Probe Interrogation Position | SEQ ID NO: |
|---|---|---|---|---|
| CTGTCCGAAGCGGCAAGTGCGTCCA | 44 | 401 | 1400 | 768 |
| GTCCACTACCACTCATGCTGGAGAG | 80 | 761 | 1420 | 769 |
| GAGAGGACAGGCCGCCTGTCTTCTG | 229 | 643 | 1440 | 770 |
| CACCCTCAGACCTCTGAGAACTGCC | 841 | 317 | 1490 | 771 |
| CTCTCCTCAGCCTTACAGCTGGAGG | 416 | 383 | 1584 | 772 |
| CCGAGGCCCAGGAGCTTCAAAAGTC | 858 | 435 | 1729 | 773 |
| GACCAAGACTGTCCTTGGTCCCACA | 37 | 625 | 1755 | 774 |
| CAGAGGTGAGATCTGTGCGTGCCCC | 52 | 331 | 1784 | 775 |
| TCCACACTCACGGGGACAGGGCGTG | 533 | 975 | 1812 | 776 |
| CAGGGCGTGAGATCTTTGCGCCCCC | 961 | 335 | 1828 | 777 |
| TGATCTCCCTTTCCAGATTTTCAAA | 693 | 935 | 1859 | 778 |

HG-U133_PLUS_2:241485_AT
SEQ ID NO: 779
gggtttggttaatttgtcctgcagcagcatcgtccctgattaacatcgtgatattaagcc
attcactgtgtcctgtaacagtctctaatcgttcataaacacatagtagaaagtgggccc
caattaccccaaaattattctctacaatacatgtcagctaacaaatggaactttctgga
aattttcttcttgtcacttccaacactgaattgtgatattt ggcctttaacaggacattc
ttgatca Cluster Members
Consensus/Exemplar
BLASTn GenBank NR
Probe Info

| Probe Sequence(5'-3') | Probe X | Probe Y | Probe Interrogation Position | SEQ ID NO: |
|---|---|---|---|---|
| GGGTTTGGTTAATTTGTCCTGCAGC | 618 | 807 | 18 | 780 |
| CAGCAGCATCGTCCCTGATTAACAT | 36 | 327 | 39 | 781 |
| ATCGTCCCTGATTAACATCGTGATA | 772 | 47 | 46 | 782 |
| GATATTAAGCCATTCACTGTGTCCT | 235 | 687 | 67 | 783 |
| CACTGTGTCCTGTAACAGTCTCTAA | 734 | 315 | 81 | 784 |
| ACAGTCTCTAATCGTTCATAAACAC | 845 | 185 | 95 | 785 |
| ACATAGTAGAAAGTGGGCCCCAATT | 651 | 177 | 118 | 786 |
| TACCCCCAAAATTATTCTCTACAAT | 881 | 1059 | 142 | 787 |
| TATTCTCTACAATACATGTCAGCTA | 1076 | 1087 | 154 | 788 |
| ATGTCAGCTAACAAATGGAACTTTC | 333 | 63 | 169 | 789 |
| GCCTTTAACAGGACATTCTTGATCA | 870 | 475 | 240 | 790 |

>HG-U133_PLUS_2:241873_AT
SEQ ID NO:791
aacaccagcaatacatcagctttacacagcaggcaagtttcctgctctctacaagtacag
atggaacttgtcttgtgaattaacatcctgactactttgttgatcatcacatttttcc
tcatgagagaaataatagtgtttataggctcctgagaataggtttactaaagtcatcga
gatctgggttcaaatgacactgcttagggaggcattcactgatcaagttacctaaaatag
caacaatctatcatccaaaatatcatttgccagctttgattttgcatataacacttactt -continued

```
tatatatgtacatatatgtgtatatatatatttgtgtgtgtgtgtgtatacatgtata
tatatatgcagtctgcaataaaatgtatgcttntcaggggagaaannnnnttntaataca
ttcagtgctctatacccagaacctg
```

Cluster Members
Consensus/Exemplar
BLASTn GenBank NR
Note: "n"'s represent regions that are not probed by the probe sequences.
Probe Info

| Probe Sequence(5'-3') | Probe X | Probe Y | Probe Interrogation Position | SEQ ID NO: |
|---|---|---|---|---|
| AACACCAGCAATACATCAGCTTTAC | 511 | 229 | 52 | 792 |
| AGCTTTACACAGCAGGCAAGTTTCC | 440 | 137 | 69 | 793 |
| AGTTTCCTGCTCTCTACAAGTACAG | 955 | 101 | 87 | 794 |
| ACATCCTGACTACTTTTGTTGATCA | 1018 | 181 | 134 | 795 |
| GATCATCACATTTTTTCCTCATGAG | 771 | 679 | 154 | 796 |
| AATAGTGTTTTATAGGCTCCTGAGA | 180 | 285 | 185 | 797 |
| GATCTGGGTTCAAATGACACTGCTT | 933 | 677 | 232 | 798 |
| GACACTGCTTAGGGAGGCATTCACT | 644 | 601 | 247 | 799 |
| GGCATTCACTGATCAAGTTACCTAA | 158 | 879 | 262 | 800 |
| TCATTTGCCAGCTTTGATTTTGCAT | 86 | 1017 | 314 | 801 |
| TTCAGTGCTCTATACCCAGAACCTG | 599 | 1129 | 472 | 802 |

>HG-U133_PLUS_2:232522_AT
SEQ ID NO: 803
```
atcctcccttgattcgtggatggacaactatggaggccaatctggctgaggtgaagactg
cttgagtctaaattcctctctcctcaaacccaattcaaactggcctgagcaaaatgaatg
tattgatccataactgaaaagtccagaatgatcaggcatcaggcatggttgcatccaggg
gcccatgtattagaaccatctccttccagttctgggctctgcttgcctcccagttggttt
tactgcacagaggcttattcaagtccagagatcttatctttccctacaagtctgtgac
cttgattctgaacctgcatctatgggaagggcttgcagtgtctgagtgagcttggactgt
gtaaactttcccacttctgaagctgggg
```

Cluster Members
Consensus/Exemplar
BLASTn GenBank NR
Probe Info

| Probe Sequence(5'-3') | Probe X | Probe Y | Probe Interrogation Position | SEQ ID NO: |
|---|---|---|---|---|
| ATCCTCCCTTGATTCGTGGATGGAC | 1033 | 49 | 1465 | 804 |
| TGCTTGAGTCTAAATTCCTCTCTCC | 418 | 961 | 1523 | 805 |
| CTCTCCTCAAACCCAATTCAAACTG | 804 | 381 | 1542 | 806 |
| GGCATCAGGCATGGTTGCATCCAGG | 170 | 877 | 1619 | 807 |
| GGGCCCATGTATTAGAACCATCTCC | 257 | 793 | 1643 | 808 |
| TGCCTCCCAGTTGGTTTTACTGCAC | 112 | 971 | 1688 | 809 |
| GCACAGAGGCTTATTCAAGTCCAGA | 1118 | 539 | 1709 | 810 |
| TATCTTTCCCTACAAGTCTGTGACC | 727 | 1053 | 1741 | 811 |
| GATTCTGAACCTGCATCTATGGGAA | 54 | 693 | 1768 | 812 |
| GTGAGCTTGGACTGTGTAAACTTTC | 788 | 769 | 1810 | 813 |
| AACTTTCCCACTTCTGAAGCTGGGG | 510 | 233 | 1828 | 814 |

HG-U133_PLUS_2:233266_AT
SEQ ID NO: 815
```
tcccttatccagatgcaggtgcctatagctgaagccatgtgtggtacatttggtccagc
canagccttgcatgaagctggcacttgtgctggtgcctgnagctgtctgccttgccacag
cagctagcatgcgtggctgtgcacagtggctggaccccatgctcattcgctcatacactc
tttgccactccgtgcctggctcccccttggcaggtgtgagatcgaggccagtagtgtgag
ccaagcgcagcctgccaggccaagtgggtggaacgagccctgtgggcgcgagcaatactc
aggcagaaggcgctgcctgccacagaggtttctggctggcaaatcgacatcccaagggtc
ccgtgacaattatagcccctgcttctggatagagt
```

Cluster Members
Consensus/Exemplar
BLASTn GenBank NR
Note: "n"'s represent regions that are not probed by the probe sequences.
Probe Info

| Probe Sequence(5'-3') | Probe X | Probe Y | Probe Interrogation Position | SEQ ID NO: |
|---|---|---|---|---|
| TCCCCTTATCCAGATGCAGGTGCCT | 423 | 987 | 1464 | 816 |
| ATGTGTGGTACATTTGGTCCAGCCA | 147 | 67 | 1501 | 817 |
| AAGCTGGCACTTGTGCTGGTGCCTG | 759 | 247 | 1538 | 818 |

-continued

| | | | |
|---|---|---|---|
| CTAGCATGCGTGGCTGTGCACAGTG | 892 | 371 | 1587 | 819 |
| GCAGGTGTGAGATCGAGGCCAGTAG | 797 | 527 | 1673 | 820 |
| CAGTAGTGTGAGCCAAGCGCAGCCT | 901 | 333 | 1692 | 821 |
| TGGGCGCGAGCAATACTCAGGCAGA | 280 | 915 | 1746 | 822 |
| GGTTTCTGGCTGGCAAATCGACATC | 944 | 829 | 1790 | 823 |
| CAAATCGACATCCCAAGGGTCCCGT | 308 | 307 | 1803 | 824 |
| GGGTCCCGTGACAATTATAGCCCCT | 863 | 807 | 1819 | 825 |
| TATAGCCCCTGCTTCTGGATAGAGT | 888 | 1083 | 1834 | 826 |

>HG-U133_PLUS_2:232649_AT
SEQ ID NO: 827
aattgtcgagcacctctgacacttggcagtgcctacctgnttgtgttccagngggcagnt
tcagagaaaacgggnananacnntccaagccnagntcaatcntcagangggccagtaatta
ccnattggaattacacagcagcaatggatngttcatataggataataatnataattatac
atgagcatcgctgtagaataatgatgcctattggcttatcctgggaagactccaaaaatg
tgattcagtcctgaggcctcggcaatgggcatgatgagggcaggctcaggggcaggaggg
caccctgctagagctgggtgtggggcacgtaggaaaggggtggttttcaaaaaggcttga
gacagatccctggccttgaggacgtgcttcgcatgcagcctgcaacccagggagtgcaga
aaagaaaaagtgcatttgtttatggagcacatatttgtgtggcaggtaccattctagatn
ctggagattcagaaataagcccccctcc Cluster Members
Consensus/Exemplar
BLASTn GenBank NR
Note: "n"'s represent regions that are not probed by the probe sequences.
Probe Info

| Probe Sequence(5'-3') | Probe X | Probe Y | Probe Interrogation Position | SEQ ID NO: |
|---|---|---|---|---|
| AATTGTCGAGCACCTCTGACACTTG | 1160 | 291 | 1474 | 828 |
| TCTGACACTTGGCAGTGCCTACCTG | 317 | 1001 | 1488 | 829 |
| ATGCCTATTGGCTTATCCTGGGAAG | 897 | 51 | 1677 | 830 |
| AATGTGATTCAGTCCTGAGGCCTCG | 120 | 273 | 1710 | 831 |
| GAGGCCTCGGCAATGGGCATGATGA | 1056 | 663 | 1726 | 832 |
| GAGGGCACCCTGCTAGAGCTGGGTG | 894 | 653 | 1769 | 833 |
| GCTGGGTGTGGGGCACGTAGGAAAG | 657 | 495 | 1786 | 834 |
| AGGCTTGAGACAGATCCCTGGCCTT | 709 | 75 | 1826 | 835 |
| TGCAGCCTGCAACCCAGGGAGTGCA | 686 | 957 | 1867 | 836 |
| TTGTGTGGCAGGTACCATTCTAGAT | 875 | 1157 | 1928 | 837 |
| GAGATTCAGAAATAAGCCCCCCTCC | 958 | 643 | 1957 | 838 |

>HG-U133_PLUS_2:241887_AT
SEQ ID NO: 839
atgacatcacttgtcagattttctggtgtatggaaagatttaataatcctgcctcttttg
aagcctgaaacttacaatttaaagcctgaaatctaccataaggaacttggtaaattgtgt
cagataccatgaaaatgcatcttttcatagttaaccacagattgtttatgtaaaggcaaa
ttggtggtcaggttcaaggtaaaatggattattgggttgattagtagccaaaaactaaat
gcatgttcaggtcaaaatgaatttgtttgttttagttggtgccattttcctttttattatt
cagaactacagagtgtgcatttttattaataggaatgaaagctcatgcttgaggatttgaa
tagggtggatgtatatattttataaactcaagttgcaaaatatgtaaagtcactactttt
taaatagaatataaatgttaaaacagacaaatctatgttatatattttttaatacatgta
tcagacttgttagttgaatgcagattac Cluster Members
Consensus/Exemplar
BLASTn GenBank NR
Probe Info

| Probe Sequence(5'-3') | Probe X | Probe Y | Probe Interrogation Position | SEQ ID NO: |
|---|---|---|---|---|
| ATGACATCACTTGTCAGATTTTCTG | 737 | 57 | 187 | 840 |
| CTCTTTTGAAGCCTGAAACTTACAA | 160 | 381 | 239 | 841 |
| TTTAAAGCCTGAAATCTACCATAAG | 444 | 1103 | 264 | 842 |
| GCATCTTTTCATAGTTAACCACAGA | 329 | 523 | 323 | 843 |
| GGCAAATTGGTGGTCAGGTTCAAGG | 624 | 871 | 361 | 844 |
| ACTAAATGCATGTTCAGGTCAAAAT | 570 | 173 | 420 | 845 |
| TTTCCTTTTATTATTCAGAACTACA | 224 | 1097 | 472 | 846 |
| GAACTACAGAGTGTGCATTTTATTA | 834 | 577 | 489 | 847 |
| GAAAGCTCATGCTTGAGGATTTGAA | 748 | 589 | 522 | 848 |
| AATACATGTATCAGACTTGTTAGTT | 165 | 283 | 657 | 849 |
| GACTTGTTAGTTGAATGCAGATTAC | 1145 | 607 | 670 | 850 |

>HG-U133_PLUS_2:1570330_AT
SEQ ID NO: 851
agagctctgcaaagaacaccgccagctctttccttccgggtgctcttgctgggggtcag
gctggtcccctctgactggcactgccacgctgggacatggaggagggccatctgggca -continued

```
ctgcaggagcagatcctgggtgcacatggggagacaggtgtgctggcaggaacagcaggc
ggggctgagctcaggaggcgcctcacagcgggtgcctccagcctggtctgagcacgggat
gaagaaccaggcaccgctcatcgtgcatctccacaaggcactgtgtgacttcatgcaagc
cgctcaacctctctggcccacgtcctTgtccacaggggcagagtggactgaatggaggc
tgaggtccctctcagcttgggtggtgtggcagagggtgaggaggagcccatgggccctgg
atcaccagcctcctccacccagaatgccccgtccactccactgcccacnancctctgtg
caattgacaaacgtcctggntgttaacgcctaagcataaagagtcgg
```

Cluster Members  
Consensus/Exemplar  
BLASTn GenBank NR  
Note: "n"'s represent regions that are not probed by the probe sequences.  
Probe Info

| Probe Sequence(5'-3') | Probe X | Probe Y | Probe Interrogation Position | SEQ ID NO: |
|---|---|---|---|---|
| AGAGCTCTGCAAAGAACACCGCCAG | 274 | 117 | 168 | 852 |
| AAAGAACACCGCCAGCTCTTTCCTT | 356 | 211 | 178 | 853 |
| TTTCCTTCCGGGTGCTCTTGCTGGG | 325 | 1097 | 196 | 854 |
| AGGCTGGTCCCCTCTGACTGGCACT | 437 | 1 | 226 | 855 |
| CAGCCTGGTCTGAGCACGGGATGAA | 162 | 323 | 386 | 856 |
| GTCTGAGCACGGGATGAAGAACCAG | 866 | 753 | 393 | 857 |
| GAAGAACCAGGCACCGCTCATCGTG | 603 | 567 | 408 | 858 |
| GTGTGACTTCATGCAAGCCGCTCAA | 996 | 781 | 450 | 859 |
| TGAATGGAGGCTGAGGTCCCTCTCA | 994 | 953 | 517 | 860 |
| AGGTCCCTCTCAGCTTGGGTGGTGT | 662 | 85 | 530 | 861 |
| TTAACGCCTAAGCATAAAGAGTCGG | 404 | 1111 | 670 | 862 |

HG-U133_PLUS_2:214570_X_AT  
SEQ ID NO: 863

```
ccttcccagctgcaagcatggatgcgggcatgagaagaacaagncntggcacttctgctc
ctgcagctgccgcagcagcccctccccccctccncattgaacccacgttggggtcactac
tngagtggatngaggcccttcacatttctgggcctcagccacagctgcagcaggtgccca
gaggtcagaaccagagatcncagacctcccggaccagctcgtgccccaaangaaaggcca
tctccagctcctacagctctacgggaggcctcccggaacgaaagcggaggagggggccag
cctcatcccactgccagctgaccctcagttcctcaaacacagacccagggtgcgtgccca
tctccagcccagggcagctcccctgtaagctgggtgagctactgaagccaaggcgggagg
cagctgacaacacccacggcccatgtggaggtggtggaaaggctggactcagcagcaaca
ccaaatcccggaccaggcagaaacca
```

Cluster Members  
Consensus/Exemplar  
Group Members  
BLASTn GenBank NR  
Note: "n"'s represent regions that are not probed by the probe sequences.  
Probe Info

| Probe Sequence(5'-3') | Probe X | Probe Y | Probe Interrogation Position | SEQ ID NO: |
|---|---|---|---|---|
| CCTTCCCAGCTGCAAGCATGGATGC | 992 | 451 | 1067 | 864 |
| AGGCCCTTCACATTTCTGGGCCTCA | 291 | 73 | 1199 | 865 |
| GCAGGTGCCCAGAGGTCAGAACCAG | 587 | 527 | 1236 | 866 |
| GAAAGCGGAGGAGGGGGCCAGCCTC | 308 | 591 | 1346 | 867 |
| AAACACAGACCCAGGGTGCGTGCCC | 344 | 219 | 1401 | 868 |
| GCAGCTCCCCTGTAAGCTGGGTGAG | 150 | 535 | 1440 | 869 |
| GGTGAGCTACTGAAGCCAAGGCGGG | 390 | 815 | 1459 | 870 |
| AGGCGGGAGGCAGCTGACAACACCC | 916 | 73 | 1477 | 871 |
| CACCCACGGCCCATGTGGAGGTGGT | 643 | 317 | 1497 | 872 |
| AAGGCTGGACTCAGCAGCAACACCA | 636 | 269 | 1525 | 873 |
| CAAATCCCGGACCAGGCAGAAACCA | 143 | 301 | 1548 | 874 |

>HG-U133_PLUS_2:1570227_AT  
SEQ ID NO: 875

```
ggatgggccgtcaaagtctaagtcagagcatcctgatgttggaggcaaagcaggagagtg
tggattaagcagctagacattggttactggggcaacaaccgtttgggtggagaactggat
cagaaatcaactggagtggatcgaggtgtgcatagaaggcgaggaagtggcgaggcgttt
ggctgcgaggggtagaactagggtgcaccaagcaggagaaacagatggaagtttggacat
gattgaacacaaatgggaagagtacagaaacaagagtggaccaggctcatatgtgtaatc
ccagcacttggggaggctgaggcgggaggattgcttgacactaggagtttgaggccaacc
tgggcaatatggcgagacccccatctctacaaaaaacatttaaaaattagccagatgcggtg
gcgcatacctgtggtcccaggctaagatgggacgattgcttgagcccaggaggtcaaggc
ctcagtcatgccactgcttgagtgacag
```

Cluster Members  
Consensus/Exemplar

-continued

BLASTn GenBank NR
Probe Info

| Probe Sequence(5'-3') | Probe X | Probe Y | Probe Interrogation Position | SEQ ID NO: |
|---|---|---|---|---|
| GGATGGGCCGTCAAAGTCTAAGTCA | 383 | 841 | 678 | 876 |
| AAGTCTAAGTCAGAGCATCCTGATG | 44 | 261 | 691 | 877 |
| GATTAAGCAGCTAGACATTGGTTAC | 97 | 691 | 740 | 878 |
| CAACCGTTTGGGTGGAGAACTGGAT | 581 | 301 | 773 | 879 |
| AATCAACTGGAGTGGATCGAGGTGT | 426 | 281 | 802 | 880 |
| GGTAGAACTAGGGTGCACCAAGCAG | 1156 | 825 | 868 | 881 |
| GTGCACCAAGCAGGAGAAACAGATG | 451 | 765 | 880 | 882 |
| AGTGGACCAGGCTCATATGTGTAAT | 803 | 91 | 952 | 883 |
| TACCTGTGGTCCCAGGCTAAGATGG | 138 | 1043 | 1103 | 884 |
| AGGTCAAGGCCTCAGTCATGCCACT | 837 | 83 | 1148 | 885 |
| AGTCATGCCACTGCTTGAGTGACAG | 197 | 99 | 1161 | 886 |

>HG-U133_PLUS_2:225716_AT
SEQ ID NO:887
gcattgtctactgaaaagctgtggcagcgagtggtattattgaccatgtgttctcatgtc
tttttgcagatttaaaggtttttattgtagtgtccatttaatatctgcatgtgtgtttaat
ctctgaataccatgtaattaaactgattaacttgtgatggtgatggtgattagcacacac
taaaaacccaatgaagcaattgtctccctcttcttaactggaaatcacacttgtgaggta
tggtatccattatcaacagtggattcatgattgacttcatattttgtgtatctggttata
aattttgtatagcatttaatttggcacttaatataaatccatttgatttgaatagtgtgt
gtgtgtacatggtgtgtgtgtgtgtgcactttagtttcgtgagccttgggaaactgat
tctacaaatatcttatatagagataaatgtatcaggcatttttttgcaaagcgatatata
cattcctct Cluster Members
Consensus/Exemplar
BLASTn GenBank NR
Probe Info

| Probe Sequence(5'-3') | Probe X | Probe Y | Probe Interrogation Position | SEQ ID NO: |
|---|---|---|---|---|
| GCATTGTCTACTGAAAAGCTGTGGC | 764 | 519 | 1139 | 888 |
| GCTGTGGCAGCGAGTGGTATTATTG | 1081 | 497 | 1156 | 889 |
| GGTATTATTGACCATGTGTTCTCAT | 645 | 829 | 1171 | 890 |
| TGTAGTGTCCATTTAATATCTGCAT | 718 | 927 | 1223 | 891 |
| ATCTGCATGTGTGTTTAATCTCTGA | 716 | 45 | 1240 | 892 |
| AATGAAGCAATTGTCTCCCTCTTCT | 219 | 275 | 1328 | 893 |
| GTCTCCCTCTTCTTAACTGGAAATC | 689 | 751 | 1340 | 894 |
| TTGACTTCATATTTTGTGTATCTGG | 381 | 1153 | 1409 | 895 |
| GTGTGCACTTTAGTTTCGTGAGCCT | 668 | 781 | 1522 | 896 |
| GTGAGCCTTGGGAAACTGATTCTAC | 806 | 771 | 1539 | 897 |
| TGCAAAGCGATATATACATTCCTCT | 582 | 955 | 1603 | 898 |

>HG-U133_PLUS_2:244659_AT
SEQ ID NO: 899
agacttcctgagttcagatctctcagccataactagctatctgaccttggccaagtatgc
tcaaagtcacaaaaccttagtttccttatgtgcatgatgattataataccttttgtacag
ttatgaggaaacttagacaatgcctgtgttgtatggtaagcgttttcataaatgctgcct
acctgtaagtagcattatagtgtgtagttattggttaatttccttttctttaccagaag
tgtgggttttgcccagcctttatacaacttcagtatttctggttaatctgtctctctatg
gctctaaacttttcagagtggtgggggagttaccaacacttttgtaaaaggccagatagt
aaatgttttatgctttatgtagtctctgttgcaagtactcaattctgtaattatagcgtg
aaagcggccacagacttgtaaatgaatgagtacagctatgttctaataaaatttttattt
acaaaannnatgtggtggactggatttggcctttgggccatattttgctgacc Cluster Members
Consensus/Exemplar
BLASTn GenBank NR
Note: "n"'s represent regions that are not probed by the probe
sequences.
Probe Info

| Probe Sequence(5'-3') | Probe X | Probe Y | Probe Interrogation Position | SEQ ID NO: |
|---|---|---|---|---|
| AGACTTCCTGAGTTCAGATCTCTCA | 921 | 119 | 116 | 900 |
| TAACTAGCTATCTGACCTTGGCCAA | 379 | 1043 | 145 | 901 |
| ACCTTGGCCAAGTATGCTCAAAGTC | 712 | 153 | 159 | 902 |
| AACCTTAGTTTCCTTATGTGCATGA | 435 | 243 | 188 | 903 |
| GCGTTTTCATAAATGCTGCCTACCT | 349 | 493 | 275 | 904 |
| TGCCCAGCCTTTATACAACTTCAGT | 676 | 967 | 365 | 905 |
| TTTCTGGTTAATCTGTCTCTCTATG | 1022 | 1097 | 391 | 906 |

-continued

| | | | |
|---|---|---|---|
| GTCTCTCTATGGCTCTAAACTTTTC | 180 | 753 | 405 | 907 |
| GTAGTCTCTGTTGCAAGTACTCAAT | 81 | 729 | 494 | 908 |
| GCGTGAAAGCGGCCACAGACTTGTA | 669 | 493 | 531 | 909 |
| GCCTTTGGGCCATATTTTGCTGACC | 844 | 475 | 624 | 910 |

>HG-U133_PLUS_2:241737_X_AT
SEQ ID NO: 911
gcgtggtgactgatgtgtgcctgtagtctcagctactcaggaggctgaggcaggaggatc
acttgagcccaggagtttgagtcnagtctgggcnaacantagnaaacccatctctaaaa
taaataaaataaatgactgagctgttgtgaaagggttagtgatagaganccagaactctt
aactgtcaggccaatgtctttnccacttcctcacactgatcccacataactctgggtatg
atagtgagtgtcaggggtcagacatgggtctgntnnngctgagctgcctgattgttcctt
ataaagtttgtcaacctcttcttttttttgaacaagttaagaggaaaggaattaaagctt
tatggatgatcactttcaa Cluster Members
Consensus/Exemplar
Group Members
BLASTn GenBank NR
Note: "n"'s represent regions that are not probed by the probe
sequences.
Probe Info

| Probe Sequence(5'-3') | Probe X | Probe Y | Probe Interrogation Position | SEQ ID NO: |
|---|---|---|---|---|
| GCGTGGTGACTGATGTGTGCCTGTA | 967 | 493 | 13 | 912 |
| ATGACTGAGCTGTTGTGAAAGGGTT | 158 | 57 | 145 | 913 |
| CCAGAACTCTTAACTGTCAGGCCAA | 948 | 459 | 182 | 914 |
| TCTTAACTGTCAGGCCAATGTCTTT | 156 | 1013 | 189 | 915 |
| TCACACTGATCCCACATAACTCTGG | 578 | 1029 | 223 | 916 |
| TCCCACATAACTCTGGGTATGATAG | 1137 | 991 | 232 | 917 |
| GGTATGATAGTGAGTGTCAGGGGTC | 1160 | 827 | 247 | 918 |
| GTGTCAGGGGTCAGACATGGGTCTG | 764 | 779 | 260 | 919 |
| AGCTGCCTGATTGTTCCTTATAAAG | 6 | 139 | 294 | 920 |
| TTATAAAGTTTGTCAACCTCTTCTT | 1092 | 1113 | 311 | 921 |
| AGCTTTATGGATGATCACTTTTCAA | 507 | 137 | 368 | 922 |

>HG-U133_PLUS_2:232433_AT
SEQ ID NO:923
tgggcttggggacatctcaatggccatagataggtagcctgggtttggggacacctcagt
gggctgatatgaataggctgcacttggggacacctcagtgggctgatatgggtgggctgg
gcttggagatacctcagtgggctgaaatggctgngccaggggttgggtactccctaatggc
ctgagatgggtaggttggacttggggacacctcagtgggctgaaatggctgagccagcat
tgggtactccccaacagactgagatgggtagtctggacttggagacaccccnnanngctt
gagatggctgggccagatttgaggttacccccaggggcttggatggctgggctaggcttg
agggctccccactgtccatagatggctgggctaggttttgggaccccccagttagccattg
attggtgaccttggtctgaggccactctaaaggtccttgatgggtgtcctcg Cluster Members
Consensus/Exemplar
BLASTn GenBank NR
Note: "n"'s represent regions that are not probed by the probe
sequences.
Probe Info

| Probe Sequence(5'-3') | Probe X | Probe Y | Probe Interrogation Position | SEQ ID NO: |
|---|---|---|---|---|
| TGGGCTTGGGGACATCTCAATGGCC | 138 | 915 | 4990 | 924 |
| TGGGCTGGGCTTGGAGATACCTCAG | 405 | 915 | 5102 | 925 |
| GCCAGGGTTGGGTACTCCCTAATGG | 561 | 455 | 5144 | 926 |
| TGGCTGAGCCAGCATTGGGTACTCC | 3 | 897 | 5215 | 927 |
| GGTACTCCCCAACAGACTGAGATGG | 305 | 825 | 5232 | 928 |
| GATTTGAGGTTACCCCAGGGGCTTG | 1003 | 685 | 5305 | 929 |
| GGGCTTGAGATGGCTGGGCTAGGCT | 601 | 793 | 5323 | 930 |
| GATGGCTGGGCTAGGTTTTGGGACC | 363 | 665 | 5370 | 931 |
| GACCCCCAGTTAGCCATTGATTGGT | 168 | 619 | 5391 | 932 |
| TTGGTGACCTTGGTCTGAGGCCACT | 612 | 1161 | 5411 | 933 |
| TAAAGGTCCTTGATGGGTGTCCTCG | 584 | 1047 | 5437 | 934 |

>HG-U133_PLUS_2:240224_AT
SEQ ID NO: 935
acaatgggagcccttcatcacagctttgtagttacctcaactctggctgttgagtaattt
gctcagttaaatctgtttgtgggtgtagtgaattacaacctcctctggttccctcgagat
caagtctaacctggtgattgcgtcatctggtgggagagcacggctacaacagcaggtgga
aaccatgctcgggtcctggccacttttgcctaggatgaaagctgttgtggcaaacagggga
aagagcttcaagctttgtagtaaaaggaatctgggcttaaattcctcttatcagcactgt -continued

```
gaccttggagaattaatcattcttggttgtggtgagggttaattgagatcaggtatttaa
aggacatctgacagtgcctggcacgggataggtgctcc
```

Cluster Members
Consensus/Exemplar
BLASTn GenBank NR
Probe Info

| Probe Sequence(5'-3') | Probe X | Probe Y | Probe Interrogation Position | SEQ ID NO: |
|---|---|---|---|---|
| ACAATGGGAGCCCTTCATCACAGCT | 202 | 197 | 127 | 936 |
| GCTTTGTAGTTACCTCAACTCTGGC | 711 | 513 | 149 | 937 |
| AGTGAATTACAACCTCCTCTGGTTC | 953 | 93 | 213 | 938 |
| GTTCCCTCGAGATCAAGTCTAACCT | 1151 | 701 | 234 | 939 |
| GTCTAACCTGGTGATTGCGTCATCT | 20 | 751 | 250 | 940 |
| GGTGGGAGAGCACGGCTACAACAGC | 382 | 817 | 275 | 941 |
| TCCTGGCCACTTTGCCTAGGATGAA | 617 | 985 | 320 | 942 |
| ATCTGGGCTTAAATTCCTCTTATCA | 59 | 47 | 395 | 943 |
| CCTCTTATCAGCACTGTGACCTTGG | 715 | 445 | 410 | 944 |
| AAGGACATCTGACAGTGCCTGGCAC | 688 | 267 | 486 | 945 |
| GTGCCTGGCACGGGATAGGTGCTCC | 216 | 763 | 500 | 946 |

>HG-U133_PLUS_2:241674_S_AT
SEQ ID NO:947
```
tttttttttaccaactattgtcacatacatataacgcatatagacatatggacacacagaa
gatacttcttacctggagttatatactagcaatattttc
```

Cluster Members
Consensus/Exemplar
BLASTn GenBank NR
Probe Info

| Probe Sequence(5'-3') | Probe X | Probe Y | Probe Interrogation Position | SEQ ID NO: |
|---|---|---|---|---|
| TTTTTTTTACCAACTATTGTCACAT | 866 | 1107 | 48 | 948 |
| TTTTACCAACTATTGTCACATACAT | 230 | 1109 | 52 | 949 |
| TACCAACTATTGTCACATACATATA | 394 | 1063 | 55 | 950 |
| ACTATTGTCACATACATATAACGCA | 540 | 175 | 60 | 951 |
| GTCACATACATATAACGCATATAGA | 831 | 743 | 66 | 952 |
| AACGCATATAGACATATGGACACAC | 63 | 241 | 79 | 953 |
| CATATGGACACACAGAAGATACTTC | 219 | 351 | 91 | 954 |
| GAAGATACTTCTTACCTGGAGTTAT | 415 | 565 | 105 | 955 |
| GATACTTCTTACCTGGAGTTATATA | 320 | 683 | 108 | 956 |
| TCTTACCTGGAGTTATATACTAGCA | 879 | 1011 | 114 | 957 |
| GGAGTTATATACTAGCAATATTTTC | 1117 | 845 | 122 | 958 |

>HG-U133_PLUS_2:240617_AT
SEQ ID NO: 959
```
cccagccgaggaagagccgggaaagggcgtcgncgctcatgtaggctcacctttcgagtg
cggagggtgacggacgcccccgttcaagcagcagctcagccacctcgaagtggncacag
ttgagggcatcgtggagggggggtgatgccttcgcagccctggccacctgggtcgtccact
gcggccccgtggtccagcaggaagcggacaatttctgcagaccaggagacgtaagcccag
ctcccgatgccccgccaggactgactcttcgcccacgtgtccaccaagggtctcactcc
agcctgggtgacagagcgagactccatctcaagaaaaaaaaacaacacaacatggatggt
gcctggctcaaagtgagggctgacggctgccaacctccaatggtggtctctgccatcagc
actcctggaccacgcgtgccatctcctctcccaccctgggaggctaggggtacaactact
gtctccagt
```

Cluster Members
Consensus/Exemplar
BLASTn GenBank NR
Note: "n"'s represent regions that are not probed by the probe sequences.
Probe Info

| Probe Sequence(5'-3') | Probe X | Probe Y | Probe Interrogation Position | SEQ ID NO: |
|---|---|---|---|---|
| CCCAGCCGAGGAAGAGCCGGGAAAG | 196 | 421 | 72 | 960 |
| TCATGTAGGCTCACCTTTCGAGTGC | 1111 | 1017 | 108 | 961 |
| CGAGTGCGGAGGGTGACGGACGCCC | 197 | 415 | 126 | 962 |
| ATCGTGGAGGGGGGTGATGCCTTCG | 331 | 47 | 200 | 963 |
| GGAAGCGGACAATTTCTGCAGACCA | 166 | 865 | 271 | 964 |
| GCAGACCAGGAGACGTAAGCCCAGC | 485 | 531 | 288 | 965 |
| AACAACACAACATGGATGGTGCCTG | 589 | 227 | 412 | 966 |
| GGTGCCTGGCTCAAAGTGAGGGCTG | 733 | 821 | 429 | 967 |
| AAAGTGAGGGCTGACGGCTGCCAAC | 876 | 207 | 441 | 968 |

-continued

| | | | |
|---|---|---|---|
| GGAGGCTAGGGGTACAACTACTGTC | 1130 | 839 | 530 | 969 |
| TAGGGGTACAACTACTGTCTCCAGT | 605 | 1073 | 536 | 970 |

>HG-U133_PLUS_2:230640_AT
SEQ ID NO: 971
ggcagcgtatccagaagggggcagggaatgggtgaagaggttgtgctctagggcagagct
gagctctgatctagaaaggacagcaaagatacctggaaggcctcccgattcttgcgttgt
tggcgtcgctcccgaagccgggcccgctcccgttcctcctcctcttccctctccaaagct
cggatgtgctcctcaaaacagatcagtgcatcttccttgtccatgtctaaagacaggcag
gaggttccgcgggcattgtcccagcaggatacccctcagacccagcacccctaatgtt
tcaacgatgctgtcctacaggtgctagggatacccagggtggtgggggaagggcctggag
ggggctctgtgggagcagccactgcaatggtagttct Cluster Members
Consensus/Exemplar
BLASTn GenBank NR
Probe Info

| Probe Sequence(5'-3') | Probe X | Probe Y | Probe Interrogation Position | SEQ ID NO: |
|---|---|---|---|---|
| GGCAGCGTATCCAGAAGGGGGCAGG | 1008 | 873 | 41 | 972 |
| GAGGTTGTGCTCTAGGGCAGAGCTG | 1069 | 657 | 77 | 973 |
| GAGCTCTGATCTAGAAAGGA | 236 | 629 | 96 | 974 |
| AGCAAAGATACCTGGAAGGCCTCCC | 6 | 129 | 122 | 975 |
| CGATTCTTGCGTTGTTGGCGTCGCT | 856 | 413 | 146 | 976 |
| ATGTGCTCCTCAAAACAGATCAGTG | 610 | 65 | 224 | 977 |
| AACAGATCAGTGCATCTTCCTTGTC | 1146 | 229 | 237 | 978 |
| AGCACCCCTAATGTTTCAACGATGC | 503 | 131 | 326 | 979 |
| TGTTTCAACGATGCTGTCCTACAGG | 521 | 929 | 337 | 980 |
| GTCCTACAGGTGCTAGGGATACCCA | 948 | 755 | 352 | 981 |
| GAGCAGCCACTGCAATGGTAGTTCT | 177 | 631 | 413 | 982 |

>HG-U133_PLUS_2:241760_X_AT
SEQ ID NO: 983
acaatgataacaacagctaacacttagaaaggaaatacaatgaactgttctcttcgagat
ccagaataaaagtctggcagctagaacnccgtttttatacaccgaacccctcgtgctctc
cctgcntttttttttgttgttgntgttgtgcttaatgttagaaaataacattactactatg
aaacgaanagaattttttttcaaaaccatgtcttgccattacagatgagacaag Cluster Members
Consensus/Exemplar
Group Members
BLASTn GenBank NR
Note: "n"'s represent regions that are not probed by the probe
sequences.
Probe Info

| Probe Sequence(5'-3') | Probe X | Probe Y | Probe Interrogation Position | SEQ ID NO: |
|---|---|---|---|---|
| ACAATGATAACAACAGCTAACACTT | 508 | 197 | 15 | 984 |
| AAGGAAATACAATGAACTGTTCTCT | 834 | 267 | 43 | 985 |
| TGAACTGTTCTCTTCGAGATCCAGA | 448 | 951 | 55 | 986 |
| AACTGTTCTCTTCGAGATCCAGAAT | 952 | 237 | 57 | 987 |
| TGTTCTCTTCGAGATCCAGAATAAA | 365 | 931 | 60 | 988 |
| AGAATAAAAGTCTGGCAGCTAGAAC | 927 | 127 | 77 | 989 |
| AATAACATTACTACTATGAAACGAA | 199 | 283 | 177 | 990 |
| TTTTTTCAAAACCATGTCTTGCCAT | 360 | 1107 | 209 | 991 |
| TTCAAAACCATGTCTTGCCATTACA | 79 | 1127 | 213 | 992 |
| ACCATGTCTTGCCATTACAGATGAG | 1057 | 151 | 219 | 993 |
| GTCTTGCCATTACAGATGAGACAAG | 555 | 749 | 224 | 994 |

>HG-U133_PLUS_2:221871_S_AT
SEQ ID NO: 995
ccctaccatccacagtatcattttcaggaatattggtggaaggtcctggttctccaggtg
gttccaagctatccaataaacgattcactttattcgaagttctatcagttctcgacgga
gatatttcacctgacttgattcaaggggtcttggctggccattaacaaataatgtcagtt
tcagtatcctactgcactgaattgcaaaggaaaggtcagaactatcaaaaattgttataa
gatctccatcttcatctttatactttattgttacttcatcattactcagaagttttcctc
tgaaaactcgttgcatcattagcactaattcatcataagtaatatcttcattatgaatag
gaattcgccgaatatcctccccaagttgagctttgatgattagcttcccacttagatcca
actgtccgttcatggtg Cluster Members
Consensus/Exemplar
BLASTn GenBank NR
Probe Info -continued

| Probe Sequence(5'-3') | Probe X | Probe Y | Probe Interrogation Position | SEQ ID NO: |
|---|---|---|---|---|
| CCCTACCATCCACAGTATCATTTTC | 975 | 425 | 27 | 996 |
| GGTGGTTCCAAGCTATCCAATAAAC | 151 | 815 | 83 | 997 |
| GAAGTTCTATCAGTTCTCGACGGAG | 592 | 565 | 123 | 998 |
| CTCGACGGAGATATTTCACCTGACT | 17 | 385 | 138 | 999 |
| TGATTCAAGGGGTCTTGGCTGGCCA | 458 | 931 | 163 | 1000 |
| CAGTATCCTACTGCACTGAATTGCA | 474 | 333 | 208 | 1001 |
| TTTCCTCTGAAAACTCGTTGCATCA | 631 | 1097 | 320 | 1002 |
| TAGGAATTCGCCGAATATCCTCCCC | 1011 | 1073 | 384 | 1003 |
| TATCCTCCCCAAGTTGAGCTTTGAT | 961 | 1079 | 399 | 1004 |
| GATGATTAGCTTCCCACTTAGATCC | 223 | 671 | 421 | 1005 |
| TAGATCCAACTGTCCGTTCATGGTG | 828 | 1067 | 439 | 1006 |

>HG-U133_PLUS_2:241532_AT
SEQ ID NO: 1007
aactcccaggtttctatatgccagccaagaggtgactttgtnaagcaggactttnctaag
ggtagtagtnctatgancctgctgtgttaactccttnctgcacatncgtggtanccccag
ggaagtttgttttcttctacctctttatatggaatatgaagcatttgcactaaatcatct
ctcttgaggaaatttagtaacaaccagaacgttttgagaatgacttgaacagtgtaactg
ggtttaataagtgagtttattcacttagacatatttctcaaaaataatactgccttgac
agtattattcacagcctgtgctggttgttgtaatgata Cluster Members
Consensus/Exemplr
BLASTn GenBank NR
Note: "n"'s represent regions that are not probed by the probe sequences.
Probe Info

| Probe Sequence(5'-3') | Probe X | Probe Y | Probe Interrogation Position | SEQ ID NO: |
|---|---|---|---|---|
| AACTCCCAGGTTTCTATATGCCAGC | 488 | 237 | 20 | 1008 |
| TCTTCTACCTCTTTATATGGAATAT | 576 | 1013 | 152 | 1009 |
| GCATTTGCACTAAATCATCTCTCTT | 532 | 521 | 180 | 1010 |
| AAATCATCTCTCTTGAGGAAATTTA | 418 | 201 | 191 | 1011 |
| ATCTCTCTTGAGGAAATTTAGTAAC | 698 | 41 | 196 | 1012 |
| TAGTAACAACCAGAACGTTTTGAGA | 735 | 1043 | 214 | 1013 |
| ACCAGAACGTTTTGAGAATGACTTG | 688 | 151 | 222 | 1014 |
| GAATGACTTGAACAGTGTAACTGGG | 120 | 557 | 237 | 1015 |
| GAGTTTATTCACTTAGACATATTTT | 674 | 647 | 272 | 1016 |
| GCCTTGACAGTATTATTCACAGCCT | 21 | 477 | 312 | 1017 |
| GCCTGTGCTGGTTGTTGTAATGATA | 955 | 481 | 333 | 1018 |

>HG-U133_PLUS_2:240277_AT
SEQ ID NO:1019
gaaagcaattgtatttgtgcaaagcntaaacaggaaaacaaagtggatgacttggcattt
gaagaatgaaaaagccaaacagcactgtcacaaccatttctgccttcagtctccagtgcc
tttttctttcattataaaatccatagaaatggcaaggaaagatataggaaagtttatcac
agatacagtagctattacagaaatttggaattcagcagatgttttaagtcaaaattttct
gtgtaacagatgaatttgcaaagttttgaaaacacagtccacaaagtaatttaaaatgtg
ataattaaatttgttttaaaaagcaaattaacaccttttattttctgtgaagataaaaca
ataaaagaaaaatgttcatatatccaaacctatgctggaagtacacaaaaagacaatttg
tatacattactggcaatagtcttgtttt Cluster Members
Consensus/Exemplar
BLASTn GenBank NR
Note: "n"'s represent regions that are not probed by the probe sequences.
Probe Info

| Probe Sequence(5'-3') | Probe X | Probe Y | Probe Interrogation Position | SEQ ID NO: |
|---|---|---|---|---|
| GAAAGCAATTGTATTTGTGCAAAGC | 745 | 591 | 14 | 1020 |
| AAGTGGATGACTTGGCATTTGAAGA | 705 | 263 | 54 | 1021 |
| ACAGCACTGTCACAACCATTTCTGC | 235 | 189 | 92 | 1022 |
| ATCACAGATACAGTAGCTATTACAG | 729 | 37 | 189 | 1023 |
| TTTGGAATTCAGCAGATGTTTTAAG | 833 | 1089 | 217 | 1024 |
| CTGTGTAACAGATGAATTTGCAAAG | 527 | 403 | 252 | 1025 |
| GTTTTGAAAACACAGTCCACAAAGT | 48 | 713 | 276 | 1026 |
| ATGTTCATATATCCAAACCTATGCT | 22 | 63 | 385 | 1027 |
| AAACCTATGCTGGAAGTACACAAAA | 375 | 215 | 399 | 1028 |
| GACAATTTGTATACATTACTGGCAA | 1064 | 597 | 425 | 1029 |
| ACATTACTGGCAATAGTCTTGTTTT | 1046 | 179 | 437 | 1030 |

```
>HG-U133_PLUS_2:230576_AT
SEQ ID NO: 1031
ctcagaaccaggcggcagggtcaggatcgggagaggaaccagatctaaggatagtggggc
cctggtctccgcagtaggggttgaactatatccaatataaagcattatccaaggggaccg
gattagcccccatgggtgacaccaagatgggagcggggtggggggtgataagagacaca
ggagacagagtcaggtcccagaggcagcaaggcctaccccaaattgcagtcaggttggg
aagtagaatcatggctaggcccgcggcccgggtctttctcaggcccggtccctggcacg
ccgcggatgtccggcagcaggcggcagccagccacgatgtccagacgctcggccagcgca
caaaggtccccgcgcgccaggcgcacgctgtgggccgccgccagccccgccgcctgggct
gccgccagcctactagccagggcggccacgtcgcggcctgcacggcggtagacaccgctc
ac
```

Cluster Members
Consensus/Exemplar
BLASTn GenBank NR
Probe Info

| Probe Sequence(5'-3') | Probe X | Probe Y | Probe Interrogation Position | SEQ ID NO: |
|---|---|---|---|---|
| CTCAGAACCAGGCGGCAGGGTCAGG | 52 | 379 | 26 | 1032 |
| GGCAGGGTCAGGATCGGGAGAGGAA | 338 | 875 | 39 | 1033 |
| TAAGGATAGTGGGGCCCTGGTCTCC | 1131 | 1037 | 71 | 1034 |
| CCTGGTCTCCGCAGTAGGGGTTGAA | 39 | 439 | 86 | 1035 |
| GTAGGGGTTGAACTATATCCAATAT | 4 | 727 | 99 | 1036 |
| TAAAGCATTATCCAAGGGGACCGGA | 581 | 1043 | 123 | 1037 |
| GGGTGACACCAAGATGGGAGCGGGG | 879 | 809 | 159 | 1038 |
| GGAGACAGAGTCAGGTCCCAGAGGC | 128 | 849 | 206 | 1039 |
| CCTACCCCCAAATTGCAGTCAGGTT 7 | 64 | 447 | 238 | 1040 |
| GAAGTAGAATCATGGCTAGGCCCGC | 978 | 563 | 265 | 1041 |
| CTGCACGGCGGTAGACACCGCTCAC | 92 | 395 | 483 | 1042 |

```
>HG-U133_PLUS_2:222042_X_AT
SEQ ID NO:1043
gtggtccgcgctctaggaaaagatatgaatggcctgggtggccggcgtgcggcaggcggg
acactcgggctcgctcttgccgcagatgcggacggcgcagtccatgcagaagaggttgtg
gccgcaggggaccagcgcagccatcacctcgccctcggcgcacaccacgcactctcgcgc
cagggccggggccgaggacgccgaaggggggcttgcggctgttc
```

Cluster Members
Consensus/Exemplar
BLASTn GenBank NR
Probe Info

| Probe Sequence(5'-3') | Probe X | Probe Y | Probe Interrogation Position | SEQ ID NO: |
|---|---|---|---|---|
| GTGGTCCGCGCTCTAGGAAAAGATA | 1039 | 785 | 106 | 1044 |
| AAAAGATATGAATGGCCTGGGTGGC | 910 | 221 | 123 | 1045 |
| TATGAATGGCCTGGGTGGCCGGCGT | 850 | 1077 | 129 | 1046 |
| CTCGCTCTTGCCGCAGATGCGGACG | 542 | 385 | 175 | 1047 |
| GCTCTTGCCGCAGATGCGGACGGCG | 712 | 507 | 178 | 1048 |
| TGCCGCAGATGCGGACGGCGCAGTC | 37 | 971 | 183 | 1049 |
| ACGGCGCAGTCCATGCAGAAGAGGT | 992 | 163 | 197 | 1050 |
| GCAGAAGAGGTTGTGGCCGCAGGGG | 488 | 531 | 211 | 1051 |
| GAGGACGCCGAAGGGGGCTrGCGGC | 215 | 661 | 299 | 1052 |
| GACGCCGAAGGGGGCTTGCGGCTGT | 780 | 617 | 302 | 1053 |
| CGCCGAAGGGGGCTTGCGGCTGTTC | 389 | 419 | 304 | 1054 |

```
HG-U133_PLUS_2:241677_X_AT
SEQ ID NO: 1055
cggccgcctactactactatacggctgcgagaagacgacagaaggggcaagaacgactgg
agaaggaagaacaagataggctggagagagaggaattgaaaagaaaggcagaggaggaaa
ggcttcgcctagaagaggaagcccgaaagcaggaagaag
```

Cluster Members
Consensus/Exemplar
BLASTn GenBank NR
Probe Info

| Probe Sequence(5'-3') | Probe X | Probe Y | Probe Interrogation Position | SEQ ID NO: |
|---|---|---|---|---|
| CGGCCGCCTACTACTACTATACGGC | 778 | 407 | 14 | 1056 |
| CCTACTACTACTATACGGCTGCGAG | 38 | 449 | 20 | 1057 |
| ACTACTATACGGCTGCGAGAAGACG | 226 | 173 | 26 | 1058 |
| ATACGGCTGCGAGAAGACGACAGAA | 116 | 29 | 32 | 1059 |
| GACAGAAGGGGCAAGAACGACTGGA | 527 | 603 | 50 | 1060 |

-continued

| | | | |
|---|---|---|---|
| GGGGCAAGAACGACTGGAGAAGGAA | 1055 | 813 | 57 | 1061 |
| GGAAGAACAAGATAGGCTGGAGAGA | 684 | 865 | 78 | 1062 |
| GCAGAGGAGGAAAGGCTTCGCCTAG | 43 | 531 | 121 | 1063 |
| GGAGGAAAGGCTTCGCCTAGAAGAG | 783 | 843 | 126 | 1064 |
| GCCTAGAAGAGGAAGCCCGAAAGCA | 951 | 477 | 140 | 1065 |
| GAGGAAGCCCGAAAGCAGGAAGAAG | 865 | 659 | 148 | 1066 |

>HG-U133_PLUS_2:240630_AT
SEQ ID NO: 1067
agctctgagacaccctaggagggcccacacttctagtacaacaaggctgtcttctcacag
cctgtggaaactcctgaagaacagcattaagtgatactccgaagagatgatgagaagcaa
ttggccctccaagaccatggtgcgggagtttgttggaaccagctccagctgactcctctt
cccctcccaagcctcctagctcatcccaaaaggagctcctcccacaagtaccttaatagt
cccactccatttgattctcacagtcctgaaggggcaggctcctgttgccattgtagagat
gaaaaaactgaggctcaaaaagaaaattgccttcctcaacgtcatacagcttgtcaatgg
cagggctgggattcaaacccaggcaggtatggtggctcacacctttaattctagcactt
tgggaggccaagatgggacgccaggagttgcttgac Cluster Members
Consensus/Exemplar
BLASTn GenBank NR
Probe Info

| Probe Sequence(5'-3') | Probe X | Probe Y | Probe Interrogation Position | SEQ ID NO: |
|---|---|---|---|---|
| AGCTCTGAGACACCCTAGGAGGGCC | 146 | 139 | 22 | 1068 |
| GGCCCACACTTCTAGTACAACAAGG | 987 | 887 | 43 | 1069 |
| TAGTACAACAAGGCTGTCTTCTCAC | 517 | 1071 | 55 | 1070 |
| CTCACAGCCTGTGGAAACTCCTGAA | 270 | 377 | 75 | 1071 |
| GATGAGAAGCAATTGGCCCTCCAAG | 106 | 671 | 130 | 1072 |
| GCCCTCCAAGACCATGGTGCGGGAG | 1091 | 485 | 145 | 1073 |
| CTCCTCCCACAAGTACCTTAATAGT | 527 | 387 | 237 | 1074 |
| TAATAGTCCCACTCCATTTGATTCT | 570 | 1035 | 255 | 1075 |
| GATTCTCACAGTCCTGAAGGGGCAG | 1106 | 691 | 274 | 1076 |
| CTTCCTCAACGTCATACAGCTTGTC | 758 | 359 | 352 | 1077 |
| GATGGGACGCCAGGAGTTGCTTGAC | 351 | 667 | 453 | 1078 |

HG-U133_PLUS_2:230651_AT
SEQ ID NO:1079
attattttggtgggcttgatttttatagtttctcttaaaaattgtttggttgccatccaga
gggctcttttatgaagaatctatataaactactaaaacatttcttaggacctttttggtg
aatttgatcataaaattaaaaagcgtgtatgtgttttataaaggcatacctctgttaaga
aggctggttttatgtttgccttttcttctctactttgatcaccaccctagctgttccttt
ctccagaccaccttacttttcaaacttgattcttgctatcacagctctctgtaacatcag
ttaaaatcagctgcctcaactctttgaggatgtttgtgcataggacggcattgtgaaaca
tagggaaatggcagtcttactaacaaaacaggacctatctctggc Cluster Members
Consensus/Exemplar
BLASTn GenBank NR
Probe Info

| Probe Sequence(5'-3') | Probe X | Probe Y | Probe Interrogation Position | SEQ ID NO: |
|---|---|---|---|---|
| ATTATTTTGGTGGGCTTGATTTTAT | 413 | 15 | 72 | 1080 |
| TTGTTTGGTTGCCATCCAGAGGGCT | 1154 | 1155 | 112 | 1081 |
| GGCATACCTCTGTTAAGAAGGCTGG | 982 | 877 | 234 | 1082 |
| CAGACCACCTTACTTTTCAAACTTG | 225 | 329 | 315 | 1083 |
| CTTGATTCTTGCTATCACAGCTCTC | 846 | 357 | 336 | 1084 |
| CACAGCTCTCTGTAACATCAGTTAA | 865 | 309 | 351 | 1085 |
| ATCAGTTAAAATCAGCTGCCTCAAC | 245 | 39 | 367 | 1086 |
| CAACTCTTTGAGGATGTTTGTGCAT | 455 | 301 | 388 | 1087 |
| GTTTGTGCATAGGACGGCATTGTGA | 262 | 719 | 403 | 1088 |
| CATAGGGAAATGGCAGTCTTACTAA | 101 | 351 | 430 | 1089 |
| TAACAAAACAGGACCTATCTCTGGC | 980 | 1043 | 452 | 1090 |

>HG-U133_PLUS_2:241861_AT
SEQ ID NO: 1091
tttcctgtcttgaataatcccaacaaaaccatttgaatcctcaagtaaaaatatatttat
cacttaaatcagaaacaatgaattcaaaatggnaaagtagttaaagtctaaaatgttttt
tcccataaaacttagaaagaattatcttctacttccataaatatattatgttttataacga
tgtattgtgttaccacatacaacaaacctttatgaactgctcatataactgtttaattgt
tttcaatctctggctctgaacaattctag Cluster Members
Consensus/Exemplar
BLASTn GenBank NR Note: "n"'s represent regions that are not probed by the probe sequences.
Probe Info

| Probe Sequence(5'-3') | Probe X | Probe Y | Probe Interrogation Position | SEQ ID NO: |
|---|---|---|---|---|
| TTTCCTGTCTTGAATAATCCCAACA | 837 | 1097 | 133 | 1092 |
| GAATAATCCCAACAAAACCATTTGA | 950 | 551 | 144 | 1093 |
| CAAAACCATTTGAATCCTCAAGTAA | 752 | 303 | 156 | 1094 |
| GAAAGAATTATCTTCTACTTCCATA | 968 | 591 | 266 | 1095 |
| ATTATCTTCTACTTCCATAAATATA | 356 | 15 | 272 | 1096 |
| ATAACGATGTATTGTGTTACCACAT | 1106 | 33 | 306 | 1097 |
| GTTACCACATACAACAAACCTTTAT | 599 | 709 | 321 | 1098 |
| CAACAAACCTTTATGAACTGCTCAT | 223 | 303 | 332 | 1099 |
| GAACTGCTCATATAACTGTTTAATT | 960 | 577 | 346 | 1100 |
| TTAATTGTTTTCAATCTCTGGCTCT | 935 | 1125 | 365 | 1101 |
| AATCTCTGGCTCTGAACAATTCTAG | 624 | 279 | 377 | 1102 |

>HG-U133_PLUS_2:241566_AT
SEQ ID NO: 1103
ttcattcaaacatttcttattatcatttattgcacatagcatggattaatcaaataagtt
taaaataaaataatagactagagaaaggtgctttattttaaaaacagaaacaaaaagaag
gtacgtggattatctgatgctacatcacactctgggagagacttcccttctttcagagag
cctctcatttcttaatgtggatcattttgctctttcccccctgataatgctcacttactct
ctttcataatctcccctctttcacttgttcttttctttccaatcatccaatgatccatc
aaggtactttggtgttcagtgctttctcatatggttcaactcagatcatgtagtctttct
cacccaaccaattcaactactgtttcctgagaccc Cluster Members
Consensus/Exemplar
BLASTn GenBank NR
Probe Info

| Probe Sequence(5'-3') | Probe X | Probe Y | Probe Interrogation Position | SEQ ID NO: |
|---|---|---|---|---|
| TTCATTCAAACATTTCTTATTATCA | 994 | 1131 | 28 | 1104 |
| GGTACGTGGATTATCTGATGCTACA | 789 | 827 | 147 | 1105 |
| ATGCTACATCACACTCTGGGAGAGA | 50 | 55 | 164 | 1106 |
| CTTTCAGAGAGCCTCTCATTTCTTA | 1022 | 365 | 197 | 1107 |
| CTTTTCTTTCCAATCATCCAATGAT | 683 | 365 | 298 | 1108 |
| CAATGATCCATCAAGGTACTTTGGT | 838 | 293 | 316 | 1109 |
| GTACTTTGGTGTTCAGTGCTTTCTC | 153 | 735 | 331 | 1110 |
| GTGCTTTCTCATATGGTTCAACTCA | 352 | 765 | 346 | 1111 |
| TGGTTCAACTCAGATCATGTAGTCT | 1044 | 905 | 359 | 1112 |
| CTCACCCAACCAATTCAACTACTGT | 109 | 373 | 386 | 1113 |
| ATTCAACTACTGTTTCCTGAGACCC | 355 | 11 | 398 | 1114 |

>HG-U133_PLUS_2:240780_AT
SEQ ID NO:1115
ggggcacgcttttcacaacgtggagatgcagggtcatgggctgcctgctaccacgangcn
gaaggggatggtgctgggcaccagnncctgccccnggggctgggtttctcctgggcctggg
ccgagggggtggaggcctgtgggtgacgtgttcaagacggctcagcaanccccacctgaca
gtgtccaggtggggcctcntnncccncccccaggctcccagggagcacagcctccactc
ctacacactggctactctgccggagggggaggccgtgctggagtgatgcctggcgcgtgt
tgtgtgatgggagaattgggtatttacagtttaataacgagatctcgatgccgtcgatcg
gcc Cluster Members
Consensus/Exemplar
BLASTn GenBank NR
Note: "n"'s represent regions that are not probed by the probe sequences.
Probe Info

| Probe Sequence(5'-3') | Probe X | Probe Y | Probe Interrogation Position | SEQ ID NO: |
|---|---|---|---|---|
| GGGGCACGCTTTTCACAACGTGGAG | 1041 | 813 | 31 | 1116 |
| GCTTTTCACAACGTGGAGATGCAGG | 966 | 513 | 38 | 1117 |
| GAGATGCAGGGTCATGGGCTGCCTG | 96 | 643 | 53 | 1118 |
| TGCAGGGTCATGGGCTGCCTGCTAC | 445 | 959 | 57 | 1119 |
| GGCCTGTGGGTGACGTGTTCAAGAC | 555 | 889 | 163 | 1120 |
| GTGACGTGTTCAAGACGGCTCAGCA | 258 | 771 | 172 | 1121 |
| AGGCCGTGCTGGAGTGATGCCTGGC | 465 | 73 | 300 | 1122 |
| CTGGCGCGTGTTGTGTGATGGGAGA | 1085 | 407 | 320 | 1123 |
| GAGAATTGGGTATTTACAGTTTAAT | 431 | 633 | 341 | 1124 |

-continued

| | | | |
|---|---|---|---|
| TAACGAGATCTCGATGCCGTCGATC | 264 | 1043 | 365 | 1125 |
| GAGATCTCGATGCCGTCGATCGGCC | 150 | 643 | 369 | 1126 |

>HG-U133_PLUS_2:244862_AT
SEQ ID NO:1127
ggcactgggaacaggcatgctcccagctaggaagaagccggggacataaagctagcagct
gtggtgaggataccagggtgagtgctgagggtgagggacctggcttcctgttttaatg
attaagcctcagcctcaaaaagcttttgacagcctggacaacatggccagaccctatc Cluster Members
Consensus/Exemplar
BLASTn GenBank NR
Probe Info

| Probe Sequence(5'-3') | Probe X | Probe Y | Probe Interrogation Position | SEQ ID NO: |
|---|---|---|---|---|
| GGCACTGGGAACAGGCATGCTCCCA | 451 | 873 | 90 | 1128 |
| GCATGCTCCCAGCTAGGAAGAAGCC | 778 | 523 | 104 | 1129 |
| GCCGGGGACATAAAGCTAGCAGCTG | 549 | 483 | 126 | 1130 |
| AGCTAGCAGCTGTGGTGAGGATACC | 610 | 137 | 139 | 1131 |
| GAGGATACCAGGGTGAGTGCTGAGG | 377 | 659 | 155 | 1132 |
| GTGCTGAGGGTGAGGGACCTGGGCT | 982 | 761 | 171 | 1133 |
| CTGGGCTTCCTGTTTTTAATGATTA | 17 | 405 | 189 | 1134 |
| TTAATGATTAAGCCTCAGCCTCAAA | 585 | 1125 | 204 | 1135 |
| AAGCCTCAGCCTCAAAAAGCTTTTG | 250 | 245 | 213 | 1136 |
| AAAAAGCTTTTGACAGCCTGGACAA | 1046 | 219 | 226 | 1137 |
| CTGGACAACATGGCCAGACCCTATC | 70 | 407 | 243 | 1138 |

>HG-U133_PLUS_2:241864_X_AT
SEQ ID NO: 1139
ggccccgtattcatttttatactggaaaacatttttttgtaattttctttgcaaaga
aatgagcataaaaatgaatactccaaagaaaaggaattattatggcaaattaaaagggac
acggtactatgatttaattactgtcttgtctttttaaaatgtcatctcttgttttacccct
tttttaaataaaagctttaaaaacanntctttgggtattattctggaggtatgtttctt
ttatataagatttcaagtttaaacatttacaataagtaataatatttaaattcttataac
aagtaatgaaatatttggtttagtaattagcntagtctattttnaaaaatcattaaaatt
tncttttgttttaagaatgccatactacaaatgatgttatttggttttaatggtgttttg
tg Cluster Members
Consensus/Exemplar
Group Members
BLASTn GenBank NR
Note: "n"'s represent regions that are not probed by the probe
sequences.
Probe Info

| Probe Sequence(5'-3') | Probe X | Probe Y | Probe Interrogation Position | SEQ ID NO: |
|---|---|---|---|---|
| GGCCCCGTATTCATTTTTTATACTG | 541 | 697 | 192 | 1140 |
| AAGGGACACGGTACTATGATTTAAT | 1118 | 263 | 305 | 1141 |
| TATGATTTAATTACTGTCTTGTCTT | 1098 | 1077 | 319 | 1142 |
| TACTGTCTTGTCTTTTAAAATGTC | 918 | 1057 | 330 | 1143 |
| AAAATGTCATCTCTTGTTTTACCCT | 965 | 223 | 347 | 1144 |
| TCTTTGGGTATTATTCTGGAGGTAT | 878 | 1009 | 400 | 1145 |
| GTATTATTCTGGAGGTATGTTTCTT | 919 | 719 | 407 | 1146 |
| TCTGGAGGTATGTTTCTTTTATATA | 60 | 997 | 414 | 1147 |
| TTTGTTTTTAAGAATGCCATACTAC | 414 | 1093 | 555 | 1148 |
| GAATGCCATACTACAAATGATGTTA | 1063 | 555 | 566 | 1149 |
| TATTTGGTTTTAATGGTGTTTTGTG 7 | 48 | 1085 | 589 | 1150 |

>HG-U133_PLUS_2:241643_AT
SEQ ID NO: 1151
ctcttgatctctcaaccttgtgatctgcccgcctcgacctcccaaagtgctgggattaca
ggcatgagccactgcgcctggcctagctacagatttttttacaatgctaagtattttctg
aacagtttgactgttgccaaataatttattcaatttttttccctctatgactcattact
taccctgagcaaatcatctatacgtccctccttcttttccaggtcctgggttttattact
ttctaatgctgctaatttcagcattgtgagatcagtctaaatgaaaaaagttattttat
tatctccattatatatgttgtttcaagcaaacataaaactagattttactccaaattcaa
aaggtaaagaaaaataatttgtgtgtatatgtaaagtgaatctcaaaaagtttgtcgac Cluster Members
Consensus/Exemplar
BLASTn GenBank NR
Probe Info -continued

| Probe Sequence(5'-3') | Probe X | Probe Y | Probe Interrogation Position | SEQ ID NO: |
|---|---|---|---|---|
| CTCTTGATCTCTCAACCTTGTGATC | 1017 | 379 | 255 | 1152 |
| CGCCTGGCCTAGCTACAGATTTTTT | 595 | 419 | 329 | 1153 |
| TGGCCTAGCTACAGATTTTTTACA | 690 | 893 | 333 | 1154 |
| TACAGATTTTTTACAATGCTAAGT | 233 | 1053 | 342 | 1155 |
| TTCTGAACAGTTTGACTGTTGCCAA | 13 | 1137 | 370 | 1156 |
| CTCTATGACTCATTACTTACCCTGA | 80 | 381 | 418 | 1157 |
| ATGACTCATTACTTACCCTGAGCAA | 507 | 57 | 422 | 1158 |
| TCATTACTTACCCTGAGCAAATCAT | 1079 | 1015 | 427 | 1159 |
| AAGTTATTTTATTATCTCCATTATA | 418 | 259 | 543 | 1160 |
| CTAGATTTTACTCCAAATTCAAAAG | 976 | 365 | 593 | 1161 |
| AGTGAATCTCAAAAAGTTTGTCGAC | 502 | 75 | 650 | 1162 |

>HG-U133_PLUS_2:240452_AT
SEQ ID NO: 1163
gtacacggtcacagttttcatcatactaatctctcttcaagaaatcttcaaaatttgatt
tacttctgaaaatacgtttcaccttttctctcctgttgctattatctattaccatgtcag
aacttagtctccattaaatgccaagcccaccgttaggcaccatgggtaaaaaatgaatag
gaaaccatctgtttcatacggtcttcagtcatttgcgcttttcacaatgtactggtagt
agatcacaattttttttcctttgtagttacaatagctagaaagtaaatgttggaatttta
aaatatgcaggtatactagattttgggaatgtggggattggaagcatctagacattgtt
tgatttgtgacattcaaaagcaggtacgtcataactcgtttgcttctattttc Cluster Members
Consensus/Exemplar
BLASTn GenBank NR
Probe Info

| Probe Sequence(5'-3') | Probe X | Probe Y | Probe Interrogation Position | SEQ ID NO: |
|---|---|---|---|---|
| GTACACGGTCACAGTTTTCATCATA | 820 | 735 | 69 | 1164 |
| TTTCATCATACTAATCTCTCTTCAA | 490 | 1101 | 84 | 1165 |
| ACCATGTCAGAACTTAGTCTCCATT | 59 | 153 | 179 | 1166 |
| GTCTCCATTAAATGCCAAGCCCACC | 932 | 751 | 195 | 1167 |
| GCCCACCGTTAGGCACCATGGGTAA | 370 | 487 | 213 | 1168 |
| AAACCATCTGTTTCATACGGTCTTC | 856 | 213 | 250 | 1169 |
| TACGGTCTTCAGTCATTTTGCGCTT | 371 | 1059 | 265 | 1170 |
| TTTGCGCTTTTCACAATGTACTGGT | 309 | 1095 | 281 | 1171 |
| GGAAGCATCTAGACATTGTTTGATT | 218 | 865 | 409 | 1172 |
| GCAGGTACGTCATAACTCGTTTGCT | 946 | 525 | 448 | 1173 |
| TCATAACTCGTTTGCTTCTATTTTC | 563 | 1017 | 457 | 1174 |

While the invention has been described in terms of its preferred embodiments, those skilled in the art will recognize that the invention can be practiced with modification within the spirit and scope of the appended claims.

REFERENCES

1. American Heart Association. 2002 Heart and Stroke Statistical Update. 2001
2. Safian R D. Zidar J, Hermiller et al. Manual of Interventional Cardiology. 3rd Edition, p 511. Physicians Press, Royal Oak, Mich. 2110.
3. Betriu A, Masotti M, Serra, A et al. Randomized comparison of coronary stent implantation and balloon angioplasty in the treatment of de novo coronary artery lesions (START). A four year follow-up. J Am Coll Cardiol. 1999; 34: 1498-506.
4. Morphologic predictors of restenosis after coronary stenting in humans. Circ. 2002; 105:2974-2980.
5. Bauters C, Hubert C, Prat A et al. Predictors of restenosis after coronary stent implantation. J Am Coll Cardiol. 1998; 31:1291-1298.
6. Kastrati A, Schgomig A, Elezi S et al. Predictive factors of restenosis after coronary stent placement. J Am Coll Cardiol. 1997; 30:1428-1436.
7. Morice M C, Serruys P W, Sousa J E et al. A randomized comparison of a Sirolimus-eluting stent with a standard stent for coronary revascularization. N Eng J Med. 200; 346:1773-1780.
8. Grube E, Silber S, Hauptman K E et al. TAXUS I: six and twelve month results from a randomized, double blind trial on a slow release paclitaxel-eluting stent for de novo coronary lesions. Circ. 2003; 107:38-42.
9. Windecker S, Remondino A, Eberli F R et al. Sirolimus-eluting and paclitaxel-eluting stents for coronary revascularization. N Eng J Med 2005; 353:653-662.

Serruys P W, de Jaegere P, Kiemeneji F et al. A comparison of balloon expandable stent implantation and balloon angioplasty in patients with coronary artery disease. The BENESTNR Study Group. N Eng J Med 1994; 34: 1498-506.

11. Pfisterer M, Brunner-LaRocca H P, Buser P T et al. Late clinical events after clopidogrel discontinuation may limit the benefit of drug eluting stents Vs bare metal stents. J Am Coll Cardiol 2006; 48(12):2584-2591.
12. Walter D H, Schachinger V, Elsner M et al. Statin therapy is associated with reduced restenosis rates after coronary stent implantation in carriers of the PI(A2) allele of the platelet glycoprotein IIIa gene. Eur Heart J. 2001; 22:587-95.

13. Banters C, Lamblin N, Amouyel P. Gene polymorphisms and outcome after coronary angioplasty. Curr Interven Cardiol Rep 2001; 22:587-95.
14. Mamotte C D, van Bockxmeer F M, roger R. PIa1/a2 polymorphism of glycoprotein IIIa and risk of coronary artery disease and restenosis following coronary angioplasty. Am J Cardiol 1998; 82:13-16.
15. de Maat M P, Jukema J W, Ye S et al. Effect of stromelysin-1 promoter on efficacy of pravastatin in coronary atherosclerosis and restenosis. Am J Cardiol 1999; 83:852-856.
16. Kastrati A, Werner K, Berger P et al. Protective role against restenosis from an interleukin-1 receptor antagonist gene polymorphism in patients treated with coronary stenting. J Am Coll Cardiol 2000; 36:2168-73.
17. Zohlnhofer D, Klein C A, Richter T et al. Gene expression profiling of human stent induced neointima by cDNA array analysis of microscopic specimens retrieved by helix cutter atherectomy: detection of FK506-binding protein 12 upregulation. Circ. 2001; 103:1396-1402.
18. Irizarry R A, Hobbs B, Collin F et al. Exploration, normalization, and summaries of high density oligonucleotide array probe level data. Biostatistics 2003; 4(2); 249-264.
19. Kyoto Encyclopedia of Genes and Genomics. www-.genomejp/KEGG.
20. Boulesteix A 1, Strimmer K. Partial Least Squares: A versatile tool for the ananlysis of high dimensional genomic data. Briefings in Bioinformatics 2007; 8(1):32-44.
21. Hoang A. Optimal multi-class classification with principal components. Proc of International Conf on Data Mining 2206. Las Vegas, Nev.
22. Rosipal R, Kramer N. Overview and Recent Advances in Partial Least Squares in C. Saunders et al (eds) "Subspace, latent structure and feature selection techniques, Lecture Note in Computer Science. Spring 2006:34-51.

We claim:

1. A genomic based profiling method for predicting whether a patient that is a candidate for a coronary artery stent will experience restenosis if he or she receives a bare metal stent, comprising the steps of
   i) obtaining a biological sample associated with a patient that is currently not suffering from an active infection, and does not have diabetes, a malignancy, a genetic based disease or a chronic inflammatory disease, said biological sample being leukocytes present in circulating whole blood;
   ii) establishing a gene expression profile from a plurality of nucleic acids representative of genes expressed in said leukocytes; and
   iii) using a trained partial least squares component based regression model with an accuracy as measured by the receiver operating characteristic (PLS-ROC) of 0.76 or greater to provide a probability output for restenosis in said patient based on said gene expression profile.

2. The method of claim 1, wherein said plurality of nucleic acids are expressed from said leukocytes and are selected from one or more molecular pathways or molecular families selected from the group consisting of: molecular target of rapamycin; leukocyte trans-endothelial migration; TGFβ signaling; T cell antigen processing; T cell signaling; mitogen activated protein kinase (MAPK); and cell adhesion molecules.

3. The method of claim 1, wherein said step of determining a gene expression profile is carried out using a whole human genome chip.

* * * * *